United States Patent
Wegmann et al.

(10) Patent No.: US 11,229,693 B2
(45) Date of Patent: Jan. 25, 2022

(54) POXVIRUS VECTORS ENCODING HIV ANTIGENS, AND METHODS OF USE THEREOF

(71) Applicants: Janssen Vaccines & Prevention B.V., Leiden (NL); Bavarian Nordic A/S, Kvistgaard (DK)

(72) Inventors: Frank Wegmann, Leiden (NL); Johannes Petrus Maria Langedijk, Amsterdam (NL); Jerôme Hubertina Henricus Victor Custers, Alphen aan den Rijn (NL); Viki Bockstal, Borgerhout (BE); Markus Kalla, Penzberg (DE)

(73) Assignees: Janssen Vaccines & Prevention B.V., Leiden (NL); Bavarian Nordic A/S, Kvistgaard (DK)

(*) Notice: Subject to any disclaimer, the term of this patent is extended or adjusted under 35 U.S.C. 154(b) by 41 days.

(21) Appl. No.: 16/620,669

(22) PCT Filed: Jun. 14, 2018

(86) PCT No.: PCT/IB2018/054386
§ 371 (c)(1),
(2) Date: Dec. 9, 2019

(87) PCT Pub. No.: WO2018/229711
PCT Pub. Date: Dec. 20, 2018

(65) Prior Publication Data
US 2020/0138938 A1    May 7, 2020

Related U.S. Application Data

(60) Provisional application No. 62/520,079, filed on Jun. 15, 2017.

(51) Int. Cl.
| | | |
|---|---|---|
| *A61K 39/00* | (2006.01) | |
| *A61K 39/21* | (2006.01) | |
| *A61K 39/12* | (2006.01) | |
| *C07K 14/005* | (2006.01) | |
| *C12N 7/00* | (2006.01) | |
| *A61P 31/18* | (2006.01) | |
| *C12N 15/86* | (2006.01) | |

(52) U.S. Cl.
CPC .............. *A61K 39/12* (2013.01); *A61P 31/18* (2018.01); *C12N 15/86* (2013.01); *C07K 2319/00* (2013.01); *C12N 2710/24043* (2013.01); *C12N 2740/16134* (2013.01); *C12N 2740/16234* (2013.01); *C12N 2740/16334* (2013.01)

(58) Field of Classification Search
CPC ......... A61K 39/12; A61K 39/21; A61P 31/18; A61P 37/04; C07K 14/005
See application file for complete search history.

(56) References Cited

U.S. PATENT DOCUMENTS

| | | |
|---|---|---|
| 4,603,112 A | 7/1986 | Paoletti et al. |
| 5,185,146 A | 2/1993 | Altenburger |
| 5,639,649 A | 6/1997 | Almond et al. |
| 5,643,576 A | 7/1997 | Johnston et al. |
| 6,761,893 B2 | 7/2004 | Chaplin et al. |
| 6,911,205 B2 | 6/2005 | Sodroski et al. |
| 7,270,811 B2 | 9/2007 | Bout et al. |
| 7,429,653 B2 | 9/2008 | Sodroski et al. |
| 7,592,014 B2 | 9/2009 | Binley et al. |
| 7,901,690 B2 | 3/2011 | Lu et al. |
| 7,939,083 B2 | 5/2011 | Dey et al. |
| 8,034,378 B2 | 10/2011 | O'Hagan |
| 8,197,825 B2 | 6/2012 | Sutter et al. |
| 9,017,691 B2 | 4/2015 | Barouch et al. |
| 2003/0206926 A1 | 11/2003 | Chaplin et al. |
| 2003/0207287 A1 | 11/2003 | Short |
| 2006/0159699 A1 | 7/2006 | Howley et al. |
| 2007/0166784 A1 | 7/2007 | Barnett et al. |
| 2007/0298051 A1 | 12/2007 | Barouch et al. |
| 2008/0199939 A1 | 8/2008 | Havenga et al. |
| 2008/0279879 A1 | 11/2008 | Zolla-Pazner |
| 2011/0159036 A1 | 6/2011 | Moss et al. |
| 2011/0250220 A1 | 10/2011 | Dey et al. |

(Continued)

FOREIGN PATENT DOCUMENTS

| | | |
|---|---|---|
| CN | 102282175 A | 12/2011 |
| EP | 2292772 A1 | 3/2011 |

(Continued)

OTHER PUBLICATIONS

Goujard et al., "HIV-1 Control After Transient Antiretroviral Treatment Initiated in Primary Infection: Role of Patient Characteristics and Effect of Therapy", Antiviral Therapy, vol. 17, No. 6, pp. 1001-1009 (2012).

(Continued)

*Primary Examiner* — Barry A Chestnut
(74) *Attorney, Agent, or Firm* — Ice Miller LLP

(57) ABSTRACT

Poxvirus vectors encoding a synthetic HIV envelope antigen and other HIV antigens, as well as compositions containing such poxvirus vectors and uses of such poxvirus vectors as vaccines to provide improved immunity against HIV, are provided. Also provided are vaccine combinations containing the disclosed poxvirus vectors, adenovirus vectors encoding one or more HIV antigens, and one or more isolated HIV antigenic polypeptides, and methods of using the vaccine combinations to provide improved immunity against HIV.

20 Claims, 10 Drawing Sheets
Specification includes a Sequence Listing.

(56) References Cited

U.S. PATENT DOCUMENTS

| | | |
|---|---|---|
| 2012/0045472 A1 | 2/2012 | Harrison et al. |
| 2012/0076812 A1 | 3/2012 | Barouch et al. |
| 2013/0189754 A1 | 7/2013 | Parks et al. |
| 2014/0302080 A1 | 10/2014 | Barouch et al. |
| 2014/0348791 A1 | 11/2014 | Barouch et al. |
| 2015/0246112 A1 | 9/2015 | Barouch et al. |
| 2015/0291935 A1 | 10/2015 | Barouch et al. |
| 2016/0024156 A1 | 1/2016 | Barouch et al. |
| 2016/0122392 A1 | 5/2016 | Baker et al. |
| 2017/0165355 A1 | 6/2017 | Langedijk |
| 2017/0362280 A1 | 12/2017 | Nguyen et al. |
| 2018/0064803 A1 | 3/2018 | Tomaka et al. |
| 2018/0072777 A1 | 3/2018 | Rutten et al. |

FOREIGN PATENT DOCUMENTS

| | | | |
|---|---|---|---|
| EP | 2319860 A2 | | 5/2011 |
| WO | 2000/70071 A1 | | 11/2000 |
| WO | 0119958 | | 3/2001 |
| WO | 200242480 A2 | | 5/2002 |
| WO | 2003048184 A2 | | 6/2003 |
| WO | 2003/104467 A1 | | 12/2003 |
| WO | 2004/001032 A2 | | 12/2003 |
| WO | 2004/0044155 | | 5/2004 |
| WO | 2006002079 | | 1/2006 |
| WO | 2006020071 | | 2/2006 |
| WO | 2006/040330 | | 4/2006 |
| WO | 2007005934 | | 1/2007 |
| WO | 2007/024941 A2 | | 3/2007 |
| WO | 2007/104792 A2 | | 9/2007 |
| WO | 2007/149491 | | 12/2007 |
| WO | 2008063331 | | 5/2008 |
| WO | 2008/107370 A1 | | 9/2008 |
| WO | 2010/042942 A2 | | 4/2010 |
| WO | 2010/059732 A1 | | 5/2010 |
| WO | WO2010059732 | * | 5/2010 |
| WO | 2010096561 A1 | | 8/2010 |
| WO | 2011/082087 A2 | | 7/2011 |
| WO | 2011/092029 A1 | | 8/2011 |
| WO | 2012/030904 | | 3/2012 |
| WO | 2012/048817 A2 | | 4/2012 |
| WO | WO2012048817 | * | 4/2012 |
| WO | 2012/082918 A1 | | 6/2012 |
| WO | 2013055908 | | 4/2013 |
| WO | 2014/047261 | | 3/2014 |
| WO | 2014/107744 A1 | | 7/2014 |
| WO | 2014/124301 A1 | | 8/2014 |
| WO | 2015/048770 | | 4/2015 |
| WO | 2016/049287 A1 | | 3/2016 |
| WO | 2016037154 A1 | | 3/2016 |
| WO | 2016146844 A1 | | 9/2016 |
| WO | WO2016/146844 | * | 9/2016 |
| WO | WO2016146844 | * | 9/2016 |
| WO | 2017102929 A1 | | 6/2017 |

OTHER PUBLICATIONS

Hamlyn et al., "Plasma HIV Viral Rebound Following Protocol-Indicated Cessation of ART Commenced in Primary and Chronic HIV Infection", PLOS One, vol. 7, No. 8, 8 pgs (Aug. 2012).
Havenga et al., "Novel Replication-Incompetent Adenoviral B-Group Vectors: High Vector Stability and Yield in PER. C6 Cells", Journ. of Gen Viro., vol. 87, pp. 2135-2143 (2006).
Lodi et al., "Immunovirologic Control 24 Months After Interruption of Antiretroviral Therapy Initiated Close to HIV Seroconversion", Archives of Internal Medicine, vol. 172, No. 16, pp. 1252-1255 (2012).
Saez-Cirion et al., "Post-Treatment HIV-1 Controllers with a Long-Term Virological Remission after the Interruption of Early Initiated Antiretroviral Therapy ANRS Visconti Study", PLOS Pathogens, vol. 9, No. 3, 12 pgs (Mar. 2013).
Unaids, "Report on the Global AIDS Epidemic", 198 pgs (2013).
Williams et al., "HIV-1 DNA Predicts Disease Progression and Post-Treatment Virological Control", eLife, vol. 3, 16 pgs (2014).
Stickl, "Smallpox Vaccination and it's Consequences: First Experiences with the Highly Attenuated Smallpox Vaccine MVA", Preventive Medicine, vol. 3, pp. 97-101 (1974).
Blondelle et al., "Immunogenically Optimized Peptides Derived from Natural Mutants of HIV CTL Epitopes and Peptide Combinational Libraries", Biopolymers, vol. 90(5), pp. 683-694 (2008).
Fischer et al., "Coping with Viral Diversity in HIV vaccine Design: A Response to Nickle et al.," PLoS Comput Bioi., vol. 4, No. 1, pp. 175-179 (2008).
Kong et al., "Expanded Breadth of the T-Cell Response to Mosaic Human Immunodeficiency Virus Type 1 Envelope DNA Vaccination," J. Viral., vol. 83, No. 5, pp. 2201-2215 (2009).
Korber et al., "T-Cell Vaccine Strategies for Human Immunodeficiency Virus, The Virus with a Thousand Faces," J. Viral., vol. 83, No. 17, pp. 8300-8314 (2009).
NCBI Blast for GenBank AAY23526.1, Jul. 2016, "Envelope glycoprotein Human immunodeficiency virus 1", downloaded from web page: http://www.ncbi.nlm.nih.gov/protein/62956393, Download date: Feb. 8, 2018 (2 pages).
Thurmond et al., "Web-Based Design and Evaluation of T-cell Vaccine Candidates," Bioinformatics, vol. 24, No. 14, pp. 1639-1640 (2008).
Gotch et al., "Candidate Vaccines for Immunotherapy in HIV", HIV Medicine, vol. 2, pp. 260-265 (2001).
Girard et al., A Review of Vaccine Research and Development: The Human Immunodeficiency Virus (HIV), Vaccine, vol. 24, pp. 4062-4081 (2006).
Barouch, "Challenges in the Development of an HIV-1 Vaccine", Nature, vol. 455, No. 2, pp. 613-619 (2008).
Cohen, "Did Merck's Failed HIV Vaccine Cause Harm?" Science, vol. 318, pp. 1048-1049 (2007).
Abrahams et al., "Quantitating the Multiplicity of Infection with Human Immunodeficiency Virus Type 1 Subtype C Reveals a Non-Poisson Distribution of Transmitted Variants," Journal of Virology, vol. 83, No. 8, pp. 3556-3567 (Apr. 2009).
Amanna et al., "Contributions of Humoral and Cellular Immunity to Vaccine-Induced Protection in Humans," Virology, vol. 411, No. 2, pp. 206-215 (2011).
Baba et al, "Human Neutralizing Monoclonal Antibodies of the IgG1 Subtype Protect Against Mucosal Simian-Human Immunodeficiency Virus Infection," Nature Medicine, vol. 6, No. 2, pp. 200-206 (2000).
Calarese et al, "Antibody Domain Exchange is an Immunological Solution to Carbohydrate Cluster Recognition," Science, vol. 300, No. 5628, pp. 2065-2071 (2003).
Cardoso et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Cardoso et al, "Structural Basis of Enhanced Binding of Extended and Helically Constrained Peptide Epitopes of the Broadly Neutralizing HIV-1 Antibody 4E1 0," Journal of Molecular Biology, vol. 365, No. 5, pp. 1533-1544 (2007).
Catanzaro et al, "Phase I Clinical Evaluation of a Six-Plasmid Multiclade HIV-1 DNA Candidate Vaccine," Vaccine, vol. 25, No. 20, pp. 4085-4092 (2007).
Checkley et al, "HIV-1 Envelope Glycoprotein Biosynthesis, Trafficking, and Incorporation," Journal of Molecular Biology, vol. 410, No. 4, pp. 582-608 (2011).
Cho et al, "Polyvalent Envelope Glycoprotein Vaccine Elicits a Broader Neutralizing Antibody Response But is Unable to Provide Sterilizing Protection Against Heterologous Simian/Human Immunodeficiency Virus Infection in Pigtailed Macaques," Journal of Virology, vol. 75, No. 5, pp. 2224-2234 (Mar. 2001).
Cohen, "Naked DNA Points Way to Vaccines," Science, vol. 259, pp. 1691-1692 (Mar. 1993).
Davenport et al, "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107 (Jul. 2011).

(56) References Cited

OTHER PUBLICATIONS

Doores et al, "Antibody 2G12 Recognizes Di-Mannose Equivalently in Domain- and Nondomain-Exchanged Forms but Only Binds the HIV-1 Glycan Shield if Domain Exchanged," Journal of Virology, vol. 84, No. 20, pp. 10690-10699 (2010).
Doria-Rose et al, "Frequency and Phenotype of Human Immunodeficiency Virus Envelope-Specific B Cells from Patients with Broadly Cross-Neutralizing Antibodies," Journal of Virology, vol. 83, No. 1, pp. 188-199 (Jan. 2009).
Engelhardt et al, "Ablation of E2A in Recombinant Adenoviruses Improves Transgene Persistence and Decreases Inflammatory Response in Mouse Liver," Proceedings of the National Academy of Sciences of the United States of America, vol. 91, No. 13, pp. 6196-6200 (Jun. 1994).
Falkowska et al, "PGV04, an HIV-1 gp120 CD4 Binding Site Antibody, is Broad and Potent in Neutralization but Does Not Induce Conformational Changes Characteristic of CD4," Journal of Virology, vol. 86, No. 8, pp. 4394-4403 (2012).
Fiebig et al, "Neutralizing Antibodies Against Conserved Domains of p15E of Porcine Endogenous Retroviruses: Basis for a Vaccine for Xenotransplantation?" Virology, vol. 307, No. 2, pp. 406-413 (2003).
Fischer et al, "Identification of a Peptide Mimicking the Binding Pattern of an Antiphospholipid Antibody," Immunobiology, vol. 211, No. 9, pp. 695-699 (2006).
Freeman et al, "Crystal Structure of HIV-1 Primary Receptor CD4 in Complex with a Potent Antiviral Antibody," Structure, vol. 18, No. 12, pp. 1632-1641 (Dec. 8, 2010).
Frey et al, "A Fusion-Intermediate State of HIV-1 gp41 Targeted by Broadly Neutralizing Antibodies," Proceedings of the National Academy of Sciences of the United States of America, vol. 105, No. 10, pp. 3739-3744 (Mar. 11, 2008).
Fynan et al, "DNA Vaccines: Protective Immunizations by Parenteral, Mucosal, and Gene-Gun Inoculations," Proceedings of the National Academy of Sciences of the United States of America, vol. 90, No. 24, p. 11478-11482 (Dec. 1993).
Gao et al, "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).
Gao et al, "Centralized HIV-1 Envelope Immunogens and Neutralizing Antibodies," Current HIV Research, vol. 5, No. 6, pp. 572-577 (2007).
Gao et al, "Molecular Cloning and Analysis of Functional Envelope Genes from Human Immunodeficiency Virus Type 1 Sequence Subtypes A through G" Journal of Virology, vol. 70, No. 3, pp. 1651-1667 (Mar. 1996).
Gaschen et al, "Diversity Consideration in HIV-1 Vaccine Selection," Science, vol. 296, No. 5577, pp. 2354-2360 (Jun. 28, 2002).
GenBank Accession No. KC769514. Retrieved on Dec. 30, 2014 (2 pages).
Georgiev et al, "Delineating Antibody Recognition in Polyclonal Sera from Patterns of HIV-1 Isolate Neutralization," Science, vol. 340, No. 6133, pp. 751-756 (2013).
Graham et al, "Phase 1 Safety and Immunogenicity Evaluation of a Multiclade HIV-1 DNA Candidate Vaccine," The Journal of Infectious Diseases, vol. 194, No. 12, pp. 1650-1660 (Dec. 15, 2006).
Gray et al, "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Grundner et al, "Analysis of the Neutralizing Antibody Response Elicited in Rabbits by Repeated Inoculation with Trimeric HIV-1 Envelope Glycoproteins," Virology, vol. 331, No. 1, pp. 33-46 (2005).
Hammer et al, "Efficacy Trial of a DNA/rAd5 HIV-1 Preventive Vaccine," The New England Journal of Medicine, vol. 369, No. 22, pp. 2083-2092 (Nov. 28, 2013).

Huang et al, "Broad and Potent Neutralization of HIV-1 by a gp41-Specific Human Antibody," Nature, vol. 491, No. 7424, pp. 406-412 (2012).
Julien et al, "Asymmetric Recognition of the HIV-1 Trimer by Broadly Neutralizing Antibody PG9," Proceedings of the National Academy of Sciences of the United States of America, vol. 110, No. 11, pp. 4351-4356 (Mar. 12, 2013).
Haynes et al, "Immune-Correlates Analysis of an HIV-1 Vaccine Efficacy Trial," The New England Journal of Medicine, vol. 366, No. 14, pp. 1275-1286 (2012).
Sarzotti-Kelsoe et al, "Optimization and Validation of the TZM-bl Assay for Standardized Assessments of Neutralizing Antibodies Against HIV-1," Journal of Immunological Methods, vol. 409, pp. 131-146 (2014).
Schnierle et al, "Pseudotyping of Murine Leukemia Virus with the Envelope Glycoproteins of HIV Generates a Retroviral Vector with Specificity of infection for CD4-Expressing Cells," Proceedings of the National Academy of Sciences of the United States of America, vol. 94, pp. 8640-8645 (Aug. 1997).
Walker et al, "Broad and Potent Neutralizing Antibodies from an African Donor Reveal a New HIV-1 Vaccine Target," Science, vol. 326, No. 5950, pp. 285-289 (Oct. 9, 2009).
Baicu et al., "Acid-base Buffering in Organ Preservation Solutions as a Function of Temperature: New Parameters for Comparing Buffer Capacity and Effciency", Cryobiology, vol. 45, pp. 33-48 (2002).
Barouch et al., "Protective Efficacy of Adenovirus/Protein Vaccines Against SIV Challenges in Rhesus Monkeys", Science, vol. 349, No. 6245, pp. 320-324 (Jul. 2015).
Barouch et al., "Protective Efficacy of a Global HIV-1 Mosaic Vaccine against Heterologous SHIV Challenges in Rhesus Monkeys," Cell, vol. 155, pp. 531-539 (Oct. 2013).
Hoganson et al., "Development of a Stable Adenoviral Vector Formulation", BioProcessing Journ., pp. 43-48 (Mar. 2002).
Kamerzell et al., "Protein-Excipient Interactions: Mechanisms and Biophysical Characterization Applied to Protein Formulation Development", Advanced Drug Delivery Review, vol. 63, pp. 1118-1159 (2011).
Kovacs et al., "HIV-1 Envelope Trimer Elicits more Potent Neutralizing Antibody Responses than Monomeric gp120", Proc. Natl. Acac. Sci., vol. 109, No. 30, pp. 12111-12116 (2012).
Lepe-Zuniga et al., "Toxicity of Light-Exposed Hepes Media", Journ. of Immun. Methods, vol. 103, pp. 145 (1987).
Sanders et al., "Brunenders: A Partially Attenuated Historic Poliovirus Type 1 Vaccine Strain", Journ. of General Viro., vol. 96, pp. 2614-2622 (2015).
Nkolola et al., "Breadth of Neutralizing Antibodies Elicited by Stable, Homogeneous Clade A and Clade C HIV-1 gp140 Envelope Trimers in Guinea Pigs", Journ. of Viro., vol. 84. No. 7, pp. 3270-3279 (Apr. 2010).
Nkolola et al., "Characterization and Immunogenicity of a Novel Mosaic M HIV-1 gp140 Trimer", Journ. of Virology, vol. 88, No. 17, pp. 9538-9552 (Sep. 2014).
Uchiyama, "Liquid Formulation for Antibody Drugs", Biochimica Biophysica, vol. 1844, pp. 2041-2052 (2014).
Zigler et al., "Analysis of the Cytotoxic Effects of Light-Exposed Hepes-Containing Culture Medium", In Vitro Cell Dev. Biol., vol. 21, No. 5, pp. 282-287 (1985).
Clapp et al. "Vaccines with Aluminum-Containing Adjuvants: Optimizing Vaccine Efficacy and Thermal Stability", J. Pharm. Sci. vol. 100, No. 2: pp. 388-401 (2011).
Wiggan et al. "Novel Formulations Enhance the Thermal Stability of Live-Attenuated Flavivirus Vaccines," Vaccine, vol. 29, pp. 7456-7462 (2011).
De Taeye et al, "Immunogenicity of Stabilized HIV-1 Envelope Trimers With Reduced Exposure of Non-Neutralizing Epitopes," Cell, vol. 163, pp. 1702-1715 (2015).
Julien et al, "Design and Structure of Two HIV-1 Clade C SOSIP. 664 Trimers That Increase the Arsenal of Native-Like Env Immunogens," PNAS, vol. 112, No. 38, pp. 11947-11952 (2015).
Kwon et al, "Crystal Structure, Conformational Fixation and Entry-Related Interactions of Mature Ligand-Free HIV-1 Env," Nature Structural & Molecular Biology, vol. 22, No. 7, pp. 522-531 (2015).

(56) References Cited

OTHER PUBLICATIONS

Pugach et al, "A Native-Like SOSIP.664 Trimer Based on an HIV-1 Subtype B Env Gene," Journal of Virology, vol. 39, No. 6, pp. 3380-3395 (2015).
Altschul et al, "Gapped BLAST and PSI-BLAST: a new generation of protein database search programs," Nucleic Acids Research, vol. 25, No. 17, pp. 3389-3402 (1997).
Eglen et al, "The Use of AlphaScreen Technology in HTS: Current Status," Current Chemical Genomics, vol. 1, pp. 2-10 (2008).
Abbink et al, "Comparative seroprevalence and immunogenicity of six rare serotype recombinant adenovirus vaccine vectors from subgroups B and D," Journal of Virology, vol. 81, No. 9, pp. 4654-4663 (2007).
Barouch et al, "Mosaic HIV-1 Vaccines Expand the Breadth and Depth of Cellular Immune Responses in Rhesus Monkeys," Nat. Med., vol. 16, No. 3, pp. 319-323 (2010).
Georgiev et al, "Single-Chain Soluble BG505.SOSIP gp140 Trimers as Structural and Antigenic Mimics of Mature Closed HIV-1 Env," Journal of Virology, vol. 89, pp. 5318-5329 (2015).
Bale et al, "Covalent Linkage of HIV-1 Trimers To Synthetic Liposomes Elicits Improved B Cell and Antibody Responses," Journal of Virology, vol. 91, No. 16, pp. e00443 17 (2017).
Harris et al, "Trimeric HIV-1 Glycoprotein gp140 Immunogens and Native HIV-1 Envelope Glycoproteins Display The Same Closed and Open Quaternary Molecular Architectures," PNAS, vol. 108, No. 28, pp. 11440-11445 (2011).
Guenaga et al, "Glycine Substitution at Helix-To-Coil Transitions Facilitates the Structural Determination of A Stabilized Subtype C HIV Envelope Glycoprotein," Immunity, vol. 46, pp. 792-803 (2017).
Lopez-Sagaseta et al, "Self-Assembling Protein Nanoparticles in the Design of Vaccines," Computational and Structural Biotechnology Journal, vol. 14, pp. 58-68 (2016).
Kesavardhana et al, "Stabilizing The Native Trimer of HIV-1 Env By Destabilizing The Heterodimeric Interface of The gp41 Postfusion Six-Helix Bundle," Journal of Virology, vol. 88, No. 17, pp. 9590-9604 (2014).
He et al, "Presenting Native-Like Trimeric HIV-1 Antigens With Self-Assembling Nanoparticles," Nature Communications, vol. 7, No. 1, pp. 1-15 (2016).
Sanders et al, "Stabilization of The Solubale, Cleaved, Trimeric Form of The Envelope Glycoprotein Complex of Human Immunodeficiency Virus Type 1," Journal of Virology, vol. 76, No. 17, pp. 8875-8889 (2002).
Kong et al, "Uncleaved Prefusion-Optimized gp140 Trimers Derived From Analysis of HIV-1 Envelope Metastability," Nature Communications, vol. 7, No. 1, pp. 1-15 (2016).
Zhang et al, "Expression, Purification, and Characterization of Recombinant HIV gp140," Journal of Biological Chemistry, vol. 276, No. 43, p. 39577-39585 (2001).
Sanders et al, "HIV-1 Neutralizing Antibodies Induced by Native-Like Envelope Trimers," Science, vol. 349, Issue 6244, pp. 1-17 (2015).
Zhao et al, "Nanoparticle Vaccines," Vaccines, vol. 32, pp. 327-337 (2014).
Sharma et al, "Cleavage-Independent HIV-1 Env Trimers Engineered As Soluble Native Spike Mimetics For Vaccines Design," Cell Reports, vol. 11, pp. 1-12 (2015).
Kushnir et al, "Virus-Like Particles As a Highly Efficient Vaccine Platform: Diversity of Targets and Production Systems and Advances in Clinical Development," Vaccine, vol. 31, pp. 58-83 (2012).
Achenbach et al., "Effect of Therapeutic Intensification Followed by HIV DNA Prime and rAd5 Boost Vaccination on HIV-specific Immunity and HIV Reservoir (EraMune 02): a Multicentre Randomised Clinical Trial", The Lancet, vol. 2, No. 3, pp. e82-e91 (Mar. 2015).
Gach et al., "HIV-1-Specific Antibody Response and Function after DNA Prime and Recombinant Adenovirus 5 Boost HIV Vaccine in HIV-Infected Subjects", PLOS One, vol. 11, No. 8, p. 17 (Aug. 2016).
Katlama et al., "Barriers to a Cure for HIV: New Ways to Target and Eradicate HIV-1 Reservoirs", The Lancet, vol. 381, No. 988., pp. 2109-2117 (Jun. 2013).
Thompson et al., "DNA/MVA Vaccination of HIV-1 Infected Participants with Viral Suppression on Antiretroviral Therapy, Followed by Treatment Interruption: Elicitation of Immune Responses without Control of Re-Emergent Virus", Plos One, vol. 11, No. 10, pp. 25 (Oct. 2016).
Blanchard et al., "Modified Vaccinia Virus Ankara Undergoes Limited Replication in Human Cells and Lacks Several Immunomodulatory Proteins: Implications for Use as a Human Vaccine", Journ. of Gen. Viro., vol. 79, pp. 1159-1167 (1998).
Carcelain et al., "Immune Interventions in HIV Infection", Immunol Rev., vol. 254, No. 1, pp. 355-371 (2013).
Carroll et al., "Host Range and Cytopathogenicity of the Highly Attenuated MVA Strain of Vaccinia Virus: Propagation and Generation of Recombinant Viruses in a Nonhuman Mammalian Cell Line", Virology, vol. 238, pp. 198-211 (1997).
Chen et al., "Protection of Rhesus Macaques Against Disease Progression from Pathogenic SHIV-89.6PD by Vaccination with Phage-Displayed HIV-1 Epitopes", Nat. Med., vol. 7, No. 11, pp. 1225-1231 (2001).
Fischer et al., "Polyvalent Vaccines for Optimal Coverage of Potential T-Cell Epitopes in Global HIV-1 Variants", Nat. Med., vol. 13, No. 1, pp. 100-106 (Jan. 2007).
Gianella et al., "Effect of Early Antiretroviral Therapy During Primary HIV-1 Infection on Cell-Associated HIV-1 DNA and Plasma HIV-1 RNA", Antiviral Therapy, vol. 16, No. 4, pp. 535-545 (2011).
Julien et al, "Broadly Neutralizing Antibody PGT121 Allosterically Modulates CD4 Binding via Recognition of the HIV-1 gp120 V3 Base and Multiple Surrounding Glycans," PLOS Pathogens, vol. 9, No. 5, pp. e1003342 (May 2013).
Kochanek et al, "A New Adenoviral Vector: Replacement of All Viral Coding Sequences with 28 kb of DNA Independently Expressing Both Full-Length Dystrophin and Beta-Galactosidase," Proceedings of the National Academy of Sciences of the United States of America, vol. 93, No. 12, pp. 5731-5736 (Jun. 1996).
Kothe et al, "Ancestral and Consensus Envelope Immunogens for HIV-1 Subtype C," Virology, vol. 352, No. 2, pp. 438-449 (2006).
Kothe et al, "Antigenicity and Immunogenicity of HIV-1 Consensus Subtype B Envelope Glycoproteins," Virology, vol. 360, No. 1, pp. 218-234 (Mar. 30, 2007).
Kwong et al, "Structure of an HIV gp120 Envelope Glycoprotein in Complex with the CD4 Receptor and a Neutralizing Human Antibody," Nature, vol. 393, No. 6686, pp. 648-659 (Jun. 18, 1998).
Li et al, "Broad HIV-1 Neutralization Mediated by CD4-Binding Site Antibodies," Nature Medicine, vol. 13, No. 9, pp. 1032-1039 (Sep. 2007).
Li et al, "Characterization of Antibody Responses Elicited by Human Immunodeficiency Virus Type 1 Primary Isolate Trimeric and Monomeric Envelope Glycoproteins in Selected Adjuvants," Journal of Virology, vol. 80, No. 3, pp. 1414-1426 (Feb. 2006).
Li et al, "Evidence for Potent Autologous Neutralizing Antibody Titers and Compact Envelopes in Early Infection with Subtype C Human Immunodeficiency Virus Type 1," Journal of Virology, vol. 80, No. 11, pp. 5211-5218 (Jun. 2006).
Li et al, "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).
Li et al, "Removal of a Single N-Linked Glycan in Human Immunodeficiency Virus Type 1 gp120 Results in an Enhanced Ability to Induce Neutralizing Antibody Responses," Journal of Virology, vol. 82, No. 2, pp. 638-651 (Jan. 2008).
Liao et al, "A Group M Consensus Envelope Glycoprotein Induces Antibodies That Neutralize Subsets of Subtype B and C HIV-1 Primary Viruses," Virology, vol. 353, No. 2, pp. 268-282 (Sep. 30, 2006).
Liao et al, "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 (Apr. 2013).

(56) References Cited

OTHER PUBLICATIONS

Liao et al, "Co-Evolution of a Broadly Neutralizing HIV-1 Antibody and Founder Virus," Nature, vol. 496, No. 7446, pp. 469-476 (Apr. 25, 2013).
Lin et al, "Designing Immunogens to Elicit Broadly Neutralizing Antibodies to the HIV-1 Envelope Glycoprotein," Current HIV Research, vol. 5, No. 6, pp. 514-541 (2007).
Lynch et al, "The Development of CD4 Binding Site Antibodies During HIV-1 Infection," Journal of Virology, vol. 86, No. 14, pp. 7588-7595 (Jul. 2012).
Malherbe et al, "Sequential Immunization with a Subtype B HIV-1 Envelope Quasispecies Partially Mimics the In Vivo Development of Neutralizing Antibodies," Journal of Virology, vol. 85, No. 11, pp. 5262-5274 (Jun. 2011).
Mangeat et al, "Lentiviral Vectors and Antiretroviral Intrinsic Immunity," Human Gene Therapy, vol. 16, No. 8, pp. 913-920 (Aug. 2005).
Mascola et al, "Protection of Macaques Against Pathogenic Simian/Human Immunodeficiency Virus 89.6PD by Passive Transfer of Neutralizing Antibodies," Journal of Virology, vol. 73, No. 5, pp. 4009-4018 (May 1999).
Mascola et al, "Protection of Macaques Against Vaginal Transmission of a Pathogenic HIV-1/SIV Chimeric Virus by Passive Infusion of Neutralizing Antibodies," Nature Medicine, vol. 6, No. 2, pp. 207-210 (Feb. 2000).
McBurney et al, "Evaluation of Heterologous Vaginal SHIV SF162p4 Infection Following Vaccination with a Polyvalent Clade B Virus-Like Particle Vaccine," AIDS Research and Humam Retroviruses, vol. 28, No. 9, pp. 863-872 (2012).
McBurney et al, "Human Immunodeficiency Virus-Like Particles with Consensus Envelopes Elicited Broader Cell-Mediated Peripheral and Mucosal Immune Responses than Polyvalent and Monovalent Env Vaccines," Vaccine, vol. 27, No. 32, pp. 4337-4349 (2009).
McCoy et al, "Potent and Broad Neutralization of HIV-1 by a Llama Antibody Elicited by Immunization," The Journal of Experimental Medicine, vol. 209, No. 6, pp. 1091-1103 (2012).
McGuire et al, "Engineering HIV Envelope Protein to Activate Germline B Cell Receptors of Broadly Neutralizing Anti-CD4 Binding Site Antibodies," The Journal of Experimental Medicine, vol. 210, No. 4, pp. 655-663 (2013).
Pancera et al, "Crystal Structure of PG16 and Chimeric Dissection with Somatically Related PG9: Structure-Function Analysis of Two Quaternary-Specific Antibodies That Effectively Neutralize HIV-1," Journal of Virology, vol. 84, No. 16, pp. 8098-8110 (Aug. 2010).
McLellan et al, "Structure of HIV-1 gp120 V1/V2 Domain with Broadly Neutralizing Antibody PG9," Nature, vol. 480, No. 7377, pp. 336-343 (2011).
Montefiori, "Evaluating Neutralizing Antibodies Against Hiv, Siv, and SHIV in Luciferase Reporter Gene Assays," Current Protocols in Immunology, vol. 12, No. 11, pp. 1-17 (2004).
Mouquet et al, "Complex-Type N-Glycan Recognition by Potent Broadly Neutralizing HIV Antibodies," Proceedings of the National Academy of Sciences of the United States of America, vol. 109, No. 47, pp. E3268-E3277 (2012).
Ofek et al, "Structure and Mechanistic Analysis of the Anti-Human Immunodeficiency Virus Type 1 Antibody 2F5 in Complex with Its gp41 Epitope," Journal of Virology, vol. 78, No. 19, pp. 10724-10737 (Oct. 2004).
Pancera et al, "Structure of HIV-1 gp120 with gp41-Interactive Region Reveals Layered Envelope Architecture and Basis of Conformational Mobility," Procedures of the National Academy of Sciences of the United States of America, vol. 107, No. 3, pp. 1166-1171 (2010).
Pejchal et al, "A Potent and Broad Neutralizing Antibody Recognizes and Penetrates the HIV Glycan Shield," Science, vol. 334, No. 6059, pp. 1097-1103 (2011).
Pejchal et al, "Structure and Function of Broadly Reactive Antibody PG16 Reveal an H3 Subdomain that Mediates Potent Neutralization of HIV-1," Proceedings of the National Academy of Sciences of the United States of America, vol. 107, No. 25, pp. 11483-11488 (2010).

Plotkin et al, "Postscript Relating to New Allegations Made by Edward Hooper at The Royal Society Discussion Meeting on Sep. 11, 2000," Philosophical Transactions of the Royal Society of London B: Biological Sciences, vol. 356, No. 1410, pp. 825-829 (2001).
Plotkin, "Correlates of Protection Induced by Vaccination," Clinical and Vaccine Immunology, vol. 17, No. 7, pp. 1055-1065 (Jul. 2010).
Plotkin, "Immunologic Correlates of Protection Induced by Vaccination," Pediatric Infectious Disease Journal, vol. 20, No. 1, pp. 63-75 (2001).
Plotkin, "The RV144 Thai HIV Vaccine Trial," Human Vaccines, vol. 6, No. 2, p. 159 (Feb. 2010).
Saphire et al, "Crystal Structure of a Neutralizing Human IgG Against HIV-1: A Template for Vaccine Design," Science, vol. 293, No. 5532, pp. 1155-1159 (2001).
Scheid et al, "Sequence and Structural Convergence of Broad and Potent HIV Antibodies That Mimic CD4 Binding," Science, vol. 333, pp. 1633-1637 (2011).
Seaman et al, "Multiclade Human Immunodeficiency Virus Type 1 Envelope Immunogens Elicit Broad Cellular and Humoral Immunity in Rhesus Monkeys," Journal of Virology, vol. 79, No. 5, pp. 2956-2963 (2005).
Seaman et al, "Standardized Assessment of NAb Responses Elicited in Rhesus Monkeys Immunized with Single- or Multi-Clade HIV-1 Envelope Immunogens," Virology, vol. 367, pp. 175-186 (2007).
Simek et al, "Human Immunodeficiency Virus Type 1 Elite Neutralizers: Individuals With Broad and Potent Neutralizing Activity Identified by Using a High-Throughput Neutralization Assay Together With an Analytical Selection Algorithm," Journal of Virology, vol. 83, No. 14, pp. 7337-7748 (2009).
Sok et al, "Promiscuous Glycan Site Recognition by Antibodies to the High-Mannose Patch of gp120 Broadens Neutralization of HIV," Science Translational Medicine, vol. 6, No. 236, p. 236ra63 (May 14, 2014).
Stamatatos et al, "Neutralizing Antibodies Generated During Natural HIV-1 Infection: Good News for an HIV-1 Vaccine?," Nature Medicine, vol. 15, No. 8, pp. 866-870 (2009).
Vaine et al, "Antibody Responses Elicited through Homologous or Heterologous Prime-Boost DNA and Protein Vaccinations Differ in Functional Activity and Avidity," Vaccine, vol. 28, No. 17, pp. 2999-3007 (2010).
Vaine et al, "Profiles of Human Serum Antibody Responses Elicited by Three Leading HIV Vaccines Focusing on the nduction of Env-Specific Antibodies," PLoS One, vol. 5, No. 11, pp. e13916 (Nov. 2010).
Walker et al, "Broad Neutralization Coverage of HIV by Multiple Highly Potent Antibodies," Nature, vol. 477, No. 7365, pp. 466-470 (Sep. 22, 2011).
Wang et al, "Cross-Subtype Antibody and Cellular Immune Responses Induced by a Polyvalent DNA Prime-Protein Boost HIV-1 Vaccine in Healthy Human Volunteers," Vaccine, vol. 26, No. 31, pp. 3947-3957 (Jul. 23, 2008).
Wang et al, "Enhanced Immunogenicity of gp120 Protein when Combined with Recombinant DNA Priming to Generate Antibodies that Neutralize the JR-FL Primary Isolate of Human Immunodeficiency Virus Type 1," Journal of Virology, vol. 79, No. 12, pp. 7933-7937 (Jun. 2005).
Wang et al, "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates from Subtypes A, B, C, D and E," Virology, vol. 350, No. 1, pp. 34-47 (2006).
Wattanapitayakul et al, "Recent Developments in Gene Therapy for Cardiac Disease," Biomed & Pharmacother, vol. 54, No. 1, pp. 487-504 (2000).
Wiznerowicz et al, "Harnessing HIV for Therapy, Basic Research and Biotechnology," TRENDS in Biotechnology, vol. 23, No. 1, pp. 42-47 (Jan. 2005).
Gurwith et al, "Safety and Immunogenicity of an Oral, Replicating Adenovirus Serotype 4 Vector Vaccine for H5N1 Influenza: A Randomised, Double-Blind, Placebo-Controlled, Phase 1 Study", Lancet Infect Dis, vol. 13, No. 3, pp. 238-250 (2013).

(56) References Cited

OTHER PUBLICATIONS

Centlivre et al., "In HIV-1 Pathogenesis the Die is Cast During Primary Infections", AIDS, vol. 21, No. 1, pp. 1-11 (2007).
Flynn et al., "Placebo-controlled phase 3 trial of a recombinant glycoprotein 120 vaccine to prevent HIV-1 infection",. J. Infect Dis, vol. 191, No. 5, pp. 654-665 (2005).
Pitisuttihum et al., "Randomized, Double-Blind, Placebo-Controlled Efficacy Trial of a Bivalent Recombinant Glycoprotein 120 HIV-1 Vaccine Among Injection Drug Users in Bangkok, Thailand", J. Infect. Dis., vol. 194, No. 12, pp. 1661-1671 (2006).
Gray et al., "Safety and Efficacy of the HVTN 503/Phambili Study of a Clade-B-based HIV-1 Vaccine in South Africa: A Double-Blind, Randomised, Placebo-Controlled Test-of-Concept Phase 2b Study", Lancet Infect Dis, vol. 11, No. 7, pp. 507-515 (2011).
Buchbinder et al., Efficacy Assessment of a Cell-Mediated Immunity HIV-1 Vaccine (The Step Study): A Double-Blind, Randomised, Placebo-Controlled, Test-of-Concept Trial, Lancet, vol. 372 No. 9653, pp. 1881-1893 (2008).
Rerks-Ngarm et al.", Vaccination with ALVAC and AIDSVAX to Prevent HIV-1 Infection in Thailand", N. Engl J Med., vol. 361, No. 23, pp. 2209-2220 (2009).
McElrath et al., "HIV-1 Vaccine-Induced Immunity in the Test-of-Concept Step Study: A Case-Cohort Analysis", Lancet, vol. 372, No. 9653, pp. 1894-1905 (2008).
Vogels et al., "Replication-Deficient Human Adenovirus Type 35 Vecotrs for Gene Transfer and Vaccination: Efficient Human Cell Infection and Bypass of Preexisting Adenovirus Immunity", J. Virol, vol. 77, No. 15, pp. 8263-8271 (2003).
Farina et al., "Replication-defective Vector Based on a Chimpanzee Adenovirus", J. Virol, vol. 75, No. 23, p. 11603-11613 (2001).
Barouch et al., "International Seroepidemiology of Adenovirus Serotypes 5, 36, 35 and 48 in Pediatric and Adult Populations", Vaccine, vol. 29: pp. 5203-5209 (2011).
Chen et al., "Adenovirus-Based Vaccines: Comparison of Vectors from Three Species of Adenoviridae", J. Virol, vol. 34, No. 20, p. 10522-10532 (2010).
Thorner et al., "Age Dependence of Adenovirus-Specific Neutralizing Antibody Titer in Individuals From Sub-Saharan Africa", J. Clin. Microbiol, vol. 44, No. 10, pp. 3781-3783 (2006).
Spranger et al., "Quantifying Adenovirus-Neutralizing Antibodies by Luciferase Transgene Detection: Addressing Preexisting Immunity to Vaccine and Gene Therapy Vectors", J. Clin. Microbiol, vol. 41, No. 11, pp. 5046-5052 (2003).
Liu et al., "Magnitude and Phenotype of Cellular Immune Responses Elicited by Recombinant Adenovirus Vectors and Heterologous Prime-Boost Regimens in Rhesus Monkeys", J. Viol., vol. 82, No. 10, p. 4844 4852 (2008).
Liu et al., Immune Control of an SIV Challenge by a T-Cell-Based Vaccine in Rhesus Monkeys, Nature, vol. 457, No. 7225, pp. 87-91(2009).
Lore et al., "Myeloid and Plasmacytoid Dendritic Cells are Susceptible to Recombinant Adenovirus Vectors and Stimulate Polyfunctional Memory T Cell Responses", J. Immunol, vol. 179, No. 3, pp. 1721-1729 (2007).
Kuschner et al., "A Phase 3, Randomized, Double-Blind, Placebo-Controlled Study of the Safety and Efficacy of the Live, Oral Adenovirus Type 4 and Type 7 Vaccine, in U.S. Military Recruits", Vaccine, vol. 31(28), pp. 2963-2971 (2013).
Masopust et al., "Hidden Memories: Frontline Memory T Cells and Early Pathogen Interception", J. Immunol., vol. 188, No. 12, pp. 5811-5817 (2012).
Mast et al., "International Epidemiology of Human Pre-Existing Adenovirus (Ad) Type-5, Type-6, Type-26 and Type-36 Neutralizing Antibodies: Correlates of High Ad5 Titers and Implications for Potential HIV Vaccine Trials", Vaccine, vol. 28: pp. 950-957 (2010).
Hierholzer et al., "Adenoviruses from Patients with Aids: A Plethora of Serotypes and a Description of Five New Serotypes of Subgenus D (types 43-47).", J. Infect. Dis., vol. 158, No. 4 pp. 804-813 (1988) (Abstract Only).

Khoo et al., "Adenovirus Infections in Human Immunodeficiency Virus-Positive Patients: Clinical Features and Molecular Epidemiology", J. Infect. Dis, vol. 172, No. 3, pp. 629-637 (1995) (Abstract Only).
Janes et al., "MRKAd5 HIV-1 Gag/Pol/Nef Vaccine-Induced T-cell Responses Inadequately Predict Distance of Breakthrough HIV-1 Sequences to the Vaccine or Viral Load", PLoS One, vol. 7, No. 8, pp. e43396 (2012).
Santra et al., "Mosaic Vaccines Elicit CD8+ T Lymphocyte Responses That Confer Enhanced Immune Coverage of Diverse HIV Strains in Monkeys", Nat Med., vol. 16, No. 3, pp. 324-328 (2010).
Li et al., "Visualizing Antigen-Specific and Infected Cells in Situ Predicts Outcomes in Early Viral Infection", Science, vol. 323, No. 5922, pp. 1726-1729 (2009).
Baden et al., "First-in-human Evaluation of the Safety and Immunogenicity of a Recombinant Adenovirus Serotype 26 HIV-1 Env Vaccine (IPCAVD 001)", J. Infect. Dis., vol. 207, No. 2, pp. 240-247 (2013).
Barouch et al., "Characterization of Humoral and Cellular Immune Responses Elicited by a Recombinant Adenovirus Serotype 26 HIV-1 Env Vaccine in Healthy Adults (IPCAVD 001)", J. Infect. Dis, vol. 207, No. 2, pp. 248-256 (2013).
Jin et al., "Stabilizing Formulations for Inhalable Powders of an Adenovirus 35-Vectored Tuberculosis (TB) Vaccine (AERAS-402)", Vaccine, vol. 28, No. 27, pp. 4369-4375 (2010).
De Gruijl et al., Intradermal Delivery of Adenoviral Type-35 Vectors Leads to High Efficiency Transduction of Mature, CD8+ T Cell-Stimulating Skin-Emigrated Dendritic Cells, J. Immunol, vol. 177, No. 4, pp. 2208-2215 (2006).
Haslett et al., "Strong Human Immunodeficiency Virus (HIV)-Specific CD4+ T Cell Responses in a Cohort of Chronically Infected Patients are Associated with Interruptions in Anti-HIV Chemotherapy,"J. Infect. Dis, vol. 81, No. 4, pp. 1264-1272 (2000).
Yang et al., "Highly Stable Trimers Formed by Human Immunodeficiency Virus Type 1 Envelope Glycoproteins Fused with the Trimeric Motif of T4 Bacteriophage Fibritin", J. Virol., vol. 76, No. 9, pp. 4634-4642 (2002).
Chen et al., A Chimeric Protein of Simian Immunodeficiency Virus Envelope Glycoprotein gp140 and *Escherichia coli* Asparatate Transcarbamoylase, J. Virol, vol. 78, No. 9, pp. 4508-4516 (2004).
Cohen et al, "Chimpanzee Adenovirus CV-68 Adapted as a Gene Delivery Vector Interacts with the Coxsackievirus and Adenovirus Receptor", J. Gen. Virol., vol. 83, pp. 151-155 (2002).
Kobinger et al, "Chimpanzee Adenovirus Vaccine Protects Against Zaire Ebola Virus", Virology, vol. 346, pp. 394-401 (2006).
Tatsis et al., "A CD46-binding Chimpanzee Adenovirus Vector as a Vaccine Carrier", Molecular Therapy, vol. 15, No. 3, pp. 608-617 (2007).
Bangari et al., "Development of Nonhuman Adenoviruses as Vaccine Vectors", Vaccine, vol. 24, No. 7, pp. 849-826 (2006).
Lasaro et al., "New Insights on Adenovirus as Vaccine Vectors", Mol. Ther., vol. 17, No. 8, pp. 1333-1339 (2009).
Mayr et al., "The Small Pox Vaccination Strain MVA: Marker, Genetic Structure, Experience Gained with the Parenteral Vaccination and Behavior in Organisms with a Debilitated Defence Mechanism," Zentralbl Bacteriol. vol. 167, pp. 375-390 (1978) (Abstract Only).
Ambrosini et al., "Gene Transfer in Astrocytes: Comparison Between Different Delivering Methods and Expression of the HIV-1 Protein Nef.", J. Neurosci. Res., vol. 55, p. 569 (1999) (Abstract Only).
Letvin et al., "Potent, Protective Anti-HIV Immune Responses Generated by Bimodal HIV Envelope DNA Plus Protein Vaccination", Proc. Natl. Acad Sci., vol. 94, pp. 9378-9383 (1997).
Patterson et al. "Protection Against Mucosal Simian Immunodeficiency Virus SIVmac251 Challenge by Using Replicating Adenovirus-SIV Multigene Vaccine Priming and Subunit Boosting," Journal of Virology, vol. 78, No. 5, pp. 2212-2221 (Mar. 2004).
Burke et al. "Neutralizing Antibody Responses to Subtype B and C Adjuvanted HIV Envelope Protein Vaccination in Rabbits," Virology, vol. 387, No. 1, pp. 147-156 (Apr. 2009).
Peng et al. "Replicating Rather than Nonreplicating Adenovirus-Human Immunodeficiency Virus Recombinant Vaccines Are Better

(56) References Cited

OTHER PUBLICATIONS at Eliciting Potent Cellular Immunity and Priming High-Titer Antibodies," Journal of Virology, vol. 79, No. 16, p. 10200-10209 (Aug. 2005).
Lian et al., "Evaluation of Envelope Vaccines Derived from the South African Subtype C Human Immunodeficiency Virus Type 1 TV1 Strain," Journal of Virology, vol. 79, No. 21, p. 13338-13349 (Nov. 2005).
Gomez-Roman et al., "An Adenovirus-Based HIV Subtype B Prime/Boost Vaccine Regimen Elicits Antibodies Mediating Broad Antibody-Dependent Cellular Cytotoxicity Against Non-Subtype B HIV Strains", J. Acquir. Immune Defic. Syndr., vol. 43, No. 3, pp. 270-277 (Nov. 2006).
"Endogenous Retrovirus Group K Member 25 Env Polyprotein", Database UNIPROT, Accession No. Q5GI17, 2 pages (Mar. 1, 2005).
"Recombinant Protein gp41 Heterologous Transmembrane Region, Seq ID1," Database Geneseq, Accession No. AUR74751, 1 page, (Mar. 19, 2009).
"Transmembrane Domain Peptide, Seq ID 14," Database Geneseq, Accession No. AEF06609, 1 page (Mar. 23, 2006).
"GCN4 Fusion Linker Peptide, Seq ID No. 3," Database Geneseq, Accession No. AEN61500, 1 page (Mar. 8, 2007).
Abrahamyan et al., "The Cytoplasmic Tail Slows the Folding of Human Immunodeficiency Virus Type 1 Env from a late Prebundle Configuration into the Six-Helix Bundle", Journal of Virology, vol. 79, No. 1, pp. 106-115 (2005).
Wu et al, "Rational Design of Envelope Identifies Broadly Neutralizing Human Monoclonal Antibodies to HIV-1," Science, vol. 329, No. 5993, pp. 856-861 (Aug. 13, 2010).
Yang et al, "Improved Elicitation of Neutralizing Antibodies Against Primary Human Immunodeficiency Viruses by Soluble Stabilized Envelope Glycoprotein Trimers," Journal of Virology, vol. 75, No. 3, pp. 1165-1171 (Feb. 2001).
Yasmeen et al, "Differential Binding of Neutralizing and Non-Neutralizing Antibodies to Native-Like Soluble HIV-1 Env Trimers, Uncleaved Env Proteins, and Monomeric Subunits," Retrovirology, vol. 11, No. 41 (2014).
Zhou et al, "Structural Basis for Broad and Potent Neutralization of HIV-1 by Antibody VRC01," Science, vol. 329, No. 5993, pp. 811-817 (Aug. 13, 2010).
Lee et al, "A Single Point Mutation in HIV-1 V3 Loop Alters the Immunogenic Properties of rgp120," Archives of Virology, vol. 145, pp. 2087-2103 (2000).
Walker et al, "Toward an AIDS Vaccine," Science, vol. 320, pp. 760-764 (May 9, 2008).
McElrath et al, "Induction of Immunity to Human Immunodeficiency Virus Type-1 by Vaccination," Immunity, vol. 33, pp. 542-554 (Oct. 29, 2010).
Watkins et al, "Immune Escape by Human Immunodeficiency Virus Type 1 from Neutralizing Antibodies: Evidence for Multiple Pathways," Journal of Virology, vol. 67, No. 12, pp. 7493-7500 (Dec. 1993).
Sattentau, "Envelope Glycoprotein Trimers as HIV-1 Vaccine Immunogens", Vaccines, vol. 1, pp. 497-512 (2013).
Barnett et al, "Development of V2-deleted trimeric envelope vaccine candidates from human immunodeficiency virus type 1 (HIV-1) subtypes Band C," Microbes Infect, vol. 7, vol. 14, pp. 1386-1391 (2005).
Gao et al, "A Comprehensive Panel of Near-Full-Length Clones and Reference Sequences for Non-Subtype B Isolates of Human Immunodeficiency Virus Type 1, "Journal of Virology, vol. 72, No. 7, pp. 5680-5698 (1998).
Yang et al, "Modifications That Stabilize Human Immunodeficiency Virus Envelope Glycoprotein Trimers in Solution," Journal of Virology, vol. 74, No. 10, pp. 4746-4754 (2000).
Desrosiers, "Prospects for an AIDS Vaccine", Nature Medicine, vol. 10, No. 3, pp. 221-223 (2004).
Gallo, "The End or the Beginning of the Drive to an HIV-Preventive Vaccine: A View from over 20 Years", The Lancet, vol. 366, No. 9500, pp. 1894-1898 (Nov. 2005).
Levine, "Why Do We Not Yet Have a Human Immunodeficiency Virus Vaccine," J. Virol., vol. 82, No. 24, pp. 11998-12000 (Dec. 2008).
Zhang et al, "Extensively Cross-Reactive Anti-HIV-1 Neutralizing Antibodies Induced by gp140 Immunization," PNAS, vol. 104, No. 24, pp. 10193-10198 (2007).
Beddows et al, "A Comparative Immunogenicity Study in Rabbits of Disulfide-Stablized, Proteolytically Cleaved, Soluble Trimeric Human Immunodeficiency Virus Type 1 gp140, Trimeric Cleavage-Defective gp140 and Monomeric gp120," Virology, vol. 360, pp. 329-340 (2007).
Berger et al, "Chemokine Receptors as HIV-1 Coreceptors: Roles in Viral Entry, Tropism and Disease," Annu. Rev. Immunol., vol. 17, pp. 657-700 (1999).
Berman et al, "Comparison of the Immune Response to Recombinant gp120 in Humans and Chimpanzees," AIDS, vol. 8, pp. 591-601 (1994).
Binley et al "A Recombinant Human Immunodeficiency Virus Type 1 Envelope Glycoprotein Complex Stabilized by 6 an Intermolecular Disulfide Bond Between the gp120 and gp41 Subunits is an Antigenic Mimic of the Trimeric Virion-Associated Structure," Journal of Virology, vol. 74, No. 2, pp. 627-643 (Jan. 2000).
Bower et al, "HIV-1 Env gp 140 Trimers Elicit Neutralizing Antibodies Without Efficient Induction of Conformational Antibodies," Vaccine, vol. 24, pp. 5442-5451 (2006).
Burton et al, "HIV Vaccine Design and the Neutralizing Antibody Problem," Nature Immunology, vol. 5, No. 3, pp. 233-236 (Mar. 2004).
Carrow et al, "High Prevalance of Antibodies to the gp120 V3 Regional Principal Neutralizing Determinant of HIV-1 MN in Sera from Africa and the Americas," Aids Research and Human Retroviruses, vol. 7, No. 10, pp. 831-838 (1991).
Chen et al, "Expression, Purification, and Characterization of gp160e, the Soluble, Trimeric Ectodomain of the Simian mmunodeficiency Virus Envelope Glycoprotein, gp160," The Journal of Biological Chemistry, vol. 275, No. 45, pp. 34946-34953 (Nov. 10, 2000).
Crooks et al, "A Comparative Immunogenicity Study of HIV-1 Virus-Like Particles Bearing Various Forms of Envelope Proteins, Particles Bearing No Envelope and Soluble Monomeric gp120," ScienceDirect, Virology vol. 366, pp. 245-262 (2007).
Derby et al, "Isolation and Characterization of Monoclonal Antibodies Elicited by Trimeric HIV-1 Env gp140 Protein 14 Immunogens," Virology, vol. 366, pp. 433-445 (2007).
Dey et al, "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, vol. 81, No. 11, pp. 5579-5593 (Jun. 2007).
Gallo et al, "The HIV Env-mediated Fusion Reaction," Biochemics et Biophysica Acta, pp. 36-50 (2003).
Kang et al, "Structural and Immunogenicity Studies of a Cleaved, Stabilized Envelope Trimer Derived from Subtype A HIV-1," Vaccine, vol. 27, pp. 5120-5132 (2009).
Kim et al, "Comparison of HIV Type 1 ADA gp120 Monomers Versus gp140 Trimers as Immunogens for the Induction of Neutralizing Antibodies," AIDS Research and Human Retroviruses, vol. 21, No. 1, pp. 58-67 (2005).
Li et al, "Genetic and Neutralization Properties of Subtype C Human Immunodeficiency Virus Type 1 Molecular env Clones From Acute Early Heterosexually Acquired Infections in Southern Africa," Journal of Virology, vol. 80, No. 23, 11776-11790 (Dec. 2006).
Montefiori et al, "Antibody-Based HIV-1 Vaccines: Recent Developments and Future Directions," PLOS Medicine, vol. 4, No. 12, pp. e348 (2007).
Montefiori, "Measuring HIV Neutralization in a Luciferase Reporter Gene Assay," HIV Protocols Second 25 Edition, vol. 485, pp. 395-405 (2009).

(56) References Cited

OTHER PUBLICATIONS

Morner et al, "Human Immunodeficiency Virus Type 1 ENV Trimer Immunization of Macaques and Impact of D Priming with Viral Vector or Stabilized Core Protein," Journal of Virology, vol. 83, No. 2, pp. 540-551 (Jan. 2009).
Nara et al, "Purified Envelope Glycoproteins from Human Immunodeficiency Virus Type 1 Variants Induce Individual, Type-Specific Neutralizing Antibodies," Journal of Virology, vol. 62, No. 8, pp. 2622-2628 (Aug. 1988).
Page et al, "Studies on the Immunogenicity of Chinese Hamster Ovary Cell-Derived Recombinant gp120 (HIV-1111B)," Vaccine, vol. 9, pp. 47-52 (Jan. 1991).
Pantophlet et al, "GP120: Target for Neutralizing HIV-1 Antibodies," Annu. Rev. Immunol., vol. 24, pp. 739-769 (2006).
Polonis et al, "Recent Advances in the Characterization of HIV-1 Neutralization Assays for Standardized Evaluation of the Antibody Response to Infection and Vaccination," Virology, vol. 375, pp. 315-320 (2008).
Rodenburg et al, "Near Full-Length Clones and Reference Sequences for Subtype C Isolates of HIV Type 1 from Three Different Continents," AIDS Research and Human Retroviruses, vol. 17, No. 2, pp. 161-168 (2001).
Scheid et al, "Broad Diversity of Neutralizing Antibodies Isolated From Memory B Cells in HIV-Infected Individuals," D Nature, vol. 458, pp. 636-640 (Apr. 2, 2009).
Vaine et al, "Improved Induction of Antibodies Against Key Neutralizing Epitopes by Human Immunodeficiency Virus Type 1 gp120 DNA Prime-Protein Boost Vaccination Compared to gp120 Protein-Only Vaccination," Journal of Virology, vol. 82, No. 15, pp. 7369-7378 (Aug. 2008).
Vogel et al, "The Majority of Neutralizing Abs in HIV-1-Infected Patients Recognize Linear V3 Loop Sequences," The Journal of Immunology, vol. 153, pp. 1895-1904 (1994).
Wyatt et al, "The Antigenic Structure of the HIV gp120 Envelope Glycoprotein," Nature, vol. 393, pp. 705-711 (Jun. 18, 1998).
Zolla-Pazner et al, "Focusing the Immune Response on the V3 Loop, a Neutralizing Epitope of the HIV-1 gp210 Envelope," Virology, vol. 372, pp. 233-246 (2008).
Jeffs et al, "Expression and Characterization of Recombinant Oligomeric Envelope Glycoproteins Derived From Primary Isolates of HIV-1," Vaccine, vol. 22, No. 8, pp. 1032-1046 (2004).
Genbank Accession No. AF286227.1, "HIV-1 strain 97Za012 from South Africa, complete genome." Accessed Jan. 6, 2016.
Salminen et al, "Full-length Sequence of an Ethiopian Human Immunodeficiency Virus Type 1 (HIV-1) Isolate of Genetic Subtype C," AIDS Res. Human Retroviruses, vol. 12, No. 14, pp. 1329-1339 (1996).
Bower et al, "Elicitation of Neutralizing Antibodies with DNA Vaccines Expressing Soluble Stabilized Human mmunodefiency Virus Type 1 Envelope Glycoprotein Trimers Conjugated to C3d", Journ. of Viro., vol. 78, No. 9, pp. 4710-4719 (May 2004).
Nkolola et al, "Stability and Neutralization Capacity of a Novel Mosaic HIV-1 gp140 trimer in a Guinea Pig Model" AIDS Vaccine Poster, Ragon Institute, 1 pg. (2012).
Borducchi, E. N., Dec. 2016, Ad26/MVA therapeutic vaccination with TLR7 stimulation in SIV-infected rhesus monkeys, Nature 540:284-299.

Franchini, G., and M. L. Bosch, 1989, Genetic relatedness of the human immunodeficiency viruses type 1 and 2 (HIV-1, HIV-2) and the simian immunodeficiency virus (SIV), Annal New York Acad. Sci. 554(1):81-87.
Guyader, M., et al., 1987, Genome organization and transactivation of the human immunodeficiency virus type 2, Nature 326:662-669.
Johannes et al., "HIV-1-Specific antibody response and function after DNA Prima nd Recombinant Adenovirus 5 boost HIV Vaccine in HIV-infected subjects", PloS One, 2016, 11 (8):pdf pp. 1-17.
Li, Q. et al. Visualizing antigen-specific and infected cells in situ predicts outcomes in early viral infection. Science, 2009. 323(5922): p. 1726-9.
Liu, J, et al. Magnitude and phenotype of cellular immune responses elicited by recombinant adenovirus vectors and heterologous prime-boost regimens in rhesus monkeys. J Virol, 2008. 82(10): p. 4844-52.
Lore, K et al. Myeloid and plasmacytoid dendritic cells are susceptible to recombinant adenovirus vectors and stimulate polyfunctional memory T cell responses. J. Immunol, 2007. 179(3): p. 1721-9.
Rios, A., 2018, Fundamental challenges to the development of a preventive HIV vaccine, Curr. Opin. Virol. 29:26-32.
Subbaraman, H., et al., 2018, Broadly neutralizing antibodies: What is needed to move from a rare event in HIV-1 infection to vaccine efficacy, Retroviral. 15:52, pp. 1-14.
Nkolola et al, "Stability and Neutralization Capacity of a Novel Mosaic HIV-1 gp140 Trimer in a Guinea Pig Model," Retrovirology, vol. 9, Supp. 2, pp. 299 (2012).
Pinter, "Roles of HIV-1 Env Variable Regions in Viral Neutralization and Vaccine Development", Current HIV Research, vol. 5, No. 6, pp. 542-553 (2007).
Shu et al., "Efficient Boosting After Plasmid DNA or Recombinant Adenovirus Immunization with HIV-1 Vaccine Constructs", Vaccine, vol. 25, No. 8, pp. 1398-1408 (2007).
Muthumani et al., "HIV-1 Env DNA Vaccine plus PRotein Boost Delivered by EP Expands B- and T-Cell Responses and Neutralizing Phenotype in Vivo", PLOS One, vol. 8, No. 12, 12 pgs (Dec. 2013).
Barouch et al., "Accelerating HIV-1 Vaccine Efficacy Trials", Cell, vol. 159, No. 5, pp. 969-792 (Nov. 2014).
Int'l Search Report and Written Opinion dated Sep. 10, 2018 in PCT/US2018/043016.
Int'l Search Report and Written Opinion dated Dec. 11, 2018 in Int'l Application PCT/US2018/051274.
Schuitemaker, "Evaluation of lead HIV-1 Vaccine Regimen in APPROACH: Phase 1/2a study testing heterologous prime boost regimens using mosaic Ad26 and MVA vectors combined with Env protein", Jul. 24, 2017, Retrived from the Internet: https://www.avac.org/sites/default/files/u3/hiv-1_APPROACH.pdf, Retrived Nov. 29, 2018.
Int'l Preliminary Report on Patentability dated Mar. 14, 2019 in Int'l Appliction No. PCT/US2017/049817.
Int'l Search Report and Written Opinion dated Oct. 4, 2018 in Int'l Application No. PCT/IB2018/054386.
Edwards et al., "Truncation of the Cytoplasmic Domain Induces Exposure of Conserved Regions in the Ectodomain of Human Immunodeficiency Virus Type 1 Envelope Protein" Journal of Virology, vol. 76, No. 6, pp. 2683-2691, 2002.

\* cited by examiner

○ 3-valent
□ 4-valent (C4D7)
△ 4-valent (sC4)
▼ control (Ad26.empty)

IGR 44/45

IGR 88/89

Group 1: Prime: Ad26
Boost: Ad26

Group 2: Prime: Ad26
Boost: MVA

Group 3: Prime: Ad26
Boost: MVA + GP140

Group 4: Prime: Ad26 low dose
Boost: MVA + GP140 low dose

Group 5: Prime: Ad26.Empty
Boost: BN-MVA Empty

POXVIRUS VECTORS ENCODING HIV ANTIGENS, AND METHODS OF USE THEREOF

CROSS-REFERENCE TO RELATED APPLICATIONS

This application is a Section 371 of International Application No. PCT/IB2018/054386, filed Jun. 14, 2018, which was published in the English language on Dec. 20, 2018 under International Publication No. WO 2018/229711 A1, which claims the benefit of U.S. Provisional Application No. 62/520,079, filed Jun. 15, 2017, and the disclosures of which are incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688097_331U1", creation date of Dec. 3, 2019, and having a size of about 170 KB. The sequence listing submitted via EFS-Web is part of the specification and is herein incorporated by reference in its entirety.

BACKGROUND OF THE INVENTION

Human Immunodeficiency Virus (HIV) affects millions of people worldwide, and the prevention of HIV through an efficacious vaccine remains a very high priority, even in an era of widespread antiretroviral treatment. HIV-1 is the most common and pathogenic strain of the virus, with more than 90% of HIV/AIDS cases deriving from infection with HIV-1 group M. The M group is subdivided further into clades or subtypes. An efficacious vaccine ideally would be capable of eliciting both potent cellular responses and broadly neutralizing antibodies capable of neutralizing HIV-1 strains from different clades.

The high genetic variability of HIV-1 makes the development of a HIV-1 vaccine an unprecedented challenge. In order to improve coverage of potential T-cell epitopes, and improve cellular responses, "mosaic" HIV-1 Gag, Pol and Env antigens, derived from HIV Group Antigen (Gag), Polymerase (Pol), and Envelope (Env) proteins, were described by others and developed in an attempt to provide maximal coverage of potential T-cell epitopes (e.g., Barouch et al, *Nat Med* 2010, 16: 319-323). The mosaic antigens are similar in length and domain structure to wild-type, naturally occurring HIV-1 antigens.

For example, mosaic HIV antigens described and used in vaccines include those described in Barouch et al, supra, and WO 2010/059732 such as:
  (a) Gag mosaic antigens including:
    (a)(i) a first mosaic Gag sequence ("mos1Gag") having the amino acid sequence as set forth herein in SEQ ID NO: 1, and
    (a)(ii) a second mosaic Gag sequence ("mos2Gag") having the amino acid sequence as set forth herein in SEQ ID NO: 2;
  (b) Pol mosaic antigens including:
    (b)(i) a first mosaic Pol sequence ("mos1Pol") having the amino acid sequence as set forth herein in SEQ ID NO: 3, and
    (b)(ii) a second mosaic Pol sequence ("mos2Pol") having the amino acid sequence as set forth herein in SEQ ID NO: 4; and
  (c) Env mosaic antigens including:
    (c)(i) a first mosaic Env sequence ("mos1Env") having the amino acid sequence as set forth herein in SEQ ID NO: 5, and
    (c)(ii) a second mosaic Env sequence ("mos2Env") having the amino acid sequence as set forth herein in SEQ ID NO: 6.

Sequences encoding these antigens have been cloned in vectors, for example, such as recombinant adenoviral vectors, e.g., recombinant adenovirus serotype 26 (rAd26), and these recombinant vectors were previously used as vaccines to generate immune responses to the antigens (see e.g. Barouch et al, supra; and WO 2010/059732). For example, the mos1Gag and mos1Pol mosaic antigen sequences are typically combined into a fusion protein of Gag and Pol ("mos1GagPol"), and the coding sequence of which is cloned into a first Ad26 vector ("rAd26.mos1GagPol"); and the mos2Gag and mos2Pol antigen sequences are combined into another fusion protein of Gag and Pol ("mos2GagPol"), and the coding sequence of which is cloned into a second Ad26 vector ("rAd26.mos2GagPol"). Constructs encoding mos1Env and mos2Env are typically cloned into separate Ad26 vectors ("rAd26.mos1Env" and "rAd26.mos2Env", respectively).

A set of such mosaic antigens as described above gives good global coverage of Group M HIV-1 isolates, where rAd26 vectors encoding mosaic 1 antigen sequences (e.g., rAd26.mos1GagPol and rAd26.mos1Env) favor clade B and CRF01 HIV-1 subtypes, and rAd26 vectors encoding mosaic 2 antigen sequences (e.g., rAd26.mos2GagPol and rAd26.mos2Env) favor clade C strains. Mosaic HIV-1 Gag, Pol, and Env antigens expressed in rAd26 vectors can be used to improve both the breadth and depth of antigen-specific T-lymphocyte responses in rhesus monkeys, without compromising the magnitude of both cellular and humoral responses when compared with consensus or natural sequence HIV-1 antigens (Barouch et al, supra; and WO 2010/059732).

However, upon further development efforts on the vaccine components described above, it was found that rAd26.mos2Env showed non-optimal cell surface expression and immune response in non-human primates, but moreover displayed a hitherto unreported, unexpected and unpredictable non-optimal genetic stability during the manufacturing process as compared to the other rAd26 vectors, such as rAd26.mos1Env. Thus, vaccines containing rAd26.mos2Env may result in non-optimal immune responses against Clade C HIV-1 subtypes, since the mos2Env mosaic antigen favors clade C HIV-1 strains. Accordingly, there is a need for an alternative to the mos2Env antigen in vaccines against HIV that can be used to induce improved immune responses against HIV-1 clade C.

Poxvirus vectors, such as Modified Vaccinia virus Ankara (MVA), can be used to encode antigens of interest for vaccination purposes. There is a need in the art for poxvirus vectors encoding novel combinations of HIV antigens.

BRIEF SUMMARY OF THE INVENTION

The invention relates to synthetic human immunodeficiency virus (HIV) envelope proteins that have improved cell surface expression and genetic stability as compared to the previously described mos2Env antigen and a novel poxvirus vector comprising nucleic acid sequence encoding the synthetic HIV envelope proteins. The invention also relates to compositions and methods of using such novel poxvirus vectors comprising nucleic acid sequence encoding the synthetic HIV envelope proteins to induce increased immune responses against HIV-1, particularly HIV-1 clade C and B, preferably when used in combination with other HIV antigens.

In particular aspects, the invention relates to poxvirus vectors, preferably Modified Vaccinia virus Ankara (MVA) vectors, comprising nucleic acid encoding the synthetic HIV envelope protein and preferably comprising a nucleic acid sequence encoding further HIV antigens.

In one general aspect, the invention relates to a nucleic acid encoding a synthetic HIV envelope protein comprising the amino acid sequence of SEQ ID NO: 8. The synthetic HIV envelope protein can further comprise a signal sequence, for instance a signal sequence having the amino acid sequence selected from the group consisting of SEQ ID NOs: 9-12. In one embodiment, the signal sequence has the amino acid sequence of SEQ ID NO: 9.

In certain embodiments, the synthetic HIV envelope protein further comprises a transmembrane domain, preferably a transmembrane domain having the amino acid sequence of SEQ ID NO: 13. In certain embodiments, the synthetic HIV envelope protein further comprises a fragment of a cytoplasmic domain, preferably a fragment of a cytoplasmic domain comprising the amino acid sequence of SEQ ID NO: 14, or the N-terminal amino acids 1-4 thereof (i.e., NRVR). In embodiments wherein the synthetic HIV envelope protein further comprises a transmembrane domain and a fragment of a cytoplasmic domain, it is preferred that the protein also comprises the amino acid sequence of SEQ ID NO: 37, which is fused to the carboxyl-terminus (C-terminus) of SEQ ID NO: 8 and the amino-terminus (N-terminus) of the transmembrane region.

In a most preferred embodiment, the invention relates to a poxvirus vector comprising a nucleic acid sequence encoding a synthetic HIV envelope protein comprising the amino acid sequence of SEQ ID NO: 17, SEQ ID NO: 18, or aa 1-686 of SEQ ID NO: 19. Most preferably the synthetic HIV envelope protein encoded by the nucleic acid comprises or consists of the amino acid sequence of SEQ ID NO: 18.

In preferred embodiments, the poxvirus vector comprises a nucleic acid encoding a synthetic HIV envelope protein as described above, and at least one additional HIV antigen. In a preferred embodiment, the poxvirus vector is a Modified Vaccinia virus Ankara (MVA) vector. Most preferably the MVA vector comprises MVA-BN or derivatives thereof.

In one preferred embodiment, the poxvirus vector comprises (a) nucleic acid encoding a first HIV envelope (Env) antigen comprising the amino acid sequence of SEQ ID NO: 18, and preferably further comprises nucleic acid encoding: (b) a second HIV Env antigen different from the first HIV Env antigen; (c) a third antigen and fourth antigen, being two different HIV Gag antigens; and (d) a fifth antigen and sixth antigens, being two different HIV Pol antigens. In certain preferred embodiments, (b) the second HIV Env antigen comprises the amino acid sequence of SEQ ID NO: 5; (c) the third and fourth antigens comprise the amino acid sequence of SEQ ID NO: 1 and SEQ ID NO: 2, respectively; and (d) the fifth and the sixth antigens comprise the amino acid sequence of SEQ ID NO: 3 and SEQ ID NO: 4, respectively. In certain embodiments, the third and fifth antigens are fused into a first Gag-Pol fusion antigen, preferably comprising SEQ ID NO: 28; and the fourth and sixth antigens are fused into a second Gag-Pol fusion antigen, preferably comprising SEQ ID NO: 29. In certain particular embodiments, the first HIV Env antigen is encoded by SEQ ID NO: 41. In one or more particular embodiments, the second HIV Env antigen is encoded by SEQ ID NO: 39; the first Gag-Pol fusion antigen is encoded by SEQ ID NO: 38; and the second Gag-Pol fusion antigen is encoded by SEQ ID NO: 40.

In embodiments wherein the poxvirus vector is an MVA vector, such as an MVA vector comprising MVA-BN or derivatives thereof, the first Gag-Pol fusion antigen and the second Env antigen are preferably inserted into intergenic region (IGR) 44/45 of the MVA genome, and the second Gag-Pol fusion antigen and the first Env antigen are preferably inserted into IGR 88/89 of the MVA genome. More preferably, the first Gag-Pol fusion antigen and the second Gag-Pol fusion antigens are each under control of a separate promoter, preferably a Pr13.5 promoter, and the first Env antigen and the second Env antigen are each under control of a separate promoter, preferably a PrHyb promoter.

Another general aspect of the invention relates to a composition, preferably a vaccine composition, comprising an immunogenically effective amount of a poxvirus vector comprising a nucleic acid sequence encoding a synthetic HIV envelope protein according to an embodiment of the invention and preferably further comprising a nucleic acid sequence encoding one or more additional HIV antigens, and a carrier, wherein the nucleic acid encoding the synthetic HIV envelope protein is operably linked to a promoter sequence. In one embodiment, the composition further comprises an adenovirus vector, preferably an adenovirus 26 vector, encoding a synthetic HIV envelope protein comprising the amino acid sequence of SEQ ID NO: 18. In certain embodiments, the composition comprises a poxvirus vector, preferably an MVA vector, encoding a synthetic HIV envelope protein comprising the amino acid sequence of SEQ ID NO: 18, and preferably encoding further HIV antigens. In certain embodiments, the compositions of the invention further comprise additional expression vectors encoding additional HIV antigens and/or isolated HIV antigenic polypeptide.

In another general aspect, the invention relates to a vaccine combination for inducing an immune response against a human immunodeficiency virus (HIV) in a subject in need thereof. In one embodiment, the vaccine combination comprises:

(a) a first vaccine composition comprising an immunogenically effective amount of a vector, preferably a poxvirus vector, more preferably an MVA vector, encoding (i) a first HIV envelope (Env) protein being a synthetic HIV envelope protein comprising the amino acid sequence of SEQ ID NO: 18 and preferably further comprising nucleic acid encoding: (ii) a second HIV Env antigen different from the first HIV Env antigen; (iii) a third antigen and a fourth antigen, being two different HIV Gag antigens; and (iv) a fifth antigen and a sixth antigen, being two different HIV Pol antigens; and at least one of:

(b) (i) a second vaccine composition comprising an immunogenically effective amount of one or more vectors, preferably one or more adenovirus vectors, more preferably one or more adenovirus 26 vectors, encoding one or more of the first, second, third, fourth, fifth, and sixth HIV antigens, preferably encoding one or more HIV antigens comprising an amino acid sequence selected from the group consisting of SEQ ID NOs: 1-5, 18, 28, and 29; and/or (b) (ii) a third vaccine composition comprising one or more polypeptides comprising an immunogenically effective amount of an isolated HIV antigenic polypeptide, for instance, a polypeptide comprising residues 30-708 of the amino acid sequence of SEQ ID NO: 7, and/or a polypeptide comprising residues 30-724 of SEQ ID NO: 36, wherein the first composition and the second and/or third compositions are present in the same composition or in one or more different compositions.

In one embodiment wherein the vaccine combination comprises a second vaccine composition, the second vaccine composition comprises one or more recombinant adenovirus 26 vectors encoding one or more antigens comprising the amino acid sequences selected from the group consisting of SEQ ID NOs: 1-5, 18, 28, and 29, more preferably comprising two, three, or four recombinant adenovirus 26 vectors together encoding SEQ ID NOs: 1, 2, 3, 4, 5, and 18.

Yet another general aspect of the invention relates to methods of inducing an immune response against a human immunodeficiency virus (HIV) in a subject in need thereof, comprising administering to the subject a composition, such as a vaccine composition, or vaccine combination according to an embodiment of the invention. The invention also relates to methods of inducing an immune response against an HIV comprising priming and boosting the immune response using a composition or a vaccine combination according to an embodiment of the invention.

In a particular embodiment, a method of inducing an immune response against a HIV in a subject in need thereof comprises administering to the subject:
  (a) a first vaccine comprising one or more recombinant adenovirus vectors, preferably Ad26 vectors, encoding one or more of SEQ ID NOs: 1, 2, 3, 4, 5, and 18; and
  (b) a second vaccine comprising a poxvirus vector, preferably an MVA vector, encoding a first HIV envelope (Env) protein being a synthetic HIV envelope protein comprising the amino acid sequence of SEQ ID NO: 18 and preferably encoding further HIV antigens, preferably a second HIV Env antigen different from the first HIV Env antigen, a third antigen and a fourth antigen being two different HIV Gag antigens, and a fifth antigen and sixth antigen being two different HIV Pol antigens, more preferably one or more HIV antigens encoding the amino acid sequences selected from the group consisting of SEQ ID NOs: 1-5, 28, and 29, wherein the first vaccine is a priming vaccine and the second vaccine is a boosting vaccine, or wherein the second vaccine is a priming vaccine and the first vaccine is a boosting vaccine. In certain embodiments, one or more isolated HIV antigenic polypeptides preferably comprising an immunogenically effective amount of an isolated HIV antigenic polypeptide, for example, a polypeptide comprising residues 30-708 of the amino acid sequence of SEQ ID NO: 7, and/or a polypeptide comprising residues 30-724 of SEQ ID NO: 36 are administered to the subject at about the same time as the boosting vaccine in the same composition as the boosting vaccine or in a composition separate from the boosting vaccine.

Another aspect of the invention relates to a cell, preferably an isolated cell, comprising a vector according to an embodiment of the invention.

BRIEF DESCRIPTION OF THE SEVERAL VIEWS OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 1A shows a full length HIV envelope protein; FIG. 1B shows the structure of a soluble single chain HIV envelope protein according to an embodiment of the invention in which the transmembrane domain (TM) is replaced with a GCN4 trimerization domain, and the furin cleavage site is mutated (sC4); FIG. 1C shows the structure of a membrane bound HIV envelope protein according to an embodiment of the invention comprising a transmembrane domain and a fragment of a cytoplasmic domain (C4D7);

FIG. 3A shows binding of sC1; FIG. 3B shows binding of sC4;

FIG. 7A shows the results with VSV-G (negative control); and FIG. 7B shows the results with MW965.26 (Tier 1A clade C).

FIGS. 9A and 9B show clade C gp140 and Mosaic gp140-specific ELISA titers, respectively; each dot represents the log 10-transformed relative potency value (log 10 EU/ml) of an individual rabbit, with group-mean indicated as a horizontal line; ULOQ, upper limit of quantitation (upper solid line), LLOQ lower limit of quantitation (lower solid line), LOB, limit of background (dotted line); all values below the LOB were set at the LOB level; statistical analysis consisted of an across sex Tobit model; for the comparison of group 1, 2, and 3, a Tukey correction was applied; statistically significant differences are indicated in the graphs: *P<0.05, P<0.01, *P<0.001; FIG. 9C shows virus neutralization titers against HIV-1 BaL envelope pseudotyped virus particles in a TZM-bl cell-based neutralization assay using rabbit serum; each dot represents the log 10-transformed $IC_{50}$ value of an individual rabbit, with the group mean indicated by a horizontal line; HD: Highest Dilution tested (upper solid line); LD: Lowest Dilution tested (lower solid line); LOB: limit of background, 95 percentile value of compiled negative samples (dotted line); log 10 $IC_{50}$ values exceeding the LD or HD threshold were set at the corresponding line; statistical analysis consisted of an across sex Tobit model; for the comparison of group 1, 2, and 3, a Tukey correction was applied; statistically significant differences are indicated in the graphs: *P<0.05, P<0.01, *P<0.001; FIGS. 10A and 10B show Mosaic gp140-specific ELISA titers; each dot represents the log 10-transformed endpoint titer of an individual mouse, with group-mean indicated as a horizontal line; UD, upper limit of dilution; LD, lowest dilution; all values below the LD were set at the LD level; statistical analysis consisted of an across dose Tobit model; statistically significant differences are indicated in the graphs: *P<0.05, P<0.01, *P<0.001; FIGS. 10C-10E show Interferon-gamma (IFN-γ) ELISPOT data at week 7 of the study; each dot represents the spot-forming cell (SFC) count per $10^6$ splenocytes of an individual mouse, with group-mean indicated as a horizontal line; LOD: limit of detection, 95 percentile value of compiled unstimulated controls (dotted line); Env-, Gag- and Pol-specific responses were determined by stimulation with the immuno-dominant Env-, Gag- and Pol-peptides IHIGPGRAFYTAGDI (SEQ ID NO: 44), AMQMLKETI (SEQ ID NO: 45), and YYDPSKDLI (SEQ ID NO: 46), respectively; statistically significant differences are indicated in the graphs: *P<0.05, P<0.01, *P<0.001.

DETAILED DESCRIPTION OF THE INVENTION

Figures 1A, 1B, 1C:
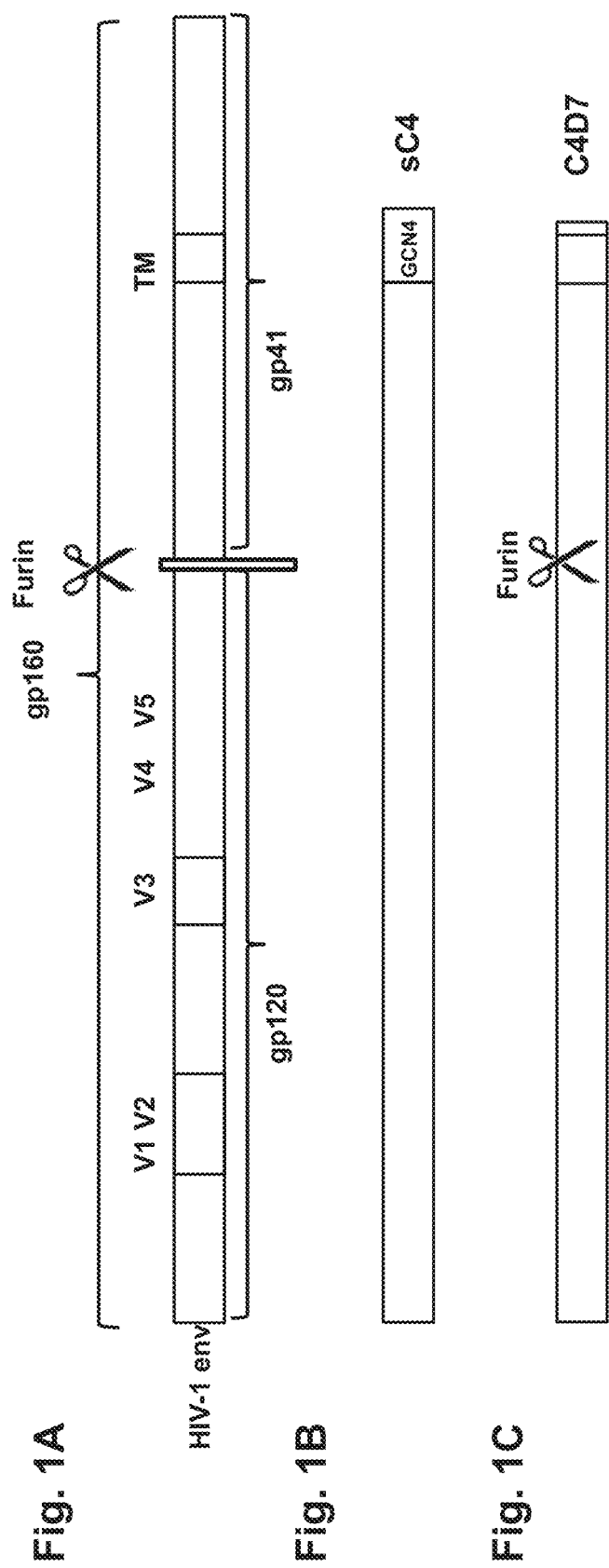
FIGS. 1A-1C are schematic representations of the structure of HIV envelope proteins.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, to who will be or has been administered a vector, composition or vaccine combination according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The invention generally relates to synthetic HIV envelope proteins, nucleic acid and vectors encoding the synthetic HIV envelope proteins, and methods of inducing an immune response against HIV with vectors encoding the synthetic HIV envelope proteins and optionally encoding further HIV antigens, alone or in combination with one or more additional vectors encoding one or more additional HIV antigens and/or in combination with one or more additional isolated HIV antigenic polypeptides.

Human immunodeficiency virus (HIV) is a member of the genus Lentivirinae, which is part of the family of Retroviridae. Two species of HIV infect humans: HIV-1 and HIV-2. HIV-1 is the most common strain of HIV virus, and is known to be more pathogenic than HIV-2. As used herein, the terms "human immunodeficiency virus" and "HIV" refer, but are not limited to, HIV-1 and HIV-2.

HIV is categorized into multiple clades with a high degree of genetic divergence. As used herein, the term "HIV clade" or "HIV subtype" refers to related human immunodeficiency viruses classified according to their degree of genetic similarity. There are currently three groups of HIV-1 isolates: M, N and O. Group M (major strains) consists of at least ten clades, A through J. Group O (outer strains) can consist of a similar number of clades. Group N is a new HIV-1 isolate that has not been categorized in either group M or 0.

As used herein, the terms "HIV antigenic polypeptide," "HIV antigenic protein," "HIV antigen," and "HIV immunogen" refer to a polypeptide capable of inducing an immune response, e.g., a humoral and/or cellular mediated response, against HIV in a subject. The antigenic polypeptide or antigen can be a protein of the HIV, a fragment or epitope thereof, or a combination of multiple HIV proteins or portions thereof that can induce an immune response or produce an immunity, e.g., protective immunity, against the HIV in a subject.

Preferably, an antigenic polypeptide or antigen is capable of raising in a host a protective immune response, e.g., inducing an immune response against a viral disease or infection, and/or producing an immunity in (i.e., vaccinates) a subject against a viral disease or infection, that protects the subject against the viral disease or infection. For example, the antigenic polypeptide or antigen can comprise a protein or fragments thereof from Simian Immunodeficiency Virus (SIV) or an HIV, such as the HIV or SIV envelope gp160 protein, the HIV or SIV matrix/capsid proteins, and the HIV or SIV gag, pol and env gene products.

An HIV antigenic polypeptide or antigen can be any HIV-1 or HIV-2 antigen or fragment thereof. Examples of HIV antigens include, but are not limited to gag, pol, and env gene products, which encode structural proteins and essential enzymes. Gag, pol, and env gene products are synthesized as polyproteins, which are further processed into multiple other protein products. The primary protein product of the gag gene is the viral structural protein gag polyprotein, which is further processed into MA, CA, SP1, NC, SP2, and P6 protein products. The pol gene encodes viral enzymes (Pol, polymerase), and the primary protein product is further processed into RT, RNase H, IN, and PR protein products. The env gene encodes structural proteins, specifically glycoproteins of the virion envelope. The primary protein product of the env gene is gp160, which is further processed into gp120 and gp41. Other examples of HIV antigens include gene regulatory proteins Tat and Rev; accessory proteins Nef, Vpr, Vif and Vpu; capsid proteins, nucleocapsid proteins, and p24 viral protein.

In certain embodiments, the HIV antigenic polypeptide or antigen comprises an HIV Gag, Env, or Pol antigen, or any antigenic portion or epitope or combination thereof, preferably an HIV-1 Gag, Env, or Pol antigen or any antigenic portion or epitope or combination thereof.

HIV antigenic polypeptides can also be mosaic HIV antigens. As used herein, "mosaic antigen" refers to a recombinant protein assembled from fragments of natural sequences. Mosaic antigens resemble natural antigens, but are optimized to maximize the coverage of potential T-cell epitopes found in the natural sequences, which improves the breadth and coverage of the immune response. Mosaic HIV antigens for use with the invention are preferably mosaic Gag, Pol, and/or Env antigens, and more preferably a mosaic HIV-1 Gag, Pol, and/or Env antigens. As used herein, "a mosaic HIV Gag, Pol, and/or Env antigen" specifically refers to a mosaic antigen comprising multiple epitopes derived from one or more of the Gag, Pol and/or Env polyprotein sequences of HIV.

In one embodiment, a mosaic HIV antigen for use with the invention is a mosaic HIV Gag antigen with epitopes derived from the sequences of gag gene products (examples are provided in SEQ ID NOs: 1, 2); a mosaic HIV Pol antigen with epitopes derived from the sequences of pol gene products (examples are provided in SEQ ID NOs: 3, 4); or a mosaic HIV Env antigen with epitopes derived from the sequences of env gene products (examples are provided in SEQ ID NOs: 5, 6; also the synthetic antigens of the invention, e.g. in SEQ ID NOs: 8, 17, 18, 19, can be considered mosaic HIV Env antigens). In certain embodiments, a mosaic HIV antigen for use with the invention comprises a combination of epitopes derived from sequences of gag, pol, and/or env gene products. Illustrative and non-limiting examples include mosaic Env-Pol antigens with epitopes derived from the sequences of env and pol gene products; mosaic Gag-Pol antigens with epitopes derived from the sequences of gag and pol gene products (examples are provided in SEQ ID NOs: 28, 29); and mosaic Gag-Env antigens with epitopes derived from the sequences of gag and env gene products. The sequences of gag, pol, and env gene products can be derived from one or more clades.

Examples of mosaic HIV Gag, Pol and/or Env antigens that can be used in the invention include those described in, e.g., US20120076812; Barouch et al., *Nat Med* 2010, 16:319-323; and Barouch et al., *Cell* 155:1-9, 2013, all of which are incorporated herein by reference in their entirety. Preferably, mosaic HIV Gag, Pol, and/or Env antigens for use with the present invention include, but are not limited to, mos1Gag (SEQ ID NO: 1), mos2Gag (SEQ ID NO: 2), mos1Pol (SEQ ID NO: 3), mos2Pol (SEQ ID NO: 4), mos1Env (SEQ ID NO: 5), mos2Env (SEQ ID NO: 6), mos1GagPol (SEQ ID NO: 28), mos2GagPol (SEQ ID NO: 29), and combinations thereof.

As used herein, each of the terms "HIV envelope protein," "env protein," and "Env" refers to a protein that is expressed on the envelope of an HIV virion and enables an HIV to target and attach to the plasma membrane of HIV infected cells, or a fragment or derivative thereof that can induce an immune response or produce an immunity against the HIV in a subject in need thereof. The HIV env gene encodes the precursor protein gp160, which is proteolytically cleaved into the two mature envelope glycoproteins, gp120 and gp41. The cleavage reaction is mediated by a host cell protease, furin, at a sequence highly conserved in retroviral envelope glycoprotein precursors. More specifically, gp160 trimerizes to (gp160)$_3$ and then undergoes cleavage into the two noncovalently associated gp120 and gp41. Viral entry is subsequently mediated by a trimer of gp120/gp41 heterodimers. Gp120 is the receptor binding fragment, and binds to the CD4 receptor on a target cell that has such a receptor, such as, e.g., a T-helper cell. Gp41, which is noncovalently bound to gp120, is the fusion fragment and provides the second step by which HIV enters the cell. Gp41 is originally buried within the viral envelope, but when gp120 binds to a CD4 receptor, gp120 changes its conformation causing gp41 to become exposed, where it can assist in fusion with the host cell. Gp140 is the uncleaved ectodomain of trimeric gp160, i.e., (gp160)$_3$, that has been used as a surrogate for the native state of the cleaved, viral spike.

According to embodiments of the invention, an "HIV envelope protein" can be a gp160, gp140, gp120, gp41 protein, combinations, fusions, truncations or derivatives thereof. For example, an "HIV envelope protein" can include a gp120 protein noncovalently associated with a gp41 protein. It can also include a stabilized trimeric gp140 protein that can have or can be modified to include a trimerization domain that stabilizes trimers of gp140. Examples of trimerization domains include, but are not limited to, the T4-fibritin "foldon" trimerization domain; the coiled-coil trimerization domain derived from GCN4; and the catalytic subunit of *E. coli* aspartate transcarbamoylase as a trimer tag. An "HIV envelope protein" can also be a truncated HIV envelope protein including, but not limited to, envelope proteins comprising a C-terminal truncation in the ectodomain (i.e. the domain that extends into the extracellular space), a truncation in the gp41, such as a truncation in the transmembrane domain of gp41, or a truncation in the cytoplasmic domain of gp41. An "HIV envelope protein" can further be a derivative of a naturally occurring HIV envelope protein having sequence mutations, e.g., in the furin cleavage sites, and/or so-called SOSIP mutations.

Preferably, an "HIV envelope protein" is a "synthetic HIV envelope protein." As used herein, the term "synthetic HIV envelope protein" refers to a non-naturally occurring HIV envelope protein that is optimized to induce an immune response or produce an immunity against one or more naturally occurring HIV strains in a subject in need thereof. Mosaic HIV Env proteins are examples of synthetic HIV Env proteins, and the invention provides synthetic HIV Env antigens, e.g. the ones comprising SEQ ID NOs: 8, 17, 18, or 19.

As used herein, "TCID$_{50}$" refers to Tissue Culture Infectious Dose 50 given as TCID$_{50}$. The TCID$_{50}$ can be determined using various methods known to the skilled person such as for example a Tissue Culture Infectious Dose 50 (TCID$_{50}$) assay. The TCID$_{50}$ assay is a method for titrating the infectivity of Modified Vaccinia virus Ankara (MVA) vectors, using 10-fold dilutions in a 96-well format as described in Example 2 of WO 03/053463. The infectivity of a poxvirus such as MVA can be determined using various methods known to the skilled person such as for example by a Flow Cytometry based assay or a Tissue Culture Infectious Dose $_{50}$ (TCID$_{50}$) assay. In one exemplary aspect, a titration of MVA is performed in a TCID$_{50}$-based assay using 10-fold dilutions in a 96-well format. At the endpoint of the assay, infected cells are visualized using an anti-vaccinia virus antibody and an appropriate staining solution. Primary CEF cells are prepared and cultivated in RPMI including 10% serum and 1% Gentamycin using T-flasks for 2-3 days at a given density following trypsinization and seeding into 96-well plates at a density of 1×10$^5$ cells/mL using RPMI with 7% serum. The expected titer of the sample dictates the number of 10-fold serial dilutions, which are performed across a deep-well plate from column 1 to e.g. 10 using 100 μL for transfer into the next well. Following dilution, 100 μL are seeded per well of 96-well plates. Cells are incubated for 5 days at 34-38° C. and 4-6% CO$_2$ to allow infection and viral replication.

Five days post infection, cells are stained with an MVA specific antibody. For the detection of the specific antibody, a horseradish peroxidase (HRP) coupled secondary antibody is used. The MVA specific antibody can be an anti-vaccinia virus antibody, rabbit polyclonal, or an IgG fraction (Quartett, Berlin, Germany #9503-2057), for example. The secondary antibody can be anti-rabbit IgG antibody, or HRP coupled goat polyclonal (Promega, Mannheim, Germany, #W4011), for example. The secondary antibody is visualized using a precipitating TMB substrate. Every well with cells that are positive in the color reaction are marked as positive for the calculation of the TCID$_{50}$. The titer is calculated by using the Spearman-Kaerber method of calculation. The data can also be represented as a log of virus titer which is the relative difference for any given time-point from T=0 time-point.

An alternative method for quantification of virus concentration is by viral plaque assay, which is a standard method well known to the skilled person to determine virus concentration in terms of infectious dose. Briefly, a confluent monolayer of host cells is infected with virus at various dilutions and covered with a semi-solid medium. A viral plaque is formed when a virus infects a cell in the cell monolayer and the number of plaques can be counted in combination with the dilution factor to calculate the number of plaque forming units per sample volume (pfu/mL). The pfu/mL represents the number of infective particles within the sample. Due to distinct differences in assay methods and principles, TCID$_{50}$ and pfu/mL or other infectivity assay results are not necessarily equivalent. For MVA, both methods (TCID$_{50}$ and viral plaque assay) can be used, and generally the dosage of an MVA vector for clinical administration to humans is provided in pfu, or in TCID$_{50}$. The dosage of an adenovirus vector can also be given in pfu or TCID$_{50}$. For administration to humans, generally the dosage of an adenovirus vector is given in viral particles (vp), and concentrations are expressed in vp/mL.

Synthetic HIV Envelope Proteins and Coding Sequences Thereof

Embodiments of the invention relate to novel poxvirus vectors, preferably MVA vectors, comprising nucleic acid sequence encoding synthetic HIV envelope proteins and preferably comprising nucleic acid sequence encoding further HIV antigens.

In one embodiment, a synthetic HIV envelope protein comprises the amino acid sequence of SEQ ID NO: 8, or SEQ ID NO:8 having one or more mutations selected from the group consisting of (i) I529P, (ii) K480E, and (iii) a combination of EK479-480RRRR, I529P, A471C and T575C. SEQ ID NO: 8 comprises a synthetic mature gp120 and a synthetic truncated gp41 without the transmembrane region, nor the cytoplasmic domain. SEQ ID NO: 8 is a non-naturally occurring sequence comprised of a chimera of sequences from the mos2Env mosaic antigen (SEQ ID NO: 6), and other HIV envelope protein sequences. The sequence of the synthetic Env antigen comprising SEQ ID NO: 8 is optimized to provide broad coverage and an enhanced T-cell response against HIV clade C (as compared to the mos2Env antigen (SEQ ID NO: 6)). In certain embodiments, further amino acids can be added to SEQ ID NO: 8 or one of its variants defined herein.

In certain embodiments, the synthetic HIV envelope protein further comprises a signal sequence. The synthetic HIV envelope protein is synthesized with a signal sequence that is cleaved from the nascent polypeptide chain during its transport into the lumen of the endoplasmic reticulum (ER). In principle, any known signal sequence could be used. Preferably an HIV Env signal sequence or a variant thereof is used. Different signal sequences have been used in the art for HIV Env proteins (see e.g. WO 2014/107744). In certain embodiments, the signal sequence comprises SEQ ID NO: 9, SEQ ID NO: 10, SEQ ID NO: 11 or SEQ ID NO: 12. In one preferred embodiment, the signal sequence comprises SEQ ID NO: 9.

In certain embodiments, the synthetic HIV envelope protein further comprises a transmembrane domain. The transmembrane domain anchors the synthetic HIV envelope protein to the ER membrane, and contributes to membrane assembly and function of the HIV envelope. Preferably, the transmembrane domain comprises SEQ ID NO: 13.

In another embodiment, the synthetic HIV envelope protein comprises a gp41 having a truncated cytoplasmic domain. The gp41 has an unusually long cytoplasmic domain at its carboxyl end, typically about 150 amino acids (Edwards et al., J. Virology, 2002, 76:2683-2691). Truncation of the cytoplasmic domain was reported to induce exposure of conserved regions in the ectodomain of HIV-1 Env protein (Id.). The truncated cytoplasmic domain in a synthetic HIV envelope of the invention can range from one to about 140 amino acids, such as 1, 2, 3, 4, 5, 6, 7, 8, 9, 10, 15, 20, 30, 40, 50, 60, 70, 80, 90, 100, 110, 120, 130, or 140 amino acids of a full-length cytoplasmic domain. In certain embodiments the truncated cytoplasmic domain is derived from amino acids 704-862 of SEQ ID NO: 17 (i.e. from the cytoplasmic domain of the C4 molecule of the invention), by truncation after a given amino acid up to the C-terminus. In a preferred embodiment, the synthetic HIV envelope protein comprises a truncated cytoplasmic domain having 1 to 10 amino acids residues, more preferably 4 to 8 amino acid residues, and most preferably 7 amino acid residues of an HIV gp41 cytoplasmic domain. The cytoplasmic domain or fragment thereof of a synthetic HIV envelope protein is located C-terminal to the extracellular domain (ectodomain), and when the synthetic HIV envelope protein also comprises a transmembrane domain, the cytoplasmic domain or fragment thereof is located C-terminal to the transmembrane domain. See, e.g., FIGS. 1A and 1C. In a particular embodiment, the synthetic HIV envelope protein comprises a gp41 with a truncated cytoplasmic domain having the amino acid sequence of SEQ ID NO: 14 or a fragment thereof, such as residues 1-4 thereof (i.e. NRVR). Other truncated cytoplasmic domains have been described and could be used (e.g. Schiernle et al., PNAS 1997; Abrahamyan et al., J Virol 2005).

In embodiments wherein the synthetic HIV envelope protein further comprises a transmembrane domain and a fragment of a cytoplasmic domain, it is preferred that the protein also comprises the amino acid sequence of SEQ ID NO: 37, which contains residues 655-682 of SEQ ID NO: 18, wherein the amino acid sequence of SEQ ID NO: 37 is fused to the C-terminus of SEQ ID NO: 8 and the N-terminus of the transmembrane domain.

In a particularly preferred embodiment of the invention, the synthetic HIV envelope protein further comprises a transmembrane domain, such as that having the amino acid sequence of SEQ ID NO: 13, and a truncated cytoplasmic domain or a fragment of a cytoplasmic domain, such as that having the amino acid sequence of SEQ ID NO: 14 or residues 1-4 of SEQ ID NO: 14 (i.e., NRVR). Most preferably, the synthetic HIV envelope protein comprises or consists of the amino acid sequence of SEQ ID NO: 18, with or without the signal sequence (i.e., amino acid resides 1-29 of SEQ ID NO: 18).

In another embodiment, the synthetic HIV envelope protein comprises a trimerization domain that replaces an Env transmembrane region. The trimerization domain increases the stability of an Env trimeric structure. Preferably, the synthetic HIV envelope protein comprises a gp140 polypeptide that is modified to include a trimerization domain that stabilizes trimers of gp140. Examples of trimerization domains include, but are not limited to, the T4-fibritin "foldon" trimerization domain, such as that comprising the amino acid sequence of SEQ ID NO: 16; the coiled-coil trimerization domain derived from GCN4, such as that comprising the amino acid sequence of SEQ ID NO: 15; the catalytic subunit of E. coli aspartate transcarbamoylase as a trimer tag; or matrillin-based trimerization motifs. If present, the trimerization domain typically is located C-terminal to the extracellular domain (see FIG. 1B). In certain preferred embodiments where the synthetic HIV envelope protein comprises a trimerization domain, the synthetic HIV envelope protein comprises the amino acid sequence of SEQ ID NO: 19, with or without the signal sequence (i.e., amino acid residues 1-29 of SEQ ID NO: 19). These embodiments with trimerization domains are mainly useful for soluble ectodomain variants of the synthetic HIV envelope protein. In certain embodiments of such soluble variants of the invention, it is possible to mutate the furin cleavage site (e.g. mutation of Lys to Glu at position 480 in SEQ ID NO: 8) to inactivate this cleavage site, so that the protein will be a single chain; this combines well with a trimerization domain, especially with the GCN4 trimerization domain of SEQ ID NO: 19.

Alternative versions of such soluble ectodomain variants of the synthetic HIV envelope protein without use of trimerization domains are also embodiments of the invention, and can be prepared from SEQ ID NO: 8 by combining mutations that optimize the furin cleavage site (e.g., replacing the Gly-Lys dipeptide at positions 479-480 by four Arg residues) as well as so-called SOSIP mutations (e.g., I to P mutation at position 529, and introduction of a disulfide bridge between positions 471 and 575 by replacement of the respective Ala and Thr at those positions in SEQ ID NO: 8 each with a Cys residue). This yields a protein having the amino acid sequence of SEQ ID NO: 8 with the following combination of mutations: EK479-480RRRR, I529P, A471C and T575C.

One possible modification to further increase the trimer content of a synthetic HIV envelope protein of the invention (comprising SEQ ID NO: 8), is modification of Ile to Pro at position 529. This can be effective for both soluble and membrane-bound variants.

Vectors

In one general aspect, the invention relates to vectors comprising nucleic acid sequence encoding a synthetic HIV envelope protein, and preferably comprising nucleic acid sequence encoding at least one additional HIV antigen. According to embodiments of the invention, the vectors can comprise any of the synthetic HIV envelope proteins described herein. In a particular embodiment of the invention, the vector is a poxvirus vector, preferably an MVA vector, comprising nucleic acid sequence encoding a synthetic HIV envelope protein comprising the amino acid sequence of SEQ ID NO: 8, SEQ ID NO: 17, SEQ ID NO: 18, or SEQ ID NO: 19, and more preferably SEQ ID NO: 18 or amino acid residues 30-711 of SEQ ID NO: 18.

According to embodiments of the invention, the nucleic acid sequence encoding the synthetic HIV envelope protein is operably linked to a promoter, meaning that the nucleic acid is under the control of a promoter. The promoter can be a homologous promoter (i.e., derived from the same genetic source as the vector) or a heterologous promoter (i.e., derived from a different vector or genetic source). Non-limiting examples of suitable promoters for the adenoviral vectors include the cytomegalovirus (CMV) promoter and the Rous Sarcoma virus (RSV) promoter. Preferably, the promoter is located upstream of the nucleic acid within an expression cassette. An exemplary CMV promoter sequence that can be operably linked to nucleic acid sequence encoding the synthetic HIV envelope protein is shown in SEQ ID NO: 24.

Non-limiting examples of suitable promoters for the poxvirus vectors include the 30K promoter, the 13 promoter, the PrS promoter, the PrS5E promoter, the Pr7.5K, the Pr13.5 long promoter, the PrHyb promoter, the 40K promoter, the MVA-40K promoter, the FPV 40K promoter, 30k promoter, the PrSynIIm promoter, and the PrLE1 promoter. Additional promoters are further described in WO 2010/060632, WO 2010/102822, WO 2013/189611 and WO 2014/063832, which are incorporated fully by reference herein. In more preferred embodiments, the HIV antigens, when incorporated as part of a poxvirus vector according to the invention, are operably linked to the Pr13.5long promoter (SEQ ID NO: 42) and/or the PrHyb promoter (SEQ ID NO: 43).

According to embodiments of the invention, a vector can be an expression vector. Expression vectors include, but are not limited to, vectors for recombinant protein expression and vectors for delivery of nucleic acid into a subject for expression in a tissue of the subject, such as a viral vector. Examples of viral vectors suitable for use with the invention include, but are not limited to adenoviral vectors, adeno-associated virus vectors, poxvirus vectors, MVA vectors, enteric virus vectors, Venezuelan Equine Encephalitis virus vectors, Semliki Forest Virus vectors, Tobacco Mosaic Virus vectors, lentiviral vectors, etc. The vector can also be a non-viral vector. Examples of non-viral vectors include, but are not limited to plasmids, bacterial artificial chromosomes, yeast artificial chromosomes, bacteriophages, etc.

In certain embodiments of the invention, the vector is an adenovirus vector. An adenovirus according to the invention belongs to the family of the Adenoviridae, and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu), or a simian adenovirus such as chimpanzee or gorilla adenovirus (ChAd, AdCh, or SAdV), or a rhesus monkey adenovirus (RhAd). In the invention, a human adenovirus is meant if referred to as Ad without indication of species, e.g. the brief notation "Ad26" means the same as HAdV26, which is human adenovirus serotype 26. Also as used herein, the notation "rAd" means recombinant adenovirus, e.g., "rAd26" refers to recombinant human adenovirus 26.

Most advanced studies have been performed using human adenoviruses, and human adenoviruses are preferred according to certain aspects of the invention. In certain preferred embodiments, a recombinant adenovirus according to the invention is based upon a human adenovirus. In preferred embodiments, the recombinant adenovirus is based upon a human adenovirus serotype 5, 11, 26, 34, 35, 48, 49, 50, 52, etc. According to a particularly preferred embodiment of the invention, an adenovirus is a human adenovirus of serotype 26. Advantages of these serotypes include a low seroprevalence and/or low pre-existing neutralizing antibody titers in the human population, and experience with use in human subjects in clinical trials.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2010085984; Farina et al, 2001, *J Virol* 75: 11603-13; Cohen et al, 2002, *J Gen Virol* 83: 151-55; Kobinger et al, 2006, *Virology* 346: 394-401; Tatsis et al., 2007, *Molecular Therapy* 15: 608-17; see also review by Bangari and Mittal, 2006, *Vaccine* 24: 849-62; and review by Lasaro and Ertl, 2009, *Mol Ther* 17: 1333-39). Hence, in other embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Preferably, the adenovirus vector is a replication deficient recombinant viral vector, such as rAd26, rAd35, rAd48, rAd5HVR48, etc.

In a preferred embodiment of the invention, the adenoviral vectors comprise capsid proteins from rare serotypes including Ad26. In the typical embodiment, the vector is an rAd26 virus. An "adenovirus capsid protein" refers to a protein on the capsid of an adenovirus (e.g., Ad26, Ad35, rAd48, rAd5HVR48 vectors) that is involved in determining the serotype and/or tropism of a particular adenovirus. Adenoviral capsid proteins typically include the fiber, penton and/or hexon proteins. As used herein a "capsid protein" for a particular adenovirus, such as an "Ad26 capsid protein" can be, for example, a chimeric capsid protein that includes at least a part of an Ad26 capsid protein. In certain embodiments, the capsid protein is an entire capsid protein of Ad26. In certain embodiments, the hexon, penton and fiber are of Ad26.

One of ordinary skill in the art will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of pre-existing immunity of a first serotype with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad26 (i.e., the vector is rAd26). In some embodiments, the adenovirus is replication deficient, e.g., because it contains a deletion in the E1 region of the genome. For adenoviruses being derived from non-group C adenovirus, such as Ad26 or Ad35, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga, et al., 2006, *J Gen Virol* 87: 2135-43; WO 03/104467). However, such adenoviruses will not be capable of replicating in non-complementing cells that do not express the E1 genes of Ad5.

The preparation of recombinant adenoviral vectors is well known in the art. Preparation of rAd26 vectors is described, for example, in WO 2007/104792 and in Abbink et al., (2007) *Virol* 81(9): 4654-63. Exemplary genome sequences of Ad26 are found in GenBank Accession EF 153474 and in SEQ ID NO: 1 of WO 2007/104792. Examples of vectors useful for the invention for instance include those described in WO2012/082918, the disclosure of which is incorporated herein by reference in its entirety.

Typically, a vector useful in the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention can be in the form of RNA or in the form of DNA obtained by cloning or produced synthetically. The DNA can be double-stranded or single-stranded.

The adenovirus vectors useful in the invention are typically replication deficient. In these embodiments, the virus is rendered replication deficient by deletion or inactivation of regions critical to replication of the virus, such as the E1 region. The regions can be substantially deleted or inactivated by, for example, inserting a gene of interest, such as a gene encoding a synthetic HIV envelope protein (usually linked to a promoter), or a gene encoding an HIV antigenic polypeptide (usually linked to a promoter) within the region. In some embodiments, the vectors of the invention can contain deletions in other regions, such as the E2, E3 or E4 regions, or insertions of heterologous genes linked to a promoter within one or more of these regions. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amounts of adenovirus vectors for use in the invention. A packaging cell is a cell that comprises those genes that have been deleted or inactivated in a replication deficient vector, thus allowing the virus to replicate in the cell. Suitable packaging cell lines for adenoviruses with a deletion in the E1 region include, for example, PER.C6, 911, 293, and E1 A549.

In a preferred embodiment of the invention, the vector is an adenovirus vector, and more preferably a rAd26 vector, most preferably a rAd26 vector with at least a deletion in the E1 region of the adenoviral genome, e.g. such as that described in Abbink, *J Virol,* 2007. 81(9): p. 4654-63, which is incorporated herein by reference. Typically, the nucleic acid sequence encoding the synthetic HIV envelope protein and/or other HIV antigens is cloned into the E1 and/or the E3 region of the adenoviral genome.

In a preferred aspect of the invention, the vector encoding the synthetic HIV antigen described herein is a poxvirus vector. In a particularly preferred aspect, the vector is a Modified Vaccinia virus Ankara (MVA) vector. In additional preferred embodiments, the MVA virus vector is MVA-BN or derivatives thereof.

MVA has been generated by more than 570 serial passages on chicken embryo fibroblasts of the dermal vaccinia strain Ankara (Chorioallantois vaccinia virus Ankara virus, CVA; for review see Mayr et al. (1975) *Infection* 3, 6-14) that was maintained in the Vaccination Institute, Ankara, Turkey for many years and used as the basis for vaccination of humans. The attenuated CVA-virus MVA (Modified Vaccinia Virus Ankara) was obtained by serial propagation (more than 570 passages) of the CVA on primary chicken embryo fibroblasts (CEF).

However, due to the often severe post-vaccination complications associated with vaccinia viruses, there were several attempts to generate a more attenuated, safer vaccine. As a result of the passaging used to attenuate MVA, there are a number of different strains or isolates, depending on the number of passages conducted in CEF cells. Strains of MVA having enhanced safety profiles for the development of safer products, such as vaccines or pharmaceuticals, have been developed, for example by Bavarian Nordic. MVA was further passaged by Bavarian Nordic and is designated MVA-BN. A representative sample of MVA-BN was deposited on Aug. 30, 2000 at the European Collection of Cell Cultures (ECACC) under Accession No. V00083008. MVA-BN is further described in WO 02/42480 (see also e.g., U.S. Pat. Nos. 6,761,893 and 6,913,752 and US 2003/0206926) and WO 03/048184 (US 2006/0159699), which are incorporated by reference herein in their entireties. MVA as well as MVA-BN lacks approximately 15% (31 kb from six regions) of the genome compared with ancestral CVA virus. The deletions affect a number of virulence and host range genes, as well as the gene for Type A inclusion bodies.

In various embodiments, the MVA or MVA used for generating the recombinants suitable for the present invention are MVA-572, MVA-575, MVA-1721, MVA as deposited as ATCC® VR-1508™, MVA as deposited as ATCC® VR-1566™, ACAM3000 MVA, MVA-BN or any similarly attenuated MVA strain. In preferred embodiments, the MVA used for generating the recombinants are MVA-575, MVA as deposited as ATCC® VR-1508™, MVA as deposited as ATCC® VR-1566™, ACAM3000 MVA and MVA-BN. More preferably the MVA used for generating the recombinants is MVA-BN.

MVA-572 was deposited at the European Collection of Animal Cell Cultures (ECACC, Vaccine Research and Production Laboratory, Public Health Laboratory Service, Centre for *Applied Microbiology* and Research, Porton Down, Salisbury, Wiltshire SP4 OJG, United Kingdom) with the deposition number ECACC V94012707 on Jan. 27, 1994. MVA-575 was deposited under ECACC V00120707 on Dec. 7, 2000. Acam3000 MVA was deposited at the American Type Culture Collection (ATCC) under Accession No.: PTA-5095 on Mar. 27, 2003 (American Type Culture Collection, 10801 University Blvd., Manassas, Va. 20110-2209, USA). MVA-1721 was deposited as CNCM 1721 at the Collection Nationale de Cultures de Microorganisms, Institute Pasteur. MVA-BN was deposited on Aug. 30, 2000 at the ECACC under number V00083008. MVA-BN has been described in WO 02/042480.

Also encompassed by the invention are derivatives or variants of any of the MVA viruses or MVA-BN described herein. "Derivatives" or "variants" of MVA or MVA-BN refer to MVA or MVA-BN viruses exhibiting essentially the same replication characteristics as the MVA or MVA-BN to which it refers, but exhibiting differences in one or more parts of their genomes. Viruses having the same "replication characteristics" as the deposited virus are viruses that replicate with similar amplification ratios as the deposited strain in CEF cells and the cell lines HaCat (Boukamp et al. (1988), *J Cell Biol* 106: 761-771), the human bone osteosarcoma cell line 143B (ECACC No. 91112502), the human embryo kidney cell line 293 (ECACC No. 85120602), and the human cervix adenocarcinoma cell line HeLa (ATCC No. CCL-2). Tests and assay to determine these properties of MVA, its derivatives and variants are well known to the skilled person, such as the cell line permissivity assay as described in WO 02/42480. In an exemplary cell line permissivity assay, mammalian cell lines are infected with the parental and derivative or variant MVA virus at a low multiplicity of infection per cell, i.e., 0.05 infectious units per cell ($5 \times 10^4$ TCID$_{50}$). Following absorption of 1 hour the virus inoculum is removed and the cells washed three times to remove any remaining unabsorbed viruses. Fresh medium supplemented with 3% FCS is added and infections are left for a total of 4 days (at 37° C., 5% $CO_2$) where viral extracts can be prepared. The infections are stopped by freezing the plates at –80° C. for three times. Virus multiplication and cytopathic effects (CPE) are subsequently determined on CEF cells using methods well known to the skilled person such as those described in Carroll and Moss (1997), *Virology* 238, 198-211.

More specifically, MVA-BN or a derivative or variant of MVA-BN preferably has the capability of reproductive replication in chicken embryo fibroblasts (CEF), but no capability of reproductive replication in the human keratinocyte cell line HaCat (Boukamp et al (1988), *J. Cell Biol.* 106:761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably three-fold less than MVA-575 in Hela cells and HaCaT cell lines. Tests and assays for these properties of MVA variants are described in WO 02/42480 or in the exemplary cell line permissivity assay as described above.

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input) referred to as the "amplification ratio." An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The recombinant poxvirus vectors provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) [J. Sambrook et al., Cold Spring Harbor Laboratory Press (1989)], and techniques for the handling and manipulation of viruses are described in Virology Methods Manual [B. W. J. Mahy et al. (eds.), Academic Press (1996)]. Similarly, techniques and know-how for the handling, manipulation and genetic engineering of MVA are described in Molecular Virology: A Practical Approach [A. J. Davison & R. M. Elliott (Eds.), The Practical Approach Series, IRL Press at Oxford University Press, Oxford, UK (1993)(see, e.g., Chapter 9: Expression of genes by Vaccinia virus vectors)] and Current Protocols in Molecular Biology [John Wiley & Son, Inc. (1998)(see, e.g., Chapter 16, Section IV: Expression of proteins in mammalian cells using vaccinia viral vector)].

For the generation of the various recombinant poxviruses disclosed herein, different methods are applicable. The DNA sequence to be inserted into the virus can be placed into an *E. coli* plasmid construct into which DNA homologous to a section of DNA of the poxvirus has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of poxviral DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with poxvirus. Recombination between homologous poxviral DNA in the plasmid and the viral genome, respectively, can generate a poxvirus modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign or heterologous gene or genes, such as one or more of the HIV antigen encoding nucleic acids provided in the present disclosure; preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In this case, this gene shall be introduced into a different insertion site of the poxviral genome, and the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a poxvirus genome cloned as a bacterial artificial chromosome (BAC) and a linear foreign sequence flanked with DNA sequences homologous to sequences flanking the desired site of integration in the vaccinia virus genome.

One or more nucleic acid sequences encoding at least one HIV antigen according to embodiments of the invention can be inserted into any suitable part of the poxvirus or poxviral vector. In a preferred aspect, the poxvirus used for the present invention includes an MVA virus. Suitable parts of the MVA virus into which one or more nucleic acids of the present disclosure can be inserted include non-essential parts of the MVA virus.

For MVA virus, non-essential parts of the MVA genome can be intergenic regions or the known deletion sites 1-6 of the MVA genome. Alternatively or additionally, non-essential parts of the recombinant MVA can be a coding region of the MVA genome which is non-essential for viral growth. However, the insertion sites are not restricted to these preferred insertion sites in the MVA genome, since it is within the scope of the present invention that the antigens and nucleic acids and any accompanying promoters as described herein can be inserted anywhere in the viral genome as long as it is possible to obtain recombinants that can be amplified and propagated in at least one cell culture system, such as Chicken Embryo Fibroblasts (CEF cells).

Preferably, the nucleic acids of the present invention are inserted into one or more intergenic regions (IGR) of the MVA. The terms "intergenic region" and "IGR" refer preferably to those parts of the viral genome located between two adjacent open reading frames (ORF) of the MVA genome, preferably between two essential ORFs of the MVA virus genome. For MVA, in certain embodiments, the IGR is selected from IGR 07/08, IGR 44/45, IGR 64/65, IGR 88/89, IGR 136/137, and IGR 148/149. In more preferred embodiments, the nucleic acids of the present invention are inserted in the IGR 44/45 and IGR 88/89 regions.

According to embodiments of the invention, and as noted above, any of the synthetic HIV envelope proteins and/or HIV antigens described herein can be expressed in the vectors of the invention. In view of the degeneracy of the genetic code, the skilled person is well aware that several nucleic acid sequences can be designed that encode the same protein, according to methods entirely routine in the art. The nucleic acid encoding the synthetic HIV envelope protein and/or HIV antigens can optionally be codon-optimized to ensure proper expression in the treated host (e.g., human). Codon-optimization is a technology widely applied in the art. Some non-limiting examples of sequences encoding a synthetic HIV envelope protein of the invention are provided in SEQ ID NOs: 26 (used in adenovirus vectors in the examples), and 41 (used in MVA vectors in the examples); and some non-limiting examples of sequences encoding further HIV antigens for use in the invention are provided in SEQ ID NOs: 20-22 (used in adenovirus vectors in the examples), and 38-40 (used in MVA vectors in the examples).

The invention also provides cells, preferably isolated cells, comprising any of the vectors described herein. The cells can be used for recombinant protein production, or for the production of viral particles.

Also disclosed is a method of making a synthetic HIV antigenic polypeptide. The method comprises transfecting a host cell with an expression vector comprising nucleic acid encoding the synthetic HIV antigenic polypeptide operably linked to a promoter, growing the transfected cell under conditions suitable for expression of the synthetic HIV antigenic polypeptide, and isolating the synthetic HIV antigenic polypeptide from the cell. The synthetic HIV antigenic polypeptide can be isolated or collected from the cell by any method known in the art including affinity chromatography, etc. Techniques used for recombinant protein expression are well known to one of ordinary skill in the art in view of the present disclosure.

The invention also relates to a method for manufacturing a vector encoding a synthetic HIV antigenic polypeptide of the invention, the method comprising culturing a cell that comprises the vector, to propagate and multiply the vector during said culturing, and isolating the vector that encodes the synthetic HIV antigenic polypeptide of the invention from the cell culture, e.g. from the cells, from the culture medium, or both. The vector can be further purified according to methods known in the art.

In certain embodiments, the invention provides a poxvirus vector, preferably an MVA vector, such as an MVA-BN vector, comprising a nucleic acid sequence encoding a synthetic HIV antigen. The poxvirus vector comprises nucleic acid sequence encoding a synthetic HIV envelope (Env) antigen according to the invention, such as that comprising the amino acid sequence of SEQ ID NO: 18, and optionally further comprises nucleic acid sequence encoding at least one additional HIV antigen. In preferred embodiments, the poxvirus vector and more preferably a MVA vector, comprises nucleic acid sequence encoding a first HIV Env antigen which is a synthetic HIV Env antigen comprising the amino acid sequence of SEQ ID NO: 18, and at least one additional HIV antigen, such as Gag, Pol, and/or Env antigens, preferably one or more additional HIV antigens comprising the amino acid sequences selected from the group consisting of SEQ ID NOs: 1-5, 28, and 29.

For example, in a particular embodiment, a poxvirus vector can comprise nucleic acid encoding a first HIV Env antigen comprising the amino acid sequence of SEQ ID NO: 18; a second HIV Env antigen different than the first HIV Env antigen; a third antigen and a fourth antigen, being two different HIV Gag antigens; and a fifth antigen and a sixth antigen, being two different HIV Pol antigens. The Gag and Pol antigens can be fused into a first Gag-Pol fusion antigen and a second Gag-Pol fusion antigen, such as those Gag-Pol fusion antigens comprising the amino acid sequence of SEQ ID NO: 28 or SEQ ID NO: 29.

In certain exemplary embodiments, the poxvirus vector comprises nucleic acid encoding one or more amino acid sequences selected from the group consisting of SEQ ID NOs: 1-5, 18, 28, and 29. In one or more specific embodiments, the poxvirus vector comprises nucleic acid encoding the amino acid sequences of SEQ ID NOs: 1-5, and 18, more preferably SEQ ID NOs: 5, 18, 28, and 29.

In other certain exemplary embodiments a vector is an adenovirus vector comprising a nucleic acid sequence selected from the group consisting of SEQ ID NOs: 25, 26 and 27, preferably SEQ ID NO: 26. Further exemplary embodiments include adenovirus vectors encoding other HIV antigens, such adenovirus vectors comprising one or more nucleic acid sequences selected from the group consisting of SEQ ID NOs: 20, 21, and 22. In other certain embodiments, the vector is a poxvirus vector, preferably an MVA vector, more preferably MVA-BN, the vector comprising one or more nucleic acid sequences selected from the group consisting of SEQ ID NOs: 38, 39, 40, and 41. In one or more specific embodiments the poxvirus vector comprises SEQ ID NOs: 38, 39, 40, and 41.

The nucleic acid sequence encoding the one more HIV antigens can be inserted into any appropriate insertion site of the poxvirus vector genome as described herein. In particular embodiments wherein the poxvirus vector is an MVA vector, such as MVA-BN or derivatives thereof, encoding one or more Gag-Pol fusion antigens, nucleic acid sequence encoding a first Gag-Pol fusion antigen can be inserted into intergenic region (IGR) 44/45 of the MVA genome and nucleic acid sequence encoding a second Gag-Pol fusion antigen can be inserted into IGR 88/89 of the MVA genome. Additionally, nucleic acid sequence encoding HIV Env antigens can be inserted into the IGR 44/45 and/or IGR 88/89 of the MVA genome. In one or more specific embodiments, the poxvirus vector comprises nucleic acid sequence encoding a Gag-Pol fusion antigen comprising SEQ ID NO: 28 and nucleic acid sequence encoding an HIV Env antigen comprising SEQ ID NO: 5 into IGR 44/45 of the MVA genome and/or nucleic acid sequence encoding a Gag-Pol fusion antigen comprising SEQ ID NO: 29 and nucleic acid sequence encoding an HIV Env antigen comprising SEQ ID NO: 18 into IGR 88/89 of the MVA genome. Preferably, the Gag-Pol fusion antigens are each under control of a separate promoter, preferably a Pr13.5 promoter, such as that shown in SEQ ID NO: 42 and/or the Env antigens are each under control of a separate promoter, preferably a PrHyb promoter, such as that shown in SEQ ID NO: 43.

Compositions

In another general aspect, the invention relates to a composition comprising a vector comprising a nucleic acid encoding a synthetic HIV envelope protein and a carrier. Preferably, the composition is a vaccine composition, which is described in greater detail below. According to embodiments of the invention, any of vectors described herein can be included in the composition. Preferably, the vector is a viral vector, more preferably an adenovirus vector or a poxvirus vector, and even more preferably an adenovirus 26 vector or an MVA vector.

In one embodiment, a composition of the invention comprises a poxvirus vector, preferably an MVA vector, comprising nucleic acid sequence encoding a synthetic HIV envelope protein comprising the amino acid sequence of SEQ ID NO: 8, SEQ ID NO: 18, or SEQ ID NO: 19, and more preferably the amino acid sequence of SEQ ID NO: 18. In certain preferred embodiments, the vector is an MVA-BN vector, or derivative thereof. In one or more specific embodiments, a composition of the invention comprises a poxvirus vector, MVA vector, or MVA-BN vector comprising nucleic acid encoding at least a first HIV envelope antigen comprising the amino acid sequence of SEQ ID NO: 18. Most preferably, such vector further comprises nucleic acid sequence encoding: (b) a second HIV Env antigen different from the first HIV Env antigen; (c) a third antigen and a fourth antigen, being two different HIV Gag antigens; and (d) a fifth antigen and a sixth antigen, being two different HIV Pol antigens. In preferred embodiments, the second HIV Env antigen comprises the amino acid sequence of SEQ ID NO: 5, the third and fourth antigens comprise the amino acid sequence of SEQ ID NO: 1 and SEQ ID NO: 2, respectively; and the fifth and the sixth antigens comprise the amino acid sequence of SEQ ID NO: 3 and SEQ ID NO: 4, respectively. In certain embodiments, the third and the fifth antigens are fused into a first Gag-Pol fusion antigen that comprises the amino acid sequence of SEQ ID NO: 28, and the fourth and the sixth antigens are fused into a second Gag-Pol fusion antigen that comprises the amino acid sequence of SEQ ID NO: 29.

According to embodiments of the invention, a composition comprising a poxvirus vector according to the invention can be used together with one or more additional vectors encoding one or more additional HIV antigens, and/or one or more isolated HIV antigenic polypeptides. The additional vectors and/or HIV antigenic polypeptides can be present in the same composition or in one or more different compositions. Preferably, the one or more additional vectors are viral vectors, such as adenovirus vectors, more preferably adenovirus 26 vectors, or poxvirus vectors, more preferably MVA vectors. The one or more additional vectors can encode any HIV antigen known to those skilled in the art in view of the present disclosure. Most preferably, the one or more additional vectors are adenovirus vectors, preferably adenovirus 26 vectors, encoding one or more HIV antigens comprising the amino acid sequences selected from the group consisting of SEQ ID NOs: 1-5, 18, 28, and 29.

In one aspect, the invention provides a combination vaccine comprising one or more vectors together comprising nucleic acid sequences encoding (a) a synthetic HIV envelope protein comprising the amino acid sequence of SEQ ID NO: 18; (b) a second HIV envelope protein, preferably comprising the amino acid sequence of SEQ ID NO: 5; (c) a third antigen and a fourth antigen, being two different HIV Gag antigens, preferably comprising the amino acid sequences of SEQ ID NOs: 1 and 2, respectively; and (d) a fifth antigen and a sixth antigen, being two different HIV Pol antigens, preferably comprising the amino acid sequences of SEQ ID NOs: 3 and 4, respectively. In one or more specific embodiments, the third and fifth antigens are fused into a first Gag-Pol fusion antigen, preferably comprising the amino acid sequence of SEQ ID NO: 28 and the fourth and sixth antigens are fused into a second Gag-Pol fusion antigen that comprises the amino acid sequence of SEQ ID NO: 29. The vectors can each be in separate compositions, or they can be combined in a single composition. The multiple nucleic acids in the vector(s) are intended to be administered to one subject, which will result in an immune response to HIV that is broader than the immune response that would be obtained upon administration of either vector alone. The multiple nucleic acid sequences could also be present on one single vector.

According to embodiments of the invention, the one or more vectors can be adenovirus vectors, preferably adenovirus 26 vectors, and/or poxvirus vectors, preferably MVA vectors. The compositions comprising adenovirus and/or poxvirus vectors can optionally further comprise one or more isolated HIV antigenic polypeptides. Any isolated HIV antigenic polypeptide can be used in the compositions of the invention in view of the present disclosure. In certain preferred embodiments, the one or more isolated HIV antigenic polypeptides comprises a polypeptide comprising residues 30-708 of the amino acid sequence of SEQ ID NO: 7, a polypeptide comprising residues 30-724 of SEQ ID NO: 36, or a combination thereof.

In one or more specific embodiments, a combination comprises an adenovirus vector, preferably an adenovirus 26 vector, comprising nucleic acid encoding one or more HIV antigens preferably selected from the group consisting of SEQ ID NOs: 1-5, 18, 28, and 29 and a poxvirus vector, preferably a MVA vector, comprising nucleic acid encoding one or more HIV antigens preferably selected from the group consisting of SEQ ID NOs: 1-5, 18, 28, and 29. Preferably, one or more adenovirus vectors, preferably adenovirus 26 vectors together encode SEQ ID NOs: 1-5 and 18; and the poxvirus vector, preferably MVA vector, encodes SEQ ID NOs: 1-5 and 18. The vectors can be present in one composition, or in one or more different compositions.

According to certain embodiments of the invention, a composition, such as a vaccine composition, comprises an immunogenically effective amount of a vector, such as a viral vector. As used herein, "an immunogenically effective amount" or "immunologically effective amount" means an amount of a composition sufficient to induce a desired immune effect or immune response in a subject in need thereof. In one embodiment, an immunogenically effective amount means an amount sufficient to induce an immune response in a subject in need thereof. In another embodiment, an immunogenically effective amount means an amount sufficient to produce immunity in a subject in need thereof, e.g., provide a protective effect against a disease such as a viral infection. An immunogenically effective amount can vary depending upon a variety of factors, such as the physical condition of the subject, age, weight, health, etc.; the particular application, whether inducing immune response or providing protective immunity; the specific recombinant vector administered; the immunogen or antigenic polypeptide encoded by the recombinant vector administered; the specific antigenic polypeptide administered; and the particular disease, e.g., viral infection, for which immunity is desired. An immunogenically effective amount can readily be determined by one of ordinary skill in the art in view of the present disclosure.

As general guidance, an immunogenically effective amount when used with reference to a recombinant viral vector such as an adenoviral vector can be for instance about $10^8$ viral particles to about $10^{12}$ viral particles, for example $10^8$, $10^9$, $10^{10}$, $10^{11}$, or $10^{12}$ viral particles. A single dose of adenoviral vectors for administration to humans in certain embodiments is between 10' and $10^{11}$ viral particles. An immunogenically effective amount when used with reference to a recombinant viral vector such as a poxviral vector can be for instance about $10^4$ to $10^{11}$ TCID$_{50}$, $10^5$ to $10^{10}$ TCID$_{50}$, $10^6$ to $10^9$ TCID$_{50}$, or $10^7$ to $10^8$ TCID$_{50}$, such as $10^4$, $10^5$, $10^6$, $10^7$, $10^8$, $10^9$, $10^{10}$, or $10^{11}$ TCID$_{50}$. A preferred dose for the subjects (preferably a human) comprises $10^5$ to $10^{10}$ TCID$_{50}$, including a dose of $10^5$ TCID$_{50}$, $10^6$ TCID$_{50}$, $10^7$ TCID$_{50}$, $10^8$ TCID$_{50}$, $10^9$ TCID$_{50}$, or $10^{10}$ TCID$_{50}$. The immunogenically effective amount of a poxviral vector such as an MVA vector can alternatively and conveniently be expressed in plaque forming units (pfu), and can for instance be about $10^5$ to about $10^{11}$ pfu, e.g. about $10^5$, $10^6$, $10^7$, $10^8$, $10^9$, $10^{10}$ or $10^{11}$ pfu, preferably about $10^7$ to $10^9$ pfu, and more preferably about $10^8$ pfu, such as for instance about $0.5\times10^8$, $1\times10^8$, $2\times10^8$, $3\times10^8$, $4\times10^8$, or $5\times10^8$ pfu. In certain embodiments, the immunogenically effective amount of an MVA vector according to the invention administered to a human subject is about $1\times10^7$ to $1\times10^9$ pfu, preferably about $1\times10^8$ pfu, preferably in a volume of 0.1 mL to 1 mL, e.g. 0.5 mL.

An immunogenically effective amount of a vector, such as an MVA vector and/or adenovirus vector, can be administered in a single composition, or in multiple compositions, such as 1, 2, 3, 4, 5, 6, 7, 8, 9, or 10 compositions (e.g., tablets, capsules or injectables), wherein the administration of the multiple capsules or injections collectively provides a subject with the immunogenically effective amount. It is also possible to administer an immunogenically effective amount to a subject, and subsequently administer another dose of an immunogenically effective amount to the same subject, in a so-called prime-boost regimen. Further booster administrations can optionally be added to the regimen, as needed. This general concept of a prime-boost regimen is well known to the skill person in the vaccine field and is described in greater detail below.

Compositions of the invention may further comprise a carrier. A carrier can include one or more pharmaceutically acceptable excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions of the invention can be formulated in any matter suitable for administration to a subject to facilitate administration and improve efficacy, including, but not limited to, oral (enteral) administration and parenteral injections. The parenteral injections include intravenous injection or infusion, intra-arterial injection, subcutaneous injection, intramuscular injection, and intra-articular injection. Compositions of the invention can also be formulated for other routes of administration including transmucosal, ocular, rectal, long acting implantation, sublingual administration, under the tongue, from oral mucosa bypassing the portal circulation, inhalation, or intranasal.

According to certain embodiments of the invention, a composition comprises an immunogenically effective amount of purified or partially purified vector, for instance adenovirus vector, such as an adenovirus 26 vector, or poxvirus vector, such as MVA or MVA-BN, the vector comprising a nucleic acid encoding a synthetic HIV envelope protein of the invention and optionally one or more additional HIV antigens. Said compositions can be formulated as a vaccine (also referred to as an "immunogenic composition") according to methods well known in the art.

In certain embodiments of the invention, a composition can further comprise one or more polypeptides comprising an immunogenically effective amount of an isolated HIV antigenic polypeptide. In general, when used with reference to a polypeptide, such as an isolated antigenic polypeptide, an immunogenically effective amount can range from, e.g. about 0.3 to about 3000 microgram (µg), e.g. 1-1000 µg, e.g.

10-500 µg, e.g. about 50 or 250 µg. As a non-limiting example, it is possible to combine administration of the one or more vectors encoding the synthetic HIV Env antigen of the invention (e.g., having SEQ ID NO: 18) and optionally one or more additional HIV antigens (e.g., having SEQ ID NOs: 1-5, 28, and/or 29) with administration of an isolated HIV Env polypeptide, e.g. 250 µg of HIV clade C Env trimer protein having amino acids 30-708 of SEQ ID NO: 7 or 250 µg of HIV mosaic Env trimer protein having amino acids 30-708 of SEQ ID NO: 36.

In some embodiments, compositions of the invention can further optionally comprise an adjuvant to enhance immune responses. The terms "adjuvant" and "immune stimulant" are used interchangeably herein, and are defined as one or more substances that cause stimulation of the immune system. In this context, an adjuvant is used to enhance an immune response to the vectors encoding synthetic HIV envelope proteins of the invention and optionally one or more additional HIV antigens and/or HIV antigenic polypeptides used in combination with vectors encoding synthetic HIV envelope proteins of the invention and optionally one or more additional HIV antigens.

Adjuvants suitable for use with the invention should be ones that are potentially safe, well tolerated and effective in people, such as for instance QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, aluminum salts (e.g. AdjuPhos), Adjuplex, and MF59. The optimal ratios of each component in the formulation can be determined by techniques well known to those skilled in the art in view of the present disclosure.

In a preferred embodiment, the adjuvant is an aluminum salt, such as aluminum phosphate, e.g. AdjuPhos. In certain embodiments, the aluminum phosphate is preferably present in or administered with a composition with isolated HIV antigenic polypeptide, such as gp140.

The preparation and use of immunogenic compositions are well known to those of ordinary skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can also be included.

For instance recombinant adenovirus vector may be stored in the buffer that is also used for the Adenovirus World Standard (Hoganson et al., 2002, *Bioprocessing J* 1: 43-8): 20 mM Tris pH 8, 25 mM NaCl, 2.5% glycerol. Another useful adenovirus formulation buffer suitable for administration to humans is 20 mM Tris, 2 mM MgCl$_2$, 25 mM NaCl, sucrose 10% w/v, polysorbate-80 0.02% w/v. Another formulation buffer that is suitable for recombinant adenovirus comprises 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Obviously, many other buffers can be used, and several examples of suitable formulations for the storage and for pharmaceutical administration of purified vectors are known.

An exemplary preparation and storage of poxviral vectors, including MVA and MVA-BN can be based on the experience in the preparation of poxvirus vaccines used for vaccination against smallpox, as described, for example, in Stickl, H. et al., Dtsch. med. Wschr. 99, 2386-2392 (1974).

In an exemplary embodiment, purified poxvirus is stored at −80° C. with a titer of 5×10$^8$ TCID$_{50}$/ml formulated in 10 mM Tris, 140 mM NaCl, pH 7.7. For the preparation of vaccine shots, e.g., 10$^2$-10$^8$ particles of the virus can be lyophilized in phosphate-buffered saline (PBS) in the presence of 2% peptone and 1% human albumin in an ampoule, preferably a glass ampoule. Alternatively, the vaccine shots can be prepared by stepwise, freeze-drying of the virus in a formulation. In certain embodiments, the formulation contains additional additives such as mannitol, dextran, sugar, glycine, lactose, polyvinylpyrrolidone, or other additives, such as, including, but not limited to, antioxidants or inert gas, stabilizers or recombinant proteins (e.g. human serum albumin) suitable for in vivo administration. The ampoule is then sealed and can be stored at a suitable temperature, for example, between 4° C. and room temperature for several months. However, as long as no need exists, the ampoule is stored preferably at temperatures below −20° C.

In various embodiments involving vaccination or therapy, the lyophilisate is dissolved in 0.1 to 0.5 ml of an aqueous solution, preferably physiological saline or Tris buffer, and administered either systemically or locally, i.e., by parenteral, subcutaneous, intravenous, intramuscular, intranasal, intradermal, or any other path of administration known to a skilled practitioner. Optimization of the mode of administration, dose, and number of administrations is within the skill and knowledge of one skilled in the art.

An advantage of embodiments wherein the vector or vector combination encodes both HIV antigens comprising SEQ ID NOs: 18 and 5, is increased breadth of the immune response (covering strains from clades B and C).

In certain embodiments, a composition or a vaccine combination of the invention further comprises on the same or other vectors, nucleic acid encoding an HIV antigenic polypeptide comprising the amino acid sequence of SEQ ID NO: 28 (mos1GagPol) and/or SEQ ID NO: 29 (mos2GagPol).

In a particular embodiment, a composition or a vaccine combination of the invention comprises a first adenovirus vector, preferably an adenovirus 26 vector, encoding an HIV antigen comprising the amino acid sequence of SEQ ID NO: 18, and further comprises a second adenovirus vector, preferably an adenovirus 26 vector, encoding an HIV antigen comprising the amino acid sequence of SEQ ID NO: 5, and one or more additional adenovirus vectors, preferably adenovirus 26 vectors, encoding one or more HIV antigens comprising the amino acid sequence selected from the group consisting of SEQ ID NO: 28 or SEQ ID NO: 29. For example, a composition or a vaccine combination according to an embodiment of the invention can comprise four adenovirus vectors, preferably adenovirus 26 vectors, with a first vector encoding a synthetic HIV envelope protein comprising the amino acid sequence of SEQ ID NO: 18; a second vector encoding an HIV antigen comprising the amino acid sequence of SEQ ID NO: 5; a third vector encoding a HIV antigen comprising the amino acid sequence of SEQ ID NO: 28; and a fourth vector encoding a HIV antigen comprising the amino acid sequence of SEQ ID NO: 29. Preferably, the poxvirus vector of the invention can be part of a vaccine combination with those adenovirus vectors. Such poxvirus vector, preferably an MVA vector, e.g. an MVA-BN vector, in a preferred embodiment encodes each of SEQ ID NOs: 18, 5, 28 and 29.

In a particularly preferred embodiment of the invention, a composition or a vaccine combination comprises a poxvirus vector, preferably an MVA vector, preferably MVA-BN, comprising nucleic acid sequence encoding six different HIV antigens, namely the antigens encoded by SEQ ID NO: 18 (mos2S Env), SEQ ID NO: 5 (mos1 Env), SEQ ID NO:

1 (mos1 Gag), SEQ ID NO: 2 (mos2 Gag), SEQ ID NO: 3 (mos1 Pol), and SEQ ID NO: 4 (mos2 Pol), wherein SEQ ID NOs: 1 and 3 can optionally be fused (SEQ ID NO: 28; mos1GagPol) and SEQ ID NOs: 2 and 4 can optionally be fused (SEQ ID NO: 29: mos2GagPol). An advantage is that only a single vector needs to be manufactured, purified, formulated, tested, stored, shipped, and administered for administering these six HIV antigens. Also, it is known that poxviral vectors, such as MVA, including MVA-BN, provide good immune responses against the antigens encoded therein. Moreover, they can typically be advantageously used together with other vector platforms, such as with adenoviral, e.g. Ad26, vectors in prime-boost regimens to generate further improved immune responses. For example, the poxvirus vector comprising nucleic acid sequence encoding the six different HIV antigens encoded by SEQ ID NOs: 1-5 and 18 can be used together with one or more adenovirus vectors, preferably adenovirus 26 vectors, encoding one or more HIV antigens encoded by SEQ ID NOs: 1-5 and 18, preferably wherein the one or more adenovirus vectors together encode SEQ ID NOs: 1-5 and 18.

As mentioned above, in some embodiments, the composition or a vaccine combination further comprises one or more isolated HIV antigenic polypeptides. Any HIV antigenic polypeptide known to those skilled in the art in view of the present disclosure can be further included in a composition or a vaccine combination of the invention, including, but not limited to an HIV envelope protein (e.g., gp160, gp140, gp120, or gp41), preferably a stabilized trimeric gp140 protein, such as a stabilized clade C or clade A gp140 protein. In a preferred embodiment, the isolated HIV antigenic polypeptide is a stabilized HIV clade C trimeric gp140 protein, such as that comprising residues 30-708 of the amino acid sequence of SEQ ID NO: 7 (residues 1-29 of SEQ ID NO: 7 are in the signal sequence). An alternative or additional HIV Env polypeptide that could be used in addition to the clade C gp140 protein or alone, is a mosaic Env trimer protein, for instance having an amino acid sequence as disclosed in amino acids 30-724 of SEQ ID NO: 36 (corresponding to SEQ ID NO: 2 of WO 2014/107744, in which residues 1-29 of SEQ ID NO: 36 are in the signal sequence). In certain embodiments, the HIV antigenic polypeptides comprise both (i) a clade C gp140 protein comprising amino acid residues 30-708 of SEQ ID NO: 7, and (ii) a mosaic gp140 protein comprising amino acid residues 30-724 of SEQ ID NO: 36.

The invention also relates to a method of producing a composition or a vaccine combination of the invention. According to embodiments of the invention, a method of producing a composition or a combination comprises combining a vector comprising nucleic acid encoding the synthetic HIV envelope protein of the invention with a carrier, and optionally one or more additional vectors encoding one or more additional HIV antigenic polypeptides and/or one or more isolated HIV antigenic polypeptides. One of ordinary skill in the art will be familiar with conventional techniques used to prepare such compositions.

Vaccine and Vaccine Combinations

Other general aspects of the invention relate to vaccines and vaccine combinations. In certain embodiments, the compositions of the invention described herein are vaccines. As used herein, the term "vaccine" refers to a composition comprising an immunologically effective amount of an expression vector, preferably a viral vector, encoding a synthetic HIV envelope protein of the invention and optionally further encoding one or more additional HIV antigens that can provide protective immunity or a protective immune response to a subject, or to vaccinate a subject. According to embodiments of the invention, upon administration of the composition to a subject, the expression vector expresses the encoded synthetic HIV envelope protein and optionally further encoded HIV antigens, and the expressed synthetic HIV envelope protein and optionally further encoded HIV antigens are presented to the immune system of the subject, thereby inducing the required response to produce immunity, or induce an immune response.

Thus, in another general aspect, the invention provides a vaccine for inducing an immune response against a human immunodeficiency virus (HIV) in a subject. According to embodiments of the invention, the vaccine comprises a composition comprising an immunogenically effective amount of an expression vector encoding a synthetic HIV envelope protein comprising the amino acid sequence of SEQ ID NO: 18. Preferably, the expression vector is a viral vector, more preferably an adenovirus vector, e.g., adenovirus 26 vector, and most preferably a poxvirus vector, e.g., MVA or MVA-BN vector.

According to embodiments of the invention, vaccine compositions can further comprise one or more additional vectors, e.g., viral vectors, such as adenovirus vectors, preferably adenovirus 26 vectors, encoding one or more additional HIV antigenic polypeptides and/or one or more isolated HIV antigenic polypeptides. The synthetic HIV envelope protein, additional vectors and/or one or more isolated HIV antigenic polypeptides can be formulated in the same composition or one or more different compositions in the vaccine.

The invention also relates to vaccine combinations for priming and boosting an immune response to one or more HIV clades in a subject in need thereof using one or more vectors, optionally in combination with an isolated antigenic polypeptide. Thus, in another general aspect, the invention provides a vaccine combination for inducing an immune response against an HIV in a subject comprising:

(a) a first vaccine composition comprising an immunologically effective amount of a poxvirus vector comprising nucleic acid sequence encoding a first HIV Env antigen comprising the amino acid sequence of SEQ ID NO: 18, and optionally further comprising nucleic acid sequence encoding further HIV antigens, preferably one or more HIV antigens comprising the amino acid sequences selected from SEQ ID NOs: 1-5, 28, and 29; and at least one of:

(b) (i) a second vaccine composition comprising an immunogenically effective amount of one or more adenovirus vectors encoding one or more HIV antigens comprising the amino acid sequences selected from the group consisting of SEQ ID NOs: 1-5, 18, 28, and 29; and (b) (ii) a third vaccine composition comprising one or more polypeptides comprising an immunogenically effective amount of an isolated HIV antigenic polypeptide, wherein the first composition, and second and/or third composition are present in the same composition or in one or more different compositions.

In certain embodiments thereof, the first vaccine composition comprises an MVA vector encoding a first HIV Env antigen comprising the amino acid sequence of SEQ ID NO: 18, a second HIV Env antigen comprising the amino acid sequence of SEQ ID NO: 5, third and fourth HIV Gag antigens comprising the amino acid sequence of SEQ ID NO: 1 and SEQ ID NO: 2, respectively, and fifth and sixth HIV Pol antigens comprising the amino acid sequence of SEQ ID NO: 3 and SEQ ID NO: 4, respectively. In certain embodiments, the Gag and Pol antigens of SEQ ID NOs: 1 and 3 are combined and present as a Gag-Pol fusion antigen comprising SEQ ID NO: 28, and/or the Gag and Pol antigens of SEQ ID NOs: 2 and 4 are combined and present as a Gag-Pol fusion antigen comprising SEQ ID NO: 29.

In certain embodiments thereof, the second vaccine composition comprises an Ad26 vector encoding an HIV antigen comprising the amino acid sequence of SEQ ID NO: 18, an Ad26 vector encoding an HIV antigen comprising the amino acid sequence of SEQ ID NO: 5, an Ad26 vector encoding an HIV antigen comprising the amino acid sequence of SEQ ID NO: 28, and an Ad26 vector encoding an HIV antigen comprising the amino acid sequence of SEQ ID NO: 29.

In certain embodiments of the invention, a vaccine combination comprises one or more polypeptides comprising an immunogenically effective amount of an isolated HIV antigenic polypeptide. Preferably an isolated HIV antigenic polypeptide comprises residues 30-708 of the amino acid sequence of SEQ ID NO: 7, or residues 30-724 of SEQ ID NO: 36. In certain embodiments, two isolated HIV antigenic polypeptides are administered together in one composition, for instance a first isolated HIV antigenic polypeptide that comprises residues 30-708 of the amino acid sequence of SEQ ID NO: 7, and a second isolated HIV antigenic polypeptide that comprises residues 30-724 of SEQ ID NO: 36. The isolated HIV antigenic polypeptide can be present in a third composition or in the first and/or second compositions. The first or second composition can be administered together with the one or more isolated HIV antigenic polypeptides, preferably gp140, for the priming and/or boosting administrations.

As used herein, the terms "co-delivery", "co-administration" or "administered together with" refers to simultaneous administration of two or more components, such as a viral expression vector and an isolated antigenic polypeptide, or multiple viral expression vectors. "Simultaneous administration" can be administration of the two or more components at least within the same day. When two components are "administered together with," they can be administered in separate compositions sequentially within a short time period, such as 24, 20, 16, 12, 8 or 4 hours, or within 1 hour or less, such as essentially simultaneously, or they can be administered in a single composition at the same time.

Another general aspect of the invention relates to a kit comprising a vaccine combination according to an embodiment of the invention.

Other embodiments of the synthetic HIV envelope protein, expression vectors, additional expression vectors, HIV antigens encoded by the expression vectors, and isolated HIV antigenic polypeptide etc. that can be used in the vaccine combinations of the invention are discussed in detail above and in the illustrative examples below.

Method for Inducing Protective Immunity Against HIV Infection

The invention also relates to a method of inducing an immune response against one or more HIV clades in a subject in need thereof. The methods described herein include methods of priming and boosting an immune response using one or more expression vectors optionally in combination with one or more isolated antigenic polypeptides.

According to embodiments of the invention, "inducing an immune response" when used with reference to the methods and compositions described herein encompasses providing protective immunity and/or vaccinating a subject against an infection, such as a HIV infection, for prophylactic purposes, as well as causing a desired immune response or effect in a subject in need thereof against an infection, such as a HIV infection, for therapeutic purposes, i.e., therapeutic vaccination. "Inducing an immune response" also encompasses providing a therapeutic immunity for treating against a pathogenic agent, i.e., HIV. Typically, for prophylactic vaccination, compositions and vaccines are administered to subjects who have not been previously infected with HIV, whereas for therapeutic vaccination, compositions and vaccines are administered to a subject already infected with HIV. The immune response can be a cellular immune response and/or a humoral immune response.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

As used herein, the term "therapeutic immunity" or "therapeutic immune response" means that the HIV infected vaccinated subject is able to control an infection with the pathogenic agent, i.e., HIV, against which the vaccination was done. Typically, the administration of the primer and booster vaccine compositions according to embodiments of the invention will have a therapeutic aim to generate an immune response against HIV after HIV infection or development of symptoms characteristic of HIV infection. Preferably, the methods of the invention are for therapeutic purposes, such as for therapeutic vaccination, in which the compositions and vaccines described herein are administered to a subject already infected with HIV. Thus, the patient population for treatment according to the methods of the invention described herein is preferably HIV-infected subjects, and more preferably HIV-infected human subjects. The terms "HIV infection" and "HIV-infected" as used herein refer to invasion of a human host by HIV. As used herein, "an HIV-infected subject" refers to a subject in whom HIV has invaded and subsequently replicated and propagated within the host, thus causing the host to be infected with HIV or have an HIV infection or symptoms thereof.

In one general aspect, a method of inducing an immune response against a human immunodeficiency virus (HIV) in a subject comprises administering to the subject a composition comprising an immunogenically effective amount of an expression vector, preferably a poxvirus vector (e.g., MVA or MVA-BN) comprising a nucleic acid sequence encoding a synthetic HIV envelope protein comprising the amino acid sequence of SEQ ID NO: 18, and preferably encoding further HIV antigens as described herein. Any of the compositions described herein can be used in a method of inducing an immune response against HIV in a subject. The composition can further comprise one or more additional vectors, for instance adenovirus, encoding the same or one or more additional HIV antigens and/or one or more additional isolated HIV antigenic polypeptides. It is also possible to encode the one or more additional HIV antigens in the same vector as the vector encoding the HIV envelope protein comprising the amino acid sequence of SEQ ID NO: 18. This is particularly suitable for poxvirus vectors such as MVA, including MVA-BN, as shown herein.

In another general aspect, a method of inducing an immune response against a human immunodeficiency virus (HIV) in a subject comprises administering to the subject:

(a) a first vaccine comprising one or more recombinant adenovirus vectors, preferably Ad26 vectors, encoding one or more of SEQ ID NOs: 1, 2, 3, 4, 5, 18, 28, and 29; and (b) a second vaccine comprising a poxvirus vector, preferably an MVA vector encoding SEQ ID NO: 18 and preferably further encoding one or more HIV antigens comprising the amino acid sequences selected from the group consisting of SEQ ID NOs: 1-5, 28, and 29, wherein steps (a) and (b) are conducted in either order, with one of the steps for priming immunization and the other step for boosting immunization.

In some embodiments, a method of inducing an immune response further comprises administering to the subject one or more isolated HIV antigenic polypeptides, preferably one or more HIV antigenic polypeptides comprising (i) a polypeptide comprising residues 30-708 of the amino acid sequence of SEQ ID NO: 7, or (ii) a polypeptide comprising residues 30-724 of SEQ ID NO: 36, or (iii) both polypeptides (i) and (ii). The one or more isolated HIV antigenic polypeptides can be present in the same composition as the first and/or second composition or in one or more additional compositions. In a preferred embodiment, the one or more isolated HIV antigenic polypeptides is administered at about the same time as the composition used for the boosting immunization. In certain embodiments, the one or more isolated HIV antigenic polypeptides are present in the same composition as the boosting vaccine. In other embodiments, the one or more isolated HIV antigenic polypeptides are present in a composition separate from the boosting vaccine. In certain embodiments, the isolated HIV antigenic polypeptide is in a composition comprising an adjuvant, for instance aluminum phosphate.

In a particular embodiment of a method of inducing an immune response according to the invention, the first composition comprises an adenovirus vector, preferably an adenovirus 26 vector, encoding a synthetic HIV envelope protein comprising the amino acid sequence of SEQ ID NO: 18 and a second adenovirus vector, preferably an adenovirus 26 vector, encoding an HIV antigen comprising the amino acid sequence of SEQ ID NO: 5; the second composition comprises a poxvirus vector, preferably an MVA vector, such as an MVA-BN vector, according to the invention comprising nucleic acid encoding the synthetic HIV antigen comprising the amino acid of SEQ ID NO: 18, and preferably further comprises nucleic acid sequence encoding one or more HIV antigens comprising the amino acid sequences of SEQ ID NOs: 1-5, 28, and 29, more preferably HIV antigens comprising the amino acid sequences of SEQ ID NOs: 5, 28, and 29; wherein the first composition is administered to the subject one or more times for priming immunization, and the second composition is administered to the subject one or more times for boosting immunization, or wherein the first composition is administered to the subject one or more times for boosting immunization and the second composition is administered to the subject one or more times for priming immunization. In preferred embodiments, the first composition further comprises a third adenovirus vector, preferably an Ad26 vector, encoding an HIV antigenic polypeptide comprising the amino acid sequence of SEQ ID NO: 28, and a fourth adenovirus vector, preferably an Ad26 vector, encoding an HIV antigenic polypeptide comprising the amino acid sequence of SEQ ID NO: 29.

In another particular embodiment of a method of inducing an immune response, the first composition comprises a first adenovirus vector, preferably an adenovirus 26 vector, encoding a synthetic HIV envelope protein comprising the amino acid sequence of SEQ ID NO: 18 and a second adenovirus vector, preferably an adenovirus 26 vector, encoding a HIV antigenic polypeptide comprising the amino acid sequence of SEQ ID NO: 5; the second composition comprises a poxvirus vector, preferably a MVA vector, more preferably MVA-BN, comprising nucleic acid sequence encoding HIV antigens comprising the amino acid sequences of SEQ ID NOs: 1-5 and 18, more preferably SEQ ID NOs: 5, 18, 28, and 29, and combinations thereof; wherein the first composition is administered to the subject, one or more times for priming immunization, and the second composition is administered to the subject one or more times for boosting immunization, optionally together with one or more isolated HIV antigenic polypeptides; or wherein the second composition is administered to the subject, one or more times for priming immunization, and the first composition is administered to the subject one or more times for boosting immunization, optionally together with one or more isolated HIV antigenic polypeptides. In preferred embodiments, the first composition further comprises a third adenovirus vector, preferably an Ad26 vector, encoding a HIV antigenic polypeptide comprising the amino acid sequence of SEQ ID NO: 28, and a fourth adenovirus vector, preferably an Ad26 vector, encoding a HIV antigenic polypeptide comprising the amino acid sequence of SEQ ID NO: 29.

Administration of the immunogenic compositions comprising the expression vectors and/or antigenic polypeptides is typically intramuscular, intradermal or subcutaneous. However, other modes of administration such as intravenous, rectal, cutaneous, oral, nasal, etc. can be envisaged as well. Intramuscular administration of the immunogenic compositions can be achieved by using a needle to inject a suspension of the expression vectors, e.g. adenovirus vectors, and/or antigenic polypeptides. An alternative is the use of a needleless injection device to administer the composition (using, e.g., Biojector™) or a freeze-dried powder containing the vaccine.

For intramuscular, intravenous, cutaneous or subcutaneous injection, or injection at the site of affliction, the vector will be in the form of a parenterally acceptable aqueous solution which is pyrogen-free and has suitable pH, isotonicity and stability. Likewise, the isolated antigenic polypeptide will be in the form of a parenterally acceptable solution having a suitable pH, isotonicity, and stability. Those of ordinary skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation can also be employed.

Typically, administration of the vaccine compositions according to embodiments of the invention will have a therapeutic aim to generate an immune response against an HIV antigen after infection or development of symptoms. In other embodiments, the expression vectors, e.g., adenovirus vectors and/or poxvirus vectors, and/or HIV antigenic polypeptides can be administered for prophylactic purposes before infection or development of symptoms.

The immunogenic compositions containing the expression vectors, e.g., adenovirus vectors and/or poxvirus vectors, and/or antigenic polypeptides are administered to a subject, giving rise to an anti-HIV immune response in the subject. An amount of a composition sufficient to induce a detectable immune response is defined to be an "immunogenically effective dose" or "immunogenically effective amount." In a typical embodiment of the invention, the immune response is a therapeutic immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences*, 16th edition, Osol, A. ed., 1980.

Following production of adenovirus vectors and/or poxvirus vectors such as MVA vectors and optional formulation of such particles into compositions, the vectors can be administered to an individual, particularly a human or other primate. Delivery to a non-human mammal need not be for a therapeutic purpose, but can be for use in an experimental context, for instance in investigation of mechanisms of immune responses to the synthetic HIV envelope protein and other HIV antigens expressed by the adenovirus vectors and/or poxvirus vectors of the invention.

In one embodiment of the disclosed methods, one or more adenovirus vectors encoding one or more HIV antigens disclosed herein are used to prime the immune response. One or more isolated HIV antigenic polypeptides can be used together with the one or more adenovirus vectors for the priming immunization. In another embodiment, one or more poxviral vectors, preferably MVA or MVA-BN, the poxviral vectors encoding one or more HIV antigens of the present invention are used to prime the immune response. One or more isolated HIV antigenic polypeptides can be used together with the one or more poxviral vectors for the priming immunization. The priming immunization can be administered only once, but can optionally also be administered multiple times, for example, initial priming administration at time 0, followed by another priming administration about 1-24 weeks after the initial priming administration. One or more isolated HIV antigenic polypeptides optionally together with one or more additional adenovirus or poxvirus vectors encoding one or more additional HIV antigens can be used to boost the immune response.

Following the priming administration, one or more of the adenoviral vectors of the present invention or the poxviral vectors of the present invention can be used in one or more boosting immunizations. A boosting immunization can also be administered once or multiple times, for example, first at about 4-52 weeks after the initial priming administration, optionally followed by another boosting administration at for instance about 8-100 weeks after the initial priming administration. In certain other embodiments, one or more adenovirus vectors of the present invention are administered together with one or more poxviral vectors of the present invention for the priming and/or boosting immunization. The immune response induced by the immunization is monitored.

Prime-boost regimens are generally preferred for generation of strong immune responses. It is possible to administer the same vector multiple times, referred to as homologous prime-boost. It is typically preferred according to the invention to apply a heterologous prime-boost regimen, which in this context indicates that the priming and boosting vectors are different. In certain such heterologous prime-boost regimen embodiments for instance, the priming is with adenoviral vector, e.g. Ad26, and boosting is with poxviral vector, e.g. MVA, for instance MVA-BN. In other such heterologous prime-boost regimen embodiments for instance, the priming is with poxviral vector, e.g. MVA, such as MVA-BN, and boosting is with adenoviral vector, e.g. Ad26. Optionally in prime-boost regimens, isolated HIV antigenic polypeptide such as gp140 can be administered at about the same time as the priming or boosting administration of such adenoviral or poxviral vector.

In one exemplary and non-limiting embodiment, a subject is administered four different adenovirus 26 vectors, together encoding HIV antigens comprising SEQ ID NOs: 5, 18, 28 and 29, wherein the vectors are present in a 1:1:1:1 ratio and are administered at a total dose of $5 \times 10^{10}$ viral particles in 0.5 mL by intramuscular injection at weeks 0 and 12, followed by administration of an MVA vector encoding HIV antigens comprising SEQ ID NOs: 5, 18, 28 and 29, at a dose of about $10^8$ plaque forming units per 0.5 mL injection administered intramuscularly at weeks 24 and 48.

It is readily appreciated by those skilled in the art that the regimen for the priming and boosting administrations can be adjusted based on the measured immune responses after the administrations. For example, the boosting compositions are generally administered weeks or months or even years after administration of the priming composition.

According to embodiments of the invention, an adjuvant can be administered together with the isolated HIV antigenic polypeptide as part of the priming and/or boosting immunization. Any adjuvant can be used together with the isolated HIV antigenic polypeptide in view of the present disclosure, and in certain embodiments the adjuvant is an aluminum salt, such as aluminum phosphate.

In a preferred embodiment of the invention, the adenovirus vectors used in the methods disclosed herein include a rAd26 vector and the poxvirus vectors used in the methods disclosed herein include an MVA vector.

In one exemplary embodiment, an rAd26 vector encoding a synthetic HIV envelope protein comprising the amino acid sequence of SEQ ID NO: 18 is used to prime the immune response in combination with an rAd26 vector encoding an HIV antigen having the amino acid sequence of SEQ ID NO: 5. One or more additional rAd26 vectors encoding one or more additional HIV antigens having the amino acid sequences selected from the group consisting SEQ ID NOs: 1-4, 28 and 29 can also be administered together with the other rAd26 vectors to prime the immune response. In certain embodiments, the priming administration can be re-administered before any boosting immunization is administered. An MVA vector encoding a synthetic HIV envelope protein comprising the amino acid sequence of SEQ ID NO: 18 and further encoding SEQ ID NOs: 5, 28, and 29 is used to boost the immune response in these embodiments. Optionally, an isolated HIV antigenic polypeptide, such as that comprising residues 30-708 of the amino acid sequence of SEQ ID NO: 7, or that comprising residues 30-724 of the amino acid sequence of SEQ ID NO: 36, or a combination of at least two of such isolated HIV antigenic polypeptides, is administered together with the MVA vector to boost the immune response. Preferably, an adjuvant is further administered with the isolated HIV antigenic polypeptide in the boosting immunization.

In another exemplary embodiment, an MVA or MVA-BN vector encoding a synthetic HIV envelope protein comprising the amino acid sequence of SEQ ID NO: 18 and further encoding SEQ ID NOs: 5, 28, and 29 is used to prime the immune response. In certain embodiments, the priming administration is re-administered before any boosting immunization is administered. Subsequent to the priming administration one or more boosting immunization(s) is/are administered, the boosting immunization comprises an rAd26 vector encoding a synthetic HIV envelope protein comprising the amino acid sequence of SEQ ID NO: 18 in combination with an rAd26 vector encoding an HIV antigen having the amino acid sequence of SEQ ID NO: 5. One or more additional rAd26 vectors encoding one or more additional HIV antigenic polypeptides having the amino acid sequences selected from the group consisting SEQ ID NOs: 1-4, 28 and 29 preferably are also administered together with the other rAd26 vectors to boost the immune response. Optionally, an isolated HIV antigenic polypeptide, such as that comprising residues 30-708 of the amino acid sequence of SEQ ID NO: 7, or that comprising residues 30-724 of the amino acid sequence of SEQ ID NO: 36, or a combination of at least two of such isolated HIV antigenic polypeptides, is administered together with the rAd26 vectors to boost the immune response.

In a particularly exemplary embodiment, an immune response is primed by administration of four HIV antigens encoded on adenoviral vectors, preferably rAd26 vectors, the four antigens that are encoded being: (i) a synthetic HIV envelope protein comprising the amino acid sequence of SEQ ID NO: 18, (ii) HIV Env antigen having the amino acid sequence of SEQ ID NO: 5, (iii) HIV Gag-Pol fusion antigen having the amino acid sequence of SEQ ID NO: 28, and (iv) HIV Gag-Pol fusion antigen having the amino acid sequence of SEQ ID NO: 29. Each of these four antigens can be encoded on a separate adenoviral vector, preferably a rAd26 vector, administered at a total dose of about 1, 2, 3, 4, 5, 6, 7, 8, 9, or $10 \times 10^{10}$ viral particles (vp), e.g. about $5 \times 10^{10}$ vp (for all vectors together). The vectors can be pre-mixed, e.g. in a 1:1:1:1 ratio. The administration of adenovirus vectors is preferably via intramuscular injection. The priming administration can be re-administered after the initial priming administration. In this embodiment, an immune response is boosted by administration of an MVA or MVA-BN vector encoding four HIV antigens comprising SEQ ID NO: 18, SEQ ID NO: 5, SEQ ID NO: 28, and SEQ ID NO: 29 at a dosage of $10^5$ to $10^{11}$ pfu, e.g. a dose of $10^7$ pfu, $10^8$ pfu, or $10^9$ pfu, or at a dosage of $10^5$ to $10^{10}$ $TCID_{50}$, e.g $10^7$, $10^8$ or $10^9$ $TCID_{50}$. Preferably, the dosage is $2 \times 10^5$ to $5 \times 10^8$ pfu. Preferably, the dose for humans comprises at least $5 \times 10^7$ pfu, e.g., at least $1 \times 10^8$ pfu, or alternatively at least $2 \times 10^7$ $TCID_{50}$, at least $3 \times 10^7$ $TCID_{50}$, at least $5 \times 10^7$ $TCID_{50}$, e.g. at least $1 \times 10^8$ $TCID_{50}$, or at least $2 \times 10^8$ $TCID_{50}$. The MVA or MVA-BN administration to boost the immune response can be performed any time after the initial priming administration. The boosting administration can be repeated after the initial boosting administration. All administrations of MVA according to this embodiment can be performed, for instance, via the intramuscular or subcutaneous route.

Alternatively, the MVA vector can be used for priming administration and the Ad26 vectors for boosting administration, all essentially as indicated above except in reversed order of administering the adenoviral and poxviral vector types. Optionally, isolated gp140 protein can be administered together with boosting administration. For example, isolated Env gp140 protein, e.g. clade C gp140 protein (comprising residues 30-708 of the amino acid sequence of SEQ ID NO: 7), or mosaic gp140 protein (comprising residues 30-724 of the amino acid sequence of SEQ ID NO: 36), or clade C gp140 protein and mosaic gp140 protein, at a total dose of about 50-300 μg protein, e.g. 50 or 250 microgram of clade C gp140 protein, or e.g. 50 or 250 microgram of mosaic gp140 protein, or e.g. 50 or 250 microgram of a combination of clade C gp140 protein and mosaic gp140 protein (e.g. in a 1:1 ratio, either mixed together or separately administered) can be administered together with the poxvirus vector for the boosting immunization. Preferably, the gp140 protein is administered together with an adjuvant, e.g. aluminum phosphate.

In certain embodiments, a method of inducing an immune response according to the invention further comprises administering a latent viral reservoir purging agent. Cells latently infected with HIV carry integrated virus that is transcriptionally silent, making it difficult to effectively eradicate HIV infection in treated subjects. As used herein, "reservoir purging agent" and "latent viral reservoir purging agent" refer to a substance that reduces the latent pool of HIV by reactivating HIV reservoirs, such as by inducing expression of quiescent HIV. Examples of latent viral reservoir purging agents suitable for use with the invention include, but are not limited to, histone deacetylase (HDAC) inhibitors and modulators of toll-like receptors (e.g., TLR7), such as those described in WO2016/007765 and WO2016/177833, which are herein incorporated by reference in their entireties. The latent viral reservoir purging agent can be administered before, after, or co-administered with one or more of the priming and boosting immunizations described herein. The vaccination of a combination of adenovirus 26 vectors encoding Gag, Pol and Env antigens as a prime, followed by MVA vectors encoding such antigens as a boost, in combination with TLR7 stimulation has shown to result in improved virologic control and delayed viral rebound following discontinuation of antiretroviral therapy in rhesus monkey model studies, demonstrating the potential of therapeutic vaccination combined with innate immune stimulation to aim at functional cure for HIV infection (Borducchi E. N., et al, 2016, Nature 540: 284-287 (doi: 10/1038/nature20583)).

In certain embodiments of the invention, the priming and boosting immunizations described herein for inducing an immune response can be combined with standard treatment, e.g., antiretroviral therapy (ART). Subjects treated according to the priming/boosting immunizations of the invention can also undergo ART with any antiretroviral drugs known in the art in view of the present disclosure. ART are medications that treat HIV, although the drugs do not kill or cure the virus. However, when taken in combination they can prevent the growth of the virus. When the virus is slowed down, so is HIV disease. Antiretroviral drugs are referred to as ARV. Combination ARV therapy (cART) is referred to as highly active ART (HAART). One of ordinary skill in the art will be able to determine the appropriate antiretroviral treatment, frequency of administration, dosage of the ART, etc. so as to be compatible with administration of the priming/boosting immunizations of the invention.

Examples of antiretroviral drugs used for ART include, but are not limited to nucleoside reverse transcriptase inhibitors (NRTIs, non-limiting examples of which include zidovudine, didanosine, stavudine, lamivudine, abacavir, tenofovir, combivir [combination of zidovudine and lamivudine], trizivir [combination of zidovudine, lamivudine and abacavir], emtricitabine, truvada [combination of emtricitabine and tenofovir], and epzicom [combination of abacavir and lamivudine]), non-nucleoside reverse transcriptase inhibitors (NNRTIs, non-limiting examples of which include nevirapine, delavirdine, efavirenz, etravirine, and rilpivirine), protease inhibitors (PIs, non-limiting examples of which include saquinavir, indinavir, ritonavir, nelfinavir, amprenavir, lopinavir/ritonavir, atazanavir, fosamprenavir, tipranavir, darunavir), integrase inhibitors (INSTIs, non-limiting examples including raltegravir, elvitegravir, and dolutegravir), and fusion inhibitors, entry inhibitors and/or chemokine receptor antagonists (FIs, CCR5 antagonists; non-limiting examples including enfuvirtide, aplaviroc, maraviroc, vicriviroc, and cnicriviroc).

In other embodiments, subjects undergo interruption (also referred to as discontinuation, used interchangeably herein) of ART after completion of a priming/boosting immunization according to embodiments of the invention. In some embodiments, subjects can undergo antiretroviral analytical treatment interruption (ARV ATI) after completion of a priming boosting immunization according to embodiments of the invention. "Antiretroviral analytical treatment interruption" and "ARV ATI" as used in the invention refer to discontinuation of treatment with antiretroviral drugs in order to assess viral suppression and viremic control in the absence of continued ART. Typically, subjects can undergo ARV ATI, i.e., ART can be discontinued, when the subject has plasma HIV RNA levels at less than 50 copies/mL for at least about 52 weeks, but a subject can still undergo ARV ATI even if the subject has one or more blips (i.e., instances) of plasma HIV RNA greater than 50 copies/ml to less than 200 copies/ml within this period, provided that the screening immediately prior to ARV ATI shows less than 50 copies/ml of plasma HIV RNA.

According to embodiments of the invention, the ART can be stopped at about 4-20 weeks after the last booster vaccine is administered. In certain embodiments, for subjects who are on non-nucleoside reverse transcriptase inhibitor (NNRTI)-based ART, a boosted protease inhibitor can be administered in place of the NNRTI for about 1-2 weeks prior to stopping ART to reduce the risk of developing NNRTI resistance. It is also possible to administer an activator (e.g. a histone deacetylase inhibitor or TLR7 modulator) during the ATI stage to activate any (e.g. latent) HIV reservoir and thereby improve the immune response.

Subjects undergoing ARV ATI can be monitored, e.g., by measuring plasma HIV RNA levels. For example, monitoring after the initiation of ARV ATI can occur up to two times per week during the first six weeks when rebound viremia is most likely to occur. "Rebound viremia" is defined as plasma HIV RNA levels of greater than 1,000 copies/ml after ARV ATI. ART can be re-initiated in subjects with rebound viremia. Preferably, a subject treated according to the methods of the invention will maintain viremic control after ART interruption. As used herein, "maintain viremic control" is defined as at least 24 weeks with plasma HIV RNA of less than 50 copies/mL after ARV ATI. The "maintained viremic control" criterion is still deemed to be met if there are one or more instances of plasma HIV RNA greater than 50 copies/ml to less than 1000 copies/ml, as long as the subject does not have plasma HIV RNA levels above 1000 copies/ml on two consecutive determinations at least one week apart.

Typically (not using the methods of the instant invention) human HIV-infected subjects have a return of viremia after 2-3 weeks following ART interruption. Without wishing to be bound by any theories, it is believed that the priming/boosting immunization according to embodiments of the invention among individuals with fully suppressed HIV will result in a measurable immune response and maintain viremic control after ARV ATI in at least certain individuals. In some embodiments, subjects can discontinue ART after being treated according to a method of the invention. Discontinuation of ART can be for long periods of time (e.g., at least 24 weeks, preferably longer, e.g. at least about 28, 32, 36, 40, 44, 48, 52 weeks, 16 months, 18, 20, 22, 24 months, or even longer). Such periods of time in which ART is stopped or discontinued are referred to as a "holiday" or "ART holiday" or "treatment holiday". In other embodiments, vaccine therapy according to the methods of the invention can provide HIV remission, meaning that viral suppression is maintained in the absence of ART.

EMBODIMENTS

Embodiment 1 is a poxvirus vector comprising nucleic acid encoding a synthetic HIV envelope protein comprising the amino acid sequence of SEQ ID NO: 18.

Embodiment 2 is a poxvirus vector comprising nucleic acid encoding:
(a) a first HIV envelope (Env) antigen comprising the amino acid sequence of SEQ ID NO: 18;
(b) a second HIV Env antigen different from the first HIV Env antigen;
(c) a third antigen and a fourth antigen, being two different HIV Gag antigens; and
(d) a fifth antigen and a sixth antigen, being two different HIV Pol antigens.

Embodiment 3 is the poxvirus vector of embodiment 2, wherein the second HIV Env antigen comprises the amino acid sequence of SEQ ID NO: 5, the third and fourth antigens comprise the amino acid sequence of SEQ ID NO: 1 and SEQ ID NO: 2, respectively; and the fifth and the sixth antigens comprise the amino acid sequence of SEQ ID NO: 3 and SEQ ID NO: 4, respectively.

Embodiment 4 is the poxvirus vector of embodiments 2 or 3, wherein the third and the fifth antigens are fused into a first Gag-Pol fusion antigen that comprises the amino acid sequence of SEQ ID NO: 28, and the fourth and the sixth antigens are fused into a second Gag-Pol fusion antigen that comprises the amino acid sequence of SEQ ID NO: 29.

Embodiment 5 is the poxvirus vector of any one of embodiments 1-4, wherein the first HIV Env antigen is encoded by SEQ ID NO: 41.

Embodiment 6 is the poxvirus vector of any one of embodiments 4-5, wherein the first HIV Env antigen is encoded by SEQ ID NO: 41; the second HIV Env antigen is encoded by SEQ ID NO: 39; the first Gag-Pol fusion antigen is encoded by SEQ ID NO: 38; and the second Gag-Pol fusion antigen is encoded by SEQ ID NO: 40.

Embodiment 7 is the poxvirus vector of any one of embodiments 1-6, wherein the nucleic acid encoding the antigen(s) is operably linked to a promoter sequence.

Embodiment 8 is the poxvirus vector of any one of embodiments 1-7, wherein the poxvirus vector is a recombinant Modified Vaccinia virus Ankara (MVA) vector.

Embodiment 9 is the poxvirus vector of embodiment 8, wherein the MVA vector comprises MVA-BN or derivatives thereof.

Embodiment 10 is the poxvirus vector of embodiment 8 or 9, wherein the first Gag-Pol fusion antigen and the second Env antigen are inserted into intergenic region (IGR) 44/45 of the MVA genome, and the second Gag-Pol fusion antigen and the first Env antigen are inserted into IGR 88/89 of the MVA genome.

Embodiment 11 is the poxvirus vector of any one of embodiments 7-10, wherein the first Gag-Pol fusion antigen and the second Gag-Pol fusion antigens are each under control of a separate Pr13.5 promoter, and the first Env and the second Env antigens are each under control of a separate PrHyb promoter.

Embodiment 12 is an isolated cell comprising the poxvirus vector of any one of embodiments 1-11.

Embodiment 13 is a composition comprising a vector of any one of embodiments 1-11, and a carrier.

Embodiment 14 is a vaccine comprising an immunogenically effective amount of a poxvirus vector according to any one of embodiments 1-11, and a pharmaceutically acceptable carrier.

Embodiment 15 is a vaccine combination, comprising:
(a) a first vaccine composition comprising an immunogenically effective amount of a poxvirus vector, preferably a MVA vector, according to any one of embodiments 1-11; and at least one of
(b) (i) a second vaccine composition comprising an immunogenically effective amount of one or more adenovirus vectors, preferably adenovirus 26 vectors, encoding one or more HIV antigens, the one or more HIV antigens preferably comprising an amino acid sequence selected from the group consisting of SEQ ID NOs: 1-5, 18, 28, and 29; and
(b) (ii) a third vaccine composition comprising one or more polypeptides comprising an immunogenically effective amount of an isolated HIV antigenic polypeptide optionally further comprising an adjuvant, preferably aluminum phosphate, wherein the first composition, and second and/or third composition are present in the same composition or in one or more different compositions.

Embodiment 16 is the vaccine combination according to embodiment 15, wherein the one or more isolated HIV antigenic polypeptides in the third vaccine composition comprises (i) a polypeptide comprising residues 30-708 of the amino acid sequence of SEQ ID NO: 7, or (ii) a polypeptide comprising residues 30-724 of the amino acid sequence of SEQ ID NO: 36, or (iii) both polypeptides (i) and (ii).

Embodiment 17 is the vaccine combination of any one of embodiments 15-16, wherein the second vaccine composition comprises recombinant adenovirus 26 vectors together encoding SEQ ID NOs: 1-5 and 18, preferably wherein SEQ ID NOs: 1 and 3 are fused together as SEQ ID NO: 28 and/or SEQ ID NOs: 2 and 4 are fused together as SEQ ID NO: 29.

Embodiment 18 is the vaccine combination of embodiment 17, wherein the second vaccine composition comprise four recombinant Ad26 vectors, the first recombinant Ad26 vector encoding SEQ ID NO: 5; the second recombinant Ad26 vector encoding SEQ ID NO: 18; the third recombinant Ad26 vector encoding SEQ ID NOs: 1 and 3, preferably SEQ ID NO: 28; and the fourth recombinant Ad26 vector encoding SEQ ID NOs: 2 and 4, preferably SEQ ID NO: 29.

Embodiment 19 is a method of inducing an immune response against a human immunodeficiency virus (HIV) in a subject in need thereof, the method comprising administering to the subject the composition of embodiment 13, the vaccine of embodiment 14, or the vaccine combination of any one of embodiments 15-18.

Embodiment 20 is a composition of embodiment 13, a vaccine of embodiment 14, or a vaccine combination of any one of embodiments 15-18 for use in inducing an immune response against a human immunodeficiency virus (HIV).

Embodiment 21 is a composition of embodiment 13 or a vaccine of embodiment 14, further comprising one or more additional expression vectors encoding one or more additional HIV antigens, and/or one or more isolated HIV antigenic polypeptides.

Embodiment 22 is a composition of embodiment 13 or a vaccine of embodiment 14, further comprising an adenovirus vector, preferably an adenovirus 26 vector, encoding a synthetic HIV envelope protein comprising or consisting of the amino acid sequence of SEQ ID NO: 18.

Embodiment 23 is a composition or vaccine according to embodiment 22, further comprising a second adenovirus vector, preferably an adenovirus 26 vector, encoding an HIV antigen comprising the amino acid sequence of SEQ ID NO: 5, and optionally one or more additional adenovirus vectors, preferably adenovirus 26 vectors, encoding one or more additional HIV antigens comprising the amino acid sequences of SEQ ID NOs: 1-4, 28 and 29, preferably SEQ ID NOs: 28 and 29, more preferably wherein SEQ ID NOs: 28 and 29 are encoded separately on a third and fourth adenovirus vector, preferably adenovirus 26 vectors.

Embodiment 24 is a method of producing an immune response against a human immunodeficiency virus (HIV) in a subject in need thereof, the method comprising administering to the subject a composition or vaccine or vaccine combination according to any one of embodiments 13-23.

Embodiment 25 is a method of producing a composition or a vaccine combination, comprising combining the poxvirus vector of any one of embodiments 1-11 with a carrier, and optionally one or more additional vectors encoding one or more additional HIV antigens and/or one or more isolated HIV antigenic polypeptides in one or more compositions, together with a carrier. 10208f Embodiment 26 is a method of inducing an immune response against a human immunodeficiency virus (HIV) in a subject in need thereof, the method comprising administering to the subject:
(i) a first vaccine comprising an immunogenically effective amount of one or more recombinant adenovirus vectors, preferably Ad26 vectors, encoding one or more HIV antigens comprising an amino acid sequence of any one or more of SEQ ID NOs: 1-5, 18, 28, and 29, and a carrier;
(ii) a second vaccine comprising a poxvirus vector according to any one of embodiments 1-11, and a carrier; and
(iii) optionally, a third vaccine comprising one or more polypeptides comprising an immunogenically effective amount of an isolated HIV antigenic polypeptides, and a carrier and optionally further comprising an adjuvant, preferably aluminum phosphate,
wherein steps (i) and (ii) are conducted in either order, with one of the steps for priming immunization and the other step for boosting immunization, and wherein the optional third vaccine is administered together with the first composition or the second composition for the priming and/or boosting immunization.

Embodiment 27 is a method according to embodiment 26, wherein the third composition is administered at about the same time as the composition used for the boosting vaccine.

Embodiment 28 is a method according to embodiment 26 or 27, wherein the one or more isolated HIV antigenic polypeptides comprise (i) a polypeptide comprising residues 30-708 of the amino acid sequence of SEQ ID NO: 7; or (ii) a polypeptide comprising residues 30-724 of SEQ ID NO: 36; or (iii) both polypeptides (i) and (ii), and wherein the one or more isolated HIV antigenic polypeptides are in the same composition as the boosting vaccine and/or priming vaccine or in a composition separate from the boosting vaccine and/or priming vaccine.

Embodiment 29 is a method according to any one of embodiments 26-28, wherein (i) the first vaccine comprises an adenovirus vector, preferably an adenovirus 26 vector, encoding a synthetic HIV envelope protein comprising the amino acid sequence of SEQ ID NO: 18 and a second adenovirus vector, preferably an adenovirus 26 vector, encoding a HIV antigen comprising the amino acid sequence of SEQ ID NO: 5, and optionally one or more additional expression vectors, preferably adenovirus vectors, more preferably adenovirus 26 vectors, encoding one or more additional HIV antigens; (ii) the second vaccine comprises a poxvirus vector, preferably an MVA vector, encoding a synthetic HIV envelope protein comprising the amino acid sequence of SEQ ID NO: 18 and preferably encoding further HIV antigens comprising one or more of the amino acid sequences of SEQ ID NOs: 1-5, 28 and 29; and (iii) the third vaccine comprises an isolated HIV antigenic polypeptide having residues 30-708 of the amino acid sequence of SEQ ID NO: 7, or residues 30-724 of SEQ ID NO: 36; wherein the first vaccine is administered to the subject one or more times for priming immunization, the second vaccine is administered to the subject one or more times for boosting immunization, and the third vaccine is administered to the subject together with the second vaccine one or more times for the boosting immunization.

Embodiment 30 is a method according to embodiment 29, wherein the first vaccine comprises one or more additional adenovirus 26 vectors encoding one or more HIV antigens comprising the amino acid sequences of SEQ ID NOs: 1-4, 28, and 29, preferably SEQ ID NOs: 28 and 29.

Embodiment 31 is a method according to embodiment 30, wherein the first vaccine comprises a third adenovirus vector encoding SEQ ID NO: 28 and a fourth adenovirus vector encoding SEQ ID NO: 29.

Embodiment 32 is a vaccine combination comprising the following components:
(i) an Ad26 vector encoding a synthetic HIV envelope protein comprising the amino acid sequence of SEQ ID NO: 18;
(ii) an Ad26 vector encoding an HIV envelope protein comprising the amino acid sequence of SEQ ID NO: 5;
(iii) an Ad26 vector encoding an HIV Gag-Pol fusion protein comprising the amino acid sequence of SEQ ID NO: 28;
(iv) an Ad26 vector encoding an HIV Gag-Pol fusion protein comprising the amino acid sequence of SEQ ID NO: 29, and
(v) an MVA vector encoding a first HIV envelope protein comprising the amino acid sequence of SEQ ID NO: 18, a second HIV envelope protein comprising the amino acid sequence of SEQ ID NO: 5, a first Gag-Pol fusion protein comprising the amino acid sequence of SEQ ID NO: 28 and a second Gag-Pol fusion protein comprising the amino acid sequence of SEQ ID NO: 29.

Embodiment 33 is a vaccine combination according to embodiment 32, further comprising the following component:
(vi) (vi, a): isolated HIV antigenic polypeptide having residues 30-708 of the amino acid sequence of SEQ ID NO: 7, or (vi, b): residues 30-724 of the amino acid sequence of SEQ ID NO: 36, or (vi, c): both (vi, a) and (vi, b), wherein (vi, a), (vi, b), or (vi, c) optionally further comprise an adjuvant.

Embodiment 34 is a method of inducing an immune response against a human immunodeficiency virus (HIV) in a human subject in need thereof, the method comprising: (a) administering to the subject: (i) a rAd26 vector encoding a synthetic HIV envelope protein comprising the amino acid sequence of SEQ ID NO: 18; (ii) a rAd26 vector encoding an antigen comprising the amino acid sequence of SEQ ID NO: 5; (iii) a rAd26 vector encoding an antigen comprising the amino acid sequence of SEQ ID NO: 28; and (iv) a rAd26 vector encoding an antigen comprising the amino acid sequence of SEQ ID NO: 29; preferably wherein the rAd26 vectors are administered in a ratio of about 1:1:1:1 at a total dose of about $1-10 \times 10^{10}$ viral particles (vp), e.g. $5 \times 10^{10}$ vp;
(b) optionally repeating step (a);
(c) administering to the subject: (i) an MVA or MVA-BN vector comprising nucleic acid encoding (i,a) a synthetic HIV envelope protein comprising the amino acid sequence of SEQ ID NO: 18; (i,b) a HIV Env antigen comprising the amino acid sequence of SEQ ID NO: 5; (i,c) a HIV Gag-Pol fusion antigen comprising the amino acid sequence of SEQ ID NO: 28; (i,d) a HIV Gag-Pol fusion antigen comprising the amino acid sequence of SEQ ID NO: 29; preferably wherein the MVA is administered at a dose of $10^5$ to $10^{11}$ pfu, e.g., at a dose of $10^7$ pfu, $10^8$ pfu, $10^9$ pfu, or $10^{10}$ pfu, or at a dose of $10^6$ to $10^{10}$ TCID$_{50}$, e.g. between $10^7$ and $10^9$ TCID$_{50}$; and
(d) optionally repeating step (c).

Embodiment 35 is a method of inducing an immune response against a human immunodeficiency virus (HIV) in a human subject in need thereof, the method comprising: (a) administering to the subject: (i) an MVA or MVA-BN vector comprising nucleic acid encoding (i,a) a synthetic HIV envelope protein comprising the amino acid sequence of SEQ ID NO: 18; (i,b) a HIV Env antigen comprising the amino acid sequence of SEQ ID NO: 5; (i,c) a HIV Gag-Pol fusion antigen comprising the amino acid sequence of SEQ ID NO: 28; (i,d) a HIV Gag-Pol fusion antigen comprising the amino acid sequence of SEQ ID NO: 29; preferably wherein the MVA is administered at a dose of $10^5$ to $10^{11}$ pfu, e.g., at a dose of $10^7$ pfu, $10^8$ pfu, $10^9$ pfu, or $10^{10}$ pfu, or at a dose of $10^6$ to $10^{10}$ TCID$_{50}$, e.g. between $10^7$ and $10^9$ TCID$_{50}$;
(b) optionally repeating step (a);
(c) administering to the subject: (i) an MVA or MVA-BN vector comprising nucleic acid encoding (i,a) a synthetic HIV envelope protein comprising the amino acid sequence of SEQ ID NO: 18; (i,b) a HIV Env antigen comprising the amino acid sequence of SEQ ID NO: 5; (i,c) a HIV Gag-Pol fusion antigen comprising the amino acid sequence of SEQ ID NO: 28; (i,d) a HIV Gag-Pol fusion antigen comprising the amino acid sequence of SEQ ID NO: 29; preferably wherein the MVA is administered at a dose of $10^5$ to $10^{11}$ pfu, e.g., at a dose of $10^7$ pfu, $10^8$ pfu, $10^9$ pfu, or $10^{10}$ pfu, or at a dose of $10^6$ to $10^{10}$ TCID$_{50}$, e.g. between $10^7$ and $10^9$ TCID$_{50}$; and optionally one or more of (ii, a) isolated HIV gp140 protein having the sequence of amino acids 30-708 of SEQ ID NO: 7; (ii, b) isolated HIV gp140 protein having the sequence of amino acids 30-724 of SEQ ID NO: 36; and (iii) aluminum phosphate adjuvant; wherein optionally the isolated HIV gp140 proteins are administered in a ratio of about 1:1 at a total dose of about 50-300 microgram, e.g. 250 microgram; and
(d) optionally repeating step (c).

Embodiment 36 is a method of inducing an immune response against HIV in a human subject in need thereof, the method comprising:
(a) administering to the subject a MVA or MVA-BN vector encoding a synthetic HIV envelope protein comprising the amino acid sequence of SEQ ID NO: 18, SEQ ID NO: 5, SEQ ID NO: 28, and SEQ ID NO: 29, wherein the MVA or MVA-BN vector is administered at a dose of $10^5$ to $10^{11}$ pfu, e.g. at a dose of $10^7$ pfu, $10^8$ pfu, $10^9$ pfu, or $10^{10}$ pfu, e.g. at a dose of $2 \times 10^7$ to $5 \times 10^8$ pfu, e.g. at a dose of about $1 \times 10^8$ pfu, or at a dose of $10^6$ to $10^{10}$ TCID$_{50}$, e.g. between $10^7$ and $10^9$ TCID$_{50}$;

(b) optionally repeating step (a);
(c) administering to the subject: (i) a rAd26 vector encoding a synthetic HIV envelope protein comprising the amino acid sequence of SEQ ID NO: 18; (ii) a rAd26 vector encoding an antigen comprising the amino acid sequence of SEQ ID NO: 5; (iii) a rAd26 vector encoding an antigen comprising the amino acid sequence of SEQ ID NO: 28; (iv) a rAd26 vector encoding an antigen comprising the amino acid sequence of SEQ ID NO: 29; and optionally one or more of: (v, a) isolated HIV gp140 protein having the sequence of amino acids 30-708 of SEQ ID NO: 7; (v, b) isolated HIV gp140 protein having the sequence of amino acids 30-724 of SEQ ID NO: 36; (v, c) both (v, a) and (v, b); and (v, d) aluminum phosphate adjuvant; preferably wherein the rAd26 vectors are administered in a ratio of about 1:1:1:1 at a total dose of about $1-10 \times 10^{10}$ viral particles (vp), e.g. $5 \times 10^{10}$ vp and wherein optionally the isolated HIV gp140 proteins are administered in a ratio of about 1:1 at a total dose of about 50-300 microgram, e.g. 250 microgram; and (d) optionally repeating step (c).

Embodiment 37 is a method of inducing an immune response against HIV in a human subject in need thereof, the method comprising:
(a) administering to the subject: (i) a rAd26 vector encoding a synthetic HIV envelope protein comprising the amino acid sequence of SEQ ID NO: 18; (ii) a rAd26 vector encoding an antigen comprising the amino acid sequence of SEQ ID NO: 5; (iii) a rAd26 vector encoding an antigen comprising the amino acid sequence of SEQ ID NO: 28; and (iv) a rAd26 vector encoding an antigen comprising the amino acid sequence of SEQ ID NO: 29; preferably wherein the rAd26 vectors are administered in a ratio of about 1:1:1:1 at a total dose of about $1-10 \times 10^{10}$ viral particles (vp), e.g. $5 \times 10^{10}$ vp;
(b) optionally repeating step (a);
(c) administering to the subject (i) an MVA or MVA-BN vector encoding a synthetic HIV envelope protein comprising the amino acid sequence of SEQ ID NO: 18, SEQ ID NO: 5, SEQ ID NO: 28, and SEQ ID NO: 29, wherein preferably the MVA or MVA-BN vector is administered at a dose of $10^5$ to $10^{11}$ pfu, e.g. at a dose of $10^7$ pfu, $10^8$ pfu, $10^9$ pfu, or $10^{10}$ pfu, e.g. at a dose of $2 \times 10^7$ to $5 \times 10^8$ pfu, e.g. at a dose of about $1 \times 10^8$ pfu, or at a dose of $10^6$ to $10^{10}$ TCID$_{50}$, e.g. between $10^7$ and $10^9$ TCID$_{50}$; and (ii, a) isolated HIV gp140 protein having the sequence of amino acids 30-708 of SEQ ID NO: 7; or (ii, b) isolated HIV gp140 protein having the sequence of amino acids 30-724 of SEQ ID NO: 36; or (ii, c) two isolated HIV gp140 proteins wherein a first isolated HIV gp140 protein has the sequence of amino acids 30-708 of SEQ ID NO: 7 and a second isolated HIV gp140 protein has the sequence of amino acids 30-724 of SEQ ID NO: 36, preferably wherein these proteins are administered in a ratio of about 1:1; and (iii) aluminum phosphate adjuvant; preferably wherein the isolated HIV gp140 protein is or isolated HIV gp140 proteins are administered at a total dose of about 50-300 microgram, e.g. 250 microgram; and (d) optionally repeating step (c).

Embodiment 38 is the method of any of embodiments 26-31 or 34-37, wherein the subject has been infected with HIV prior to the first step of administering a vector or vaccine component.

Embodiment 39 is the method of any of embodiments 26-31 or 34-38, further comprising administering a latent viral reservoir purging agent to the subject.

Embodiment 40 is the method of embodiment 39, wherein the latent viral reservoir purging agent is a TLR7 modulator.

Embodiment 41 is the method of any of embodiments 26-31 or 34-40, wherein the subject is further undergoing antiretroviral therapy (ART).

Embodiment 42 is the method of embodiment 41, wherein the subject undergoes interruption of ART after completion of a priming/boosting immunization.

Embodiment 43 is the method of embodiment 42, wherein the interruption of ART is initiated after completion of an Ad26 priming immunization and MVA boosting immunization, optionally wherein the MVA boosting immunization is administered together with one or more isolated HIV Env gp140 proteins.

Embodiment 44 is a composition of any one of embodiments 13 or 21-23, a vaccine of any one of embodiments 14 or 21-23, or a vaccine combination of any one of embodiments 15-18 or 32-33, for use in treating and/or preventing a human immunodeficiency virus (HIV) infection and/or disease.

Embodiment 45 is a composition of any one of embodiments 13 or 21-23, a vaccine of any one of embodiments 14 or 21-23, or a vaccine combination of any one of embodiments 15-18 or 32-33, for use in manufacturing a medicament for treating and/or preventing a human immunodeficiency virus (HIV) infection and/or disease.

Embodiment 46 is use of a composition of any one of embodiments 13 or 21-23, a vaccine of any one of embodiments 14 or 21-23, or a vaccine combination of any one of embodiments 15-18 or 32-33, for manufacturing a medicament for treating and/or preventing a human immunodeficiency virus (HIV) infection and/or disease.

EXAMPLES

Example 1: Design of HIV Envelope Antigen Sequences

Several HIV envelope antigen sequences were designed having sequence similarity to the mosaic HIV antigen mos2Env (SEQ ID NO: 6; previously also described in WO 2010/059732). The newly designed, membrane bound, sequences were based on (a combination of) fully natural wild-type sequences from HIV envelope proteins, or a chimera of mos2Env sequence and wild-type HIV envelope protein sequences. In addition to full length envelope protein sequences (see FIG. 1A), sequences having a C-terminal truncations of the cytoplasmic domain were also designed (see, e.g., FIG. 1C). See also e.g., Schiernle et al., PNAS 1997; Abrahamyan et al., J Virol 2005; Edwards et al., *J Virology*, 2002, 76:2683-2691. Soluble variants were also prepared by C-terminal truncation before the transmembrane (TM) region, which was replaced by a trimerization domain, such as a GCN4 trimerization domain (see, e.g., FIG. 1B). These soluble variants were further converted into a single chain variant by mutation of the furin-cleavage site, thus inhibiting the processing of the extracellular domain of the envelope protein into gp120 and gp41 subunits.

Of all constructs generated and tested, constructs based on C4 had the most optimal properties, e.g., good manufacturability, folding, immunogenicity, etc. and these were selected for further studies. A soluble variant of the C4 construct having a GCN4 trimerization domain in place of the transmembrane domain (sC4, FIG. 1B), and a variant comprising a 7-amino acid fragment of the cytoplasmic domain (C4D7, FIG. 1C) were also generated and tested in further studies. The amino acid sequences of C4, sC4, and C4D7 are shown in SEQ ID NOs: 17, 19, and 18, respectively. Sequences encoding these are shown in SEQ ID NOs:

25, 27, and 26, respectively. Construct C1 has an extracellular domain sequence based on the mos2Env sequence (SEQ ID NO: 6). A soluble variant of construct C1 having a GCN4 trimerization domain in place of the transmembrane domain (sC1), and a variant comprising a 7-amino acid fragment of the cytoplasmic domain (C1D7), similar to sC4 and C4D7 as shown in FIGS. 1B and 1C, respectively, were also generated. Construct C1 and its variants were used in further studies for comparison purposes, since these are essentially based on the mos2Env sequence of the prior art. The amino acid sequences of C1, sC1 and C1D7 are shown in SEQ ID NOs: 31, 30, and 32, respectively. Nucleic acid sequences encoding these are shown in SEQ ID NOs: 34, 33, and 35, respectively. Other constructs that were tested were less optimal than the ones based on construct C4, and were not taken into further development.

Example 2: Expression and Folding of Synthetic HIV Envelope Proteins

The expression level, folding, and cell-surface expression of synthetic HIV envelope proteins were measured.

Expression Levels

Figure 2:
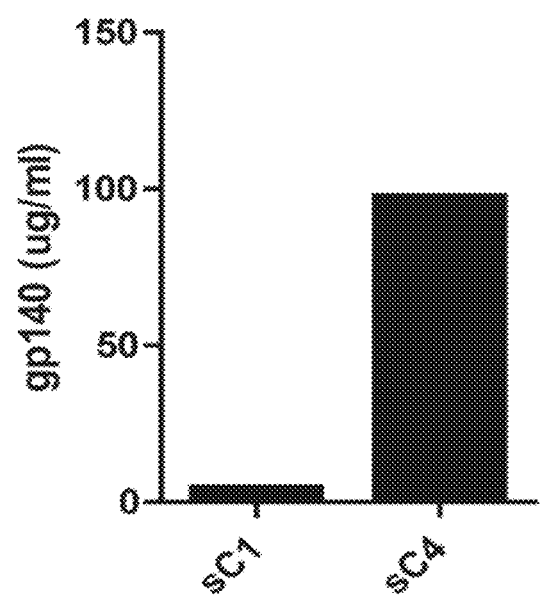
FIG. 2 shows expression levels of the soluble sC1 HIV envelope protein, which is based on the mos2Env mosaic antigen sequence with an additional C-terminal trimerization domain, and a soluble synthetic HIV envelope protein (sC4) according to an embodiment of the invention; expression was measured by quantitative Western blot using a polyclonal antibody against gp120; plasmids encoding sC1 or sC4 were transiently expressed twice, and each transfection was quantified twice by densitometry; the sC1 protein showed very low expression levels compared to the sC4 synthetic HIV envelope protein, which showed relatively high expression levels.

HEK293F cells were transiently transfected with a plasmid encoding the soluble synthetic HIV envelope proteins sC1 and sC4 as described in Example 1. Expression levels of the soluble protein were measured in the supernatant using quantitative Western blot (QWB). The results are shown in FIG. 2. The low expression levels for sC1 (which essentially corresponds to mos2Env with an added transmembrane domain) are in line with our recent insights for mos2Env. As demonstrated by the results, the sC4 variant of the invention showed significantly higher expression levels than the sC1 variant (control).

Protein Folding

Figure 3A:
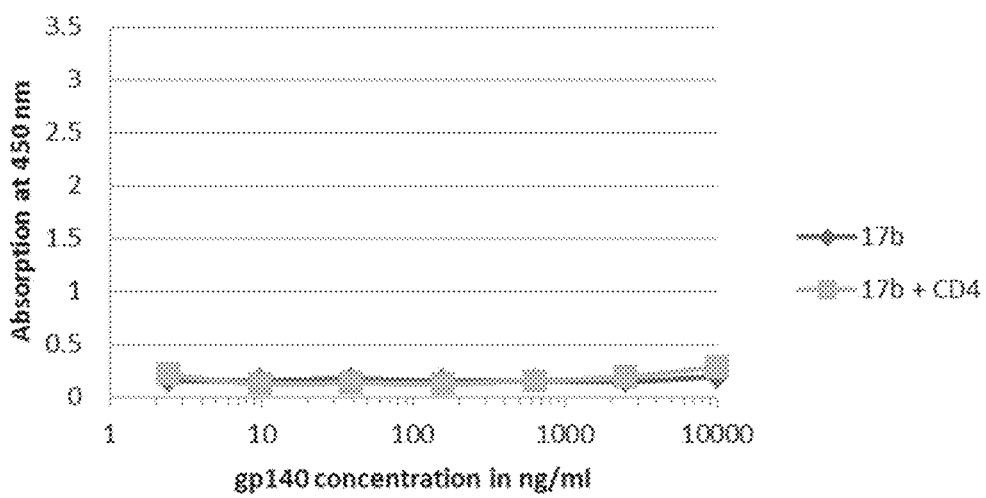
FIGS. 3A and 3B show the binding of synthetic HIV envelope proteins with monoclonal antibody 17b (mAb17b) in the presence (light gray) and absence (dark gray) of soluble CD4 as determined by ELISA assay.

Protein folding was tested by measuring the binding of soluble synthetic HIV envelope proteins to an antibody (MAb 17b) known to bind the co-receptor binding site of the HIV envelope protein, which is exposed only after binding of CD4, by enzyme-linked immunosorbent assay (ELISA). In particular, binding of purified sC4 was tested for binding to MAb 17b with prior binding of sC4 to CD4, and without prior binding of sC4 to CD4. Purified sC1 was used as a control. Binding of MAb 17b to sC4 without prior CD4 binding to the envelope protein is an indication of partially unfolded or pre-triggered envelope protein (i.e., an unstable Env that adopts the "open" conformation in the absence of CD4 binding). The results of the ELISA assay are shown in FIGS. 3A and 3B.

Figure 3B:
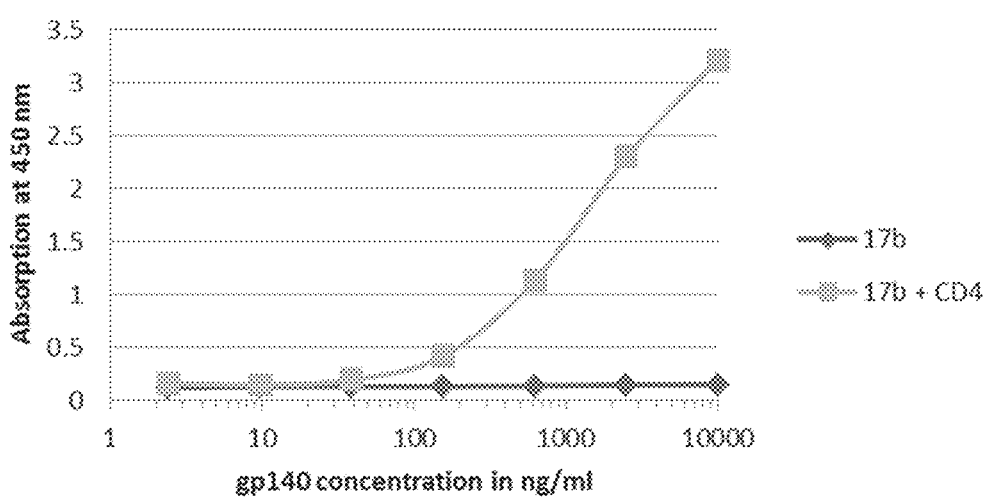

As shown in FIG. 3B, sC4 shows strong binding to MAb 17b with prior binding to CD4, but no detectable binding to MAb 17b without prior binding to CD4. In contrast, as shown in FIG. 3A, sC1 showed much lower binding to MAb 17 both with and without prior binding to CD4. The results suggest that sC4 has a correct folding pattern, with no exposure of the co-receptor binding site prior to CD4 binding.

Figure 4:
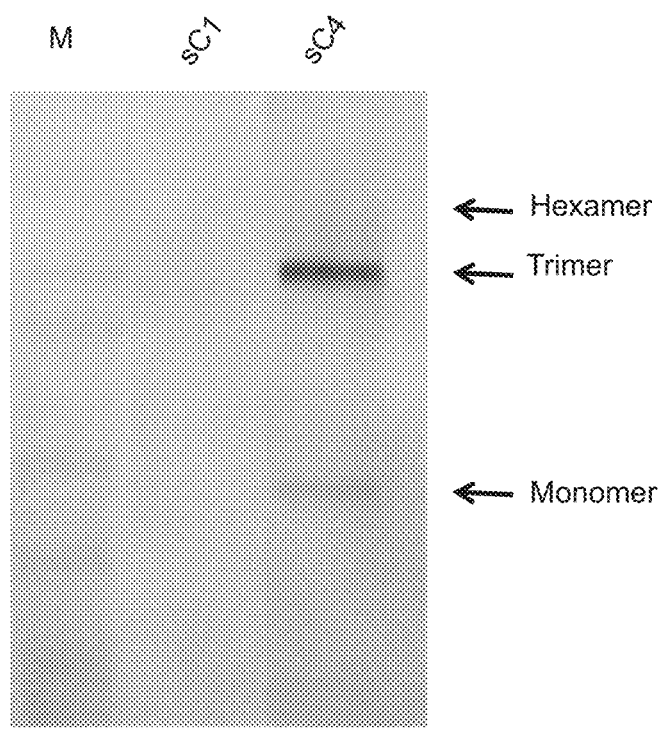
FIG. 4 is an image of a Western blot from a native polyacrylamide gel electrophoresis of the sC1 protein, and the sC4 synthetic HIV envelope protein.

Protein folding was also analyzed by native polyacrylamide gel electrophoresis (PAGE) of sC1 and sC4 to evaluate the quaternary structure of the soluble protein variants, and possible incorrect disulfide bridge formation between protomers. After electrophoresis on a native gel, protein in the gel was detected by Western blot analysis. As shown by the results in FIG. 4, the majority of sC4 is present in a trimeric state, which is the correct quaternary structure.

Taken together, the results of the protein folding experiments demonstrate that the sC4 soluble synthetic HIV envelope protein has the desired folding profile, which is improved as compared to the folding profile of the existing mos2Env antigen (represented by sC1).

Cell Surface Expression

Cell surface expression of the membrane-bound variants of HIV envelope proteins C1 (full length), C4 (full length, see FIG. 1A), C1D7, and C4D7 was also studied. HEK293T cells were transiently transfected with only eGFP-encoding plasmid (negative control, NC), or with eGFP-encoding plasmid together with an expression construct encoding an HIV envelope protein variant. Two days post-transfection, cells were subjected to fluorescence activated cell sorting (FACS)-analysis upon exposure to several poly- and monoclonal antibodies directed against gp120, and secondary antibodies, and then examined for envelope protein cell-surface expression levels. Quality of the envelope variants was assessed by determining the overall expression levels using an anti-gp120 polyclonal antibody, and by assessing relative binding of the broadly neutralizing antibodies PG9 and PG16, which are quaternary-structure dependent, and preferentially bind to correctly folded envelope trimer.

Figure 5:
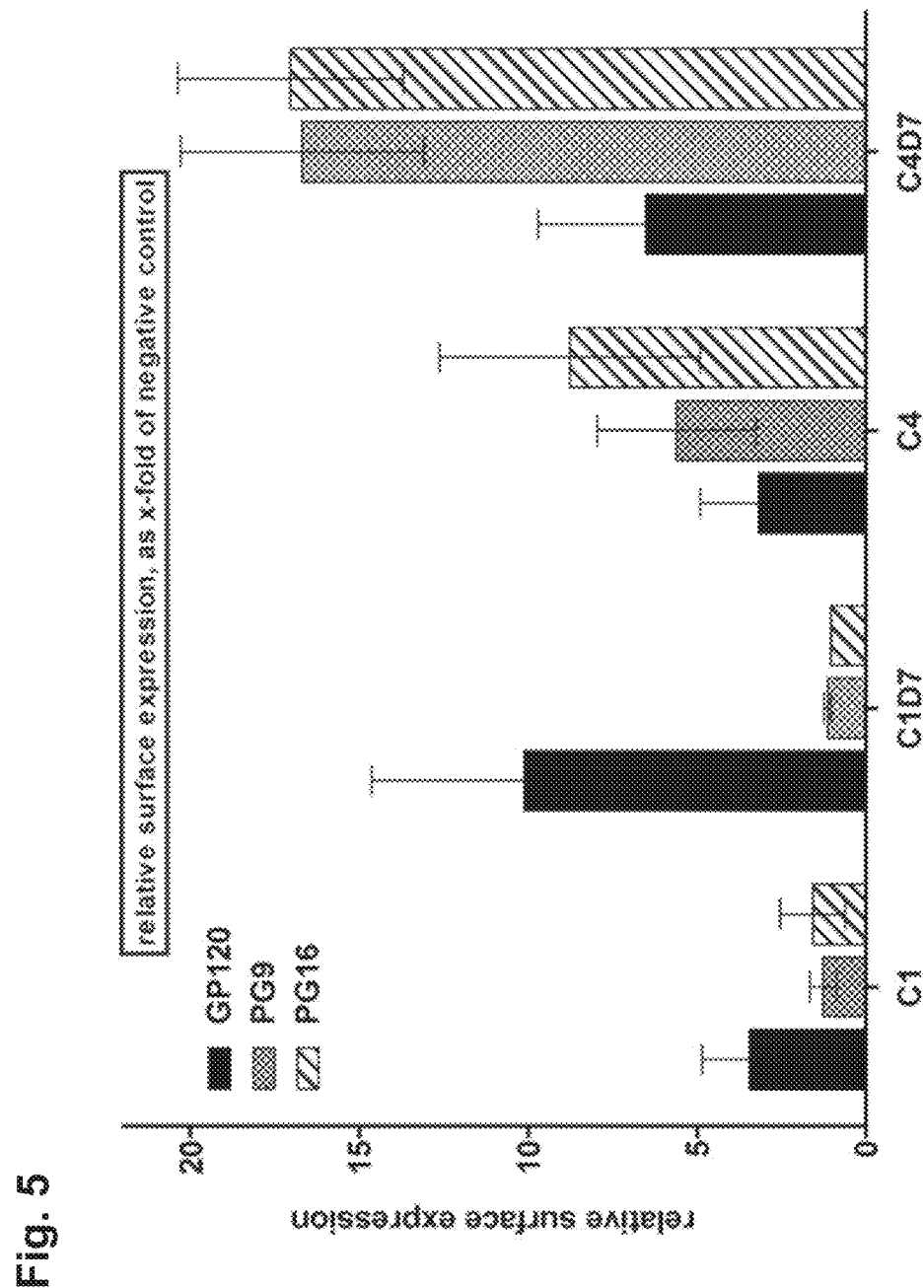
FIG. 5 shows the relative cell surface expression levels of the membrane-bound C1, C1D7, C4 and C4D7 synthetic HIV envelope proteins by FACS analysis of cells expressing these proteins using an anti-gp120 polyclonal antibody (GP120), and by binding to broadly neutralizing antibodies PG9 (PG9) and PG16 (PG16) that are quaternary-structure dependent and preferentially bind to correctly folded Env trimer.

The results of the cell surface expression experiments are shown in FIG. 5. The surface expression levels of truncated variants C1D7 and C4D7 as measured using an anti-gp120 antibody, are much higher than the surface expression levels of their full length counterparts, C1 and C4, respectively. This confirms that deletion of 144 residues from the carboxy-terminus of Env increases envelope surface expression levels. The full length C4 construct of the invention also showed improved PG9 and PG16 binding as compared to full length C1, suggesting that the C4 envelope sequence is properly folded (i.e., a trimer) on the cell surface.

The results also demonstrate that the C1D7 variant, which is essentially Mos2Env with an added transmembrane domain and 7 amino acids of the cytoplasmic domain, can be surface-expressed on HEK293T cells. This is in contrast to the soluble construct in Ad26.mos2Env, which cannot be expressed at detectable levels on the surface when transfected to A549 cells. However, relative binding to PG9 and PG16 is barely detectable above background, suggesting that the C1D7 envelope sequence is poorly folded and is probably not present as an intact trimer on the cell surface.

Overall, the C4D7 envelope variant has the most optimal antibody binding profile, with higher gp120 expression than its full-length counterpart C4, and with greater than 15-fold increased PG9 and PG16 binding compared to C1 and C1D7 (FIG. 5).

Example 3: Stability of Vectors Encoding HIV Envelope Sequences

Previous work in our laboratories (unpublished) indicated that adenovirus 26 (Ad26) vectors encoding the mos2Env antigen sequence showed relatively high VP/IU ratios (indicating lower quality of adenovirus product batches) and moreover that such vectors displayed stability issues. Accordingly, it was important to test the stability of the synthetic HIV envelope protein constructs of the invention in an adenovirus background.

Recombinant Ad26 (rAd26) vectors encoding HIV antigen sequences of the invention C4, C4D7, and sC4 as described above in Example 1 were generated in PER.C6 cells (referred to as "rAd26.C4", "rAd26.C4D7", and "rAd26.sC4", respectively). Vector clones (plaques) were picked and scaled-up for the generation of research batches. A maximum of 5 viral clones (plaques) were scaled-up to T25 format and serially passaged for 10 passages in T25 format (passages 1-3 being the transfection and plaque purification steps, followed by 10 passages in T25 format, resulting in a total of 13 passages). Genetic stability was assessed at viral passage number (vpn) 3, 5, 10 and 13 by an E1 transgene cassette PCR assay, followed by sequencing at vpn 13. The results are shown in FIG. 6.

Figure 6:
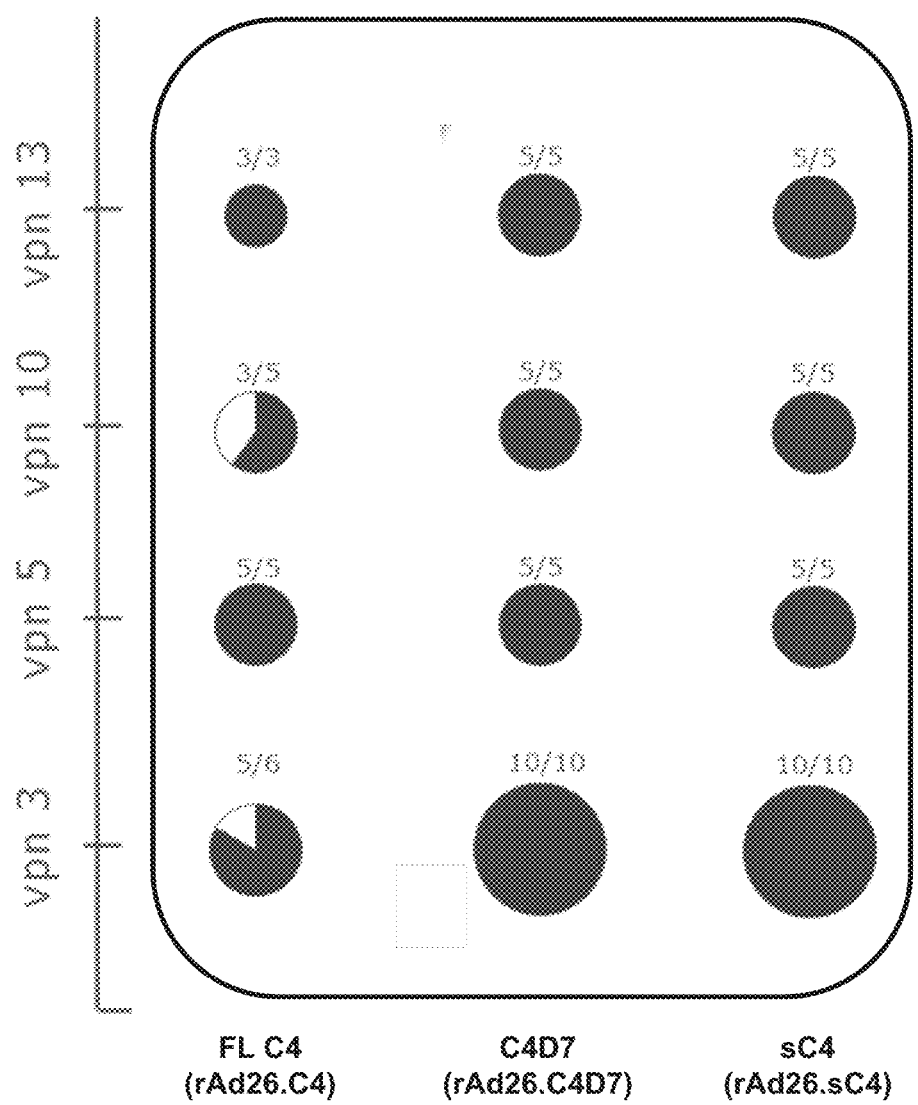
FIG. 6 is a graphical representation of the stability of adenovirus vectors containing sequences encoding synthetic HIV envelope proteins of the invention including full-length C4 (FLC4), C4D7, and sC4 after multiple viral passages; recombinant adenovirus 26 vectors were generated in PER.C6 cells; after the initial 3 passages for transfection and plaque purification, 5 plaques were selected and upscaled for 10 passages in T25 format, resulting in a total viral passage number (vpn) of 13; the stability after vpn 3, 5, 10, and 13 as determined by E1 transgene cassette polymerase chain reaction (PCR) is shown; for example, 3/5 means 3 plaques were stable out of 5 plaques tested, and 5/5 means 5 plaques were stable out of 5 plaques tested.

The rAd26 vectors encoding full length C4 (rAd26.C4) showed poor growth characteristics, as determined by no full cytopathogenic effect (CPE) in 2-3 days; genetic instability, as determined by deletions of the E1 transgene cassette region; or a combination thereof (FIG. 6). Due to the poor growth characteristics and observed genetic instability, this vector encoding full length C4 was not pursued further.

In contrast, for the rAd26 vectors encoding C4D7 (rAd26.C4D7) and sC4 (rAd26.sC4), all propagated plaques remained genetically stable during the course of the experiment (FIG. 6). Thus, the novel sC4 and C4D7 constructs outperform the original mos2Env construct with respect to stability in an adenoviral vector background. The genetic stability testing up to vpn 13 represents propagation several passages beyond that used in the industrial scale preparation of the vectors.

Example 4: Expression and in Vivo Antigenicity of HIV Envelope Sequences in Adenovirus Vectors Expression and antigenicity of rAd26.C4D7 and rAd26.sC4 were assessed separately or in combination with a recombinant Ad26 vector encoding mos1Env (SEQ ID NO: 5) (hereinafter "rAd26.mos1Env") in vector-transduced A549 cells (human cell line) in vitro (data not shown). Flow cytometry analysis demonstrated that all antigens were expressed in cell cultures transduced with either $2 \times 10^4$ viral particles (vp) of the single envelope antigens as controls, or with $1 \times 10^4$ vp of the 2 combined Env antigens by adenovirus transduction. All transductions additionally contained single doses ($1 \times 10^4$ vp) of adenovirus vectors encoding mos1GagPol ("rAd26.mos1GagPol") and mos2GagPol ("rAd26.mos2GagPol") (Barouch et al, Nat Med 2010, 16:319-323), so that the assessed vector combinations exhibited the same relative ratios of the different adenoviral vectors as intended for pre-clinical and clinical use. Preferably, the vectors encoding synthetic HIV envelope proteins of the invention are combined with vectors encoding the mos1GagPol and the mos2GagPol antigens for clinical use.

The combination of rAd26.mos1Env and rAd26.C4D7 yielded a maximal coverage of the assessed epitopes as determined by monoclonal antibody binding. Particularly, the exposure of the PG16 epitope, which was contributed by transformation with Ad26.C4D7 is promising for vaccine use since PG16 represents a broadly neutralizing monoclonal antibody recognizing the V1/V2 loop region of HIV-1 Env (Walker et al, Science 326:258-9, 2009). Hence, the synthetic HIV envelope protein of the invention derived from the C4 sequence increases the breadth of the immune response against the HIV envelope protein compared to the immune response generated by mos1Env only. Vaccine-induced antibody responses directed towards the envelope protein region have been shown to correlate with protection from HIV-1 infection in the RV144 study (Haynes et al, N Engl J Med. 336:1275-86, 2012), and thus the synthetic HIV envelope protein of the invention is a promising candidate to include in HIV vaccine regimens.

Example 5: Immunogenicity of Vectors Encoding Synthetic HIV Envelope Proteins

The synthetic HIV envelope protein sequences of the invention in an Ad26 vector background were tested in rabbits to determine if these constructs were an immunogenic alternative to the rAd26.mos2Env construct.

The immunogenicity of adenovirus vector encoding mos1Env (rAd26.mos1Env; SEQ ID NO: 5) was tested alone, and in combination with adenovirus vectors encoding synthetic HIV envelope proteins of the invention (rAd26.C4D7 and rAd26.sC4; comprising SEQ ID NO: 8, in particular SEQ ID NOs: 18 and 19, respectively). In all cases, adenovirus 26 vectors encoding mos1GagPol and mos2GagPol antigens (rAd26.mos1GagPol [SEQ ID NO: 28] and rAd26.mos2GagPol [SEQ ID NO: 29], respectively) were also administered. More specifically, the immunogenicity of rAd26.mos1Env alone (trivalent vaccine: rAd26.mos1GagPol, rAd26.mos2GagPol and rAd26.mos1Env) was compared to the immunogenicity of rAd26.mos1Env in combination with one of rAd26.C4D7 or rAd26.sC4 (tetravalent vaccine: administration of either rAd26.mos1GagPol, rAd26.mos2GagPol, rAd26.mos1Env and rAd26.C4D7; or administration of rAd26.mos1GagPol, rAd26.mos2GagPol, rAd26.mos1Env and rAd26.sC4). This comparison of the trivalent vaccine, which lacks any vectors encoding the synthetic HIV envelope proteins of the invention, with the tetravalent vaccine, which contains vectors encoding the synthetic HIV envelope proteins of the invention, allows for a determination of whether the HIV envelope proteins of the invention contribute to the breadth of protection.

Administration was done in vaccine regimens, wherein these Ad26 vectors were administered at weeks 0 and 6 as a double prime, and a clade C gp140 protein (a trivalent Env gp140 protein having SEQ ID NO: 7 without the signal peptide sequence of residues 1-29, see also WO 2010/042942) at weeks 12 and 18 as a double boost (see e.g. Barouch et al, 2015, Science 349: 320-324). Table 1 describes the vaccine regimens used for the current study. rAd26.Empty refers to a control vector lacking any gene encoding a sequence for an HIV antigenic protein. Each group contained six rabbits.

TABLE 1

Vaccine regimens tested in immunogenicity study in rabbits

| | First and second Immunizations | | | Third and fourth immunizations | | | |
|---|---|---|---|---|---|---|---|
| Group | adeno vectors | Dose (vp) | Total dose (vp) | protein boost | Dose (ug) | Adjuvant | N= |
| 1 | rAd26.Mos1Env<br>rAd26.Mos1GagPol<br>rAd26.Mos2GagPol | $2.5 \times 10^{10}$<br>$1.25 \times 10^{10}$<br>$1.25 \times 10^{10}$ | $5 \times 10^{10}$ | GP140 (clade C) | 10 | AdjuPhos 250 μg | 6 |

TABLE 1-continued

Vaccine regimens tested in immunogenicity study in rabbits

| Group | adeno vectors | Dose (vp) | Total dose (vp) | protein boost | Dose (ug) | Adjuvant | N= |
|---|---|---|---|---|---|---|---|
| 2 | rAd26.Mos1Env | $1.25 \times 10^{10}$ | $5 \times 10^{10}$ | GP140 (clade C) | 10 | AdjuPhos 250 µg | 6 |
|   | rAd26.C4D7 | $1.25 \times 10^{10}$ | | | | | |
|   | rAd26.Mos1GagPol | $1.25 \times 10^{10}$ | | | | | |
|   | rAd26.Mos2GagPol | $1.25 \times 10^{10}$ | | | | | |
| 3 | rAd26.Mos1Env | $1.25 \times 10^{10}$ | $5 \times 10^{10}$ | GP140 (clade C) | 10 | AdjuPhos 250 µg | 6 |
|   | rAd26.sC4 | $1.25 \times 10^{10}$ | | | | | |
|   | rAd26.Mos1GagPol | $1.25 \times 10^{10}$ | | | | | |
|   | rAd26.Mos2GagPol | $1.25 \times 10^{10}$ | | | | | |
| control | rAd26 Empty | $5 \times 10^{10}$ | $5 \times 10^{10}$ | NA | 0 | AdjuPhos 250 µg | 6 |

The comparison of the trivalent Ad26 vaccine (lacking the novel Env antigens of the invention) with the tetravalent Ad26 vaccine (which comprises the novel sC4 or C4D7 Env antigens) allows for testing whether the novel antigens of the invention contribute to breadth of protection. An established TZM-bl cell-based neutralization assay [Montefiori D C. Methods Mol Biol 2009, 485:395-405; Sarzotti-Kelsoe M et al., J Immunol Methods 2014, 409:131-146] was used to measure neutralizing activity of the vaccine candidates.

Figure 7A:
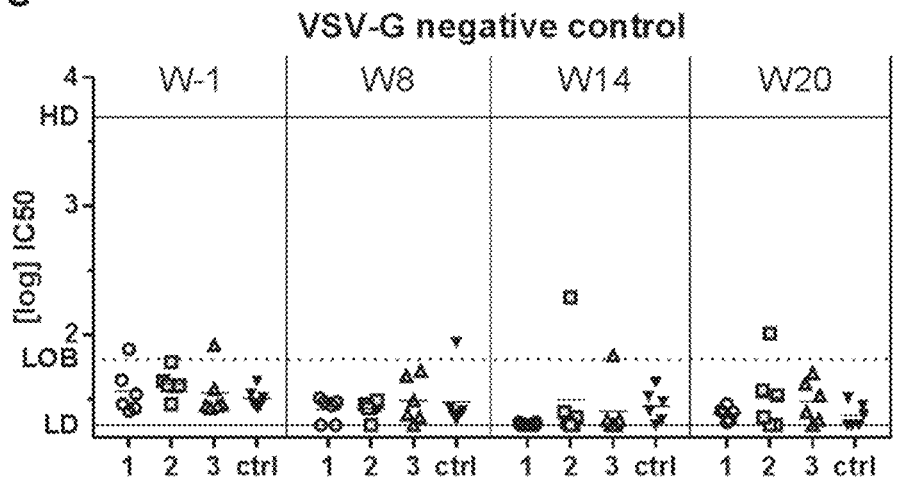
FIGS. 7A and 7B show virus neutralization titers against HIV-1 envelope pseudotyped virus particles (EVPs) in a TZM-bl cell-based neutralization assay in rabbits; log 10-transformed $IC_{50}$ values of the high-adenoviral vector dosed groups were measured against EVPs VSV-G (negative control) and MW965.26 (Tier 1A clade C) at weeks 1, 8, 14, and 20; each dot represents the log 10-transformed $IC_{50}$ value of an individual rabbit, with the group mean indicated by a horizontal line; HD: Highest Dilution tested (upper solid line); LD: Lowest Dilution tested (lower solid line); LOB: limit of background, 95 percentile value of compiled negative samples (dotted line); Log 10 $IC_{50}$ values exceeding the LD or HD threshold were set at the corresponding line; a one-way non-parametric comparison with control using the Dunn method for joint ranking was done for each time point; statistically significant differences are indicated in the graphs: *=P<0.05, =P<0.01, and *=P<0.001.

The results are shown in FIG. 7, and were statistically analyzed by using the trivalent vaccine (group 1 in Table 1) as control group and comparing to each of the novel tetravalent vaccines (groups 2 and 3 in Table 1).

Overall, the novel C4-derived (i.e. encoding Env proteins comprising SEQ ID NO: 8, being an alternative for mos2Env) adenovirus constructs were immunogenic after two homologous intramuscular immunizations in rabbits.

Neutralization capacity of rabbit immune sera against Tier 1B pseudoviruses was absent (data not shown), which is not unexpected as it was known that such viruses are more difficult to neutralize.

Pseudovirus neutralization capacity of rabbit immune sera against a clade B Tier 1A virus was unaffected by the addition of new components (data not shown). This demonstrates that the novel antigen did not negatively interfere with immunogenicity of the existing clade B antigen present in the vaccine (although the new components were directed to clade C, such undesirable interference could not be excluded a priori before it had been tested).

Pseudovirus neutralization capacity of rabbit immune sera against a clade C Tier 1A virus was significantly enhanced in the quadrivalent novel C4D7 containing adeno (quadrivalent, group 2), compared to trivalent (having only mos1Env) immunization alone (group 1) (FIG. 7 panel B). In addition, pseudovirus neutralization capacity of rabbit immune sera against a clade C Tier 1A virus at week 8 was significantly enhanced in the tetravalent novel sC4 containing adenovirus (quadrivalent, group 3), compared to trivalent (having only mos1Env) immunization alone (group 1) (FIG. 7 panel B).

Figure 7B:
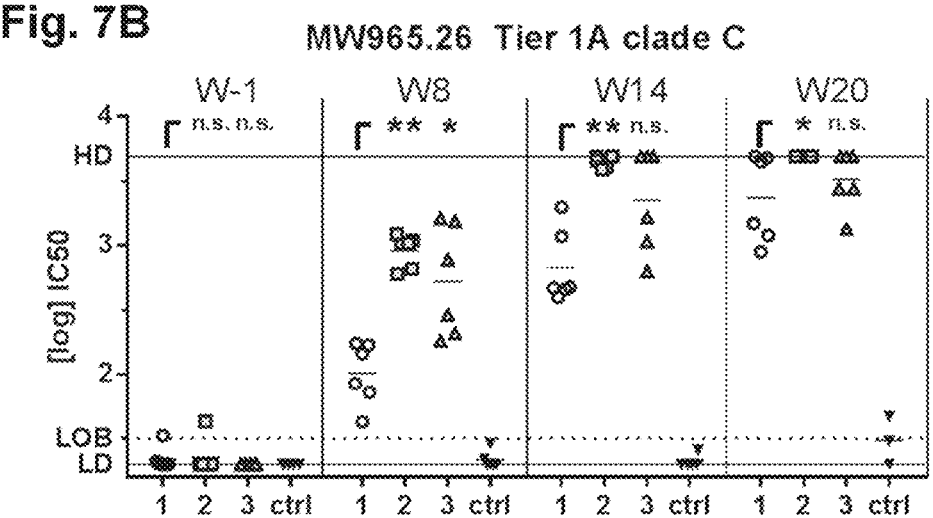

In conclusion, the C4D7 and sC4 constructs encoded in Ad26 were immunogenic and addition thereof expanded the binding- and neutralization capacity of a vaccine that has mos1Env (mainly clade B) as sole Ad26-encoded Env component, towards clade C strains (FIG. 7B).

Example 6: Immunogenicity of Vaccine Regimens Including Vectors Encoding Synthetic HIV Envelope Proteins of the Invention One further rabbit study assessed the tetravalent vector combination Ad26.Mos4.HIV (consisting of four adenoviral vectors: Ad26.Mos1GagPol [encoding SEQ ID NO: 28], Ad26.Mos2GagPol [encoding SEQ ID NO: 29], Ad26.Mos1Env [encoding SEQ ID NO: 5] and Ad26.Mos2SEnv [the name "C4D7" as used above is also referred to as "Mos2S"; this vector encodes the novel SEQ ID NO: 18 according to the invention], in a 1:1:1:1 mixture at a total dose of $5 \times 10^9$ vp,) applied intramuscularly as double prime immunizations in weeks 0 and 6, in combination with recombinant HIV-1 Env protein boosts using clade C gp140 [having the sequence of amino acid residues 30-708 of SEQ ID NO: 7], Mosaic gp140 [having the sequence of amino acid residues 30-724 of SEQ ID NO: 36], or a combination of clade C gp140 and Mosaic gp140, in weeks 13 and 19. These protein boosts were applied intramuscularly at a total dose of 10 or 50 micrograms of protein combined with 250 micrograms aluminum phosphate adjuvant formulated on the day of immunization.

Results indicate that all tested regimens were immunogenic in all animals, inducing high antibody titers and moderate neutralization activity against Tier 1 Env pseudotyped viruses. If Mosaic gp140 was used as vaccine antigen, either alone or in combination with clade C gp140, Mosaic gp140-specific ELISA titers and clade B pseudovirus recognition were significantly increased at week 15 in comparison to the reference group boosted with clade C gp140 alone. The overall effect size of the improvement was moderate, and bigger for the group boosted with the bivalent clade C gp140-Mosaic gp140 combination compared to Mosaic gp140 alone. At week 21 of the study, these differences were lost and immune responses measured for the cohorts receiving bivalent clade C gp140-Mosaic gp140 boosts or monovalent clade C gp140 boosts were statistically indistinguishable.

The bivalent protein regimen showed comparable induction of clade C ELISA titers and pseudovirus recognition as the clade C gp140 alone boosted regimen, indicating that the inclusion of the clade B-related immunogen Mosaic gp140 had no negative effect on clade C antigen coverage, whilst significantly enhancing clade B coverage at week 15 of the study.

The data confirm that the Ad26.Mos2SEnv vector encoding a synthetic Env antigen according to the invention can be successfully used in vaccine regimens.

Figure 8:
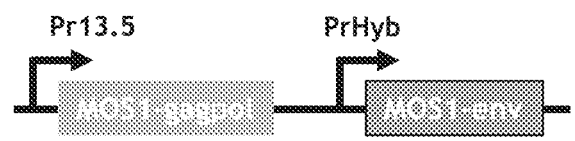
FIG. 8 is a graphical representation of inserts into specified locations of the MVA genome for vector MVA-mBN414; Pr13.5 and PrHyb are promoter sequences; IGRs are intergenic regions.
Figure 8:
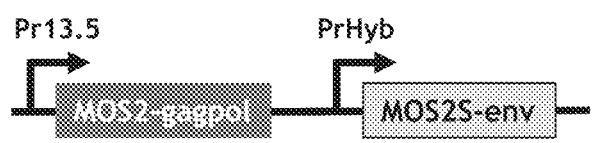

Example 7: Construction of MVA Vectors Encoding Synthetic HIV Envelope Proteins of the Invention in Combination with Other HIV Antigens In the instant example, an MVA-BN vector was generated (termed "MVA-mBN414"), comprising a nucleic acid encoding the novel HIV mos2SEnv antigen described herein as SEQ ID NO: 18 (also referred to as C4D7). The MVA-mBN414 vector additionally comprised nucleic acids encoding the following HIV antigens: mos1Env (SEQ ID NO: 5); mos1Gag (SEQ ID NO: 1); mos2Gag (SEQ ID NO: 2); mos1Pol (SEQ ID NO: 3); and mos2Pol (SEQ ID NO: 4). In MVA-mBN414 the mos1Gag (SEQ ID NO:1) and mos1Pol (SEQ ID NO: 3) were encoded as a fusion protein (SEQ ID NO:28, "mos1GagPol") and the mos2Gag and mos2Pol were encoded as a fusion protein (SEQ ID NO: 29, "mos2GagPol"). See FIG. 8 for a schematic representation of the inserts into regions of the MVA genome.

We designed a novel nucleic acid (SEQ ID NO: 41) coding for the HIV antigen mos2SEnv (SEQ ID NO: 18); a novel nucleic acid (SEQ ID NO: 39) coding for the HIV antigen mos1Env (SEQ ID NO: 5); a novel nucleic acid (SEQ ID NO: 38) coding for the HIV antigen mos1GagPol (SEQ ID NO: 28); and a novel nucleic acid (SEQ ID NO: 40) coding for the HIV antigen mos2GagPol (SEQ ID NO: 29). The novel nucleic acids were designed for human expression, minimal homology among each other, and reduced poly-nt stretches as well as repetitive elements.

The PrMVA13.5 long promoter (SEQ ID NO: 42) was included in front of the ATG start codon of both the mos1GagPol and mos2GagPol antigen sequences. The PrHyb promoter (SEQ ID NO: 43) was included in front of the ATG start codon of both the mos2SEnv and the mos1Env antigen sequences.

The mos1GagPol and mos1Env coding sequences were inserted via SacII and PacI into pBNX208, a transfer vector encoding IGR 44/45 MVA-BN homologous regions, thus allowing insertion into the targeted region (IGR 44/45) of MVA-BN via homologous recombination. Moreover, pBNX208 encodes heGFP and nptII for positive selection as well as repetitive sequences of the IGR 44/45 MVA-BN homologous region Flank 2 or later excision of the selection cassette via homologous recombination in the absence of selective pressure. The mos2GagPol and mos2Env coding sequences were inserted via NotI into pBNX227, a transfer vector encoding IGR88/89 MVA-BN homologous regions, thus allowing insertion into of the targeted region (IGR 88/89) of MVA-BN via homologous recombination. Moreover, pBNX227 encodes mRFP1 and ecogpt for positive selection, which are flanked by two loxP sites for later excision of the selection cassette in the absence of selective pressure following transfection with a plasmid encoding the CRE-recombinase, which catalyzes the precise excision of nucleic acid sequences flanked by their target sequence loxP.

The MVA based vectors were generated in primary chicken fibroblasts (CEF) and produced as described herein. The CEF cells were isolated weekly from chicken embryos and maintained in VP-SFM medium without FBS. Briefly, CEF cells were transfected with MVA vector plasmid, using Fugene according to the instructions provided by the manufacturer (Promega) and a coinfection with MVA-BN was performed. Cells were harvested after two or three days, sonified and further passaged. The virus was plaque purified in CEF cells cultured in a multi-well 96-tissue culture plate following amplification within a single well of a multi-well 12-tissue culture plate. Further amplification was carried out in CEF cells cultured in a single well of a multiwell 6-tissue plate and subsequently in a T175 tissue culture flask.

The MVA-mBN414 is thus an MVA-BN comprising in its IGR 44/45 region a nucleic acid encoding mos1GagPol (SEQ ID NO: 28) under control of a PrMVA13.5long promoter (SEQ ID NO: 42) and a nucleic acid encoding mos1Env (SEQ ID NO: 5) under control of a PrHyb promoter (SEQ ID NO: 43). In the IGR 88/89 region there is a nucleic acid encoding the mos2GagPol (SEQ ID NO: 29) under control of a PrMVA13.5long promoter (SEQ ID NO: 42) and a nucleic acid encoding mos2SEnv (SEQ ID NO: 18) under control of a PrHyb promoter (SEQ ID NO: 43). The MVA-mBN414 vector was used in subsequent experiments in prime-boost regimens with adenovirus vectors encoding antigens described herein.

Example 8: Immunogenicity of MVA-mBN414 in Rabbits

The immunogenicity of MVA-mBN414 (see Example 7) in New Zealand White (NZW) rabbits was assessed in the context of Ad26.Mos.HIV (a trivalent vaccine having 3 Ad26 vectors together encoding HIV antigens having SEQ ID NOs: 1, 2, 3, 4 and 5; in the form of antigens mos1GagPol (SEQ ID NO: 28), mos2GagPol (SEQ ID NO: 29), and mos1Env (SEQ ID NO: 5)) prime, and in comparison to homologous prime-boost with Ad26.Mos.HIV. In addition, the added benefit of co-application of clade C gp140 protein (adjuvanted with aluminum phosphate) at day 42 and day 62 (injection into contra-lateral muscles (i.e., in separate limbs)) was assessed.

The immunization schedule that was used is provided in the following Table 2:

TABLE 2

Immunization schedule for immunogenicity study in rabbits

| Group | Immunization day 0 + 22 | Immunization day 43 + 64 | N (female) | N (male) |
|---|---|---|---|---|
| 1 | Ad26.Mos.HIV $5 \times 10^{10}$ vp | Ad26.Mos.HIV $5 \times 10^{10}$ vp | 7 | 7 |
| 2 | | MVA-mBN414 $1.8 \times 10^8$ TCID$_{50}$ | 7 | 7 |
| 3 | | MVA-mBN414 $1.8 \times 10^8$ TCID$_{50}$ + clade C gp140 250 µg in AdjuPhos ® 425 µg | 7 | 7 |
| 4 | Ad26.Mos.HIV $5 \times 10^9$ vp | MVA-mBN414 $1.8 \times 10^7$ TCID$_{50}$ + clade C gp140 25 µg in AdjuPhos ® 42.5 µg | 7 | 7 |
| 5 | Ad26.Empty $5 \times 10^9$ vp | BN-MVA.Empty $1.8 \times 10^8$ TCID$_{50}$ | 3 | 3 |

The readout assays were a clade C (aa residues 30-708 of SEQ ID NO: 7) and mosaic gp140 (aa residues 30-724 of SEQ ID NO: 36) ELISA, and an HIV-1 pseudovirus neutralization assay. Neutralization capacity of sera from immunized rabbits was tested against HIV-1 ENV pseudotyped virus particles (EPVs) by inhibition of entry to TZM-bl cells. TZM-bl cells express high levels of CD4 and the co-receptors CCR5 and CXCR4 and contain an integrated tat-responsive Luciferase reporter gene under control of an HIV long-terminal repeat sequence. A neutralizing effect of serum-containing HIV-1 Env antibodies against the EPV's results in reduced luciferase expression and thereby a reduced luminescence signal in combination with the luciferin containing substrate. Serum or antibodies were tested in a three-fold serial dilution over 6 steps, starting at 1/20. The maximal luciferase expression was measured by adding only cells+EPVs within one well without serum or antibodies. The background luciferase expression was measured by adding only cells to a well, without serum/antibodies and EPVs. A non-linear 4 parameter curve was fitted between the maximal and background luciferase signal and log 10-transformed $IC_{50}$ values were determined as reportable value.

Figure 9A:
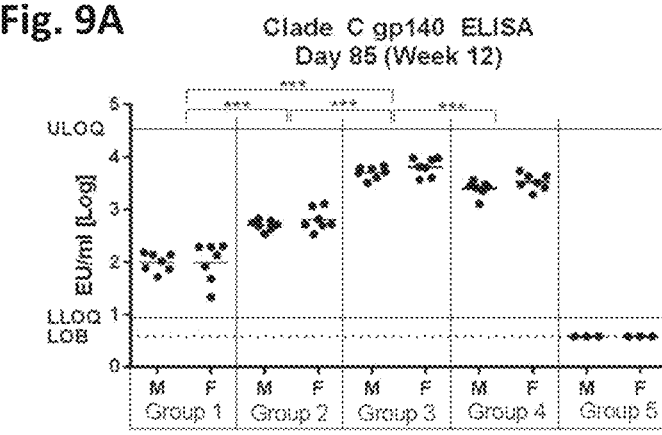
FIGS. 9A, 9B and 9C show immune responses raised in rabbits on day 85 following immunization with Ad26.Mos.HIV (abbreviated as Ad26), either alone or combined with MVA-mBN414 (abbreviated in FIGS. 9A-9C as "MVA"), clade C gp140 (abbreviated as GP140) or a combination thereof; Males (M) and Females (F) are shown separately.
Figure 9B:
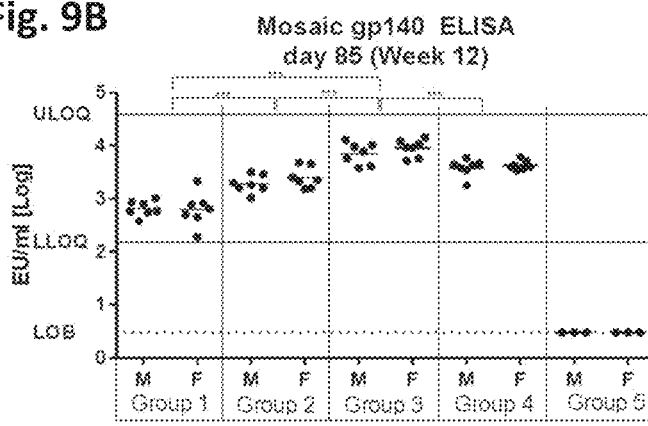
Figure 9C:
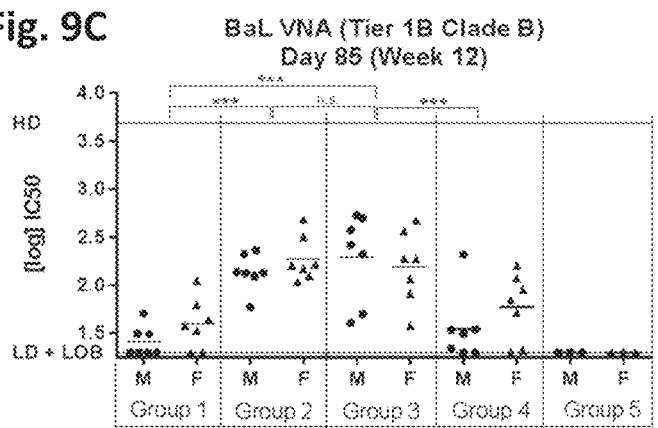

The results are shown in FIG. 9.

The results show that MVA-mBN414 was immunogenic in all rabbits. There was no obvious difference in immunogenicity between male and female animals. The MVA boost in the context of Ad26 prime induced an increase in the HIV-specific humoral immune response (measurable in clade C ELISA, clade B-like Mosaic ELISA and in clade B VNA) compared to homologous Ad26 prime-boost.

Co-administration of clade C gp140 protein with MVA as a boost induced an increase in (homologous) clade C gp140 ELISA and (heterologous) Mosaic gp140 ELISA titers compared to a boost with MVA only.

Example 9: Immunogenicity of MVA-mBN414 in Mice

The immunogenicity of MVA-mBN414 was also evaluated in CBF1 mice, with the aim to assess the immunogenicity of a heterologous Ad26.Mos4.HIV (see Example 6) prime and MVA-mBN414 (see Example 7) boost, in comparison to a homologous MVA prime-boost (i.e. both priming and boosting with MVA-mBN414).

The immunization schedule that was used is provided in the following Table 3:

TABLE 3

Immunization schedule for immunogenicity study in rabbits

| Group | Week 0 | | Week 5 | | N= |
|---|---|---|---|---|---|
| | Test article: | Dose: | Test article: | Dose: | |
| 1 | Ad26.Mos4.HIV | $2.5 \times 10^9$ total vp | MVA-mBN414 | $2.8 \times 10^6$ $TCID_{50}$ | 7 |
| 2 | | $2.5 \times 10^8$ total vp | | $2.8 \times 10^5$ $TCID_{50}$ | 7 |
| 3 | MVA-mBN414 | $2.8 \times 10^6$ $TCID_{50}$ | MVA-mBN414 | $2.8 \times 10^6$ $TCID_{50}$ | 7 |
| 4 | | $2.8 \times 10^5$ $TCID_{50}$ | | $2.8 \times 10^5$ $TCID_{50}$ | 7 |
| 5 | Ad26.Empty | $2 \times 10^9$ total vp | MVA BN-empty | $2.8 \times 10^6$ $TCID_{50}$ | 5 |

The readout assays for humoral immune responses (antigen-specific IgG measurement at weeks 5 and 7) was a mosaic gp140 (aa residues 30-724 of SEQ ID NO: 36) ELISA (see example 8). The readout assay for cellular immune responses (at week 7) was an IFN-γ ELISPOT (assay as described in Khan et al, Int J Cancer, 2017, Mar. 6, doi: 10.1002/ijc.30679. [Epub ahead of print]; 2017, Jul. 14, 141(2), 393-404), using Env, Gag and Pol immunodominant peptides as stimuli.

The results of the ELISPOT are shown in FIG. 10. An intracellular cytokine staining (ICS) assay was also performed, which gave similar results (not shown).

Figure 10A:
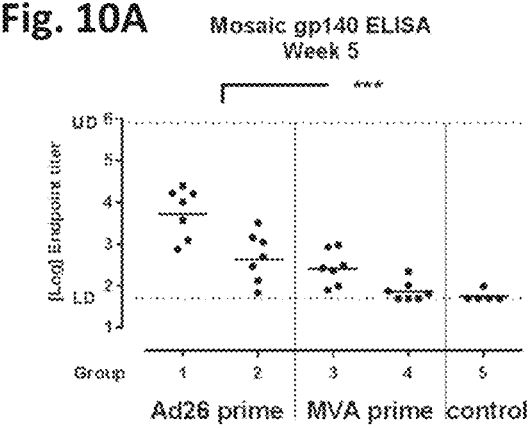
FIGS. 10A-10E show immune responses raised in mice following prime-only (week 5) or prime-boost (week 7) immunization with Ad26.Mos4.HIV (abbreviated as Ad26) followed by MVA-mBN414 prime-boost or homologous MVA-mBN414 (abbreviated in FIGS. 10A-10E as "MVA") prime-boost; Groups 1 and 2 were primed in week 0 with $2.5 \times 10^9$ or $2.5 \times 10^8$ vp of Ad26.Mos4.HIV, respectively, and boosted in week 5 with $2.8 \times 10^6$ or $2.8 \times 10^5$ $TCID_{50}$ of MVA-mBN414, respectively; Groups 3 and 4 were immunized in week 0 and week 5 with $2.8 \times 10^6$ or $2.8 \times 10^5$ $TCID_{50}$ of MVA-mBN414, respectively; Group 5 (control) was primed with $2.5 \times 10^9$ Ad26.Empty and boosted with $2.8 \times 10^6$ $TCID_{50}$ of MVA-BN-empty.
Figure 10B:
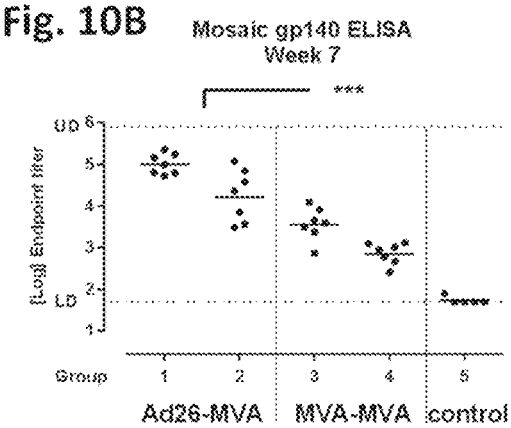
Figure 10C:
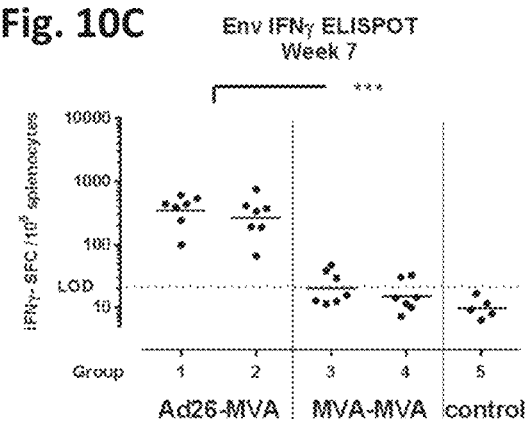
Figure 10D:
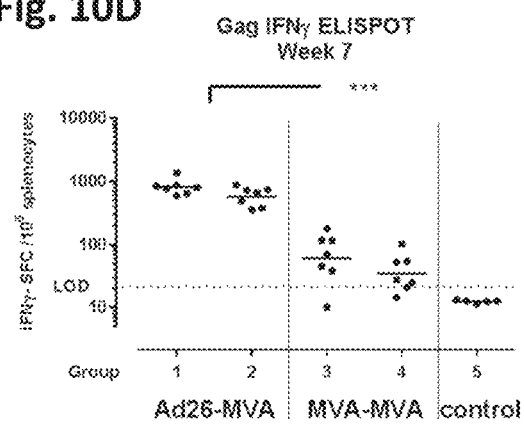
Figure 10E:
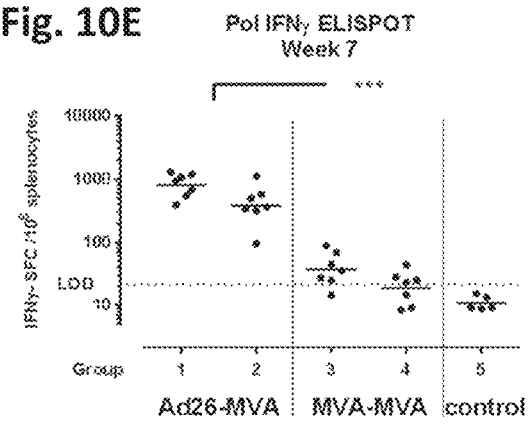

The results indicate that priming with Ad26 or MVA induced detectable immune responses at week 5 (FIG. 10A), that are further increased by boost immunization with MVA at week 7 (FIG. 10B) for both, the heterologous Ad-MVA regimen and the homologous MVA-MVA regimen. Heterologous Ad-MVA prime-boost induced significantly higher ELISA titers than the homologous MVA-MVA prime-boost regimen. This was also observed for cellular immune responses measured by ELISPOT against the antigens Env, Gag and Pol at week 7 (FIG. 10C-E). Homologous MVA prime-boost immunization induced a low but detectable cellular immune response against the antigens Gag and Pol that is clearly differentiable from control data.

All in all, the results show that an MVA with HIV antigens according to the invention is immunogenic. In addition, it is shown that such a vector can advantageously be used in prime-boost regimens with adenoviral vectors encoding HIV antigens, and/or with isolated HIV gp140 proteins.

REFERENCES

1. Barouch et al, Nat Med 2010, 16: 319-323
2. WO 2010/059732
3. Schiernle et al., PNAS 94: 8640-8645, 1997
4. Abrahamyan et al., J Virol 79: 106-115, 2005
5. US20120076812
6. Barouch et al., Cell 155:1-9, 2013
7. Havenga, et al., 2006, J Gen Virol 87: 2135-43;
8. WO 03/104467
9. WO 2004/001032
10. WO 2007/104792
11. Abbink et al., (2007) Virol 81(9): 4654-63
12. U.S. Pat. No. 7,270,811
13. Vogels et al., (2003) J Virol 77(15): 8263-71
14. WO 00/70071
15. WO2012/082918
16. Walker L M, Phogat S K, Chan-Hui P Y, Wagner D, Phung P, Goss J L, et al. Broad and potent neutralizing antibodies from an African donor reveal a new HIV-1 vaccine target. Science 2009, 326:285-289.
17. Haynes B F, Gilbert P B, McElrath M J, Zolla-Pazner S, Tomaras G D, Alam S M, et al. Immune-correlates analysis of an HIV-1 vaccine efficacy trial. N Engl J Med 2012, 366:1275-1286.
18. Barouch et al. (2015). Science 349: 320-324
19. Montefiori DC. Measuring HIV neutralization in a luciferase reporter gene assay. Methods Mol Biol 2009, 485:395-405.
20. Sarzotti-Kelsoe M, Bailer R T, Turk E, Lin CL, Bilska M, Greene K M, et al. Optimization and validation of the TZM-bl assay for standardized assessments of neutralizing antibodies against HIV-1. J Immunol Methods 2014, 409:131-146.
21. Edwards et al., J. Virology, 2002, 76:2683-2691.

The invention claimed is:

1. A poxvirus vector comprising nucleic acid encoding:
   (a) a first HIV envelope (Env) antigen comprising the amino acid sequence of SEQ ID NO: 18;

(b) a second HIV Env antigen different from the first HIV Env antigen;

(c) a third antigen and a fourth antigen, being two different HIV Gag antigens; and (d) a fifth antigen and a sixth antigen, being two different HIV Pol antigens.

2. The poxvirus vector of claim 1, wherein:

the second HIV Env antigen comprises the amino acid sequence of SEQ ID NO: 5, the third and fourth antigens comprise the amino acid sequence of SEQ ID NO: 1 and SEQ ID NO: 2, respectively; and the fifth and the sixth antigens comprise the amino acid sequence of SEQ ID NO: 3 and SEQ ID NO: 4, respectively.

3. The poxvirus vector of claim 1, wherein the third and the fifth antigens are fused into a first Gag-Pol fusion antigen that comprises the amino acid sequence of SEQ ID NO: 28, and the fourth and the sixth antigens are fused into a second Gag-Pol fusion antigen that comprises the amino acid sequence of SEQ ID NO: 29.

4. The poxvirus vector of claim 1, wherein the first HIV Env antigen is encoded by SEQ ID NO: 41.

5. The poxvirus vector of claim 3, wherein the first HIV Env antigen is encoded by SEQ ID NO: 41;

the second HIV Env antigen is encoded by SEQ ID NO: 39;

the first Gag-Pol fusion antigen is encoded by SEQ ID NO: 38; and the second Gag-Pol fusion antigen is encoded by SEQ ID NO: 40.

6. The poxvirus vector of claim 1, wherein the poxvirus vector is a recombinant Modified Vaccinia virus Ankara (MVA) vector.

7. The poxvirus vector of claim 6, wherein the MVA vector comprises MVA-BN or derivatives thereof.

8. The poxvirus vector of claim 6, wherein the poxvirus vector is a recombinant MVA vector, and wherein the first Gag-Pol fusion antigen and the second Env antigen are inserted into intergenic region (IGR) 44/45 of the MVA genome, and the second Gag-Pol fusion antigen and the first Env antigen are inserted into IGR 88/89 of the MVA genome.

9. The poxvirus vector of claim 8, wherein the first Gag-Pol fusion antigen and the second Gag-Pol fusion antigen are each under control of a separate Pr13.5 promoter, and the first Env antigen and the second Env antigen are each under control of a separate PrHyb promoter.

10. A vaccine comprising a poxvirus vector according to claim 1 and a pharmaceutically acceptable carrier.

11. A vaccine combination comprising:
 (a) a first vaccine composition comprising an immunologically effective amount of a poxvirus vector according to claim 1; and at least one of:
 (b) (i) a second vaccine composition comprising an immunogenically effective amount of one or more adenovirus vectors encoding one or more of the first, second, third, fourth, fifth and sixth antigens; and
 (b) (ii) a third vaccine composition comprising one or more polypeptides comprising an immunogenically effective amount of an isolated HIV antigenic polypeptide,
 wherein the first composition, and second and/or third composition are present in the same composition or in one or more different compositions.

12. The vaccine combination of claim 11, wherein the second vaccine composition comprises recombinant Ad26 vectors together encoding SEQ ID NOs: 18, 5, 1, 2, 3 and 4.

13. The vaccine combination of claim 11, wherein the one or more isolated HIV antigenic polypeptides in the third vaccine composition comprise:
 (i) a polypeptide comprising residues 30-708 of the amino acid sequence of SEQ ID NO: 7, or
 (ii) a polypeptide comprising residues 30-724 of SEQ ID NO: 36; or
 (iii) both polypeptides (i) and (ii).

14. A method of inducing an immune response against a human immunodeficiency virus (HIV) in a subject in need thereof, the method comprising administering to the subject the vaccine of claim 10.

15. A method of inducing an immune response against a human immunodeficiency virus in a subject in need thereof, the method comprising administering to the subject:
 (a) a first vaccine comprising one or more recombinant Ad26 adenovirus vectors, encoding one or more of SEQ ID NOs: 1, 2, 3, 4, 5 and 18; and
 (b) a second vaccine comprising a poxvirus vector according to claim 1,
wherein the first vaccine is a priming vaccine and the second vaccine is a boosting vaccine, or wherein the second vaccine is a priming vaccine and the first vaccine is a boosting vaccine.

16. The method of claim 15, further comprising administering to the subject one or more isolated HIV antigenic polypeptides, at about the same time as the boosting vaccine, wherein the one or more HIV antigenic polypeptides comprise
 (i) a polypeptide comprising residues 30-708 of the amino acid sequence of SEQ ID NO: 7, or
 (ii) a polypeptide comprising residues 30-724 of SEQ ID NO: 36; or
 (iii) both polypeptides (i) and (ii),
 and wherein the one or more isolated HIV antigenic polypeptides is in the same composition as the boosting vaccine or in a composition separate from the boosting vaccine.

17. The method according to claim 14, wherein the subject is a subject that has been infected with HIV.

18. A method of inducing an immune response against a human immunodeficiency virus (HIV) in a subject in need thereof, the method comprising administering to the subject the vaccine combination of claim 11.

19. A method of inducing an immune response against a human immunodeficiency virus (HIV) in a subject in need thereof, the method comprising administering to the subject the vaccine combination of claim 12.

20. A method of inducing an immune response against a human immunodeficiency virus (HIV) in a subject in need thereof, the method comprising administering to the subject the vaccine combination of claim 13.

* * * * *

SEQUENCE LISTING

<160> NUMBER OF SEQ ID NOS: 46

<210> SEQ ID NO 1
<211> LENGTH: 500
<212> TYPE: PRT
<213> ORGANISM: Artificial Sequence
<220> FEATURE:

<223> OTHER INFORMATION: mos1Gag mosaic antigen sequence

<400> SEQUENCE: 1

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400
```

```
Ile Ala Lys Asn Cys Arg Ala Pro Arg Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
            435                 440                 445

Leu Gln Asn Arg Pro Glu Pro Thr Ala Pro Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln
            500

<210> SEQ ID NO 2
<211> LENGTH: 491
<212> TYPE: PRT
<213> ORGANISM: Artificial Sequence
<220> FEATURE:
<223> OTHER INFORMATION: mos2Gag mosaic antigen sequence

<400> SEQUENCE: 2

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255
```

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
            290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
            325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
            355                 360                 365

Ser Thr Ile Leu Met Gln Arg Ser Asn Phe Lys Gly Ser Lys Arg Ile
            370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
            405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
            435                 440                 445

Glu Pro Thr Ala Pro Pro Ala Glu Ser Phe Arg Phe Glu Glu Thr Thr
450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln
            485                 490

<210> SEQ ID NO 3
<211> LENGTH: 850
<212> TYPE: PRT
<213> ORGANISM: Artificial Sequence
<220> FEATURE:
<223> OTHER INFORMATION: mos1Pol mosaic antigen sequence

<400> SEQUENCE: 3

Met Ala Pro Ile Ser Pro Ile Glu Thr Val Pro Val Lys Leu Lys Pro
1               5                   10                  15

Gly Met Asp Gly Pro Arg Val Lys Gln Trp Pro Leu Thr Glu Glu Lys
            20                  25                  30

Ile Lys Ala Leu Thr Ala Ile Cys Glu Glu Met Glu Lys Glu Gly Lys
            35                  40                  45

Ile Thr Lys Ile Gly Pro Glu Asn Pro Tyr Asn Thr Pro Val Phe Ala
        50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
            85                  90                  95

Pro His Pro Ala Gly Leu Lys Lys Lys Lys Ser Val Thr Val Leu Ala
            100                 105                 110

Val Gly Asp Ala Tyr Phe Ser Val Pro Leu Asp Glu Gly Phe Arg Lys
            115                 120                 125

```
Tyr Thr Ala Phe Thr Ile Pro Ser Thr Asn Asn Glu Thr Pro Gly Ile
130                 135                 140

Arg Tyr Gln Tyr Asn Val Leu Pro Gln Gly Trp Lys Gly Ser Pro Ala
145                 150                 155                 160

Ile Phe Gln Cys Ser Met Thr Arg Ile Leu Glu Pro Phe Arg Ala Lys
                165                 170                 175

Asn Pro Glu Ile Val Ile Tyr Gln Tyr Met Ala Ala Leu Tyr Val Gly
                180                 185                 190

Ser Asp Leu Glu Ile Gly Gln His Arg Ala Lys Ile Glu Glu Leu Arg
            195                 200                 205

Glu His Leu Leu Lys Trp Gly Phe Thr Thr Pro Asp Lys Lys His Gln
210                 215                 220

Lys Glu Pro Pro Phe Leu Trp Met Gly Tyr Glu Leu His Pro Asp Lys
225                 230                 235                 240

Trp Thr Val Gln Pro Ile Gln Leu Pro Glu Lys Asp Ser Trp Thr Val
                245                 250                 255

Asn Asp Ile Gln Lys Leu Val Gly Lys Leu Asn Trp Ala Ser Gln Ile
                260                 265                 270

Tyr Pro Gly Ile Lys Val Arg Gln Leu Cys Lys Leu Leu Arg Gly Ala
            275                 280                 285

Lys Ala Leu Thr Asp Ile Val Pro Leu Thr Glu Glu Ala Glu Leu Glu
290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly His
                325                 330                 335

Asp Gln Trp Thr Tyr Gln Ile Tyr Gln Glu Pro Phe Lys Asn Leu Lys
                340                 345                 350

Thr Gly Lys Tyr Ala Lys Met Arg Thr Ala His Thr Asn Asp Val Lys
            355                 360                 365

Gln Leu Thr Glu Ala Val Gln Lys Ile Ala Met Glu Ser Ile Val Ile
370                 375                 380

Trp Gly Lys Thr Pro Lys Phe Arg Leu Pro Ile Gln Lys Glu Thr Trp
385                 390                 395                 400

Glu Thr Trp Trp Thr Asp Tyr Trp Gln Ala Thr Trp Ile Pro Glu Trp
                405                 410                 415

Glu Phe Val Asn Thr Pro Pro Leu Val Lys Leu Trp Tyr Gln Leu Glu
                420                 425                 430

Lys Asp Pro Ile Ala Gly Val Glu Thr Phe Tyr Val Ala Gly Ala Ala
            435                 440                 445

Asn Arg Glu Thr Lys Leu Gly Lys Ala Gly Tyr Val Thr Asp Arg Gly
450                 455                 460

Arg Gln Lys Ile Val Ser Leu Thr Glu Thr Thr Asn Gln Lys Thr Ala
465                 470                 475                 480

Leu Gln Ala Ile Tyr Leu Ala Leu Gln Asp Ser Gly Ser Glu Val Asn
                485                 490                 495

Ile Val Thr Ala Ser Gln Tyr Ala Leu Gly Ile Ile Gln Ala Gln Pro
                500                 505                 510

Asp Lys Ser Glu Ser Glu Leu Val Asn Gln Ile Ile Glu Gln Leu Ile
            515                 520                 525

Lys Lys Glu Arg Val Tyr Leu Ser Trp Val Pro Ala His Lys Gly Ile
530                 535                 540

Gly Gly Asn Glu Gln Val Asp Lys Leu Val Ser Ser Gly Ile Arg Lys
```

```
            545                 550                 555                 560
Val Leu Phe Leu Asp Gly Ile Asp Lys Ala Gln Glu Glu His Glu Lys
                565                 570                 575

Tyr His Ser Asn Trp Arg Ala Met Ala Ser Asp Phe Asn Leu Pro Pro
                580                 585                 590

Val Val Ala Lys Glu Ile Val Ala Ser Cys Asp Gln Cys Gln Leu Lys
                595                 600                 605

Gly Glu Ala Met His Gly Gln Val Asp Cys Ser Pro Gly Ile Trp Gln
                610                 615                 620

Leu Ala Cys Thr His Leu Glu Gly Lys Ile Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Ile Leu Lys Leu Ala Gly Arg Trp Pro Val
                660                 665                 670

Lys Val Ile His Thr Ala Asn Gly Ser Asn Phe Thr Ser Ala Ala Val
                675                 680                 685

Lys Ala Ala Cys Trp Trp Ala Gly Ile Gln Gln Glu Phe Gly Ile Pro
                690                 695                 700

Tyr Asn Pro Gln Ser Gln Gly Val Val Ala Ser Met Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
                740                 745                 750

Ile Gly Gly Tyr Ser Ala Gly Glu Arg Ile Ile Asp Ile Ile Ala Thr
                755                 760                 765

Asp Ile Gln Thr Lys Glu Leu Gln Lys Gln Ile Ile Lys Ile Gln Asn
                770                 775                 780

Phe Arg Val Tyr Tyr Arg Asp Ser Arg Asp Pro Ile Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Val Lys Ile Ile Lys Asp
                820                 825                 830

Tyr Gly Lys Gln Met Ala Gly Ala Asp Cys Val Ala Gly Arg Gln Asp
                835                 840                 845

Glu Asp
    850

<210> SEQ ID NO 4
<211> LENGTH: 850
<212> TYPE: PRT
<213> ORGANISM: Artificial Sequence
<220> FEATURE:
<223> OTHER INFORMATION: mos2Pol mosaic antigen sequence

<400> SEQUENCE: 4

Met Ala Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
                20                  25                  30

Ile Lys Ala Leu Val Glu Ile Cys Thr Glu Met Glu Lys Glu Gly Lys
            35                  40                  45

Ile Ser Lys Ile Gly Pro Glu Asn Pro Tyr Asn Thr Pro Ile Phe Ala
```

```
                50                  55                  60
Ile Lys Lys Lys Asp Ser Thr Lys Trp Arg Lys Leu Val Asp Phe Arg
 65                  70                  75                  80

Glu Leu Asn Lys Arg Thr Gln Asp Phe Trp Glu Val Gln Leu Gly Ile
                 85                  90                  95

Pro His Pro Ala Gly Leu Lys Lys Lys Ser Val Thr Val Leu Ala
                100                 105                 110

Val Gly Asp Ala Tyr Phe Ser Val Pro Leu Asp Glu Asp Phe Arg Lys
                115                 120                 125

Tyr Thr Ala Phe Thr Ile Pro Ser Ile Asn Asn Glu Thr Pro Gly Ile
                130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Ala Ala Leu Tyr Val Gly
                180                 185                 190

Ser Asp Leu Glu Ile Gly Gln His Arg Thr Lys Ile Glu Glu Leu Arg
                195                 200                 205

Gln His Leu Leu Arg Trp Gly Phe Thr Thr Pro Asp Lys Lys His Gln
                210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
                260                 265                 270

Tyr Ala Gly Ile Lys Val Lys Gln Leu Cys Lys Leu Leu Arg Gly Thr
                275                 280                 285

Lys Ala Leu Thr Glu Val Val Pro Leu Thr Glu Glu Ala Glu Leu Glu
                290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
                340                 345                 350

Thr Gly Lys Tyr Ala Arg Met Arg Gly Ala His Thr Asn Asp Val Lys
                355                 360                 365

Gln Leu Thr Glu Ala Val Gln Lys Ile Ala Thr Glu Ser Ile Val Ile
                370                 375                 380

Trp Gly Lys Thr Pro Lys Phe Lys Leu Pro Ile Gln Lys Glu Thr Trp
385                 390                 395                 400

Glu Ala Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
                420                 425                 430

Lys Glu Pro Ile Val Gly Ala Glu Thr Phe Tyr Val Ala Gly Ala Ala
                435                 440                 445

Asn Arg Glu Thr Lys Leu Gly Lys Ala Gly Tyr Val Thr Asp Arg Gly
                450                 455                 460

Arg Gln Lys Val Val Ser Leu Thr Asp Thr Thr Asn Gln Lys Thr Ala
465                 470                 475                 480
```

Leu Gln Ala Ile His Leu Ala Leu Gln Asp Ser Gly Leu Glu Val Asn
                485                 490                 495

Ile Val Thr Ala Ser Gln Tyr Ala Leu Gly Ile Ile Gln Ala Gln Pro
            500                 505                 510

Asp Lys Ser Glu Ser Glu Leu Val Ser Gln Ile Glu Gln Leu Ile
        515                 520                 525

Lys Lys Glu Lys Val Tyr Leu Ala Trp Val Pro Ala His Lys Gly Ile
530                 535                 540

Gly Gly Asn Glu Gln Val Asp Lys Leu Val Ser Arg Gly Ile Arg Lys
545                 550                 555                 560

Val Leu Phe Leu Asp Gly Ile Asp Lys Ala Gln Glu Glu His Glu Lys
                565                 570                 575

Tyr His Ser Asn Trp Arg Ala Met Ala Ser Glu Phe Asn Leu Pro Pro
            580                 585                 590

Ile Val Ala Lys Glu Ile Val Ala Ser Cys Asp Lys Cys Gln Leu Lys
        595                 600                 605

Gly Glu Ala Ile His Gly Gln Val Asp Cys Ser Pro Gly Ile Trp Gln
    610                 615                 620

Leu Ala Cys Thr His Leu Glu Gly Lys Val Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Leu Leu Lys Leu Ala Gly Arg Trp Pro Val
            660                 665                 670

Lys Thr Ile His Thr Ala Asn Gly Ser Asn Phe Thr Ser Ala Thr Val
        675                 680                 685

Lys Ala Ala Cys Trp Trp Ala Gly Ile Lys Gln Glu Phe Gly Ile Pro
    690                 695                 700

Tyr Asn Pro Gln Ser Gln Gly Val Val Ala Ser Ile Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Glu Tyr Ser Ala Gly Glu Arg Ile Val Asp Ile Ile Ala Ser
        755                 760                 765

Asp Ile Gln Thr Lys Glu Leu Gln Lys Gln Ile Thr Lys Ile Gln Asn
    770                 775                 780

Phe Arg Val Tyr Tyr Arg Asp Ser Arg Asp Pro Leu Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Ala Lys Ile Ile Arg Asp
            820                 825                 830

Tyr Gly Lys Gln Met Ala Gly Asp Asp Cys Val Ala Ser Arg Gln Asp
        835                 840                 845

Glu Asp
    850

<210> SEQ ID NO 5
<211> LENGTH: 685
<212> TYPE: PRT
<213> ORGANISM: Artificial Sequence
<220> FEATURE:

-continued

<223> OTHER INFORMATION: mos1Env mosaic antigen sequence

<400> SEQUENCE: 5

```
Met Arg Val

Trp Asn Asn Ser Thr Trp Asn Asn Thr Lys Arg Ser Asn Asp Thr Glu
            405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
            435                 440                 445

Arg Cys Ser Ser Asn Ile Thr Gly Leu Leu Leu Thr Arg Asp Gly Gly
            450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
            485                 490                 495

Glu Pro Leu Gly Val Ala Pro Thr Lys Ala Lys Arg Arg Val Val Gln
            500                 505                 510

Ser Glu Lys Ser Ala Val Gly Ile Gly Ala Val Phe Leu Gly Phe Leu
            515                 520                 525

Gly Ala Ala Gly Ser Thr Met Gly Ala Ala Ser Met Thr Leu Thr Val
            530                 535                 540

Gln Ala Arg Leu Leu Leu Ser Gly Ile Val Gln Gln Gln Asn Asn Leu
545                 550                 555                 560

Leu Arg Ala Ile Glu Ala Gln Gln His Leu Leu Gln Leu Thr Val Trp
            565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
            595                 600                 605

Cys Thr Thr Thr Val Pro Trp Asn Ala Ser Trp Ser Asn Lys Ser Leu
610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
            645                 650                 655

Gln Gln Glu Lys Asn Glu Gln Glu Leu Leu Glu Leu Asp Lys Trp Ala
            660                 665                 670

Ser Leu Trp Asn Trp Phe Asp Ile Ser Asn Trp Leu Trp
            675                 680                 685

<210> SEQ ID NO 6
<211> LENGTH: 684
<212> TYPE: PRT
<213> ORGANISM: Artificial Sequence
<220> FEATURE:
<223> OTHER INFORMATION: mos2Env mosaic antigen sequence

<400> SEQUENCE: 6

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30

Leu Trp Val Thr Val Tyr Tyr Gly Val Pro Val Trp Lys Glu Ala Lys
            35                  40                  45

Thr Thr Leu Phe Cys Ala Ser Asp Ala Lys Ala Tyr Glu Lys Glu Val
            50                  55                  60

His Asn Val Trp Ala Thr His Ala Cys Val Pro Thr Asp Pro Asn Pro
65                  70                  75                  80

```
Gln Glu Met Val Leu Glu Asn Val Thr Glu Asn Phe Asn Met Trp Lys
                85                  90                  95
Asn Asp Met Val Asp Gln Met His Glu Asp Ile Ile Arg Leu Trp Asp
            100                 105                 110
Gln Ser Leu Lys Pro Cys Val Lys Leu Thr Pro Leu Cys Val Thr Leu
        115                 120                 125
Glu Cys Arg Asn Val Arg Asn Val Ser Ser Asn Gly Thr Tyr Asn Ile
    130                 135                 140
Ile His Asn Glu Thr Tyr Lys Glu Met Lys Asn Cys Ser Phe Asn Ala
145                 150                 155                 160
Thr Thr Val Val Glu Asp Arg Lys Gln Lys Val His Ala Leu Phe Tyr
                165                 170                 175
Arg Leu Asp Ile Val Pro Leu Asp Glu Asn Asn Ser Ser Glu Lys Ser
            180                 185                 190
Ser Glu Asn Ser Ser Glu Tyr Tyr Arg Leu Ile Asn Cys Asn Thr Ser
        195                 200                 205
Ala Ile Thr Gln Ala Cys Pro Lys Val Ser Phe Asp Pro Ile Pro Ile
    210                 215                 220
His Tyr Cys Ala Pro Ala Gly Tyr Ala Ile Leu Lys Cys Asn Asn Lys
225                 230                 235                 240
Thr Phe Asn Gly Thr Gly Pro Cys Asn Asn Val Ser Thr Val Gln Cys
                245                 250                 255
Thr His Gly Ile Lys Pro Val Val Ser Thr Gln Leu Leu Asn Gly
            260                 265                 270
Ser Leu Ala Glu Glu Glu Ile Ile Ile Arg Ser Glu Asn Leu Thr Asn
        275                 280                 285
Asn Ala Lys Thr Ile Ile Val His Leu Asn Glu Thr Val Asn Ile Thr
    290                 295                 300
Cys Thr Arg Pro Asn Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Leu Ser Arg Asp Gly Trp Asn Lys Thr Leu Gln Gly
            340                 345                 350
Val Lys Lys Lys Leu Ala Glu His Phe Pro Asn Lys Thr Ile Asn Phe
        355                 360                 365
Thr Ser Ser Ser Gly Gly Asp Leu Glu Ile Thr Thr His Ser Phe Asn
    370                 375                 380
Cys Arg Gly Glu Phe Phe Tyr Cys Asn Thr Ser Gly Leu Phe Asn Gly
385                 390                 395                 400
Thr Tyr Met Pro Asn Gly Thr Asn Ser Asn Ser Ser Asn Ile Thr
                405                 410                 415
Leu Pro Cys Arg Ile Lys Gln Ile Ile Asn Met Trp Gln Glu Val Gly
            420                 425                 430
Arg Ala Met Tyr Ala Pro Pro Ile Ala Gly Asn Ile Thr Cys Arg Ser
        435                 440                 445
Asn Ile Thr Gly Leu Leu Leu Thr Arg Asp Gly Gly Ser Asn Asn Gly
    450                 455                 460
Val Pro Asn Asp Thr Glu Thr Phe Arg Pro Gly Gly Gly Asp Met Arg
465                 470                 475                 480
Asn Asn Trp Arg Ser Glu Leu Tyr Lys Tyr Lys Val Val Glu Val Lys
                485                 490                 495
Pro Leu Gly Val Ala Pro Thr Glu Ala Lys Arg Arg Val Val Glu Ser
```

```
                    500                 505                 510
Glu Lys Ser Ala Val Gly Ile Gly Ala Val Phe Leu Gly Ile Leu Gly
            515                 520                 525

Ala Ala Gly Ser Thr Met Gly Ala Ala Ser Ile Thr Leu Thr Val Gln
        530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
        595                 600                 605

Thr Thr Ala Val Pro Trp Asn Thr Ser Trp Ser Asn Lys Ser Gln Thr
    610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Ser Gln Asn Gln
                645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp
        675                 680

<210> SEQ ID NO 7
<211> LENGTH: 708
<212> TYPE: PRT
<213> ORGANISM: Artificial Sequence
<220> FEATURE:
<223> OTHER INFORMATION: stabilized clade C gp140 trimer: C97ZA012-
      gp140-foldon with cleavage mutations

<400> SEQUENCE: 7

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Gly Asn Met Trp Val Thr Val Tyr Tyr Gly Val Pro Val
        35                  40                  45

Trp Thr Asp Ala Lys Thr Thr Leu Phe Cys Ala Ser Asp Thr Lys Ala
    50                  55                  60

Tyr Asp Arg Glu Val His Asn Val Trp Ala Thr His Ala Cys Val Pro
65                  70                  75                  80

Thr Asp Pro Asn Pro Gln Glu Ile Val Leu Glu Asn Val Thr Glu Asn
                85                  90                  95

Phe Asn Met Trp Lys Asn Asp Met Val Asp Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu His Cys Thr Asn Ala Thr Phe Lys Asn Asn Val
    130                 135                 140

Thr Asn Asp Met Asn Lys Glu Ile Arg Asn Cys Ser Phe Asn Thr Thr
145                 150                 155                 160

Thr Glu Ile Arg Asp Lys Lys Gln Gln Gly Tyr Ala Leu Phe Tyr Arg
                165                 170                 175
```

-continued

Pro Asp Ile Val Leu Leu Lys Glu Asn Arg Asn Asn Ser Asn Asn Ser
        180                 185                 190

Glu Tyr Ile Leu Ile Asn Cys Asn Ala Ser Thr Ile Thr Gln Ala Cys
    195                 200                 205

Pro Lys Val Asn Phe Asp Pro Ile Pro Ile His Tyr Cys Ala Pro Ala
210                 215                 220

Gly Tyr Ala Ile Leu Lys Cys Asn Asn Lys Thr Phe Ser Gly Lys Gly
225                 230                 235                 240

Pro Cys Asn Asn Val Ser Thr Val Gln Cys Thr His Gly Ile Lys Pro
                245                 250                 255

Val Val Ser Thr Gln Leu Leu Leu Asn Gly Ser Leu Ala Glu Lys Glu
        260                 265                 270

Ile Ile Ile Arg Ser Glu Asn Leu Thr Asp Asn Val Lys Thr Ile Ile
        275                 280                 285

Val His Leu Asn Lys Ser Val Glu Ile Val Cys Thr Arg Pro Asn Asn
    290                 295                 300

Asn Thr Arg Lys Ser Met Arg Ile Gly Pro Gly Gln Thr Phe Tyr Ala
305                 310                 315                 320

Thr Gly Asp Ile Ile Gly Asp Ile Arg Gln Ala Tyr Cys Asn Ile Ser
                325                 330                 335

Gly Ser Lys Trp Asn Glu Thr Leu Lys Arg Val Lys Glu Lys Leu Gln
        340                 345                 350

Glu Asn Tyr Asn Asn Asn Lys Thr Ile Lys Phe Ala Pro Ser Ser Gly
    355                 360                 365

Gly Asp Leu Glu Ile Thr Thr His Ser Phe Asn Cys Arg Gly Glu Phe
370                 375                 380

Phe Tyr Cys Asn Thr Thr Arg Leu Phe Asn Asn Asn Ala Thr Glu Asp
385                 390                 395                 400

Glu Thr Ile Thr Leu Pro Cys Arg Ile Lys Gln Ile Ile Asn Met Trp
                405                 410                 415

Gln Gly Val Gly Arg Ala Met Tyr Ala Pro Pro Ile Ala Gly Asn Ile
        420                 425                 430

Thr Cys Lys Ser Asn Ile Thr Gly Leu Leu Leu Val Arg Asp Gly Gly
    435                 440                 445

Glu Asp Asn Lys Thr Glu Glu Ile Phe Arg Pro Gly Gly Gly Asn Met
450                 455                 460

Lys Asp Asn Trp Arg Ser Glu Leu Tyr Lys Tyr Lys Val Ile Glu Leu
465                 470                 475                 480

Lys Pro Leu Gly Ile Ala Pro Thr Gly Ala Lys Glu Arg Val Val Glu
                485                 490                 495

Arg Glu Glu Arg Ala Val Gly Ile Gly Ala Val Phe Leu Gly Phe Leu
        500                 505                 510

Gly Ala Ala Gly Ser Thr Met Gly Ala Ala Ser Leu Thr Leu Thr Val
    515                 520                 525

Gln Ala Arg Gln Leu Leu Ser Ser Ile Val Gln Gln Ser Asn Leu
530                 535                 540

Leu Arg Ala Ile Glu Ala Gln Gln His Met Leu Gln Leu Thr Val Trp
545                 550                 555                 560

Gly Ile Lys Gln Leu Gln Thr Arg Val Leu Ala Ile Glu Arg Tyr Leu
                565                 570                 575

Lys Asp Gln Gln Leu Leu Gly Ile Trp Gly Cys Ser Gly Lys Leu Ile
        580                 585                 590

Cys Thr Thr Asn Val Pro Trp Asn Ser Ser Trp Ser Asn Lys Ser Gln

```
                    595                 600                 605

Thr Asp Ile Trp Asn Asn Met Thr Trp Met Glu Trp Asp Arg Glu Ile
            610                 615                 620

Ser Asn Tyr Thr Asp Thr Ile Tyr Arg Leu Leu Glu Asp Ser Gln Thr
625                 630                 635                 640

Gln Gln Glu Lys Asn Glu Lys Asp Leu Leu Ala Leu Asp Ser Trp Lys
                645                 650                 655

Asn Leu Trp Ser Trp Phe Asp Ile Ser Asn Trp Leu Trp Tyr Ile Lys
            660                 665                 670

Ser Arg Ile Glu Gly Arg Gly Ser Gly Gly Tyr Ile Pro Glu Ala Pro
        675                 680                 685

Arg Asp Gly Gln Ala Tyr Val Arg Lys Asp Gly Glu Trp Val Leu Leu
690                 695                 700

Ser Thr Phe Leu
705

<210> SEQ ID NO 8
<211> LENGTH: 625
<212> TYPE: PRT
<213> ORGANISM: Artificial Sequence
<220> FEATURE:
<223> OTHER INFORMATION: C4 fragment: gp120-truncated gp41 without
      signal peptide and transmembrane domain

<400> SEQUENCE: 8

Met Gly Asn Leu Trp Val Thr Val Tyr Tyr Gly Val Pro Val Trp Lys
1               5                   10                  15

Asp Ala Lys Thr Thr Leu Phe Cys Ala Ser Asp Ala Lys Ala Tyr Glu
            20                  25                  30

Lys Glu Val His Asn Val Trp Ala Thr His Ala Cys Val Pro Thr Asp
        35                  40                  45

Pro Asn Pro Gln Glu Ile Val Leu Gly Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Ala Ser Leu Glu Pro Cys Val Lys Leu Thr Pro Leu Cys
                85                  90                  95

Val Thr Leu Asn Cys Arg Asn Val Arg Asn Val Ser Ser Asn Gly Thr
            100                 105                 110

Tyr Asn Ile Ile His Asn Glu Thr Tyr Lys Glu Met Lys Asn Cys Ser
        115                 120                 125

Phe Asn Ala Thr Thr Val Val Glu Asp Arg Lys Gln Lys Val His Ala
    130                 135                 140

Leu Phe Tyr Arg Leu Asp Ile Val Pro Leu Asp Glu Asn Asn Ser Ser
145                 150                 155                 160

Glu Lys Ser Ser Glu Asn Ser Ser Glu Tyr Tyr Arg Leu Ile Asn Cys
                165                 170                 175

Asn Thr Ser Ala Ile Thr Gln Ala Cys Pro Lys Val Ser Phe Asp Pro
            180                 185                 190

Ile Pro Ile His Tyr Cys Ala Pro Ala Gly Tyr Ala Ile Leu Lys Cys
        195                 200                 205

Asn Asn Lys Thr Phe Asn Gly Thr Gly Pro Cys Asn Asn Val Ser Thr
    210                 215                 220

Val Gln Cys Thr His Gly Ile Lys Pro Val Val Ser Thr Gln Leu Leu
225                 230                 235                 240
```

Leu Asn Gly Ser Leu Ala Glu Glu Ile Ile Arg Ser Glu Asn
            245                 250                 255

Leu Thr Asn Asn Ala Lys Thr Ile Ile Val His Leu Asn Glu Thr Val
        260                 265                 270

Asn Ile Thr Cys Thr Arg Pro Asn Asn Asn Thr Arg Lys Ser Ile Arg
    275                 280                 285

Ile Gly Pro Gly Gln Thr Phe Tyr Ala Thr Gly Asp Ile Ile Gly Asp
290                 295                 300

Ile Arg Gln Ala His Cys Asn Leu Ser Arg Asp Gly Trp Asn Lys Thr
305                 310                 315                 320

Leu Gln Gly Val Lys Lys Leu Ala Glu His Phe Pro Asn Lys Thr
            325                 330                 335

Ile Lys Phe Ala Pro His Ser Gly Gly Asp Leu Glu Ile Thr Thr His
            340                 345                 350

Thr Phe Asn Cys Arg Gly Glu Phe Phe Tyr Cys Asn Thr Ser Asn Leu
        355                 360                 365

Phe Asn Glu Ser Asn Ile Glu Arg Asn Asp Ser Ile Ile Thr Leu Pro
370                 375                 380

Cys Arg Ile Lys Gln Ile Ile Asn Met Trp Gln Glu Val Gly Arg Ala
385                 390                 395                 400

Ile Tyr Ala Pro Pro Ile Ala Gly Asn Ile Thr Cys Arg Ser Asn Ile
            405                 410                 415

Thr Gly Leu Leu Leu Thr Arg Asp Gly Gly Ser Asn Asn Gly Val Pro
            420                 425                 430

Asn Asp Thr Glu Thr Phe Arg Pro Gly Gly Gly Asp Met Arg Asn Asn
            435                 440                 445

Trp Arg Ser Glu Leu Tyr Lys Tyr Lys Val Val Glu Val Lys Pro Leu
450                 455                 460

Gly Val Ala Pro Thr Glu Ala Lys Arg Arg Val Val Glu Arg Glu Lys
465                 470                 475                 480

Arg Ala Val Gly Ile Gly Ala Val Phe Leu Gly Ile Leu Gly Ala Ala
            485                 490                 495

Gly Ser Thr Met Gly Ala Ala Ser Ile Thr Leu Thr Val Gln Ala Arg
            500                 505                 510

Gln Leu Leu Ser Gly Ile Val Gln Gln Gln Ser Asn Leu Leu Arg Ala
        515                 520                 525

Ile Glu Ala Gln Gln His Met Leu Gln Leu Thr Val Trp Gly Ile Lys
530                 535                 540

Gln Leu Gln Thr Arg Val Leu Ala Ile Glu Arg Tyr Leu Gln Asp Gln
545                 550                 555                 560

Gln Leu Leu Gly Leu Trp Gly Cys Ser Gly Lys Leu Ile Cys Thr Thr
            565                 570                 575

Ala Val Pro Trp Asn Thr Ser Trp Ser Asn Lys Ser Gln Thr Asp Ile
            580                 585                 590

Trp Asp Asn Met Thr Trp Met Gln Trp Asp Lys Glu Ile Gly Asn Tyr
        595                 600                 605

Thr Gly Glu Ile Tyr Arg Leu Leu Glu Glu Ser Gln Asn Gln Gln Glu
    610                 615                 620

Lys
625

<210> SEQ ID NO 9
<211> LENGTH: 29
<212> TYPE: PRT

```
<213> ORGANISM: Artificial Sequence
<220> FEATURE:
<223> OTHER INFORMATION: signal sequence

<400> SEQUENCE: 9

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val
            20                  25

<210> SEQ ID NO 10
<211> LENGTH: 29
<212> TYPE: PRT
<213> ORGANISM: Artificial Sequence
<220> FEATURE:
<223> OTHER INFORMATION: signal sequence

<400> SEQUENCE: 10

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala
            20                  25

<210> SEQ ID NO 11
<211> LENGTH: 29
<212> TYPE: PRT
<213> ORGANISM: Artificial Sequence
<220> FEATURE:
<223> OTHER INFORMATION: signal sequence

<400> SEQUENCE: 11

Met Arg Val Arg Gly Ile Gln Arg Asn Trp Pro Gln Trp Trp Ile Trp
1               5                   10                  15

Gly Ile Leu Gly Phe Trp Met Ile Ile Ile Cys Arg Val
            20                  25

<210> SEQ ID NO 12
<211> LENGTH: 29
<212> TYPE: PRT
<213> ORGANISM: Artificial Sequence
<220> FEATURE:
<223> OTHER INFORMATION: signal sequence

<400> SEQUENCE: 12

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala
            20                  25

<210> SEQ ID NO 13
<211> LENGTH: 22
<212> TYPE: PRT
<213> ORGANISM: Artificial Sequence
<220> FEATURE:
<223> OTHER INFORMATION: transmembrane domain

<400> SEQUENCE: 13

Ile Phe Ile Met Ile Val Gly Gly Leu Ile Gly Leu Arg Ile Ile Phe
1               5                   10                  15

Ala Val Leu Ser Ile Val
            20

<210> SEQ ID NO 14
<211> LENGTH: 7
```

```
<212> TYPE: PRT
<213> ORGANISM: Artificial Sequence
<220> FEATURE:
<223> OTHER INFORMATION: truncated cytoplasmic region

<400> SEQUENCE: 14

Asn Arg Val Arg Gln Gly Tyr
1               5

<210> SEQ ID NO 15
<211> LENGTH: 32
<212> TYPE: PRT
<213> ORGANISM: Artificial Sequence
<220> FEATURE:
<223> OTHER INFORMATION: GCN4 trimerization domain

<400> SEQUENCE: 15

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: foldon trimerization domain

<400> SEQUENCE: 16

Gly Ser Gly Gly Tyr Ile Pro Glu Ala Pro Arg Asp Gly Gln Ala Tyr
1               5                   10                  15

Val Arg Lys Asp Gly Glu Trp Val Leu Leu Ser Thr Phe Leu
            20                  25                  30

<210> SEQ ID NO 17
<211> LENGTH: 862
<212> TYPE: PRT
<213> ORGANISM: Artificial Sequence
<220> FEATURE:
<223> OTHER INFORMATION: C4 sequence

<400> SEQUENCE: 17

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val Met Gly Asn
            20                  25                  30

Leu Trp Val Thr Val Tyr Tyr Gly Val Pro Val Trp Lys Asp Ala Lys
            35                  40                  45

Thr Thr Leu Phe Cys Ala Ser Asp Ala Lys Ala Tyr Glu Lys Glu Val
            50                  55                  60

His Asn Val Trp Ala Thr His Ala Cys Val Pro Thr Asp Pro Asn Pro
65              70                  75                  80

Gln Glu Ile Val Leu Gly Asn Val Thr Glu Asn Phe Asn Met Trp Lys
            85                  90                  95

Asn Asp Met Val Asp Gln Met His Glu Asp Ile Ile Ser Leu Trp Asp
            100                 105                 110

Ala Ser Leu Glu Pro Cys Val Lys Leu Thr Pro Leu Cys Val Thr Leu
            115                 120                 125

Asn Cys Arg Asn Val Arg Asn Val Ser Ser Asn Gly Thr Tyr Asn Ile
            130                 135                 140
```

```
Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Lys Phe
        355                 360                 365

Ala Pro His Ser Gly Gly Asp Leu Glu Ile Thr Thr His Thr Phe Asn
    370                 375                 380

Cys Arg Gly Glu Phe Phe Tyr Cys Asn Thr Ser Asn Leu Phe Asn Glu
385                 390                 395                 400

Ser Asn Ile Glu Arg Asn Asp Ser Ile Ile Thr Leu Pro Cys Arg Ile
                405                 410                 415

Lys Gln Ile Ile Asn Met Trp Gln Glu Val Gly Arg Ala Ile Tyr Ala
            420                 425                 430

Pro Pro Ile Ala Gly Asn Ile Thr Cys Arg Ser Asn Ile Thr Gly Leu
        435                 440                 445

Leu Leu Thr Arg Asp Gly Gly Ser Asn Asn Gly Val Pro Asn Asp Thr
    450                 455                 460

Glu Thr Phe Arg Pro Gly Gly Gly Asp Met Arg Asn Asn Trp Arg Ser
465                 470                 475                 480

Glu Leu Tyr Lys Tyr Lys Val Val Glu Val Lys Pro Leu Gly Val Ala
                485                 490                 495

Pro Thr Glu Ala Lys Arg Arg Val Val Glu Arg Glu Lys Arg Ala Val
            500                 505                 510

Gly Ile Gly Ala Val Phe Leu Gly Ile Leu Gly Ala Ala Gly Ser Thr
        515                 520                 525

Met Gly Ala Ala Ser Ile Thr Leu Thr Val Gln Ala Arg Gln Leu Leu
    530                 535                 540

Ser Gly Ile Val Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
```

```
                    565                 570                 575
Thr Arg Val Leu Ala Ile Glu Arg Tyr Leu Gln Asp Gln Gln Leu Leu
                580                 585                 590

Gly Leu Trp Gly Cys Ser Gly Lys Leu Ile Cys Thr Thr Ala Val Pro
                595                 600                 605

Trp Asn Thr Ser Trp Ser Asn Lys Ser Gln Thr Asp Ile Trp Asp Asn
            610                 615                 620

Met Thr Trp Met Gln Trp Asp Lys Glu Ile Gly Asn Tyr Thr Gly Glu
625                 630                 635                 640

Ile Tyr Arg Leu Leu Glu Glu Ser Gln Asn Gln Gln Glu Lys Asn Glu
                645                 650                 655

Lys Asp Leu Leu Ala Leu Asp Ser Trp Asn Asn Leu Trp Asn Trp Phe
            660                 665                 670

Ser Ile Ser Lys Trp Leu Trp Tyr Ile Lys Ile Phe Ile Met Ile Val
        675                 680                 685

Gly Gly Leu Ile Gly Leu Arg Ile Ile Phe Ala Val Leu Ser Ile Val
    690                 695                 700

Asn Arg Val Arg Gln Gly Tyr Ser Pro Leu Ser Leu Gln Thr Leu Thr
705                 710                 715                 720

Gln Asn Pro Gly Gly Leu Asp Arg Leu Gly Arg Ile Glu Glu Glu Gly
                725                 730                 735

Gly Glu Gln Asp Lys Asp Arg Ser Ile Arg Leu Val Asn Gly Phe Phe
            740                 745                 750

Ala Leu Phe Trp Asp Asp Leu Arg Ser Leu Cys Leu Phe Ser Tyr His
        755                 760                 765

Arg Leu Arg Asp Phe Ile Leu Ile Val Ala Arg Ala Val Glu Leu Leu
    770                 775                 780

Gly Arg Ser Ser Leu Arg Gly Leu Gln Arg Gly Trp Glu Ile Leu Lys
785                 790                 795                 800

Tyr Leu Gly Ser Leu Leu Gln Tyr Trp Gly Leu Glu Leu Lys Lys Ser
                805                 810                 815

Ala Ile Asn Leu Leu Asp Thr Ile Ala Ile Ala Val Ala Glu Gly Thr
            820                 825                 830

Asp Arg Ile Ile Glu Leu Ile Gln Arg Ile Cys Arg Ala Ile Cys Asn
        835                 840                 845

Ile Pro Arg Arg Ile Arg Gln Gly Phe Glu Ala Ala Leu Gln
    850                 855                 860

<210> SEQ ID NO 18
<211> LENGTH: 711
<212> TYPE: PRT
<213> ORGANISM: Artificial Sequence
<220> FEATURE:
<223> OTHER INFORMATION: C4D7 sequence

<400> SEQUENCE: 18

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val Met Gly Asn
                20                  25                  30

Leu Trp Val Thr Val Tyr Tyr Gly Val Pro Val Trp Lys Asp Ala Lys
            35                  40                  45

Thr Thr Leu Phe Cys Ala Ser Asp Ala Lys Ala Tyr Glu Lys Glu Val
        50                  55                  60

His Asn Val Trp Ala Thr His Ala Cys Val Pro Thr Asp Pro Asn Pro
```

```
                65                  70                  75                  80
            Gln Glu Ile Val Leu Gly Asn Val Thr Glu Asn Phe Asn Met Trp Lys
                            85                  90                  95

Asn Asp Met Val Asp Gln Met His Glu Asp Ile Ile Ser Leu Trp Asp
                            100                 105                 110

Ala Ser Leu Glu Pro Cys Val Lys Leu Thr Pro Leu Cys Val Thr Leu
                            115                 120                 125

Asn Cys Arg Asn Val Arg Asn Val Ser Ser Asn Gly Thr Tyr Asn Ile
                            130                 135                 140

Ile His Asn Glu Thr Tyr Lys Glu Met Lys Asn Cys Ser Phe Asn Ala
            145                 150                 155                 160

Thr Thr Val Val Glu Asp Arg Lys Gln Lys Val His Ala Leu Phe Tyr
                            165                 170                 175

Arg Leu Asp Ile Val Pro Leu Asp Glu Asn Asn Ser Ser Glu Lys Ser
                            180                 185                 190

Ser Glu Asn Ser Ser Glu Tyr Tyr Arg Leu Ile Asn Cys Asn Thr Ser
                            195                 200                 205

Ala Ile Thr Gln Ala Cys Pro Lys Val Ser Phe Asp Pro Ile Pro Ile
                            210                 215                 220

His Tyr Cys Ala Pro Ala Gly Tyr Ala Ile Leu Lys Cys Asn Asn Lys
            225                 230                 235                 240

Thr Phe Asn Gly Thr Gly Pro Cys Asn Asn Val Ser Thr Val Gln Cys
                            245                 250                 255

Thr His Gly Ile Lys Pro Val Val Ser Thr Gln Leu Leu Leu Asn Gly
                            260                 265                 270

Ser Leu Ala Glu Glu Glu Ile Ile Arg Ser Glu Asn Leu Thr Asn
                            275                 280                 285

Asn Ala Lys Thr Ile Ile Val His Leu Asn Glu Thr Val Asn Ile Thr
                            290                 295                 300

Cys Thr Arg Pro Asn Asn Asn Thr Arg Lys Ser Ile Arg Ile Gly Pro
            305                 310                 315                 320

Gly Gln Thr Phe Tyr Ala Thr Gly Asp Ile Ile Gly Asp Ile Arg Gln
                            325                 330                 335

Ala His Cys Asn Leu Ser Arg Asp Gly Trp Asn Lys Thr Leu Gln Gly
                            340                 345                 350

Val Lys Lys Lys Leu Ala Glu His Phe Pro Asn Lys Thr Ile Lys Phe
                            355                 360                 365

Ala Pro His Ser Gly Gly Asp Leu Glu Ile Thr Thr His Thr Phe Asn
                            370                 375                 380

Cys Arg Gly Glu Phe Phe Tyr Cys Asn Thr Ser Asn Leu Phe Asn Glu
            385                 390                 395                 400

Ser Asn Ile Glu Arg Asn Asp Ser Ile Ile Thr Leu Pro Cys Arg Ile
                            405                 410                 415

Lys Gln Ile Ile Asn Met Trp Gln Glu Val Gly Arg Ala Ile Tyr Ala
                            420                 425                 430

Pro Pro Ile Ala Gly Asn Ile Thr Cys Arg Ser Asn Ile Thr Gly Leu
                            435                 440                 445

Leu Leu Thr Arg Asp Gly Gly Ser Asn Asn Gly Val Pro Asn Asp Thr
                            450                 455                 460

Glu Thr Phe Arg Pro Gly Gly Gly Asp Met Arg Asn Asn Trp Arg Ser
            465                 470                 475                 480

Glu Leu Tyr Lys Tyr Lys Val Val Glu Val Lys Pro Leu Gly Val Ala
                            485                 490                 495
```

```
Pro Thr Glu Ala Lys Arg Arg Val Val Glu Arg Glu Lys Arg Ala Val
            500                 505                 510

Gly Ile Gly Ala Val Phe Leu Gly Ile Leu Gly Ala Ala Gly Ser Thr
        515                 520                 525

Met Gly Ala Ala Ser Ile Thr Leu Thr Val Gln Ala Arg Gln Leu Leu
    530                 535                 540

Ser Gly Ile Val Gln Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
            565                 570                 575

Thr Arg Val Leu Ala Ile Glu Arg Tyr Leu Gln Asp Gln Gln Leu Leu
        580                 585                 590

Gly Leu Trp Gly Cys Ser Gly Lys Leu Ile Cys Thr Thr Ala Val Pro
    595                 600                 605

Trp Asn Thr Ser Trp Ser Asn Lys Ser Gln Thr Asp Ile Trp Asp Asn
    610                 615                 620

Met Thr Trp Met Gln Trp Asp Lys Glu Ile Gly Asn Tyr Thr Gly Glu
625                 630                 635                 640

Ile Tyr Arg Leu Leu Glu Glu Ser Gln Asn Gln Gln Glu Lys Asn Glu
            645                 650                 655

Lys Asp Leu Leu Ala Leu Asp Ser Trp Asn Asn Leu Trp Asn Trp Phe
        660                 665                 670

Ser Ile Ser Lys Trp Leu Trp Tyr Ile Lys Ile Phe Ile Met Ile Val
    675                 680                 685

Gly Gly Leu Ile Gly Leu Arg Ile Ile Phe Ala Val Leu Ser Ile Val
    690                 695                 700

Asn Arg Val Arg Gln Gly Tyr
705                 710

<210> SEQ ID NO 19
<211> LENGTH: 704
<212> TYPE: PRT
<213> ORGANISM: Artificial Sequence
<220> FEATURE:
<223> OTHER INFORMATION: sC4 sequence

<400> SEQUENCE: 19

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val Met Gly Asn
            20                  25                  30

Leu Trp Val Thr Val Tyr Tyr Gly Val Pro Val Trp Lys Asp Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
            85                  90                  95

Asn Asp Met Val Asp Gln Met His Glu Asp Ile Ile Ser Leu Trp Asp
            100                 105                 110

Ala Ser Leu Glu Pro Cys Val Lys Leu Thr Pro Leu Cys Val Thr Leu
        115                 120                 125

Asn Cys Arg Asn Val Arg Asn Val Ser Ser Asn Gly Thr Tyr Asn Ile
    130                 135                 140
```

```
Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
            165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
            195                 200                 205

Ala Ile Thr Gln Ala Cys Pro Lys Val Ser Phe Asp Pro Ile Pro Ile
        210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
            245                 250                 255

Thr His Gly Ile Lys Pro Val Val Ser Thr Gln Leu Leu Leu Asn Gly
            260                 265                 270

Ser Leu Ala Glu Glu Glu Ile Ile Arg Ser Glu Asn Leu Thr Asn
            275                 280                 285

Asn Ala Lys Thr Ile Ile Val His Leu Asn Glu Thr Val Asn Ile Thr
        290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Lys Phe
        355                 360                 365

Ala Pro His Ser Gly Gly Asp Leu Glu Ile Thr Thr His Thr Phe Asn
        370                 375                 380

Cys Arg Gly Glu Phe Phe Tyr Cys Asn Thr Ser Asn Leu Phe Asn Glu
385                 390                 395                 400

Ser Asn Ile Glu Arg Asn Asp Ser Ile Ile Thr Leu Pro Cys Arg Ile
                405                 410                 415

Lys Gln Ile Ile Asn Met Trp Gln Glu Val Gly Arg Ala Ile Tyr Ala
                420                 425                 430

Pro Pro Ile Ala Gly Asn Ile Thr Cys Arg Ser Asn Ile Thr Gly Leu
        435                 440                 445

Leu Leu Thr Arg Asp Gly Gly Ser Asn Asn Gly Val Pro Asn Asp Thr
        450                 455                 460

Glu Thr Phe Arg Pro Gly Gly Gly Asp Met Arg Asn Asn Trp Arg Ser
465                 470                 475                 480

Glu Leu Tyr Lys Tyr Lys Val Val Glu Val Lys Pro Leu Gly Val Ala
                485                 490                 495

Pro Thr Glu Ala Lys Arg Arg Val Val Glu Arg Glu Glu Arg Ala Val
            500                 505                 510

Gly Ile Gly Ala Val Phe Leu Gly Ile Leu Gly Ala Ala Gly Ser Thr
        515                 520                 525

Met Gly Ala Ala Ser Ile Thr Leu Thr Val Gln Ala Arg Gln Leu Leu
        530                 535                 540

Ser Gly Ile Val Gln Gln Ser Asn Leu Leu Arg Ala Ile Glu Ala
545                 550                 555                 560
```

```
Gln Gln His Met Leu Gln Leu Thr Val Trp Gly Ile Lys Gln Leu Gln
            565                 570                 575

Thr Arg Val Leu Ala Ile Glu Arg Tyr Leu Gln Asp Gln Gln Leu Leu
        580                 585                 590

Gly Leu Trp Gly Cys Ser Gly Lys Leu Ile Cys Thr Thr Ala Val Pro
    595                 600                 605

Trp Asn Thr Ser Trp Ser Asn Lys Ser Gln Thr Asp Ile Trp Asp Asn
    610                 615                 620

Met Thr Trp Met Gln Trp Asp Lys Glu Ile Gly Asn Tyr Thr Gly Glu
625                 630                 635                 640

Ile Tyr Arg Leu Leu Glu Glu Ser Gln Asn Gln Gln Glu Lys Met Lys
                645                 650                 655

Gln Ile Glu Asp Lys Ile Glu Glu Ile Leu Ser Lys Ile Tyr His Ile
            660                 665                 670

Glu Asn Glu Ile Ala Arg Ile Lys Lys Leu Ile Gly Glu Val Gly Ser
        675                 680                 685

Gly Ala Pro Thr Lys Ala Lys Arg Arg Val Val Gln Arg Glu Lys Arg
    690                 695                 700

<210> SEQ ID NO 20
<211> LENGTH: 4050
<212> TYPE: DNA
<213> ORGANISM: Artificial Sequence
<220> FEATURE:
<223> OTHER INFORMATION: nucleotide sequence encoding mos1GagPol

<400> SEQUENCE: 20
atgggagcca gagccagcgt gctgtccgga ggggagctgg accgctggga gaagatcagg      60
ctgaggcctg gagggaagaa gaagtacagg ctgaagcaca tcgtgtgggc cagcagagag     120
ctggaacggt ttgccgtgaa ccctggcctg ctggaaacca gcgagggctg taggcagatt     180
ctgggacagc tgcagcccag cctgcagaca ggcagcgagg aactgcggag cctgtacaac     240
accgtggcca ccctgtactg cgtgcaccag cggatcgaga tcaaggacac caaagaagcc     300
ctggaaaaga tcgaggaaga gcagaacaag agcaagaaga agcccagca ggctgccgct      360 gacacaggca acagcagcca ggtgtcccag aactacccca tcgtgcagaa catccaggga     420
cagatggtgc accaggccat cagccctcgg accctgaacg cctgggtgaa ggtggtggag     480
gaaaaggcct tcagccctga ggtgatcccc atgttctctg ccctgagcga gggagccaca     540
ccccaggacc tgaacaccat gctgaacacc gtgggagggc accaggctgc catgcagatg     600
ctgaaagaga caatcaacga ggaagctgcc gagtgggaca gggtccaccc agtgcacgct     660
ggacctatcg ctcctggcca gatgagagag cccagaggca gcgatattgc tggcaccacc     720
tccacactgc aggaacagat cggctggatg accaacaacc ctcccatccc tgtgggagag     780
atctacaagc ggtggatcat tctgggactg aacaagatcg tgcggatgta cagccctgtg     840
agcatcctgg acatcaggca gggacccaaa gagcccttca gggactacgt ggaccggttc     900
tacaagaccc tgagagccga gcaggccagc caggacgtga gaactggat gaccgagaca     960 ctgctggtgc agaacgccaa ccctgactgc aagaccatcc tgaaagccct gggacctgct    1020
gccaccctgg aagagatgat gacagcctgc caggagtgg aggacctgg ccacaaggcc     1080 agggtgctgg ccgaggccat gagccaggtg accaactctg ccaccatcat gatgcagaga    1140
ggcaacttcc ggaaccagag aaagaccgtg aagtgcttca actgtggcaa agagggacac    1200
attgccaaga actgcagggc tcccaggaag aaaggctgct ggaagtgcgg aaaagaaggc    1260
```

```
caccagatga aggactgcac cgagaggcag gccaacttcc tgggcaagat ctggcctagc    1320
aacaagggca ggcctggcaa cttcctgcag aacagaccog agcccaccgc tcctcccgag    1380
gaaagcttcc ggtttggcga ggaaaccacc acccctagcc agaagcagga acccatcgac    1440
aaagagatgt accctctggc cagcctgaag agctgttcg gcaacgaccc cagcagccag     1500
atggctccca tcagcccaat cgagacagtg cctgtgaagc tgaagcctgg catggacgga    1560
cccagggtga agcagtggcc tctgaccgag gaaaagatca agccctgac agccatctgc     1620 gaggaaatgg aaaagagggg caagatcacc aagatcggac ccgagaaccc ctacaacacc    1680
cctgtgttcg ccatcaagaa gaaagacagc accaagtgga ggaaactggt ggacttcaga    1740
gagctgaaca agcggaccca ggacttctgg gaggtgcagc tgggcatccc tcaccctgct    1800
ggcctgaaga aaaagaaaag cgtgaccgtg ctggctgtgg agatgcctac cttcagcgtg    1860
cctctggacg agggcttccg gaagtacaca gccttcacca tccccagcac caacaacgag    1920
acacctggca tcagatacca gtacaacgtg ctgcctcagg ctggaaagg cagccctgcc     1980 atcttccagt gcagcatgac cagaatcctg aacccttca gagccaagaa ccctgagatc     2040
gtgatctacc agtatatggc tgccctctac gtgggcagcg acctggaaat cggacagcac    2100
agagccaaaa tcgaagaact ccgcgagcac ctgctgaagt ggggattcac caccectgac    2160 aagaagcacc agaaagagcc tcccttcctg tggatgggct acgagctgca ccctgacaag    2220
tggaccgtgc agcccatcca gctgccagag aaggactcct ggaccgtgaa cgacatccag    2280
aaactggtcg gcaagctgaa ctgggccagc cagatctacc ctggcatcaa agtcagacag    2340
ctgtgtaagc tgctgagggg agccaaagca ctgaccgaca tcgtgcctct gacagaagaa    2400
gccgagctgg aactggccga gaacagagag atcctgaaag aacccgtgca cggagtgtac    2460 tacgaccect ccaaggacct gattgccgag atccagaaac agggacacga ccagtggacc    2520
taccagatct atcaggaacc tttcaagaac ctgaaaacag gcaagtacgc caagatgcgg    2580
acagcccaca ccaacgacgt gaagcagctg accgaagccg tgcagaaaat cgccatggaa    2640
agcatcgtga tctggggaaa gacacccaag ttcaggctgc ccatccagaa agagacatgg    2700
gaaacctggt ggaccgacta ctggcaggcc acctggattc ccgagtggga gttcgtgaac    2760
accccacccc tggtgaagct gtggtatcag ctggaaaagg accctatcgc tggcgtggag    2820
acattctacg tggctggagc tgccaacaga gagacaaagc tgggcaaggc tggctacgtg    2880
accgacagag gcagacagaa aatcgtgagc ctgaccgaaa ccaccaacca gaaaacagcc    2940
ctgcaggcca tctatctggc actgcaggac agcggaagcg aggtgaacat cgtgacagcc    3000
agccagtatg ccctgggcat catccaggcc agcctgaca agagcgagag cgagctggtg    3060
aaccagatca tcgagcagct gatcaagaaa gaacgggtgt acctgagctg ggtgccagcc    3120
cacaagggca tcggagggaa cgagcaggtg gacaagctgg tgtccagcgg aatccggaag    3180
gtgctgttcc tggacggcat cgataaagcc caggaagagc acgagaagta ccacagcaat    3240
tggagagcca tggccagcga cttcaacctg cctcccgtgg tggccaaaga aatcgtggcc    3300
agctgcgacc agtgccagct gaaaggcgag gccatgcacg gacaggtgga ctgctcccct    3360
ggcatctggc agctggcatg cacccacctg gaaggcaaga tcattctggt ggccgtgcac    3420
gtggccagcg gatacatcga agccgaagtg atccctgccg agacagggca ggaaacagcc    3480
tacttcatcc tgaagctggc tggcagatgg cctgtgaagg tgatccacac agccaacggc    3540
agcaacttca cctctgctgc cgtgaaggct gcctgttggt gggctggcat tcagcaggaa    3600
tttggcatcc cctacaatcc ccagtctcag ggagtggtgg ccagcatgaa caaagagctg    3660
```

-continued

```
aagaagatca tcggacaggt cagggatcag gccgagcacc tgaaaactgc cgtccagatg    3720
gccgtgttca tccacaactt caagcggaag ggagggatcg gagggtactc tgctggcgag    3780
cggatcatcg acatcattgc caccgatatc cagaccaaag agctgcagaa acagatcatc    3840
aagatccaga acttcagggt gtactacagg gacagcaggg accccatctg aagggacct    3900 gccaagctgc tgtggaaagg cgaaggagcc gtcgtcatcc aggacaacag cgacatcaag    3960
gtggtgccca gacggaaggt gaaaatcatc aaggactacg gcaaacagat ggctggagcc    4020
gactgtgtcg ctggcaggca ggacgaggac                                      4050
```

<210> SEQ ID NO 21
<211> LENGTH: 4023
<212> TYPE: DNA
<213> ORGANISM: Artificial Sequence
<220> FEATURE:
<223> OTHER INFORMATION: nucleotide sequence encoding mos2GagPol

<400> SEQUENCE: 21

```
atgggagcca gagccagcat cctgcgagga gggaagctgg acaagtggga aagatcagg    60 ctgaggcctg agggaagaa acactacatg ctgaagcacc tggtctgggc agcagagag     120 ctggaacggt ttgccctcaa tcctggcctg ctggaaacca gcgagggctg caagcagatc    180
atcaagcagc tgcagcctgc cctgcagaca ggcaccgagg aactgcggag cctgttcaac    240
accgtggcca ccctgtactg cgtgcatgcc gagatcgaag tgagggacac caaagaagcc    300
ctggacaaga tcgaggaaga gcagaacaag agccagcaga aacccagca ggccaaagaa     360 gccgacggca aggtctccca gaactacccc atcgtgcaga acctgcaggg acagatggtg    420
caccagccca tcagccctcg gacactgaat gcctgggtga aggtgatcga ggaaaaggcc    480
ttcagccctg aggtgatccc catgttcaca gccctgagcg agggagccac accccaggac    540
ctgaacacca tgctgaacac cgtgggaggg caccaggctg ccatgcagat gctgaaggac    600
accatcaacg aggaagctgc cgagtgggac aggctgcacc ctgtgcacgc tggacctgtg    660
gctcctggcc agatgagaga gcccagaggc agcgatattg ctggcaccac ctccaatctg    720
caggaacaga tcgcctggat gaccagcaac cctcccatcc ctgtgggaga catctacaag    780
cggtggatca tcctgggact gaacaagatc gtgcggatgt acagccctac ctccatcctg    840
gacatcaagc agggacccaa agagccttc agggactacg tggaccggtt cttcaagacc    900
ctgagagccg agcaggccac ccaggacgtg aagaactgga tgaccgacac cctgctggtg    960
cagaacgcca cccctgactg caagaccatc ctgagagccc tggacctgg agccaccctg    1020 gaagagatga tgacagcctg ccagggagtg gaggaccct ctcacaaggc tagggtgctg    1080
gccgaggcca tgagccagac caacagcacc atcctgatgc agcggagcaa cttcaagggc    1140
agcaagcgga tcgtgaagtg cttcaactgt ggcaaagagg gacacattgc cagaaactgt    1200
agggcaccca ggaagaaagg ctgctggaag tgcggaaaag aaggccacca gatgaaggac    1260
tgcaccgaga ggcaggccaa cttcctgggc aagatctggc ctagccacaa gggcagacct    1320
ggcaacttcc tgcagagcag acccgagccc accgctcctc cagccgagag cttccggttc    1380
gaggaaacca cccctgctcc caagcaggaa cctaaggaca gagagcctct gaccagcctg    1440
agaagcctgt tcggcagcga ccctctgagc cagatggctc ccatctcccc tatcgagaca    1500
gtgcctgtga agctgaagcc tggcatggac ggacccaagg tgaaacagtg gcctctgacc    1560
gaggaaaaga tcaaagccct ggtggagatc tgtaccgaga tggaaaaaga gggcaagatc    1620
```

```
agcaagatcg acccgagaa ccctacaac accctatct tcgccatcaa gaagaaagac   1680
agcaccaagt ggaggaaact ggtggacttc agagagctga acaagcggac ccaggacttc   1740
tgggaggtgc agctgggcat ccctcaccct gctggcctga gaaaaagaa aagcgtgacc   1800 gtgctggccg tgggagatgc ctacttcagc gtgcctctgg acgaggactt cagaaagtac   1860
acagccttca ccatccccag catcaacaac gagacacctg gcatcagata ccagtacaac   1920
gtgctgcctc agggatggaa gggctctcct gcaatcttcc agagcagcat gaccaagatc   1980
ctggaaccct tccggaagca gaaccctgac atcgtgatct accagtacat ggcagccctg   2040
tacgtcggca gcgacctgga atcggacag caccggacca agatcgaaga actcaggcag   2100
cacctgctgc ggtggggatt caccacccct gacaagaagc accagaaaga gcctcccttc   2160
ctgtggatgg gctacgagct gcacccagac aagtggaccg tgcagcccat cgtgctgcct   2220
gagaaggact cctggaccgt gaacgacatc cagaaactgg tcggcaagct gaactgggcc   2280
agccagatct acgctggcat caaagtgaag cagctgtgta agctcctgag aggcaccaaa   2340
gccctgaccg aggtggtgcc actgacagag gaagccgagc tggaactggc cgagaacaga   2400
gagatcctga agaaacccgt gcacggagtg tactacgacc ccagcaagga cctgattgcc   2460
gagatccaga gcagggaca gggacagtgg acctaccaga tctaccagga acccttcaag   2520
aacctgaaaa caggcaagta cgccaggatg aggggagccc acaccaacga cgtcaaacag   2580
ctgaccgaag ccgtgcagaa gatcgccacc gagagcatcg tgatttgggg aaagacaccc   2640
aagttcaagc tgcccatcca gaaagagaca tgggaggcct ggtggaccga gtactggcag   2700
gccacctgga ttcccgagtg ggagttcgtg aacacccac ccctggtgaa gctgtggtat   2760
cagctggaaa agaaccat cgtgggagcc gagacattct acgtggctgg agctgccaac   2820
agagagacaa agctgggcaa ggctggctac gtgaccgaca gaggcaggca gaaagtggtg   2880
tccctgaccc gataccacca ccagaaaaca gccctgcagg ccatccacct ggctctgcag   2940
gactctggcc tggaagtgaa catcgtgaca gccagccagt atgccctggg catcattcag   3000
gcacagcctg acaagagcga gagcgagctg gtgtctcaga tcattgagca gctgatcaag   3060
aaagaaaagg tgtacctggc ctgggtgcca gcccacaagg ggatcggagg aacgagcag   3120 gtggacaagc tggtgtccag gggcatccgg aaggtgctgt ttctggacgg catcgacaaa   3180
gcccaggaag agcacgagaa gtaccacagc aattggagag ccatggccag cgagttcaac   3240
ctgcctccca tcgtggccaa agaaatcgtg gcctcttgcg acaagtgcca gctgaaaggc   3300
gaggccattc acggacaggt ggactgcagc ccaggcatct ggcagctggc ctgcacccac   3360
ctggaaggca aggtgatcct ggtggccgtg cacgtggcct ctggatacat cgaagccgaa   3420
gtgatccctg ccgagacagg ccaggaaaca gcctacttcc tgctgaagct ggctggcagg   3480
tggcctgtga aaaccatcca cacagccaac ggcagcaact tcacctctgc caccgtgaag   3540
gctgcctgtt ggtgggctgg cattaagcag gaatttggca tccctacaa ccctcagtct   3600 cagggagtgg tggcctccat caacaaagag ctgaagaaga tcatcggaca ggtcagggat   3660
caggccgagc atctgaaaac agccgtccag atggccgtgt tcatccacaa cttcaagcgg   3720
aagggaggga tcgagagta ctctgctggc gagaggatcg tggacattat cgccagcgat   3780
atccagacca aagaactgca gaagcagatc acaaagatcc agaacttcag ggtgtactac   3840
agggacagca gagatcccct gtggaaggga cctgccaagc tgctgtggaa aggcgaagga   3900
gccgtcgtca tccaggacaa cagcgacatc aaggtggtgc ccagacgaa ggccaagatc   3960 atcagagact acggcaaaca gatggctggc gacgactgcg tcgcctctag gcaggacgag   4020
``` gac  4023

<210> SEQ ID NO 22
<211> LENGTH: 2055
<212> TYPE: DNA
<213> ORGANISM: Artificial Sequence
<220> FEATURE:
<223> OTHER INFORMATION: nucleotide sequence encoding mos1Env

<400> SEQUENCE: 22

| | | | | | | |
|---|---|---|---|---|---|---|
| atgcgggtga | ccggcatccg | gaagaactac | cagcacctgt | ggcggtgggg | caccatgctg | 60 |
| ctgggcatcc | tgatgatttg | ctctgccgcc | ggaaagctgt | gggtgaccgt | gtactacggc | 120 |
| gtgcccgtgt | ggaaagaggc | caccaccacc | ctgttctgcg | ccagcgacgc | caaggcctac | 180 |
| gacaccgagg | tgcacaacgt | gtgggccacc | cacgcctgcg | tgcccaccga | ccccaacccc | 240 |
| caggaagtgg | tcctggaaaa | cgtgaccgag | aacttcaaca | tgtggaagaa | caacatggtg | 300 |
| gagcagatgc | acgaggacat | catcagcctg | tgggaccaga | gcctgaagcc | ctgcgtgaag | 360 |
| ctgaccccc | tgtgcgtgac | cctgaactgc | accgacgacg | tgcggaacgt | gaccaacaac | 420 |
| gccaccaaca | ccaacagcag | ctggggcgag | cctatggaaa | agggcgagat | caagaactgc | 480 |
| agcttcaaca | tcaccaccct | catccggaac | aaggtgcaga | agcagtacgc | cctgttctac | 540 |
| aagctggacg | tggtgcccat | cgacaacgac | agcaacaaca | ccaactaccg | gctgatcagc | 600 |
| tgcaacacca | gcgtgatcac | ccaggcctgc | cccaaggtgt | ccttcgagcc | catccccatc | 660 |
| cactactgcg | cccctgccgg | cttcgccatc | ctgaagtgca | acgacaagaa | gttcaacggc | 720 |
| accggcccct | gcaccaacgt | gagcaccgtg | cagtgcaccc | acggcatccg | gcccgtggtg | 780 |
| tccacccagc | tgctgctgaa | cggcagcctg | gccgaggaag | aggtggtgat | cagaagcgag | 840 |
| aatttcacca | acaatgccaa | gaccatcatg | gtgcagctga | acgtgagcgt | ggagatcaac | 900 |
| tgcacccggc | ccaacaacaa | cacccggaag | agcatccaca | tcggccctgg | cagggccttc | 960 |
| tacacagccg | gcgacatcat | cggcgacatc | cggcaggccc | actgcaacat | cagccgggcc | 1020 |
| aactggaaca | cacccctgcg | gcagatcgtg | gagaagctgg | gcaagcagtt | cggcaacaac | 1080 |
| aagaccatcg | tgttcaacca | cagcagcggc | ggagaccccg | agatcgtgat | gcacagcttc | 1140 |
| aactgtggcg | gcgagttctt | ctactgcaac | agcaccaagc | tgttcaacag | cacctggacc | 1200 |
| tggaacaact | ccacctggaa | taacaccaag | cggagcaacg | acaccgaaga | gcacatcacc | 1260 |
| ctgccctgcc | ggatcaagca | gattatcaat | atgtggcagg | aggtcggcaa | ggccatgtac | 1320 |
| gcccctccca | tccggggcca | gatccggtgc | agcagcaaca | tcaccggcct | gctgctgacc | 1380 |
| cgggacggcg | gcaacgatac | cagcggcacc | gagatcttcc | ggcctggcgg | cggagatatg | 1440 |
| cgggacaact | ggcggagcga | gctgtacaag | tacaaggtgg | tgaagatcga | gcccctgggc | 1500 |
| gtggctccca | ccaaggccaa | gcggcgggtg | gtgcagagcg | agaagagcgc | cgtgggcatc | 1560 |
| ggcgccgtgt | ttctgggctt | cctggagccc | gccggaagca | ccatgggagc | cgccagcatg | 1620 |
| accctgaccg | tgcaggcccg | gctgctgctg | tccggcatcg | tgcagcagca | gaacaacctg | 1680 |
| ctccgggcca | tcgaggccca | gcagcacctg | ctgcagctga | ccgtgtgggg | catcaagcag | 1740 |
| ctgcaggcca | gggtgctggc | cgtggagaga | tacctgaagg | atcagcagct | cctgggcatc | 1800 |
| tggggctgca | gcggcaagct | gatctgcacc | accaccgtgc | cctggaacgc | cagctggtcc | 1860 |
| aacaagagcc | tggacaagat | ctggaacaat | atgacctgga | tggaatggga | gcgcgagatc | 1920 |
| aacaattaca | ccagcctgat | ctacacccty | atcgaggaaa | gccagaacca | gcaggaaaag | 1980 | aacgagcagg aactgctgga actggacaag tgggccagcc tgtggaactg gttcgacatc    2040 agcaactggc tgtgg                                                     2055

<210> SEQ ID NO 23
<211> LENGTH: 2052
<212> TYPE: DNA
<213> ORGANISM: Artificial Sequence
<220> FEATURE:
<223> OTHER INFORMATION: nucleotide sequence encoding mos2Env

<400> SEQUENCE: 23
atgagagtgc ggggcatcca gcggaactgg ccccagtggt ggatctgggg catcctgggc      60
ttttggatga tcatcatctg ccgggtgatg gcaacctgt gggtgaccgt gtactacggc     120
gtgcccgtgt ggaaagaggc caagaccacc ctgttctgcg ccagcgacgc caaggcctac    180
gagaaagagg tgcacaacgt gtgggccacc cacgcctgcg tgcccaccga ccccaacccc    240
caggaaatgg tcctggaaaa cgtgaccgag aacttcaaca tgtggaagaa cgacatggtg    300
gaccagatgc acgaggacat catccggctg tgggaccaga gcctgaagcc ctgcgtgaag    360
ctgacccccc tgtgcgtgac cctggaatgc cggaacgtga aaacgtgag cagcaacggc    420 acctacaaca tcatccacaa cgagacctac aaagagatga gaactgcag cttcaacgcc    480 accaccgtgg tggaggaccg gaagcagaag gtgcacgccc tgttctaccg gctggacatc    540
gtgcccctgg acgagaacaa cagcagcgag aagtccagcg agaacagctc cgagtactac    600
cggctgatca actgcaacac cagcgccatc acccaggcct gccccaaggt gtccttcgac    660
cccatcccca tccactactg cgcccctgcc ggctacgcca tcctgaagtg caacaacaag    720
accttcaacg gcaccggccc ctgcaacaac gtgagcaccg tgcagtgcac ccacggcatc    780
aagcccgtgt gtccaccca gctgctgctg aacggcagcc tggccgagga agagatcatc    840
atccggtccg agaacctgac caacaacgcc aagaccatca tcgtgcacct gaatgagacc    900
gtgaacatca cctgcacccg gcccaacaac acacccgga gagcatccg gatcggccct    960 ggccagacct tttacgccac cggcgacatc atcggcgaca tccggcaggc ccactgcaac    1020
ctgagccggg acggctggaa caagaccctg caggcgtga agaagaagct ggccgagcac    1080
ttccccaata agaccatcaa cttcaccagc agcagcggcg agacctgga atcaccacc     1140 cacagcttca actgcagggg cgagttcttc tactgcaata cctccggcct gttcaatggc    1200
acctacatgc ccaacggcac caacagcaac agcagcagca catcaccct gccctgccgg    1260 atcaagcaga tcatcaatat gtggcaggag gtcggcaggg ccatgtacgc ccctcccatc    1320
gccggcaata tcacctgccg gtccaacatc accggcctgc tgctgaccag ggacggcggc    1380
agcaacaacg cgtgcctaa cgacaccgag accttccggc ctggcggcgg agatatgcgg    1440
aacaactggc ggagcgagct gtacaagtac aaggtggtgg aggtgaagcc cctgggcgtg    1500
gctcctaccg aggccaagcg gcgggtggtg gagagcgaga gagcgccgt gggcatcggc    1560 gccgtgtttc tgggcattct gggagccgcc ggaagcacca tgggagccgc cagcatcacc    1620
ctgaccgtgc aggcccggca gctgctgtcc ggcatcgtgc agcagcagag caacctgctg    1680
agagccatcg aggcccagca gcacatgctg cagctgaccg tgtggggcat caagcagctg    1740
cagacccggg tgctggccat cgagagatac ctgcaggatc agcagctcct gggcctgtgg    1800
ggctgcagcg gcaagctgat ctgcaccacc gccgtgccct ggaacaccag ctggtccaac    1860
aagagccaga ccgacatctg gacaacatg acctggatgc agtgggacaa agagatcggc    1920
aactacaccg gcgagatcta caggctgctg gaagagagcc agaaccagca ggaaaagaac    1980

```
gagaaggacc tgctggccct ggacagctgg aagaacctgt ggaactggtt cgacatcacc    2040
aactggctgt gg                                                        2052

<210> SEQ ID NO 24
<211> LENGTH: 829
<212> TYPE: DNA
<213> ORGANISM: Artificial Sequence
<220> FEATURE:
<223> OTHER INFORMATION: CMV promoter used for expression of antigens in
      Ad26 vectors

<400> SEQUENCE: 24
tcaatattgg ccattagcca tattattcat tggttatata gcataaatca atattggcta      60
ttggccattg catacgttgt atccatatca taatatgtac atttatattg gctcatgtcc     120
aacattaccg ccatgttgac attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca ataggacttt ccattgacg tcaatgggtg gagtatttac ggtaaactgc     360
ccacttggca gtacatcaag tgtatcatat gccaagtacg ccccctattg acgtcaatga     420
cggtaaatgg cccgcctggc attatgccca gtacatgacc ttatgggact ttcctacttg     480
gcagtacatc tacgtattag tcatcgctat taccatggtg atgcggtttt ggcagtacat     540
caatgggcgt ggatagcggt ttgactcacg gggatttcca agtctccacc ccattgacgt     600
caatgggagt ttgttttggc accaaaatca acgggacttt ccaaaatgtc gtaacaactc     660
cgccccattg acgcaaatgg gcggtaggcg tgtacggtgg gaggtctata taagcagagc     720
tcgtttagtg aaccgtcaga tcgcctggag acgccatcca cgctgttttg acctccatag     780
aagacaccgg gaccgatcca gcctccgcgg ccgggaacgg tgcattgga                 829

<210> SEQ ID NO 25
<211> LENGTH: 2586
<212> TYPE: DNA
<213> ORGANISM: Artificial Sequence
<220> FEATURE:
<223> OTHER INFORMATION: nucleotide sequence encoding c4

<400> SEQUENCE: 25
atgagagtgc ggggcatgct gagaaactgg cagcagtggt ggatctggtc cagcctgggc      60
ttctggatgc tgatgatcta cagcgtgatg ggcaacctgt gggtcaccgt gtactacggc     120
gtgcccgtgt ggaaggacgc caagaccacc ctgttttgcg cctccgatgc caaggcctac     180
gagaaagagg tgcacaacgt ctgggccacc cacgcctgtg tgcccaccga ccccaatccc     240
caggaaatcg tcctgggcaa cgtgaccgag aacttcaaca tgtggaagaa cgacatggtc     300
gatcagatgc acgaggacat catctccctg tgggacgcct ccctggaacc tgcgtgaag     360 ctgaccccctc tgtgcgtgac cctgaactgc cggaacgtgc aacgtgtc cagcaacggc     420 acctacaaca tcatccacaa cgagacatac aaagagatga gaactgcag cttcaacgct     480 accaccgtgg tcgaggaccg gaagcagaag gtgcacgccc tgttctaccg gctggacatc     540
gtgcccctgg acgagaacaa cagcagcgag aagtcctccg agaacagctc cgagtactac     600
agactgatca actgcaacac cagcgccatc acccaggcct gccccaaggt gtccttcgac     660
cctatcccca tccactactg cgccctgcc ggctacgcca tctgaagtg caacaacaag     720 accttcaatg gcaccggccc ctgcaacaat gtgtccaccg tgcagtgcac ccacggcatc     780
```

```
aagcccgtgg tgtctaccca gctgctgctg aacggcagcc tggccgagga agagatcatt    840
atcagaagcg agaacctgac caacaacgcc aaaaccatca tcgtccacct gaacgaaacc    900
gtgaacatca cctgtacccg gcctaacaac aacacccgga agtccatccg gatcggccct    960
ggccagacct tttacgccac cggcgatatt atcggcgaca tccggcaggc ccactgcaat   1020
ctgagccggg acggctggaa caagacactg cagggcgtca agaagaagct ggccgaacac   1080
ttccctaaca agactatcaa gttcgcccct cactctggcg cgacctgga  aatcaccacc   1140 cacaccttca actgtcgggg cgagttcttc tactgcaata cctccaacct gttcaacgag   1200
agcaacatcg agcggaacga cagcatcatc acactgcctt gccggatcaa gcagattatc   1260
aatatgtggc aggaagtggg cagagccatc tacgcccctc caatcgccgg caacatcaca   1320
tgccggtcca atatcaccgg cctgctgctc accagatgc  gcggctccaa caatggcgtg   1380
ccaaacgaca ccgagacatt cagacccggc ggaggcgaca tgcggaacaa ttggcggagc   1440
gagctgtaca agtacaaggt ggtggaagtg aagcccctgg gcgtggcccc taccgaggcc   1500
aagagaagag tggtcgaacg cgagaagcgg gccgtgggaa tcggagccgt gtttctggga   1560 atcctggag  ccgctggctc taccatgggc gctgcctcta tcaccctgac agtgcaggcc   1620
agacagctgc tcagcggcat cgtgcagcag cagagcaacc tgctgagagc cattgaggcc   1680
cagcagcaca tgctgcagct gaccgtgtgg ggcattaagc agctccagac acgggtgctg   1740
gccatcgaga gatacctgca ggatcagcag ctcctgggcc tgtggggctg tagcggcaag   1800
ctgatctgta ccaccgccgt gccctggaat acctcttgga gcaacaagag ccagaccgac   1860
atctgggaca acatgacctg gatgcagtgg gacaaagaaa tcggcaacta taccggcgag   1920
atctatagac tgctggaaga gtcccagaac cagcaggaaa agaacgagaa ggacctgctg   1980
gccctggatt cttggaacaa tctgtggaac tggttcagca tctccaagtg gctgtggtac   2040
atcaagatct tcatcatgat cgtgggcggc ctgatcggcc tgcggatcat ctttgccgtg   2100
ctgagcatcg tgaaccgcgt gcggcaggga tacagccctc tgagcctgca gaccctgact   2160
cagaaccctg gcggactgga cagactgggc cggattgagg aagaaggcgg cgagcaggac   2220
aaggatcgga gcatcaggct ggtcaacggc ttcttcgctc tgttttggga cgacctgcgg   2280
agcctgtgcc tgttcagcta ccacagactg cgggacttta tcctgattgt ggccagagcc   2340
gtcgaactgc tggggagaag ctctctgaga ggcctgcagc ggggctggga gattctgaag   2400
tacctgggct ccctgctgca gtactggggc ctggaactga agaagtctgc catcaatctg   2460
ctcgacacaa tcgctattgc cgtggccgaa ggcaccgata gaatcatcga gctgatccag   2520
cggatctgcc gggccatctg caacatcccc agacggatca gacagggctt cgaggccgct   2580
ctgcag                                                              2586
```

<210> SEQ ID NO 26
<211> LENGTH: 2133
<212> TYPE: DNA
<213> ORGANISM: Artificial Sequence
<220> FEATURE:
<223> OTHER INFORMATION: nucleotide sequence encoding C4D7

<400> SEQUENCE: 26

```
atgagagtgc gggcatgct  gagaaactgg cagcagtggt ggatctggtc cagcctgggc     60
ttctggatgc tgatgatcta cagcgtgatg ggcaacctgt gggtcaccgt gtactacggc    120
gtgcccgtgt ggaaggacgc caagaccacc ctgttttgcg cctccgatgc caaggcctac    180
```

```
gagaaagagg tgcacaacgt ctgggccacc cacgcctgtg tgcccaccga ccccaatccc    240
caggaaatcg tcctgggcaa cgtgaccgag aacttcaaca tgtggaagaa cgacatggtc    300
gatcagatgc acgaggacat catctccctg tgggacgcct ccctggaacc ctgcgtgaag    360
ctgaccsctc tgtgcgtgac cctgaactgc cggaacgtgc gcaacgtgtc cagcaacggc    420
acctacaaca tcatccacaa cgagacatac aaagagatga gaactgcag cttcaacgct    480
accaccgtgg tcgaggaccg gaagcagaag gtgcacgccc tgttctaccg gctggacatc    540
gtgcccctgg acgagaacaa cagcagcgag aagtcctccg agaacagctc cgagtactac    600
agactgatca actgcaacac cagcgccatc acccaggcct gccccaaggt gtccttcgac    660
cctatcccca tccactactg cgcccctgcc ggctacgcca tcctgaagtg caacaacaag    720
accttcaatg gcaccggccc ctgcaacaat gtgtccaccg tgcagtgcac ccacggcatc    780
aagcccgtgg tgtctaccca gctgctgctg aacggcagcc tggccgagga agagatcatt    840
atcagaagcg agaacctgac caacaacgcc aaaaccatca tcgtccacct gaacgaaacc    900
gtgaacatca cctgtacccg gcctaacaac aacacccgga gtccatccg gatcggccct    960
ggccagacct tttacgccac cggcgatatt atcggcgaca tccggcaggc ccactgcaat   1020
ctgagccggg acggctggaa caagacactg cagggcgtca gaagaagct ggccgaacac   1080
ttccctaaca agactatcaa gttcgcccct cactctggcg gcgacctgga aatcaccacc   1140
cacaccttca actgtcgggg cgagttcttc tactgcaata cctccaacct gttcaacgag   1200
agcaacatcg agcggaacga cagcatcatc acactgcctt gccggatcaa gcagattatc   1260
aatatgtggc aggaagtggg cagagccatc tacgcccctc caatcgccgg caacatcaca   1320
tgccggtcca atatcaccgg cctgctgctc accagagatg gcggctccaa caatggcgtg   1380
ccaaacgaca ccgagacatt cagacccggc ggaggcgaca tgcggaacaa ttggcggagc   1440
gagctgtaca gtacaaggt ggtggaagtg aagcccctgg gcgtggcccc taccgaggcc   1500
aagagaaagag tggtcgaacg cgagaagcgg ccgtgggaa tcggagccgt gtttctggga   1560
atcctgggag ccgctggctc taccatgggc gctgcctcta tcaccctgac agtgcaggcc   1620
agacagctgc tcagcggcat cgtgcagcag cagagcaacc tgctgagagc cattgaggcc   1680
cagcagcaca tgctgcagct gaccgtgtgg ggcattaagc agctccagac acgggtgctg   1740
gccatcgaga gataccctgca ggatcagcag ctcctgggcc tgtggggctg tagcggcaag   1800
ctgatctgta ccaccgccgt gccctggaat acctcttgga caacaagag ccagaccgac   1860
atctgggaca catgacctg gatgcagtgg gacaaagaaa tcggcaacta ccggcgag    1920
atctatagac tgctggaaga gtcccagaac cagcaggaaa agaacgagaa ggacctgctg   1980
gccctggatt cttggaacaa tctgtggaac tggttcagca tctccaagtg gctgtggtac   2040
atcaagatct tcatcatgat cgtgggcggc ctgatcggcc tgcggatcat ctttgccgtg   2100
ctgagcatcg tgaaccgcgt gcggcagggc tac                                2133
```

<210> SEQ ID NO 27
<211> LENGTH: 2112
<212> TYPE: DNA
<213> ORGANISM: Artificial Sequence
<220> FEATURE:
<223> OTHER INFORMATION: nucleotide sequence encoding sC4

<400> SEQUENCE: 27

```
atgagagtgc ggggcatgct gagaaactgg cagcagtggt ggatctggtc cagcctgggc     60
ttctggatgc tgatgatcta cagcgtgatg ggcaacctgt gggtcaccgt gtactacggc    120
```

```
gtgcccgtgt ggaaggacgc caagaccacc ctgttttgcg cctccgatgc caaggcctac    180
gagaaagagg tgcacaacgt ctgggccacc cacgcctgtg tgcccaccga ccccaatccc    240
caggaaatcg tcctgggcaa cgtgaccgag aacttcaaca tgtggaagaa cgacatggtc    300
gatcagatgc acgaggacat catctccctg tgggacgcct ccctggaacc ctgcgtgaag    360
ctgaccccct gtgcgtgac cctgaactgc cggaacgtgc gcaacgtgtc cagcaacggc    420
acctacaaca tcatccacaa cgagacatac aaagagatga gaactgcag cttcaacgct    480 accaccgtgg tcgaggaccg gaagcagaag gtgcacgccc tgttctaccg gctggacatc    540
gtgcccctgg acgagaacaa cagcagcgag aagtcctccg agaacagctc cgagtactac    600
agactgatca actgcaacac cagcgccatc acccaggcct gccccaaggt gtccttcgac    660
cctatcccca tccactactg cgcccctgcc ggctacgcca tcctgaagtg caacaacaag    720
accttcaatg gcaccggccc ctgcaacaat gtgtccaccg tgcagtgcac ccacggcatc    780
aagcccgtgt gtctaccca gctgctgctg aacggcagcc tggccgagga agagatcatt    840
atcagaagcg agaacctgac caacaacgcc aaaaccatca tcgtccacct gaacgaaacc    900
gtgaacatca cctgtacccg gcctaacaac aacacccgga gtccatccg gatcggccct    960 ggccagacct tttacgccac cggcgatatt atcggcgaca tccggcaggc ccactgcaat   1020
ctgagccggg acggctggaa caagacactg cagggcgtca agaagaagct ggccgaacac   1080
ttccctaaca agactatcaa gttcgcccct cactctggcg gcgacctgga aatcaccacc   1140
cacaccttca ctgtcggggg cgagttcttc tactgcaata cctccaacct gttcaacgag   1200
agcaacatcg agcggaacga cagcatcatc acactgcctt gccggatcaa gcagattatc   1260
aatatgtggc aggaagtggg cagagccatc tacgcccctc caatcgccgg caacatcaca   1320
tgccggtcca atatcaccgg cctgctgctc accagagatg gcggctccaa caatggcgtg   1380
ccaaacgaca ccgagacatt cagacccggc ggaggcgaca tgcggaacaa ttggcggagc   1440
gagctgtaca gtacaaggt ggtggaagtg aagcccctgg gcgtggcccc taccgaggcc   1500
aagagaagag tggtcgaacg cgaggaacgg gccgtgggaa tcggagccgt gtttctggga   1560
atcctgggag ccgctggctc taccatgggc gctgcctcta tcaccctgac agtgcaggcc   1620
agacagctgc tcagcggcat cgtgcagcag cagagcaacc tgctgagagc cattgaggcc   1680
cagcagcaca tgctgcagct gaccgtgtgg ggcattaagc agctccagac acgggtgctg   1740
gccatcgaga gatacctgca ggatcagcag ctcctgggcc tgtggggctg tagcggcaag   1800
ctgatctgta ccaccgccgt gccctggaat acctcttgga gcaacaagag ccagaccgac   1860
atctgggaca catgaccctg gatgcagtgg acaaagaaa tcggcaacta taccggcgag   1920
atctatagac tgctggaaga gtcccagaac agcaggaaa agatgaagca gatcgaggac   1980
aagatcgaag agattctgag caagatctac cacatcgaga acgagatcgc ccgcatcaag   2040
aaactgatcg gcgaagtggg atccggcgct cccacaaagg ccaaaagacg ggtggtgcag   2100
cgcgagaaac gc                                                        2112
```

<210> SEQ ID NO 28
<211> LENGTH: 1350
<212> TYPE: PRT
<213> ORGANISM: Artificial Sequence
<220> FEATURE:
<223> OTHER INFORMATION: mos1GagPol mosaic antigen sequence

<400> SEQUENCE: 28

Met Gly Ala Arg Ala Ser Val Leu Ser Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65              70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
            115                 120                 125

Ser Gln Asn Tyr Pro Ile Val Gln Asn Ile Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn

```
                420             425             430
Phe Leu Gly Lys Ile Trp Pro Ser Asn Lys Gly Arg Pro Gly Asn Phe
            435             440             445

Leu Gln Asn Arg Pro Glu Pro Thr Ala Pro Pro Glu Glu Ser Phe Arg
            450             455             460

Phe Gly Glu Glu Thr Thr Thr Pro Ser Gln Lys Gln Glu Pro Ile Asp
465             470             475             480

Lys Glu Met Tyr Pro Leu Ala Ser Leu Lys Ser Leu Phe Gly Asn Asp
            485             490             495

Pro Ser Ser Gln Met Ala Pro Ile Ser Pro Ile Glu Thr Val Pro Val
            500             505             510

Lys Leu Lys Pro Gly Met Asp Gly Pro Arg Val Lys Gln Trp Pro Leu
            515             520             525

Thr Glu Glu Lys Ile Lys Ala Leu Thr Ala Ile Cys Glu Glu Met Glu
            530             535             540

Lys Glu Gly Lys Ile Thr Lys Ile Gly Pro Glu Asn Pro Tyr Asn Thr
545             550             555             560

Pro Val Phe Ala Ile Lys Lys Lys Asp Ser Thr Lys Trp Arg Lys Leu
            565             570             575

Val Asp Phe Arg Glu Leu Asn Lys Arg Thr Gln Asp Phe Trp Glu Val
            580             585             590

Gln Leu Gly Ile Pro His Pro Ala Gly Leu Lys Lys Lys Lys Ser Val
            595             600             605

Thr Val Leu Ala Val Gly Asp Ala Tyr Phe Ser Val Pro Leu Asp Glu
            610             615             620

Gly Phe Arg Lys Tyr Thr Ala Phe Thr Ile Pro Ser Thr Asn Asn Glu
625             630             635             640

Thr Pro Gly Ile Arg Tyr Gln Tyr Asn Val Leu Pro Gln Gly Trp Lys
            645             650             655

Gly Ser Pro Ala Ile Phe Gln Cys Ser Met Thr Arg Ile Leu Glu Pro
            660             665             670

Phe Arg Ala Lys Asn Pro Glu Ile Val Ile Tyr Gln Tyr Met Ala Ala
            675             680             685

Leu Tyr Val Gly Ser Asp Leu Glu Ile Gly Gln His Arg Ala Lys Ile
            690             695             700

Glu Glu Leu Arg Glu His Leu Leu Lys Trp Gly Phe Thr Thr Pro Asp
705             710             715             720

Lys Lys His Gln Lys Glu Pro Pro Phe Leu Trp Met Gly Tyr Glu Leu
            725             730             735

His Pro Asp Lys Trp Thr Val Gln Pro Ile Gln Leu Pro Glu Lys Asp
            740             745             750

Ser Trp Thr Val Asn Asp Ile Gln Lys Leu Val Gly Lys Leu Asn Trp
            755             760             765

Ala Ser Gln Ile Tyr Pro Gly Ile Lys Val Arg Gln Leu Cys Lys Leu
            770             775             780

Leu Arg Gly Ala Lys Ala Leu Thr Asp Ile Val Pro Leu Thr Glu Glu
785             790             795             800

Ala Glu Leu Glu Leu Ala Glu Asn Arg Glu Ile Leu Lys Glu Pro Val
            805             810             815

His Gly Val Tyr Tyr Asp Pro Ser Lys Asp Leu Ile Ala Glu Ile Gln
            820             825             830

Lys Gln Gly His Asp Gln Trp Thr Tyr Gln Ile Tyr Gln Glu Pro Phe
            835             840             845
```

-continued

Lys Asn Leu Lys Thr Gly Lys Tyr Ala Lys Met Arg Thr Ala His Thr
850             855             860

Asn Asp Val Lys Gln Leu Thr Glu Ala Val Gln Lys Ile Ala Met Glu
865             870             875             880

Ser Ile Val Ile Trp Gly Lys Thr Pro Lys Phe Arg Leu Pro Ile Gln
            885             890             895

Lys Glu Thr Trp Glu Thr Trp Trp Thr Asp Tyr Trp Gln Ala Thr Trp
            900             905             910

Ile Pro Glu Trp Glu Phe Val Asn Thr Pro Leu Val Lys Leu Trp
        915             920             925

Tyr Gln Leu Glu Lys Asp Pro Ile Ala Gly Val Glu Thr Phe Tyr Val
930             935             940

Ala Gly Ala Ala Asn Arg Glu Thr Lys Leu Gly Lys Ala Gly Tyr Val
945             950             955             960

Thr Asp Arg Gly Arg Gln Lys Ile Val Ser Leu Thr Glu Thr Thr Asn
            965             970             975

Gln Lys Thr Ala Leu Gln Ala Ile Tyr Leu Ala Leu Gln Asp Ser Gly
            980             985             990

Ser Glu Val Asn Ile Val Thr Ala Ser Gln Tyr Ala Leu Gly Ile Ile
        995             1000            1005

Gln Ala Gln Pro Asp Lys Ser Glu Ser Glu Leu Val Asn Gln Ile
    1010            1015            1020

Ile Glu Gln Leu Ile Lys Lys Glu Arg Val Tyr Leu Ser Trp Val
    1025            1030            1035

Pro Ala His Lys Gly Ile Gly Gly Asn Glu Gln Val Asp Lys Leu
    1040            1045            1050

Val Ser Ser Gly Ile Arg Lys Val Leu Phe Leu Asp Gly Ile Asp
    1055            1060            1065

Lys Ala Gln Glu Glu His Glu Lys Tyr His Ser Asn Trp Arg Ala
    1070            1075            1080

Met Ala Ser Asp Phe Asn Leu Pro Pro Val Val Ala Lys Glu Ile
    1085            1090            1095

Val Ala Ser Cys Asp Gln Cys Gln Leu Lys Gly Glu Ala Met His
    1100            1105            1110

Gly Gln Val Asp Cys Ser Pro Gly Ile Trp Gln Leu Ala Cys Thr
    1115            1120            1125

His Leu Glu Gly Lys Ile Ile Leu Val Ala Val His Val Ala Ser
    1130            1135            1140

Gly Tyr Ile Glu Ala Glu Val Ile Pro Ala Glu Thr Gly Gln Glu
    1145            1150            1155

Thr Ala Tyr Phe Ile Leu Lys Leu Ala Gly Arg Trp Pro Val Lys
    1160            1165            1170

Val Ile His Thr Ala Asn Gly Ser Asn Phe Thr Ser Ala Ala Val
    1175            1180            1185

Lys Ala Ala Cys Trp Trp Ala Gly Ile Gln Gln Glu Phe Gly Ile
    1190            1195            1200

Pro Tyr Asn Pro Gln Ser Gln Gly Val Val Ala Ser Met Asn Lys
    1205            1210            1215

Glu Leu Lys Lys Ile Ile Gly Gln Val Arg Asp Gln Ala Glu His
    1220            1225            1230

Leu Lys Thr Ala Val Gln Met Ala Val Phe Ile His Asn Phe Lys
    1235            1240            1245

```
Arg Lys Gly Gly Ile Gly Gly Tyr Ser Ala Gly Glu Arg Ile Ile
    1250            1255                1260

Asp Ile Ile Ala Thr Asp Ile Gln Thr Lys Glu Leu Gln Lys Gln
    1265            1270                1275

Ile Ile Lys Ile Gln Asn Phe Arg Val Tyr Tyr Arg Asp Ser Arg
    1280            1285                1290

Asp Pro Ile Trp Lys Gly Pro Ala Lys Leu Leu Trp Lys Gly Glu
    1295            1300                1305

Gly Ala Val Val Ile Gln Asp Asn Ser Asp Ile Lys Val Val Pro
    1310            1315                1320

Arg Arg Lys Val Lys Ile Ile Lys Asp Tyr Gly Lys Gln Met Ala
    1325            1330                1335

Gly Ala Asp Cys Val Ala Gly Arg Gln Asp Glu Asp
    1340            1345                1350

<210> SEQ ID NO 29
<211> LENGTH: 1341
<212> TYPE: PRT
<213> ORGANISM: Artificial Sequence
<220> FEATURE:
<223> OTHER INFORMATION: mos2GagPol mosaic antigen sequence

<400> SEQUENCE: 29

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255
```

```
Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
            290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
            325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
            355                 360                 365

Ser Thr Ile Leu Met Gln Arg Ser Asn Phe Lys Gly Ser Lys Arg Ile
            370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
            405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
            435                 440                 445

Glu Pro Thr Ala Pro Pro Ala Glu Ser Phe Arg Phe Glu Glu Thr Thr
450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
            485                 490                 495

Pro Ile Glu Thr Val Pro Val Lys Leu Lys Pro Gly Met Asp Gly Pro
            500                 505                 510

Lys Val Lys Gln Trp Pro Leu Thr Glu Glu Lys Ile Lys Ala Leu Val
            515                 520                 525

Glu Ile Cys Thr Glu Met Glu Lys Glu Gly Lys Ile Ser Lys Ile Gly
            530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
            565                 570                 575

Thr Gln Asp Phe Trp Glu Val Gln Leu Gly Ile Pro His Pro Ala Gly
            580                 585                 590

Leu Lys Lys Lys Lys Ser Val Thr Val Leu Ala Val Gly Asp Ala Tyr
            595                 600                 605

Phe Ser Val Pro Leu Asp Glu Asp Phe Arg Lys Tyr Thr Ala Phe Thr
            610                 615                 620

Ile Pro Ser Ile Asn Asn Glu Thr Pro Gly Ile Arg Tyr Gln Tyr Asn
625                 630                 635                 640

Val Leu Pro Gln Gly Trp Lys Gly Ser Pro Ala Ile Phe Gln Ser Ser
            645                 650                 655

Met Thr Lys Ile Leu Glu Pro Phe Arg Lys Gln Asn Pro Asp Ile Val
            660                 665                 670

Ile Tyr Gln Tyr Met Ala Ala Leu Tyr Val Gly Ser Asp Leu Glu Ile
```

-continued

```
            675                 680                 685
Gly Gln His Arg Thr Lys Ile Glu Glu Leu Arg Gln His Leu Leu Arg
        690                 695                 700
Trp Gly Phe Thr Thr Pro Asp Lys Lys His Gln Lys Glu Pro Pro Phe
705                 710                 715                 720
Leu Trp Met Gly Tyr Glu Leu His Pro Asp Lys Trp Thr Val Gln Pro
                725                 730                 735
Ile Val Leu Pro Glu Lys Asp Ser Trp Thr Val Asn Asp Ile Gln Lys
            740                 745                 750
Leu Val Gly Lys Leu Asn Trp Ala Ser Gln Ile Tyr Ala Gly Ile Lys
            755                 760                 765
Val Lys Gln Leu Cys Lys Leu Leu Arg Gly Thr Lys Ala Leu Thr Glu
770                 775                 780
Val Val Pro Leu Thr Glu Glu Ala Glu Leu Glu Leu Ala Glu Asn Arg
785                 790                 795                 800
Glu Ile Leu Lys Glu Pro Val His Gly Val Tyr Tyr Asp Pro Ser Lys
                805                 810                 815
Asp Leu Ile Ala Glu Ile Gln Lys Gln Gly Gln Gly Gln Trp Thr Tyr
            820                 825                 830
Gln Ile Tyr Gln Glu Pro Phe Lys Asn Leu Lys Thr Gly Lys Tyr Ala
            835                 840                 845
Arg Met Arg Gly Ala His Thr Asn Asp Val Lys Gln Leu Thr Glu Ala
850                 855                 860
Val Gln Lys Ile Ala Thr Glu Ser Ile Val Ile Trp Gly Lys Thr Pro
865                 870                 875                 880
Lys Phe Lys Leu Pro Ile Gln Lys Glu Thr Trp Ala Trp Trp Thr
                885                 890                 895
Glu Tyr Trp Gln Ala Thr Trp Ile Pro Glu Trp Glu Phe Val Asn Thr
            900                 905                 910
Pro Pro Leu Val Lys Leu Trp Tyr Gln Leu Glu Lys Glu Pro Ile Val
            915                 920                 925
Gly Ala Glu Thr Phe Tyr Val Ala Gly Ala Ala Asn Arg Glu Thr Lys
            930                 935                 940
Leu Gly Lys Ala Gly Tyr Val Thr Asp Arg Gly Arg Gln Lys Val Val
945                 950                 955                 960
Ser Leu Thr Asp Thr Thr Asn Gln Lys Thr Ala Leu Gln Ala Ile His
                965                 970                 975
Leu Ala Leu Gln Asp Ser Gly Leu Glu Val Asn Ile Val Thr Ala Ser
            980                 985                 990
Gln Tyr Ala Leu Gly Ile Ile Gln Ala Gln Pro Asp Lys Ser Glu Ser
            995                 1000                1005
Glu Leu Val Ser Gln Ile Ile Glu Gln Leu Ile Lys Lys Glu Lys
            1010                1015                1020
Val Tyr Leu Ala Trp Val Pro Ala His Lys Gly Ile Gly Gly Asn
            1025                1030                1035
Glu Gln Val Asp Lys Leu Val Ser Arg Gly Ile Arg Lys Val Leu
            1040                1045                1050
Phe Leu Asp Gly Ile Asp Lys Ala Gln Glu Glu His Glu Lys Tyr
            1055                1060                1065
His Ser Asn Trp Arg Ala Met Ala Ser Glu Phe Asn Leu Pro Pro
            1070                1075                1080
Ile Val Ala Lys Glu Ile Val Ala Ser Cys Asp Lys Cys Gln Leu
            1085                1090                1095
```

Lys Gly Glu Ala Ile His Gly Gln Val Asp Cys Ser Pro Gly Ile
    1100            1105                1110

Trp Gln Leu Ala Cys Thr His Leu Glu Gly Lys Val Ile Leu Val
    1115            1120                1125

Ala Val His Val Ala Ser Gly Tyr Ile Glu Ala Glu Val Ile Pro
    1130            1135                1140

Ala Glu Thr Gly Gln Glu Thr Ala Tyr Phe Leu Leu Lys Leu Ala
    1145            1150                1155

Gly Arg Trp Pro Val Lys Thr Ile His Thr Ala Asn Gly Ser Asn
    1160            1165                1170

Phe Thr Ser Ala Thr Val Lys Ala Ala Cys Trp Trp Ala Gly Ile
    1175            1180                1185

Lys Gln Glu Phe Gly Ile Pro Tyr Asn Pro Gln Ser Gln Gly Val
    1190            1195                1200

Val Ala Ser Ile Asn Lys Glu Leu Lys Lys Ile Ile Gly Gln Val
    1205            1210                1215

Arg Asp Gln Ala Glu His Leu Lys Thr Ala Val Gln Met Ala Val
    1220            1225                1230

Phe Ile His Asn Phe Lys Arg Lys Gly Gly Ile Gly Glu Tyr Ser
    1235            1240                1245

Ala Gly Glu Arg Ile Val Asp Ile Ile Ala Ser Asp Ile Gln Thr
    1250            1255                1260

Lys Glu Leu Gln Lys Gln Ile Thr Lys Ile Gln Asn Phe Arg Val
    1265            1270                1275

Tyr Tyr Arg Asp Ser Arg Asp Pro Leu Trp Lys Gly Pro Ala Lys
    1280            1285                1290

Leu Leu Trp Lys Gly Glu Gly Ala Val Val Ile Gln Asp Asn Ser
    1295            1300                1305

Asp Ile Lys Val Val Pro Arg Arg Lys Ala Lys Ile Ile Arg Asp
    1310            1315                1320

Tyr Gly Lys Gln Met Ala Gly Asp Asp Cys Val Ala Ser Arg Gln
    1325            1330                1335

Asp Glu Asp
    1340

<210> SEQ ID NO 30
<211> LENGTH: 709
<212> TYPE: PRT
<213> ORGANISM: Artificial Sequence
<220> FEATURE:
<223> OTHER INFORMATION: sc1 sequence

<400> SEQUENCE: 30

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

```
Asn Asp Met Val Asp Gln Met His Glu Asp Ile Ile Arg Leu Trp Asp
            100                 105                 110

Gln Ser Leu Lys Pro Cys Val Lys Leu Thr Pro Leu Cys Val Thr Leu
        115                 120                 125

Glu Cys Arg Asn Val Arg Asn Val Ser Ser Asn Gly Thr Tyr Asn Ile
    130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Glu Ile Ile Arg Ser Glu Asn Leu Thr Asn
        275                 280                 285

Asn Ala Lys Thr Ile Ile Val His Leu Asn Glu Thr Val Asn Ile Thr
            290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
        355                 360                 365

Thr Ser Ser Ser Gly Gly Asp Leu Glu Ile Thr Thr His Ser Phe Asn
    370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
        435                 440                 445

Asn Ile Thr Gly Leu Leu Leu Thr Arg Asp Gly Ser Asn Asn Gly
    450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Arg
            500                 505                 510
```

Glu Glu Arg Ala Val Gly Ile Gly Ala Val Phe Leu Gly Ile Leu Gly
            515                 520                 525

Ala Ala Gly Ser Thr Met Gly Ala Ala Ser Ile Thr Leu Thr Val Gln
530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
                580                 585                 590

Asp Gln Gln Leu Leu Gly Leu Trp Gly Cys Ser Gly Lys Leu Ile Cys
                595                 600                 605

Thr Thr Ala Val Pro Trp Asn Thr Ser Trp Ser Asn Lys Ser Gln Thr
            610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Met Lys Gln Ile Glu Asp Lys Ile Glu Glu Ile Leu Ser
                660                 665                 670

Lys Ile Tyr His Ile Glu Asn Glu Ile Ala Arg Ile Lys Lys Leu Ile
                675                 680                 685

Gly Glu Val Gly Ser Gly Ala Pro Thr Lys Ala Lys Arg Val Val
                690                 695                 700

Gln Arg Glu Lys Arg
705

<210> SEQ ID NO 31
<211> LENGTH: 867
<212> TYPE: PRT
<213> ORGANISM: Artificial Sequence
<220> FEATURE:
<223> OTHER INFORMATION: C1 sequence

<400> SEQUENCE: 31

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30

Leu Trp Val Thr Val Tyr Tyr Gly Val Pro Val Trp Lys Glu Ala Lys
            35                  40                  45

Thr Thr Leu Phe Cys Ala Ser Asp Ala Lys Ala Tyr Glu Lys Glu Val
50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
                100                 105                 110

Gln Ser Leu Lys Pro Cys Val Lys Leu Thr Pro Leu Cys Val Thr Leu
            115                 120                 125

Glu Cys Arg Asn Val Arg Asn Val Ser Ser Asn Gly Thr Tyr Asn Ile
130                 135                 140

Ile His Asn Glu Thr Tyr Lys Glu Met Lys Asn Cys Ser Phe Asn Ala
145                 150                 155                 160

```
Thr Thr Val Val Glu Asp Arg Lys Gln Lys Val His Ala Leu Phe Tyr
            165                 170                 175
Arg Leu Asp Ile Val Pro Leu Asp Glu Asn Asn Ser Ser Glu Lys Ser
        180                 185                 190
Ser Glu Asn Ser Ser Glu Tyr Tyr Arg Leu Ile Asn Cys Asn Thr Ser
    195                 200                 205
Ala Ile Thr Gln Ala Cys Pro Lys Val Ser Phe Asp Pro Ile Pro Ile
210                 215                 220
His Tyr Cys Ala Pro Ala Gly Tyr Ala Ile Leu Lys Cys Asn Asn Lys
225                 230                 235                 240
Thr Phe Asn Gly Thr Gly Pro Cys Asn Asn Val Ser Thr Val Gln Cys
            245                 250                 255
Thr His Gly Ile Lys Pro Val Val Ser Thr Gln Leu Leu Leu Asn Gly
            260                 265                 270
Ser Leu Ala Glu Glu Ile Ile Ile Arg Ser Glu Asn Leu Thr Asn
    275                 280                 285
Asn Ala Lys Thr Ile Ile Val His Leu Asn Glu Thr Val Asn Ile Thr
290                 295                 300
Cys Thr Arg Pro Asn Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
            325                 330                 335
Ala His Cys Asn Leu Ser Arg Asp Gly Trp Asn Lys Thr Leu Gln Gly
            340                 345                 350
Val Lys Lys Lys Leu Ala Glu His Phe Pro Asn Lys Thr Ile Asn Phe
            355                 360                 365
Thr Ser Ser Ser Gly Gly Asp Leu Glu Ile Thr Thr His Ser Phe Asn
    370                 375                 380
Cys Arg Gly Glu Phe Phe Tyr Cys Asn Thr Ser Gly Leu Phe Asn Gly
385                 390                 395                 400
Thr Tyr Met Pro Asn Gly Thr Asn Ser Asn Ser Ser Asn Ile Thr
            405                 410                 415
Leu Pro Cys Arg Ile Lys Gln Ile Ile Asn Met Trp Gln Glu Val Gly
            420                 425                 430
Arg Ala Met Tyr Ala Pro Pro Ile Ala Gly Asn Ile Thr Cys Arg Ser
        435                 440                 445
Asn Ile Thr Gly Leu Leu Leu Thr Arg Asp Gly Gly Ser Asn Asn Gly
    450                 455                 460
Val Pro Asn Asp Thr Glu Thr Phe Arg Pro Gly Gly Gly Asp Met Arg
465                 470                 475                 480
Asn Asn Trp Arg Ser Glu Leu Tyr Lys Tyr Lys Val Val Glu Val Lys
            485                 490                 495
Pro Leu Gly Val Ala Pro Thr Glu Ala Lys Arg Arg Val Val Glu Arg
            500                 505                 510
Glu Lys Arg Ala Val Gly Ile Gly Ala Val Phe Leu Gly Ile Leu Gly
        515                 520                 525
Ala Ala Gly Ser Thr Met Gly Ala Ala Ser Ile Thr Leu Thr Val Gln
    530                 535                 540
Ala Arg Gln Leu Leu Ser Gly Ile Val Gln Gln Ser Asn Leu Leu
545                 550                 555                 560
Arg Ala Ile Glu Ala Gln Gln His Met Leu Gln Leu Thr Val Trp Gly
            565                 570                 575
Ile Lys Gln Leu Gln Thr Arg Val Leu Ala Ile Glu Arg Tyr Leu Gln
```

```
                580             585             590
Asp Gln Gln Leu Leu Gly Leu Trp Gly Cys Ser Gly Lys Leu Ile Cys
            595                 600             605

Thr Thr Ala Val Pro Trp Asn Thr Ser Trp Ser Asn Lys Ser Gln Thr
610             615                 620

Asp Ile Trp Asp Asn Met Thr Trp Met Gln Trp Asp Lys Glu Ile Gly
625                 630              635             640

Asn Tyr Thr Gly Glu Ile Tyr Arg Leu Leu Glu Glu Ser Gln Asn Gln
                645             650             655

Gln Glu Lys Asn Glu Lys Asp Leu Leu Ala Leu Asp Ser Trp Lys Asn
            660             665             670

Leu Trp Asn Trp Phe Asp Ile Thr Asn Trp Leu Trp Tyr Ile Lys Ile
        675             680             685

Phe Ile Met Ile Val Gly Gly Leu Ile Gly Leu Arg Ile Ile Phe Ala
    690             695             700

Val Leu Ser Ile Val Asn Arg Val Arg Gln Gly Tyr Ser Pro Leu Ser
705             710             715             720

Leu Gln Thr Leu Thr Gln Asn Pro Gly Gly Leu Asp Arg Leu Gly Arg
                725             730             735

Ile Glu Glu Glu Gly Gly Glu Gln Asp Lys Asp Arg Ser Ile Arg Leu
            740             745             750

Val Asn Gly Phe Phe Ala Leu Phe Trp Asp Asp Leu Arg Ser Leu Cys
        755             760             765

Leu Phe Ser Tyr His Arg Leu Arg Asp Phe Ile Leu Ile Val Ala Arg
    770             775             780

Ala Val Glu Leu Leu Gly Arg Ser Ser Leu Arg Gly Leu Gln Arg Gly
785             790             795             800

Trp Glu Ile Leu Lys Tyr Leu Gly Ser Leu Leu Gln Tyr Trp Gly Leu
                805             810             815

Glu Leu Lys Lys Ser Ala Ile Asn Leu Leu Asp Thr Ile Ala Ile Ala
            820             825             830

Val Ala Glu Gly Thr Asp Arg Ile Ile Glu Leu Ile Gln Arg Ile Cys
        835             840             845

Arg Ala Ile Cys Asn Ile Pro Arg Arg Ile Arg Gln Gly Phe Glu Ala
    850             855             860

Ala Leu Gln
865

<210> SEQ ID NO 32
<211> LENGTH: 716
<212> TYPE: PRT
<213> ORGANISM: Artificial Sequence
<220> FEATURE:
<223> OTHER INFORMATION: C1D7 sequence

<400> SEQUENCE: 32

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
```

-continued

```
                65                  70                  75                  80
        Gln Glu Met Val Leu Glu Asn Val Thr Glu Asn Phe Asn Met Trp Lys
                        85                  90                  95

Asn Asp Met Val Asp Gln Met His Glu Asp Ile Ile Arg Leu Trp Asp
                        100                 105                 110

Gln Ser Leu Lys Pro Cys Val Lys Leu Thr Pro Leu Cys Val Thr Leu
                        115                 120                 125

Glu Cys Arg Asn Val Arg Asn Val Ser Ser Asn Gly Thr Tyr Asn Ile
                130                 135                 140

Ile His Asn Glu Thr Tyr Lys Glu Met Lys Asn Cys Ser Phe Asn Ala
        145                 150                 155                 160

Thr Thr Val Val Glu Asp Arg Lys Gln Lys Val His Ala Leu Phe Tyr
                        165                 170                 175

Arg Leu Asp Ile Val Pro Leu Asp Glu Asn Asn Ser Ser Glu Lys Ser
                        180                 185                 190

Ser Glu Asn Ser Ser Glu Tyr Tyr Arg Leu Ile Asn Cys Asn Thr Ser
                        195                 200                 205

Ala Ile Thr Gln Ala Cys Pro Lys Val Ser Phe Asp Pro Ile Pro Ile
                210                 215                 220

His Tyr Cys Ala Pro Ala Gly Tyr Ala Ile Leu Lys Cys Asn Asn Lys
        225                 230                 235                 240

Thr Phe Asn Gly Thr Gly Pro Cys Asn Asn Val Ser Thr Val Gln Cys
                        245                 250                 255

Thr His Gly Ile Lys Pro Val Val Ser Thr Gln Leu Leu Leu Asn Gly
                        260                 265                 270

Ser Leu Ala Glu Glu Glu Ile Ile Ile Arg Ser Glu Asn Leu Thr Asn
                        275                 280                 285

Asn Ala Lys Thr Ile Ile Val His Leu Asn Glu Thr Val Asn Ile Thr
                        290                 295                 300

Cys Thr Arg Pro Asn Asn Asn Thr Arg Lys Ser Ile Arg Ile Gly Pro
        305                 310                 315                 320

Gly Gln Thr Phe Tyr Ala Thr Gly Asp Ile Ile Gly Asp Ile Arg Gln
                        325                 330                 335

Ala His Cys Asn Leu Ser Arg Asp Gly Trp Asn Lys Thr Leu Gln Gly
                        340                 345                 350

Val Lys Lys Lys Leu Ala Glu His Phe Pro Asn Lys Thr Ile Asn Phe
                        355                 360                 365

Thr Ser Ser Ser Gly Gly Asp Leu Glu Ile Thr Thr His Ser Phe Asn
                        370                 375                 380

Cys Arg Gly Glu Phe Phe Tyr Cys Asn Thr Ser Gly Leu Phe Asn Gly
        385                 390                 395                 400

Thr Tyr Met Pro Asn Gly Thr Asn Ser Asn Ser Ser Asn Ile Thr
                        405                 410                 415

Leu Pro Cys Arg Ile Lys Gln Ile Ile Asn Met Trp Gln Glu Val Gly
                        420                 425                 430

Arg Ala Met Tyr Ala Pro Pro Ile Ala Gly Asn Ile Thr Cys Arg Ser
                        435                 440                 445

Asn Ile Thr Gly Leu Leu Leu Thr Arg Asp Gly Gly Ser Asn Asn Gly
                        450                 455                 460

Val Pro Asn Asp Thr Glu Thr Phe Arg Pro Gly Gly Gly Asp Met Arg
        465                 470                 475                 480

Asn Asn Trp Arg Ser Glu Leu Tyr Lys Tyr Lys Val Val Glu Val Lys
                        485                 490                 495
```

```
Pro Leu Gly Val Ala Pro Thr Glu Ala Lys Arg Arg Val Glu Arg
            500                 505                 510

Glu Lys Arg Ala Val Gly Ile Gly Ala Val Phe Leu Gly Ile Leu Gly
    515                 520                 525

Ala Ala Gly Ser Thr Met Gly Ala Ala Ser Ile Thr Leu Thr Val Gln
530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
            595                 600                 605

Thr Thr Ala Val Pro Trp Asn Thr Ser Trp Ser Asn Lys Ser Gln Thr
    610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp Tyr Ile Lys Ile
        675                 680                 685

Phe Ile Met Ile Val Gly Gly Leu Ile Gly Leu Arg Ile Ile Phe Ala
    690                 695                 700

Val Leu Ser Ile Val Asn Arg Val Arg Gln Gly Tyr
705                 710                 715

<210> SEQ ID NO 33
<211> LENGTH: 2127
<212> TYPE: DNA
<213> ORGANISM: Artificial Sequence
<220> FEATURE:
<223> OTHER INFORMATION: nucleotide sequence encoding sC1

<400> SEQUENCE: 33
atgagagtgc ggggcattca gagaaactgg ccccagtggt ggatctgggg catcctgggc      60
ttttggatga tcattatctg ccgcgtgatg ggcaacctgt gggtcaccgt gtactacggc     120
gtgcccgtgt ggaaagaggc caagaccacc ctgttctgcg ccagcgacgc caaggcctac     180
gagaaagagg tgcacaacgt ctgggccacc cacgcctgtg tgcccaccga ccccaatccc     240
caggaaatgt cctggaaaa cgtgaccgag aacttcaaca tgtggaagaa cgacatggtg     300
gaccagatgc acgaggacat catccggctg tgggaccaga gcctgaagcc ctgcgtgaag     360
ctgacccctc tgtgcgtgac cctggaatgc ggaacgtgc gcaacgtgtc cagcaacggc     420
acctacaata tcatccacaa cgagacatac aaagagatga gaactgcag cttcaacgct     480 accaccgtgg tcgaggaccg gaagcagaag gtgcacgccc tgttttaccg gctggacatc     540
gtgcccctgg acgagaacaa cagcagcgag aagtcctccg agaacagctc cgagtactac     600
agactgatca actgcaacac cagcgccatc acccaggcct gccccaaggt gtccttcgac     660
cctatcccca tccactactg cgcccctgcc ggctacgcca tcctgaagtg caacaacaag     720
accttcaatg gcaccggccc ctgcaacaat gtgtccaccg tgcagtgcac ccacggcatc     780
```

```
aagcccgtgg tgtctaccca gctgctgctg aacggcagcc tggccgagga agagatcatc    840
atcagaagcg agaacctgac caacaacgcc aagacaatca tcgtccacct gaacgaaacc    900
gtgaacatca cctgtacccg gcctaacaac aacacccgga agtccatccg gatcggccct    960
ggccagacct tttacgccac cggcgatatt atcggcgaca tccggcaggc ccactgcaat   1020
ctgagccggg acggctggaa caagacactg cagggcgtca agaagaagct ggccgaacac   1080
ttccccaaca aaaccatcaa cttcaccagc tcctctggcg gcgacctgga aatcaccacc   1140
cacagcttta actgcagagg cgagttcttc tactgcaata cctccggcct gttcaatgga   1200
acctacatgc ccaacgggac caacagcaac tccagcagca atatcaccct gccttgccgg   1260
atcaagcaga ttatcaatat gtggcaggaa gtgggcagag ctatgtacgc ccctccaatc   1320
gccggcaaca tcacatgcag aagcaacatt accggcctgc tgctcaccag ggacggcggc   1380
tctaacaatg gcgtgccaaa cgacaccgag acattcagac ccggcggagg cgacatgcgg   1440
aacaattggc ggagcgagct gtacaagtac aaggtggtgg aagtgaagcc cctgggcgtg   1500
gcccctaccg aagccaagag aagagtggtc gaacgcgagg aacgggccgt gggcattgga   1560
gccgtgtttc tgggaatcct gggagccgct ggcagcacca tgggcgctgc ctctatcaca   1620
ctgacagtgc aggccagaca gctcctgagc ggcatcgtgc agcagcagag caacctgctg   1680
agagccatcg aggcacagca gcacatgctg cagctgaccg tgtggggcat taagcagctc   1740
cagacacggg tgctggccat tgagagatac ctgcaggatc agcagctgct cggcctgtgg   1800
ggctgtagcg gcaagctgat ctgtaccacc gccgtgcctt ggaacacctc ctggtccaac   1860
aagagccaga ccgacatctg gacaacatg acctggatgc agtgggacaa agaaatcggc   1920
aactataccg gcgagatcta ccgactgctg gaagagtccc agaaccagca ggaaaagatg   1980
aagcagatcg aggacaagat cgaagagatt ctgagcaaaa tctaccacat cgagaacgag   2040
atcgcccgca tcaagaaact gatcggcgaa gtgggatccg gcgctcccac aaaggccaaa   2100
agacgggtgg tgcagcgcga gaaacgc                                       2127
```

<210> SEQ ID NO 34
<211> LENGTH: 2601
<212> TYPE: DNA
<213> ORGANISM: Artificial Sequence
<220> FEATURE:
<223> OTHER INFORMATION: nucleotide sequence encoding C1

<400> SEQUENCE: 34

```
atgagagtgc ggggcattca gagaaactgg ccccagtggt ggatctgggg catcctgggc     60
ttttggatga tcattatctg ccgcgtgatg ggcaacctgt gggtcaccgt gtactacggc    120
gtgcccgtgt ggaaagaggc caagaccacc ctgttctgcg ccagcgacgc caaggcctac    180
gagaaagagg tgcacaacgt ctgggccacc cacgcctgtg tgcccaccga ccccaatccc    240
caggaaatgg tcctgaaaaa cgtgaccgag aacttcaaca tgtggaagaa cgacatggtg    300
gaccagatgc acgaggacat catccggctg tgggaccaga gctgaagcc ctgcgtgaag    360 ctgacccctc tgtgcgtgac cctggaatgc ggaacgtgc gcaacgtgtc cagcaacggc    420
acctacaata tcatccacaa cgagacatac aaagagatga gaactgcag cttcaacgct    480 accaccgtgg tcgaggaccg gaagcagaag gtgcacgccc tgttttaccg gctggacatc    540
gtgcccctgg acgagaacaa cagcagcgag aagtcctccg agaacagctc cgagtactac    600
agactgatca actgcaacac cagcgccatc acccaggcct gccccaaggt gtccttcgac    660
cctatcccca tccactactg cgcccctgcc ggctacgcca tcctgaagtg caacaacaag    720
```

```
accttcaatg gcaccggccc ctgcaacaat gtgtccaccg tgcagtgcac ccacggcatc      780
aagcccgtgg tgtctaccca gctgctgctg aacggcagcc tggccgagga agagatcatc      840
atcagaagcg agaacctgac caacaacgcc aagacaatca tcgtccacct gaacgaaacc      900
gtgaacatca cctgtacccg gcctaacaac aacacccgga gtccatccg gatcggccct       960 ggccagacct tttacgccac cggcgatatt atcggcgaca tccggcaggc ccactgcaat     1020
ctgagccggg acggctggaa caagacactg cagggcgtca agaagaagct ggccgaacac     1080
ttccccaaca aaaccatcaa cttcaccagc tcctctggcg gcgacctgga aatcaccacc     1140
cacagcttta actgcagagg cgagttcttc tactgcaata cctccggcct gttcaatgga     1200
acctacatgc caacgggac caacagcaac tccagcagca atatcaccct gccttgccgg      1260
atcaagcaga ttatcaatat gtggcaggaa gtgggcagag ctatgtacgc ccctccaatc     1320
gccggcaaca tcacatgcag aagcaacatt accggcctgc tgctcaccag ggacggcggc     1380
tctaacaatg gcgtgccaaa cgacaccgag acattcagac cggcggagg cgacatgcgg      1440 aacaattggc ggagcgagct gtacaagtac aaggtggtgg aagtgaagcc cctgggcgtg     1500
gcccctaccg aagccaagag aagagtggtc gaacgcgaga gcggccgt gggcattgga       1560 gccgtgtttc tgggaatcct gggagccgct ggcagcacca tgggcgctgc ctctatcaca     1620
ctgacagtgc aggccagaca gctcctgagc ggcatcgtgc agcagcagag caacctgctg     1680
agagccatcg aggcacagca gcacatgctg cagctgaccg tgtgggcat taagcagctc      1740 cagacacggg tgctggccat tgagagatac ctgcaggatc agcagctgct cggcctgtgg     1800
ggctgtagcg gcaagctgat ctgtaccacc gccgtgcctt ggaacacctc ctggtccaac     1860
aagagccaga ccgacatctg gacaacatg acctggatgc agtgggacaa agaaatcggc      1920
aactataccg gcgagatcta ccgactgctg gaagagtccc agaaccagca ggaaaagaac     1980
gagaaggacc tgctggccct ggacagctgg aaaaatctgt ggaattggtt cgacatcacc     2040
aactggctgt ggtacatcaa gatcttcatc atgatcgtgg gcggcctgat cggcctgcgg     2100
atcatctttg ccgtgctgag catcgtgaac cgcgtgcggc agggatacag ccctctgagc     2160
ctgcagaccc tgacccagaa tccaggcgga ctggatcggc tgggccggat tgaggaagaa     2220
ggcggcgagc aggacaagga ccgcagcatc agactcgtga acggcttctt cgctctgttt     2280
tgggacgacc tgcggagcct gtgcctgttc tcctaccaca gactgcggga ctttatcctg     2340
attgtggcca gagccgtcga gctgctgggc agatcttctc tgagaggcct gcagcggggc     2400
tgggagattc tgaagtacct gggctccctg ctgcagtatt ggggcctgga actgaagaag     2460
tccgccatca tctgctcga cacaatcgct attgccgtgg ccgaaggcac cgacagaatc     2520
atcgagctga tccagcggat ctgccgggcc atctgcaaca tccccagacg gatcagacag     2580
ggctttgaag ccgccctcca g                                                2601
```

<210> SEQ ID NO 35
<211> LENGTH: 2148
<212> TYPE: DNA
<213> ORGANISM: Artificial Sequence
<220> FEATURE:
<223> OTHER INFORMATION: nucleotide sequence encoding C1D7

<400> SEQUENCE: 35

```
atgagagtgc gggcattca gagaaactgg ccccagtggt ggatctgggg catcctgggc       60
ttttggatga tcattatctg ccgcgtgatg ggcaacctgt gggtcaccgt gtactacggc     120
```

| | |
|---|---|
| gtgcccgtgt ggaaagaggc caagaccacc ctgttctgcg ccagcgacgc caaggcctac | 180 |
| gagaaagagg tgcacaacgt ctgggccacc cacgcctgtg tgcccaccga ccccaatccc | 240 |
| caggaaatgg tcctggaaaa cgtgaccgag aacttcaaca tgtggaagaa cgacatggtg | 300 |
| gaccagatgc acgaggacat catccggctg tgggaccaga gcctgaagcc ctgcgtgaag | 360 |
| ctgacccctc tgtgcgtgac cctggaatgc cggaacgtgc gcaacgtgtc cagcaacggc | 420 |
| acctacaata tcatccacaa cgagacatac aaagagatga gaactgcag cttcaacgct | 480 |
| accaccgtgg tcgaggaccg gaagcagaag gtgcacgccc tgttttaccg gctggacatc | 540 |
| gtgcccctgg acgagaacaa cagcagcgag aagtcctccg agaacagctc cgagtactac | 600 |
| agactgatca actgcaacac cagcgccatc acccaggcct gccccaaggt gtccttcgac | 660 |
| cctatcccca tccactactg cgcccctgcc ggctacgcca tcctgaagtg caacaacaag | 720 |
| accttcaatg gcaccggccc ctgcaacaat gtgtccaccg tgcagtgcac ccacggcatc | 780 |
| aagcccgtgg tgtctaccca gctgctgctg aacggcagcc tggccgagga agagatcatc | 840 |
| atcagaagcg agaacctgac caacaacgcc aagacaatca tcgtccacct gaacgaaacc | 900 |
| gtgaacatca cctgtacccg gcctaacaac aacacccgga agtccatccg gatcggccct | 960 |
| ggccagacct tttacgccac cggcgatatt atcggcgaca tccggcaggc ccactgcaat | 1020 |
| ctgagccggg acggctggaa caagacactg cagggcgtca agaagaagct ggccgaacac | 1080 |
| ttccccaaca aaaccatcaa cttcaccagc tcctctggcg gcgacctgga aatcaccacc | 1140 |
| cacagcttta actgcagagg cgagttcttc tactgcaata cctccggcct gttcaatgga | 1200 |
| acctacatgc caacgggac caacagcaac tccagcagca atatcaccct gccttgccgg | 1260 |
| atcaagcaga ttatcaatat gtggcaggaa gtgggcagag ctatgtacgc ccctccaatc | 1320 |
| gccggcaaca tcacatgcag aagcaacatt accggcctgc tgctcaccag ggacggcggc | 1380 |
| tctaacaatg gcgtgccaaa cgacaccgag acattcagac ccggcggagg cgacatgcgg | 1440 |
| aacaattggc ggagcgagct gtacaagtac aaggtggtgg aagtgaagcc cctgggcgtg | 1500 |
| gcccctaccg aagccaagag aagagtggtc gaacgcgaga gcgggccgt gggcattgga | 1560 |
| gccgtgtttc tgggaatcct gggagccgct ggcagcacca tggcgctgc ctctatcaca | 1620 |
| ctgacagtgc aggccagaca gctcctgagc ggcatcgtgc agcagcagag caacctgctg | 1680 |
| agagccatcg aggcacagca gcacatgctg cagctgaccg tgtggggcat taagcagctc | 1740 |
| cagacacggg tgctggccat tgagagatac ctgcaggatc agcagctgct cggcctgtgg | 1800 |
| ggctgtagcg gcaagctgat ctgtaccacc gccgtgcctt ggaacacctc ctggtccaac | 1860 |
| aagagccaga ccgacatctg gacaacatg acctggatgc agtgggacaa agaaatcggc | 1920 |
| aactataccg gcgagatcta ccgactgctg gaagagtccc agaaccagca ggaaaagaac | 1980 |
| gagaaggacc tgctggccct ggacagctgg aaaaatctgt ggaattggtt cgacatcacc | 2040 |
| aactggctgt ggtacatcaa gatcttcatc atgatcgtgg cggcctgat cggcctgcgg | 2100 |
| atcatctttg ccgtgctgag catcgtgaac cgcgtgcggc agggctac | 2148 |

<210> SEQ ID NO 36
<211> LENGTH: 724
<212> TYPE: PRT
<213> ORGANISM: Artificial Sequence
<220> FEATURE:
<223> OTHER INFORMATION: mosaic Env trimer sequence

<400> SEQUENCE: 36

Met Arg Val Arg Gly Ile Gln Arg Asn Cys Gln His Leu Trp Arg Trp

-continued

```
1               5                   10                  15
Gly Thr Leu Ile Leu Gly Met Leu Met Ile Cys Ser Ala Ala Gly Lys
                20                  25                  30

Leu Trp Val Thr Val Tyr Tyr Gly Val Pro Val Trp Lys Glu Ala Thr
                35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
 65                 70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
            115                 120                 125

Asn Cys Thr Asp Asp Val Arg Asn Val Thr Asn Asn Ala Thr Asn Thr
130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
            195                 200                 205

Ala Cys Pro Lys Val Ser Phe Glu Pro Ile Pro Ile His Tyr Cys Ala
210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
            275                 280                 285

Ile Met Val Gln Leu Asn Val Ser Val Glu Ile Asn Cys Thr Arg Pro
290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
            355                 360                 365

Ser Gly Gly Asp Pro Glu Ile Val Met His Ser Phe Asn Cys Gly Gly
370                 375                 380

Glu Phe Phe Tyr Cys Asn Ser Thr Lys Leu Phe Asn Ser Thr Trp Thr
385                 390                 395                 400

Trp Asn Asn Ser Thr Trp Asn Asn Thr Lys Arg Ser Asn Asp Thr Glu
                405                 410                 415

Glu His Ile Thr Leu Pro Cys Arg Ile Lys Gln Ile Ile Asn Met Trp
            420                 425                 430
```

```
Gln Glu Val Gly Lys Ala Met Tyr Ala Pro Pro Ile Arg Gly Gln Ile
            435                 440                 445
Arg Cys Ser Ser Asn Ile Thr Gly Leu Leu Leu Thr Arg Asp Gly Gly
        450                 455                 460
Asn Asp Thr Ser Gly Thr Glu Ile Phe Arg Pro Gly Gly Gly Asp Met
465                 470                 475                 480
Arg Asp Asn Trp Arg Ser Glu Leu Tyr Lys Tyr Lys Val Val Lys Ile
                485                 490                 495
Glu Pro Leu Gly Val Ala Pro Thr Lys Ala Lys Glu Arg Val Val Gln
            500                 505                 510
Arg Glu Glu Arg Ala Val Gly Ile Gly Ala Val Phe Leu Gly Phe Leu
        515                 520                 525
Gly Ala Ala Gly Ser Thr Met Gly Ala Ala Ser Met Thr Leu Thr Val
    530                 535                 540
Gln Ala Arg Leu Leu Leu Ser Gly Ile Val Gln Gln Gln Asn Asn Leu
545                 550                 555                 560
Leu Arg Ala Ile Glu Ala Gln Gln His Leu Leu Gln Leu Thr Val Trp
                565                 570                 575
Gly Ile Lys Gln Leu Gln Ala Arg Val Leu Ala Val Glu Arg Tyr Leu
            580                 585                 590
Lys Asp Gln Gln Leu Leu Gly Ile Trp Gly Cys Ser Gly Lys Leu Ile
        595                 600                 605
Cys Thr Thr Thr Val Pro Trp Asn Ala Ser Trp Ser Asn Lys Ser Leu
    610                 615                 620
Asp Lys Ile Trp Asn Asn Met Thr Trp Met Glu Trp Glu Arg Glu Ile
625                 630                 635                 640
Asn Asn Tyr Thr Ser Leu Ile Tyr Thr Leu Ile Glu Glu Ser Gln Asn
                645                 650                 655
Gln Gln Glu Lys Asn Glu Gln Glu Leu Leu Glu Leu Asp Lys Trp Ala
            660                 665                 670
Ser Leu Trp Asn Trp Phe Asp Ile Ser Asn Trp Leu Trp Tyr Ile Lys
        675                 680                 685
Ser Arg Ile Glu Gly Arg Gly Ser Gly Gly Tyr Ile Pro Glu Ala Pro
    690                 695                 700
Arg Asp Gly Gln Ala Tyr Val Arg Lys Asp Gly Glu Trp Val Leu Leu
705                 710                 715                 720
Ser Thr Phe Leu

<210> SEQ ID NO 37
<211> LENGTH: 28
<212> TYPE: PRT
<213> ORGANISM: Artificial Sequence
<220> FEATURE:
<223> OTHER INFORMATION: Residues 655-682 of SEQ ID NO:18

<400> SEQUENCE: 37

Asn Glu Lys Asp Leu Leu Ala Leu Asp Ser Trp Asn Asn Leu Trp Asn
1               5                   10                  15
Trp Phe Ser Ile Ser Lys Trp Leu Trp Tyr Ile Lys
            20                  25

<210> SEQ ID NO 38
<211> LENGTH: 4056
<212> TYPE: DNA
<213> ORGANISM: Artificial Sequence
<220> FEATURE:
```

<223> OTHER INFORMATION: nucleotide sequence of Mos1Gag-Pol antigen

<400> SEQUENCE: 38

```
atgggagcta gagccagtgt gctgagcggc ggagagctgg atagatggga gaaaattcgg    60
ctgcggccag gcggcaaaaa gaagtatcgc ctgaaacata ttgtgtgggc ctctcgcgag   120
ctggaaagat tgctgtgtaa tcctggactg ctcgagacat ctgaaggctg ccgccagatc   180
ctcggtcaac tgcagccatc tctgcagacc ggctcagaag agctgagatc tctgtataat   240
actgtcgcca cactctattg cgtccaccag cgcattgaaa tcaaagatac aaaggaggct   300
ctggagaaga tagaagagga acagaataag tctaaaaaga aggctcagca ggccgctgcc   360
gataccggca acagctctca ggtctcacaa aattacccta tcgttcagaa tattcaaggt   420
caaatggtcc atcaggctat cagccctcgc acactgaatg cttgggtgaa agtggtcgag   480
gaaaaagcct ttagtccaga ggttataccc atgtttagcg cactgtctga aggagccact   540
cctcaggacc tcaataccat gctgaatact gtcggaggcc atcaggccgc tatgcaaatg   600
ctgaaagaaa ccattaacga ggaagccgcc gaatgggatc gagtgcatcc agtccatgca   660
ggaccaatcg ctccaggcca gatgagagaa cctcgaggct ctgatatcgc cggaaccaca   720
agcacactgc aggaacagat tggatggatg acaaacaatc ctcctatccc tgtcggcgag   780
atctataaga gatggattat cctcggcctc aacaagattg tcagaatgta ttcacctgtg   840
tccattctgg atatccgcca aggacctaaa gagccattcc gcgattacgt cgaccgcttt   900
tacaaaaccc tgagagctga gcaggcatct caggatgtca aaattggat gacagaaact   960
ctcctggtcc agaacgctaa tcctgattgc aagacaattc tgaaggctct gggaccagcc  1020
gccactctcg aggaaatgat gaccgcttgt cagggagtcg gaggacctgg acacaaggca  1080
agagtgctcg ctgaagccat gtctcaggtc acaaacagcg ccacaattat gatgcagcgc  1140
ggtaacttca gaaaccagcg gaaaaccgtc aagtgtttta attgcggtaa agagggccat  1200
attgccaaaa attgcagagc tcctcggaaa aagggctgct ggaaatgtgg aaaagaaggt  1260
catcaaatga aggattgcac agaacgccag gccaatttcc ttgggaagat tggccttcc   1320
aacaaaggcc gaccaggaaa ctttctgcag aatcggcctg agcctaccgc tccacctgaa  1380
gagagcttta gattcggcga ggaaacaacc acaccatctc agaaacaaga gcctattgat  1440
aaggaaatgt atcctctggc ttctctgaag tctctgttcg gcaatgatcc tagctcacaa  1500
atggctccca ttagtcctat tgaaacagtg cctgtgaaac tgaaacctgg aatggacggt  1560
cctagagtca agcagtggcc tctcacagaa gagaagatta aggcactcac cgctatttgc  1620
gaagagatgg agaaagaagg caagattaca agattggac ctgagaatcc atacaataca  1680
cctgtctttg ccatcaaaaa gaaagattct accaaatggc gcaagctcgt ggatttcaga  1740
gaactcaaca acgcacaca ggattttgg gaggtccagc tcggaattcc tcatccagcc  1800
ggactgaaaa agaagaagtc cgtcacagtc ctggcagtcg cgacgcccta tttctccgtg  1860
cctctcgatg aaggttttag gaagtatacc gcctttacaa ttccatccac aaacaacgaa  1920
acaccaggca tccggtacca gtataatgtc ctgccacaag gatggaaggg atctcctgcc  1980
atctttcagt gttccatgac acggatcctt gaacctttca gagccaagaa tccagagatt  2040
gtgatctatc aatacatggc cgcactctat gtcggatctg acctcgagat ggacagcac   2100
cgcgccaaga tcgaagagct gagagaacat ctgctgaaat gggctttac aacaccagat  2160
aagaaacatc agaaagaacc tccttttctt tggatgggat atgaactgca tcccgacaaa  2220
tggacagtcc agcctatcca gctgccagag aaggatagct ggaccgttaa tgatattcag  2280
```

```
aagctcgttg gtaaactgaa ttgggccagt caaatctatc ctggaatcaa agtccgacag    2340
ctgtgcaagc tgctcagagg cgccaaggct ctcaccgata ttgtgcctct gaccgaagag    2400
gctgaactgg agctggccga gaatagagaa atcctcaagg agcctgtcca cggcgtctac    2460
tacgatcctt ctaaagacct gatcgctgaa atccaaaagc aaggacatga tcaatggaca    2520
tatcagatct accaggagcc ttttaagaat cttaagaccg gcaagtatgc caaaatgcgc    2580
accgctcata caaatgacgt gaaacagctc accgaggctg tccagaaaat tgctatggaa    2640
tctatcgtca tttggggcaa aacacctaaa ttccggcttc ctattcagaa agaaacctgg    2700
gagacatggt ggacagatta ctggcaagct acatggatcc tgaatggga atttgtgaat    2760 acacctcctc tcgtcaaact gtggtaccag ttggagaagg atccaatcgc cggcgtggaa    2820
acattctatg tggcaggcgc cgctaacaga gaaactaagc tcggcaaggc cggatatgtg    2880
acagacagag gtagacagaa gattgtatct ctgacagaga caacaaatca gaaaaccgct    2940
ctccaggcta tctacctcgc actgcaggat tccggcagcg aagtgaatat tgtgaccgcc    3000
tctcagtatg cactcggaat tattcaggca cagcctgata agtccgagtc cgagctggtc    3060
aatcagatca tcgaacagct gattaagaag gaaagagtct acctgtcttg ggtgccagca    3120
cacaagggaa tcggcggcaa tgaacaggtg gacaaacttg tgtcctccgg tattagaaag    3180
gtcctgttcc tcgatggaat tgacaaggct caggaagaac acgagaaata tcactccaac    3240
tggagagcta tggcctccga tttcaatctg ccacctgttg tggctaagga aattgtcgct    3300
tcctgcgatc agtgtcaact caaaggcgaa gctatgcatg gacaggtcga ctgttctcct    3360
ggaatatggc aactcgcttg tacacacctc gaaggcaaaa tcatcctcgt ggctgtccat    3420
gtggcctccg gctatattga agccgaagtg attcctgctg aaaccggcca ggaaaccgct    3480
tactttattc tgaaactcgc tggacggtgg cctgtgaaag tgattcatac cgccaatggc    3540
tccaacttca ccagcgccgc tgtgaaagcc gcttgctggt gggccggaat ccagcaggag    3600
ttcggaatac cgtataaccc tcagtcacaa ggagtggtcg cctctatgaa caaggaattg    3660
aagaaaatca taggtcaagt ccgagaccaa gccgaacacc tcaagaccgc tgtccagatg    3720 gcagtctttta tccacaattt caagcgcaaa ggcggcattg gcggctacag tgccggcgag    3780
agaattatcg acataatcgc cacagacatt cagacaaagg agctccagaa gcagataatc    3840
aagatacaga atttccgcgt gtactaccgc gactctagag accctatatg gaagggtcca    3900
gctaagctct tgtggaaggg cgaaggcgct gtggtcattc aggacaattc cgatatcaag    3960
gtcgttcctc ggcggaaagt caagatcatt aaggattatg gtaaacaaat ggccggagct    4020
gattgcgtgg caggccggca ggacgaagat tgataa                              4056
```

<210> SEQ ID NO 39
<211> LENGTH: 2061
<212> TYPE: DNA
<213> ORGANISM: Artificial Sequence
<220> FEATURE:
<223> OTHER INFORMATION: nucleotide sequence of Mos1Env antigen

<400> SEQUENCE: 39

```
atgcgcgtga ccggcatcag gaaaaactat cagcatctgt ggagatgggg tacaatgctc      60
ctcggaattc tcatgatctg tagcgccgct ggcaaactgt gggttacagt ctattatggc     120
gttccagtgt ggaaagaagc tacaacaaca ctgttctgtg cctccgatgc caaggcctat     180
gatacagaag tgcataacgt ctgggctaca catgcttgtg tgcctaccga tcctaatcct     240
```

```
caggaggtcg tcctcgaaaa cgtcacagaa aactttaata tgtggaaaaa caatatggtc      300
gaacagatgc acgaagatat catttctctg tgggatcaga gtctcaagcc ttgtgtgaaa      360
ctgacacctc tgtgcgtcac actcaattgc acagatgatg tccggaacgt cacaaacaat      420
gctacaaata ccaactcctc ctggggtgaa cctatggaaa aaggcgaaat caaaaattgt      480
tcctttaata tcacaaccag catccgcaac aaagtccaga acagtatgc tctcttttac       540 aaactcgacg tcgtgcctat cgataatgac tccaacaata caattaccg cctcatctcc       600 tgtaacacct ccgtgattac tcaggcctgt cctaaagtct cttttgagcc tatcccaatt      660
cactattgtg cacctgctgg atttgccatc ctcaagtgta atgacaagaa gtttaacggt      720
accggtcctt gtaccaacgt gtccacagtg cagtgtacac acggaattag acctgtggtg      780
tctactcagc tgctcctgaa tggctctctg gccgaagagg aagtcgtgat tcggagcgag      840
aactttacaa ataacgctaa acaatcatg gtccagctca atgtctccgt cgagattaac       900
tgtaccagac ctaacaataa cactcgcaag tccatccaca ttggaccagg acgcgccttt      960
tacaccgctg gtgacattat cggagatatc aggcaggcac actgtaatat ctctcgcgcc     1020
aactggaaca acactctcag acagattgtc gagaagctcg gtaaacagtt tggtaacaac     1080
aaaacaatcg tctttaatca cagctctggc ggcgatcctg agatcgtcat gcattccttc     1140
aattgcggag gggagttctt ttattgcaac tctaccaagc tctttaactc cacatggact     1200
tggaataaca gcacatggaa caataccaaa cgctccaacg atacagagga acacatcact     1260
ttgccatgca gaatcaagca aatcattaac atgtggcaag aggtgggtaa agccatgtat     1320
gctcctccta tcagaggaca gatcagatgc agctccaaca ttacaggcct gctcctgaca     1380
agagatggcg gaaacgacac ctccggaaca gagatcttca gaccaggcgg aggagacatg     1440
agagacaact ggagaagcga actctataag tataaggtcg tcaagattga gccacttgga     1500
gtggctccca caaaggccaa gagacgcgtg gtgcagtccg aaaagtccgc cgtcggaatt     1560
ggagctgtgt tctctcggatt tctgggagct gccggctcta ccatgggagc agcctccatg    1620
acactgacag tccaggctag actgctgctg agtggcattg tccagcaaca gaacaatctc     1680
ctgagagcca ttgaagctca gcaacatctc ctccagctca cagtctgggg catcaaacag     1740
ctccaggcaa gagtgctcgc cgtcgagcgg tacctgaaag accagcaact cctcggcatt     1800
tggggctgtt ccgaaaaact gatctgcacc acaacagttc cctggaatgc ctcttggagc     1860
aacaaatctc tcgataagat ttggaataac atgacttgga tggagtggga aagagaaatc     1920
aacaactaca cctctctcat ctacacactc atcgaagagt ctcaaaatca gcaagaaaag     1980
aatgaacagg agctcctcga gctggataag tgggcttctc tctggaattg gttcgatatc     2040
tctaactggc tctggtgata a                                                2061
```

<210> SEQ ID NO 40
<211> LENGTH: 4029
<212> TYPE: DNA
<213> ORGANISM: Artificial Sequence
<220> FEATURE:
<223> OTHER INFORMATION: nucleotide sequence of Mos2 Gag-Pol antigen

<400> SEQUENCE: 40

```
atgggcgcca gagcctctat cctgcgcgga ggcaaactgg ataagtggga aaagattaga      60
ctccgacctg gcggtaaaaa gcattatatg ctcaaacacc tcgtctgggc tagcagagaa     120
ctcgagagat tcgctctgaa ccctggtctc ctggaaacat ccgaagggtg taaacagatt     180
atcaaacagc tccagcctgc actccagact ggaacagagg aacttcgctc tctgtttaat     240
```

```
accgtggcta cactgtattg tgtgcacgct gaaatcgaag tccgcgacac aaaagaagct    300
ctcgacaaaa ttgaggaaga gcagaacaaa tctcagcaga agacacagca ggctaaggaa    360
gccgacggaa aagtgagcca gaattatccc attgtccaaa atctccaagg acagatggtg    420
catcagccaa tctctccaag aacactcaac gcctgggtca aggtcataga agagaaggca    480
ttctcacctg aagtcattcc aatgttcacc gctctgtccg aaggcgcaac accacaggat    540
ctgaacacta tgctcaatac cgtcggcgga caccaggcag caatgcagat gctcaaggat    600
acaatcaatg aagaggcagc tgagtgggat agactccatc ctgtgcatgc cggtccagtc    660
gcacctggac agatgcgcga gcctagaggc tccgacattg ctggcacaac cagtaacctc    720
caggagcaga tcgcttggat gacttccaat ccacctattc cagtcggaga tatctacaaa    780
cgctggatca ttctcggtct gaacaaaatc gtgcggatgt actctcctac cagcatcctc    840
gatattaagc aaggtccaaa agaaccttt cgagactatg tcgacagatt ctttaaaaca     900
ctgcgcgcag aacaggctac acaggacgtg aagaactgga tgactgatac actcctcgtg    960
cagaatgcaa atccagactg taaaacaatc ctgagagctc tcggtccagg cgctacactg   1020
gaagagatga tgactgcatg tcaaggtgtc ggtggaccta gccacaaagc tcgcgtgctg   1080
gcagaggcta tgtcacagac caattccaca atcctcatgc aacgctccaa tttcaaggc    1140
tccaagcgca ttgtcaaatg ctttaactgt ggcaaagaag acatatcgc tcggaattgc    1200
cgcgcaccac gcaagaaagg atgttggaag tgcggcaagg aaggacatca gatgaaagac   1260
tgtactgaga acaagctaa tttttctcggc aaaatctggc catctcacaa aggacgacct   1320
ggaaatttcc tgcagtctcg gccagaacct acagctcctc ctgccgagtc cttcagattc   1380
gaagagacta caccagctcc taaacaggaa cctaaggata gagaacctct gacctctctg   1440
cgcagcctgt ttggctccga tcctctgtcc cagatggcac caatttctcc aatcgaaacc   1500
gttcctgtca agctcaagcc aggcatggat ggaccaaaag tcaaacaatg gccactcact   1560
gaggagaaaa tcaaggctct ggtcgaaatc tgcacagaaa tggaaaagga aggaaagatt   1620
tccaaaatcg gaccagaaaa tccttacaac acacctatct ttgctattaa gaagaaggac   1680
tccacaaagt ggcgaaagct ggtcgacttt cgcgagctga acaagagaac tcaggacttc   1740
tgggaagtgc aactcggtat tccacatcct gcaggactca gaaaaagaa atctgtcact   1800
gtgctcgccg tcggtgacgc ttactttct gtgccactgg atgaagattt tcgcaagtac   1860
accgcattca caatcccttc cattaacaat gagacacctg gtattcgcta tcagtacaat   1920
gtgcttcctc aaggctggaa aggtagtcct gctattttcc agtcctctat gacaaagatt   1980
cttgagcctt ttcgcaaaca gaatcctgat atcgtcatct accagtatat ggcagctctg   2040
tacgtcggct ctgatctgga aatcggccag catagaacta agattgagga actccgacag   2100
cacctgctcc gctggggttt tactactcct gacaagaagc accagaagga accaccattc   2160
ctctggatgg gttacgaact tcatcctgat aagtggactg cagccaat tgtcctgcct     2220
gaaaaggatt cttggacagt caatgacatc cagaaactcg tcggaaaact caactgggct   2280
tctcagatct atgccggcat taaggtcaag cagctctgca aactcctgag aggcacaaag   2340
gcactgacag aagtggttcc tctcactgaa gaagcagaac tcgaactcgc tgagaaccgc   2400
gaaattctca agaaccagt gcatggtgtc tattatgatc caagcaaaga tctcattgca   2460
gagattcaga aacaaggcca aggccagtgg acttaccaaa tctatcagga acctttcaaa   2520
aatctcaaga caggcaaata cgctcggatg cgaggcgctc acaccaatga tgtcaagcaa   2580
```

-continued

| | |
|---|---|
| ctcacagagg cagtgcagaa gattgccaca gagtctattg tgatctgggg aaagactcca | 2640 |
| aagtttaagc ttccaatcca aaaggagact tgggaagctt ggtggactga atattggcag | 2700 |
| gcaacttgga ttccagagtg ggagtttgtc aatactccac cactcgtgaa gctctggtat | 2760 |
| cagctcgaga aagagcctat cgtcggcgcc gaaaccttt atgtcgctgg tgccgcaaac | 2820 |
| cgcgagacaa aactcggaaa agcaggatac gtcaccgata gaggacggca gaaggtcgtc | 2880 |
| agcctgaccg acactactaa ccagaagact gcacttcagg caattcatct ggctctccag | 2940 |
| gatagcggtc tggaagtcaa tatcgtcacc gctagtcagt acgctctggg tattatccag | 3000 |
| gctcagccag acaaaagcga atccgaactc gtgtctcaga ttattgagca gctcatcaag | 3060 |
| aaagagaaag tctatctcgc ctgggttccg gctcacaaag gcattggtgg aaatgagcaa | 3120 |
| gtcgataagc tcgtcagcag aggaatcagg aaagtcctct tcctggacgg tatcgataag | 3180 |
| gcacaggagg aacatgagaa gtaccacagt aactggcgcg ccatggcttc tgagtttaac | 3240 |
| ctgcctccaa tcgtcgccaa agagatcgtg gcaagctgtg acaaatgtca gctgaaagga | 3300 |
| gaggcaatcc atggccaggt tgactgctca ccaggaattt ggcagctcgc ctgcactcat | 3360 |
| ctggaaggaa aagtgattct ggtcgctgtg catgtcgcta gtggctacat cgaggctgag | 3420 |
| gtcataccag cagagacagg acaggagact gcttattttc tgctcaagct cgccggaaga | 3480 |
| tggccagtca agaccattca caccgctaac ggctctaatt tcacaagcgc cacagtcaaa | 3540 |
| gcagcatgtt ggtgggctgg tatcaaacag gaattcggca ttcctttataa tccacagtct | 3600 |
| caaggcgtcg tggctagtat caacaaagaa ctcaaaaaga tcattggcca agtcagagac | 3660 |
| caggctgagc atctcaaaac tgcagtgcaa atggctgtgt ttattcataa ctttaagaga | 3720 |
| aaaggtggca tcggcgagta cagcgctggc gagcgcatcg tggatattat tgcttcagat | 3780 |
| atacagacta aggaactgca gaaacaaatt accaagatcc agaactttag agtctactac | 3840 |
| agagattctc gagatcctct ctggaaagga ccagcaaaac ttctgtggaa aggagaaggt | 3900 |
| gcagtcgtga tccaggataa ctctgacatc aaagtggtgc ctcggagaaa ggccaaaatc | 3960 |
| attagagatt acggaaagca gatggcaggc gatgattgtg tcgctagtag acaggatgag | 4020 |
| gattgataa | 4029 |

<210> SEQ ID NO 41
<211> LENGTH: 2139
<212> TYPE: DNA
<213> ORGANISM: Artificial Sequence
<220> FEATURE:
<223> OTHER INFORMATION: nucleotide sequence of Env Mos2-C4D7 antigen

<400> SEQUENCE: 41

| | |
|---|---|
| atgcgagtca gaggtatgct gagaaattgg cagcagtggt ggatttggtc cagcctcgga | 60 |
| ttctggatgc tgatgatcta cagcgtcatg ggtaatctct gggtcacagt gtattacgga | 120 |
| gttcctgtct ggaaggacgc caagactaca ctcttttgcg cctctgacgc caaagcttac | 180 |
| gaaaaggaag tccacaatgt gtgggcaact catgcctgtg ttcctacaga tccaaatcca | 240 |
| caggagatcg tgctcggcaa tgtcaccgag aatttcaaca tgtggaagaa tgatatggtg | 300 |
| gatcaaatgc atgaggacat catttcccctc tgggacgcct ctctggaacc atgtgtcaag | 360 |
| ctcactccac tgtgtgtgac cctcaactgc agaaacgtgc gcaacgtgtc ctccaatggc | 420 |
| acatacaata tcattcataa tgagacttat aaggaaatga gaattgctc tttcaatgcc | 480 |
| accacagtcg tcgaggatcg caaacagaaa gtccatgctc tgttttaccg gctggatatc | 540 |
| gttcctctcg atgagaacaa ttcctccgag aagtcctctg agaactctag cgagtactac | 600 |

```
aggctcatta attgtaatac ctctgccatc acacaggctt gtccaaaggt ctccttcgat      660
cctattccta tccattactg tgctcctgcc ggatacgcta ttctcaaatg taacaacaag      720
acattcaatg gtactggtcc atgcaacaat gtgtctaccg tccagtgcac tcatggtatt      780
aagcctgtcg tcagtacaca gctcctgctc aatggatctc tcgctgagga agaaatcatt      840
atcagaagtg aaaacctcac taacaacgcc aaaaccatta ttgtccatct gaacgagaca      900
gtcaatatca catgcacacg acctaataac aataccagaa agtctatcag aatcggacct      960
ggccagacat tctatgccac aggcgatatc attggtgaca ttagacaggc tcattgcaat     1020
ctgtccagag atggttggaa taagacactc caaggtgtca agaagaaact cgccgaacac     1080
tttcctaaca agaccattaa gtttgcccct cactcaggcg gtgacctcga gattacaaca     1140
cacaccttta actgtagagg cgaattcttc tactgtaaca aagcaaccct cttcaacgag     1200
agcaacatcg agcggaacga cagcatcatt acacttccat gtcgcatcaa gcagatcatt     1260
aatatgtggc aggaagtcgg acgcgctatc tacgctccac ctattgccgg aaacatcaca     1320
tgtcggagca atattaccgg actcctgctc acacgcgacg gtggctctaa caatggcgtg     1380
ccaaatgata ccgaaacctt tagacctggt ggaggcgaca tgcgcaacaa ttggcgctct     1440
gaactgtaca agtacaaagt cgtcgaagtc aaacctctcg gagtcgctcc taccgaggct     1500
aaacgcagag tggtggaacg cgagaagcgg gctgtcggta tcggtgcagt gttcctaggc     1560
atcctcggcg cagccggcag cacaatgggc gctgcttcta ttacactcac tgtgcaggcc     1620
agacagctcc tgagcggaat tgtgcagcag caatcaaatc tgctgcgcgc tatcgaagca     1680
cagcagcata tgctccaact gactgtttgg ggtattaagc aactgcagac tagagtcctg     1740
gccattgaac ggtatctcca ggatcagcag ctgctcggac tctggggatg ctctggcaag     1800
ctcatctgta acagctgt gccttggaac acttcctggt ctaacaagtc tcagaccgat     1860
atttgggata atatgacatg gatgcagtgg gataaggaaa tcggtaatta tacaggcgag     1920
atctaccgac tgctcgagga atctcagaat caacaggaga gaacgaaaa ggatctcctg     1980 gctctcgact cctggaacaa tctgtggaac tggtttagca tttccaagtg gctgtggtac     2040
atcaagatct tcatcatgat cgtgggcggc ctgatcggcc tgcggatcat ctttgccgtg     2100
ctgagcatcg tgaaccgcgt gcggcagggc tactgataa                            2139
```

<210> SEQ ID NO 42
<211> LENGTH: 124
<212> TYPE: DNA
<213> ORGANISM: Artificial Sequence
<220> FEATURE:
<223> OTHER INFORMATION: Pr13.5 Long Promoter Sequence

<400> SEQUENCE: 42

```
taaaaataga aactataatc atataatagt gtaggttggt agtattgctc ttgtgactag       60
agactttagt taaggtactg taaaaataga aactataatc atataatagt gtaggttggt      120
agta                                                                   124
```

<210> SEQ ID NO 43
<211> LENGTH: 227
<212> TYPE: DNA
<213> ORGANISM: Artificial Sequence
<220> FEATURE:
<223> OTHER INFORMATION: PrHyb Promoter Sequence

<400> SEQUENCE: 43

```
gttttgaaaa ttttttata ataaatatcc ggtaaaaatt gaaaaactat tctaatttat      60
tgcacggtcc ggtaaaaatt gaaaaactat tctaatttat tgcacggtcc ggtaaaaatt    120
gaaaaactat tctaatttat tgcacggtcc ggtaaaaatt gaaaaactat tctaatttat    180
tgcacggtcc ggtaaaaatt gaaaaactat tctaatttat tgcacgg                 227

<210> SEQ ID NO 44
<211> LENGTH: 15
<212> TYPE: PRT
<213> ORGANISM: Artificial Sequence
<220> FEATURE:
<223> OTHER INFORMATION: Env peptide

<400> SEQUENCE: 44

Ile His Ile Gly Pro Gly Arg Ala Phe Tyr Thr Ala Gly Asp Ile
1               5                   10                  15

<210> SEQ ID NO 45
<211> LENGTH: 9
<212> TYPE: PRT
<213> ORGANISM: Artificial Sequence
<220> FEATURE:
<223> OTHER INFORMATION: Gag peptide

<400> SEQUENCE: 45

Ala Met Gln Met Leu Lys Glu Thr Ile
1               5

<210> SEQ ID NO 46
<211> LENGTH: 9
<212> TYPE: PRT
<213> ORGANISM: Artificial Sequence
<220> FEATURE:
<223> OTHER INFORMATION: Pol peptide

<400> SEQUENCE: 46

Tyr Tyr Asp Pro Ser Lys Asp Leu Ile
1               5
```